United States Patent
Kubo et al.

(10) Patent No.: US 7,820,673 B2
(45) Date of Patent: Oct. 26, 2010

(54) UREA DERIVATIVE, PROCESS FOR PRODUCING THE SAME, AND USE

(75) Inventors: Keiji Kubo, Osaka (JP); Yasuhiro Imaeda, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/583,046

(22) PCT Filed: Dec. 15, 2004

(86) PCT No.: PCT/JP2004/018717

§ 371 (c)(1),
(2), (4) Date: Jun. 15, 2006

(87) PCT Pub. No.: WO2005/058823

PCT Pub. Date: Jun. 30, 2005

(65) Prior Publication Data

US 2007/0093501 A1  Apr. 26, 2007

(30) Foreign Application Priority Data

Dec. 17, 2003 (JP) ............................. 2003-420031

(51) Int. Cl.
- A61K 31/4188 (2006.01)
- A61K 31/496 (2006.01)
- C07D 233/00 (2006.01)
- C07D 403/14 (2006.01)

(52) U.S. Cl. ............ 514/254.01; 514/387; 514/255.05; 514/393; 544/359; 544/360; 544/366; 544/368; 544/370; 544/371; 548/304.1; 548/360.1; 548/152; 548/306.4

(58) Field of Classification Search ............ 514/252.13, 514/254.01, 255.05, 393; 544/359, 360, 544/366, 368, 370, 371; 548/304.1, 360.1, 548/152

See application file for complete search history.

(56) References Cited

U.S. PATENT DOCUMENTS

| | | | |
|---|---|---|---|
| 4,719,200 A | 1/1988 | Eguchi et al. | |
| 5,453,423 A | 9/1995 | Long et al. | |
| 5,798,362 A | 8/1998 | Leonardi et al. | |
| 7,160,902 B2 * | 1/2007 | Dolle et al. | 514/326 |
| 2003/0187023 A1 | 10/2003 | Kubo et al. | |
| 2003/0212057 A1 | 11/2003 | Rudolf et al. | |

FOREIGN PATENT DOCUMENTS

| EP | 1 564 213 | 8/2005 |
|---|---|---|
| EP | 1 669 352 | 6/2006 |
| JP | 63-35575 | 2/1988 |
| WO | WO 92/00295 | 1/1992 |
| WO | WO 99/24421 | 5/1999 |
| WO | WO 02/06234 | 1/2002 |
| WO | WO 02/48099 | 6/2002 |
| WO | WO 02/074735 | 9/2002 |
| WO | WO 03/007888 | 1/2003 |
| WO | WO 03/010160 | 2/2003 |
| WO | WO 03/022214 | 3/2003 |
| WO | WO 03/104236 | 12/2003 |
| WO | WO 03104236 A1 * | 12/2003 |
| WO | WO 2004/048363 | 6/2004 |
| WO | WO 2005/030740 | 4/2005 |

OTHER PUBLICATIONS

U.S. Appl. No. 11/298,317, Song et al.*
Wu and Farrelly, Toxicology 236:1-6, 2007.*
Database CHEMCATS on STN, accession No. 2001:903143.

* cited by examiner

*Primary Examiner*—Yong Chu
(74) *Attorney, Agent, or Firm*—Hamre, Schumann, Mueller & Larson, P.C.

(57) ABSTRACT

The present invention provides a urea derivative or a salt thereof, which is useful as a therapeutic agent for thrombosis. The derivative is represented by Formula (I):

[Chemical formula I]

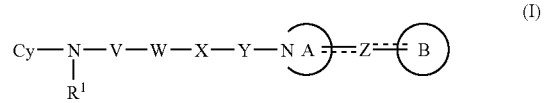

wherein Cy is an aromatic hydrocarbon group which may be substituted or an aromatic heterocyclic group which may be substituted; $R^1$ is a hydrogen atom or a hydrocarbon group which may be substituted; V is —C(O)—, —S(O)—, or —S(O)$_2$—; W is —N($R^2$)—, —O—, or a bond (wherein $R^2$ is a hydrogen atom or a hydrocarbon group which may be substituted); X is alkylene which may be substituted; Y is —C(O)—, —S(O)—, or —S(O)$_2$—; Z is a bond, a chain hydrocarbon group which may be substituted, or —N═; ring A is a non-aromatic nitrogen-containing heterocyclic ring which may be substituted; ring B is a nitrogen-containing heterocyclic ring which may be substituted; and

[Chemical formula 2]

˜˜˜, ˜˜˜ are each independently a single bond or a double bond; provided that $R^1$ may be bonded to $R^2$ to form a non-aromatic nitrogen-containing heterocyclic ring and that $R^2$ may be bonded to a substituent of X to form a non-aromatic nitrogen-containing heterocyclic ring which may be substituted.

8 Claims, No Drawings

UREA DERIVATIVE, PROCESS FOR PRODUCING THE SAME, AND USE

This application is a national stage of PCT/JP2004/18717, which was filed on Dec. 15, 2004.

TECHNICAL FIELD

The present invention relates to a novel urea derivative which inhibits activated blood coagulation factor X (FXa), thus having anticoagulation action and antithrombotic action, and is useful for the prevention and treatment of thrombotic occlusive disease, inflammation, cancer and the like in arteries and veins, a process for producing the same, and use thereof.

BACKGROUND ART

It is important to inhibit thrombus formation for the prevention and treatment of myocardial infarction, cerebral thrombosis and the like, and various antithrombin agents, platelet coagulation inhibitors and the like are being investigated and developed as antithrombotic agents. However, platelet coagulation inhibitors as well as antithrombin agents have anticoagulative action, together with their inhibition of platelet coagulation, and therefore, these drugs exhibit a tendency for hemorrhage and the like as side effects, thus presenting a safety problem. On the other hand, FXa inhibitors are thought to be safe anticoagulants because they specifically inhibit coagulation factors only.

To the present, compounds having FXa inhibitory action have been disclosed in, for example, Patent Documents 1 to 17 and Non-Patent Documents 1 and 2.

[Patent Document 1] International Patent Application Publication No. WO 96/10022

[Patent Document 2] International Patent Application Publication No. WO 02/06234

[Patent Document 3] International Patent Application Publication No. WO 03/045912

[Patent Document 4] International Patent Application Publication No. WO 02/48099

[Patent Document 5] International Patent Application Publication No. WO 00/76970

[Patent Document 6] International Patent Application Publication No. WO 00/76971

[Patent Document 7] International Patent Application Publication No. WO 01/96296

[Patent Document 8] International Patent Application Publication No. WO 01/96303

[Patent Document 9] International Patent Application Publication No. WO 01/96304

[Patent Document 10] International Patent Application Publication No. WO 01/96323

[Patent Document 11] International Patent Application Publication No. WO 03/010160

[Patent Document 12] International Patent Application Publication No. WO 03/049735

[Patent Document 13] International Patent Application Publication No. WO 03/049737

[Patent Document 14] International Patent Application Publication No. WO 03/050109

[Patent Document 15] International Patent Application Publication No. WO 02/074735

[Patent Document 16] International Patent Application Publication No. WO 2004/035579

[Patent Document 17] International Patent Application Publication No. WO 2004/048363

[Non-Patent Document 1] J. W. Liebeschuetz, et al., Journal of Medicinal Chemistry, Vol. 45, p. 1221 (2002)

[Non-Patent Document 2] W. W. K. R. Mederski, et al., Bioorganic & Medicinal Chemistry Letters, Vol. 13, p. 3715 (2003)

DISCLOSURE OF THE INVENTION

Development of a novel compound which has excellent efficacy, oral absorbability, effect sustainability and the like, with less side effects, and which is useful as a therapeutic drug for thrombosis, compared with conventional FXa inhibitors, is desired.

The present inventors had an idea that a urea derivative having high selectivity for FXa and strong inhibitory action would be able to show sustained and sufficient effect when orally administered, and would be useful for the prevention and treatment of thrombotic occlusive disease, inflammation and cancer in arteries and veins, and devotedly conducted researches.

As a result, the present inventors found that a novel urea derivative represented by the following Formula (I) or a salt thereof [hereinafter, may be referred to as Compound (I)] has specific and strong FXa inhibitory action, is highly safe, and exhibits sustained and sufficient effect when orally administered, thus completing the present invention.

That is, the invention relates to:

(1) A compound represented by Formula (1):

[Formula 1]

$$Cy-\underset{R^1}{N}-V-W-X-Y-N\overset{}{A}=Z=B \quad (I)$$

wherein Cy is an aromatic hydrocarbon group which may be substituted, or an aromatic heterocyclic group which may be substituted; $R^1$ is a hydrogen atom or a hydrocarbon group which may be substituted; V is —C(O)—, —S(O)—, or —S(O)$_2$—;

W is —N($R^2$)—, —O—, or a bond (wherein $R^2$ is a hydrogen atom or a hydrocarbon group which may be substituted); X is alkylene which may be substituted; Y is —C(O)—, —S(O)—, or —S(O)$_2$—; Z is a bond, a chain hydrocarbon group which may be substituted, or —N=; ring A is a non-aromatic nitrogen-containing heterocyclic ring which may be substituted; and ring B is a nitrogen-containing heterocyclic group which may be substituted;

-----;----- are each independently a single bond or a double bond; $R^1$ and R may be bonded to each other to form a non-aromatic nitrogen-containing heterocyclic ring which may be substituted; and $R^2$ may be bonded to a substituent of X to form a non-aromatic nitrogen-containing heterocyclic ring which may be substituted, or a salt thereof;

(2) A prodrug of the compound according to (1) above;

(3) The compound according to (1) above, wherein Cy is phenyl which may be substituted, or a 5- to 6-membered aromatic monocyclic heterocyclic group which may be substituted;

(4) The compound according to (1) above, wherein Cy is phenyl which may be substituted with a halogen atom;

(5) The compound according to (1) above, wherein $R^1$ is a hydrogen atom;

(6) The compound according to (1) above, wherein V is —C(O)—;

(7) The compound according to (1) above, wherein W is —N($R^2$)—;

(8) The compound according to (1) above, wherein X is $C_{1-4}$ alkylene which may be substituted with a hydrocarbon group which may be substituted, an aromatic heterocyclic group which may be substituted, a hydroxyl group which may be substituted, amino which may be substituted, carbamoyl which may be substituted or carboxyl which may be esterified;

(9) The compound according to (1) above, wherein X is methylene which may be substituted with a hydrocarbon group which may be substituted or an aromatic heterocyclic group which may be substituted;

(10) The compound according to (1) above, wherein Y is —C(O)—;

(11) The compound according to (1) above, wherein —W—X—Y— is an amino acid residue;

(12) The compound according to (1) above, wherein ring A is a piperidine ring which may be substituted, or a piperazine ring which may be substituted;

(13) The compound according to (1) above, wherein ring B is a monocyclic nitrogen-containing heterocyclic ring which may be substituted;

(14) The compound according to (13) above, wherein the monocyclic nitrogen-containing heterocyclic ring is a piperidine ring, a piperazine ring, a morpholine ring, an imidazoline ring, a pyrrolidine ring, a pyridine ring, an imidazole ring, or a thiazoline ring;

(15) The compound according to (1) above, wherein ring B is a fused nitrogen-containing heterocyclic ring which may be substituted;

(16) The compound according to (15) above, wherein the fused nitrogen-containing heterocyclic ring is a fused pyridine ring, a fused imidazole ring, a fused pyrazole ring, or a fused thiazoline ring;

(17) The compound according to (1) above, wherein Z is a bond or $C_{1-6}$ alkylene;

(18) A compound selected from the group consisting of N-(4-chlorophenyl)-N'-((1R)-2,2-dimethyl-1-((4-(5-methyl-3-oxo-1H-imidazo[1,5-c]imidazol-2(3H)-yl)-1-piperazinyl)carbonyl)propyl)urea, N-(4-chlorophenyl)-N'-(2-ethyl-2-hydroxy-1-((4-(5-methyl-3-oxo-1H-imidazo[1,5-c]imidazol-2(3H)-yl)-1-piperazinyl)carbonyl)butyl)urea, N-(4-chlorophenyl)-N'-((1S)-2-methyl-1-((4-(5-methyl-3-oxo-1H-imidazo[1,5-c]imidazol-2(3H)-yl)-1-piperazinyl)carbonyl)-2-(methylthio)propyl)urea, and N-(4-chlorophenyl)-N'-(2-methoxy-2-methyl-1-((4-(5-methyl-3-oxo-1H-imidazo[1,5-c]imidazol-2(3H)-yl)-1-piperazinyl)carbonyl)propyl)urea, or a salt thereof;

(19) A pharmaceutical composition comprising the compound according to (1) or (2) above;

(20) The pharmaceutical composition according to (19) above, which is an anticoagulant;

(21) The pharmaceutical composition according to (19) above, which is an activated blood coagulation factor X inhibitor;

(22) The pharmaceutical composition according to (19) above, which is a prophylactic and/or therapeutic agent for myocardial infarction, cerebral infarction, deep vein thrombosis, pulmonary thromboembolism, or arteriosclerosis obliterans;

(23) The pharmaceutical composition according to (19) above, which is a prophylactic and/or therapeutic agent for economy-class syndrome, thromboembolism during and post operation, or the secondary onset of deep vein thrombosis;

(24) A method of inhibiting blood coagulation in mammal which comprises administering an effective amount of the compound according to (1) above or a prodrug thereof to the mammal;

(25) A method of inhibiting activated blood coagulation factor X in mammal which comprises administering an effective amount of the compound according to (1) above or a prodrug thereof to the mammal;

(26) A method of preventing and/or treating myocardial infarction, cerebral infarction, deep vein thrombosis, pulmonary thromboembolism or arteriosclerosis obliterans in mammal which comprises administering an effective amount of the compound according to (1) above or a prodrug thereof to the mammal;

(27) Use of the compound according to (1) above or a prodrug thereof, for the manufacture of a medicine for inhibiting blood coagulation;

(28) Use of the compound according to (1) above or a prodrug thereof, for the manufacture of a medicine for inhibiting activated blood coagulation factor X;

(29) Use of the compound according to (1) above or a prodrug thereof, for the manufacture of a medicine for preventing and/or treating myocardial infarction, cerebral infarction, deep vein thrombosis, pulmonary thromboembolism, or arteriosclerosis obliterans;

and the like.

Effect of the Invention

The Compound (I) of the invention or a salt thereof has excellent FXa inhibitory action, with less side effects of hemorrhage, and is also useful as an orally absorbable anticoagulant.

BEST MODE FOR CARRYING OUT THE INVENTION

In the above-described formulas, Cy is an aromatic hydrocarbon group which may be substituted, or an aromatic heterocyclic group which may be substituted.

The "aromatic hydrocarbon group" of the "aromatic hydrocarbon group which may be substituted" represented by Cy may be exemplified by a monocyclic or fused polycyclic aromatic hydrocarbon group, and for example, $C_{6-14}$ aromatic hydrocarbon groups such as phenyl, naphthyl, anthryl, phenanthryl, acenaphthylenyl and the like are preferred, among which phenyl and the like are particularly preferred.

The "aromatic heterocyclic group" of the "aromatic heterocyclic group which may be substituted" represented by Cy may be exemplified by a 5- to 6-membered aromatic monocyclic heterocyclic group such as, for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl or the like; and a 8- to 16-membered (preferably, 8- to 12-membered) aromatic fused heterocyclic group such as, for example, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalizinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl or the like. Preferably, a 5- to 6-membered aromatic monocyclic heterocyclic group, and particularly preferably, pyridyl, pyrimidyl, thienyl, thiazolyl or the like may be mentioned.

The substituent (hereinafter, referred to as "substituent for Cy") which may be carried by the "aromatic hydrocarbon group" or "aromatic heterocyclic group" of the "aromatic hydrocarbon group which may be substituted" and "aromatic heterocyclic group which may be substituted" represented by Cy, may be exemplified by a hydrocarbon group which may be substituted, a heterocyclic group which may be substituted, amino which may be substituted, imidoyl which may be substituted (for example, a group represented by the formula: —C(E')=N-E [wherein E and E' are each a hydrogen atom or a substituent (E is preferably a hydrogen atom)], etc.), amidino which may be substituted (for example, a group represented by the formula: —C(NT'T")=N—T [wherein T, T' and T" are each a hydrogen atom or a substituent (T is preferably a hydrogen atom)], etc.), a hydroxyl group which may be substituted, a thiol group which may be substituted, carbamoyl which may be substituted, thiocarbamoyl which may be substituted, a sulfamoyl group which may be substituted, carboxyl which may be esterified, a halogen atom (e.g., fluorine, chlorine, bromine, iodine, etc., preferably chlorine, bromine, etc.), a cyano group, a nitro group, acyl, and the like, and any of these substituents may be used for substitution at 1 to 5 (preferably, 1 to 3) substitutable positions.

The "hydrocarbon group" of the "hydrocarbon group which may be substituted" as a substituent for Cy, may be exemplified by the same group as the "hydrocarbon group" of the "hydrocarbon group which may be substituted" represented by $R^1$ to be described below, and the like.

The substituent which may be carried by the "hydrocarbon group" may be exemplified by hydroxyl, carboxyl, $C_{1-6}$ alkoxycarbonyl, acyl (e.g., $C_{1-6}$ alkanoyl such as formyl, acetyl, propionyl, pivaloyl or the like, benzoyl, etc.), amino which may be substituted [this amino may have one or two substituents such as, for example, lower alkyl (e.g., $C_{1-6}$ alkyl such as methyl, ethyl, propyl, isopropyl, butyl, isobutyl, tert-butyl, pentyl, hexyl or the like, etc.), carboxyl, $C_{1-6}$ alkoxycarbonyl, acyl (e.g., $C_{1-6}$ alkanoyl such as formyl, acetyl, propionyl, pivaloyl or the like, benzoyl, etc.) or the like, or may be a cyclic amine such as pyrrolidinyl or piperidinyl], a halogen atom (for example, fluorine, chlorine, bromine, iodine, etc.), nitro, cyano, lower alkyl which may be substituted with 1 to 5 halogen atoms (for example, $C_{1-6}$ alkyl such as methyl, ethyl, n-propyl, isopropyl, n-butyl, isobutyl, sec-butyl, tert-butyl, pentyl, hexyl, trifluoromethyl, etc.), lower alkoxy which may be substituted with 1 to 5 halogen atoms (e.g., $C_{1-6}$ alkoxy such as methoxy, ethoxy, n-propoxy, isopropoxy, n-butoxy, isobutoxy, sec-butoxy, tert-butoxy, trifluoromethoxy or the like, etc.), oxo, thioxo, and the like. It is preferable that one to three (preferably, one or two) of these substituents, which may be identical or different, are used for substitution.

The "heterocyclic group" of the "heterocyclic group which may be substituted" as a substituent for Cy, may be exemplified by an aromatic heterocyclic group containing at least one (preferably 1 to 4, more preferably 1 to 2) of heteroatoms of 1 to 3 species (preferably, 1 to 2 species) selected from oxygen atom, sulfur atom, nitrogen atom and the like as the ring-constituting atom (ring atom), a saturated or unsaturated non-aromatic heterocyclic group (aliphatic heterocyclic group), and the like.

The "aromatic heterocyclic group" may be exemplified by a 5- to 6-membered aromatic monocyclic heterocyclic group such as, for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl or the like; and a 8- to 16-membered (preferably, 8- to 12-membered) aromatic fused heterocyclic group such as, for example, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalizinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl or the like. Preferably, a 5- to 6-membered aromatic monocyclic heterocyclic group, and particularly preferably, pyridyl, pyrimidyl, thienyl, thiazolyl or the like may be mentioned.

The "non-aromatic heterocyclic group" may be exemplified by a 3- to 8-membered (preferably, 5- to 6-membered), saturated or unsaturated (preferably, saturated) non-aromatic monocyclic heterocyclic group (aliphatic monocyclic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl or the like; a heterocyclic group in which one to two (preferably, one) of the above-mentioned non-aromatic monocyclic heterocyclic groups such as 1,3-dihydroisoindolyl are fused with one to two benzene rings (preferably, one); a heterocyclic group in which one to two (preferably, one) of the above-mentioned non-aromatic monocyclic heterocyclic group are fused with one to two (preferably, one) of heterocyclic rings of the above-mentioned 5- to 6-membered aromatic monocyclic heterocyclic groups; a non-aromatic heterocyclic group in which part or all of the double bonds of the above-mentioned aromatic monocyclic heterocyclic group such as 1,2,3,4-tetrahydroquinolyl, 1,2,3,4-tetrahydroisoquinolyl or the like, or of the above-mentioned aromatic fused heterocyclic group are saturated; or the like.

The substituent which may be carried by the "heterocyclic group" of the "heterocyclic group which may be substituted", may be exemplified by the same groups of the same number as the substituents which may be carried by the hydrocarbon group of the above-mentioned "hydrocarbon group which may be substituted" as the substituent for Cy, or the like.

The substituent for the "amino which may be substituted", "imidoyl which may be substituted", "amidino which may be substituted", "hydroxyl group which may be substituted", and "thiol group which may be substituted" as the substituent for Cy, may be exemplified by lower alkyl (e.g., $C_{1-6}$ alkyl such as methyl, ethyl, propyl, isopropyl, butyl, isobutyl, tert-butyl, pentyl, hexyl or the like, etc.) which may be substituted with a substituent selected from a halogen atom (e.g., fluorine, chlorine, bromine, iodine, etc.), and $C_{1-6}$ alkoxy which may be halogenated (e.g., methoxy, ethoxy, trifluoromethoxy, 2,2,2-trifluoroethoxy, trichloromethoxy, 2,2,2-trichloroethoxy, etc.), acyl ($C_{1-6}$ alkanoyl (e.g., formyl, acetyl, propionyl, pivaloyl, etc.), benzoyl, $C_{1-6}$ alkylsulfonyl (e.g., methanesulfonyl, etc.), benzenesulfonyl, etc.), $C_{1-6}$ alkoxycarbonyl which may be halogenated (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl, etc.), $C_{1-6}$ alkoxycarbonyl which may be substituted with phenyl (e.g., benzyloxycarbonyl, etc.), a heterocyclic group (for example, the same group as the "heterocyclic group" of the above-mentioned "heterocyclic group which may be substituted" as the substituent for Cy, etc.), or the like. The "amino" of the "amino which may be substituted" as a substituent for Cy may be substituted with imidoyl which may be substituted (e.g., $C_{1-6}$ alkanoylimidoyl (e.g., formylimidoyl, acetylimidoyl, etc.), $C_{1-6}$ alkoxyimidoyl, $C_{1-6}$ alkylthioimidoyl, amidino, etc.), amino which may be substituted with one to two of $C_{1-6}$ alkyl, or the like. Furthermore, two of the substituents may form cyclic amino, together with a nitrogen atom, and in this case, the cyclic amino may be exemplified by a 3- to 8-membered (preferably, 5- to 6-membered) cyclic amino such as 1-azetidinyl, 1-pyrrolidinyl, piperidino, thiomorpholino, morpholino, 1-piperazinyl which may be substituted at 4-position (the substituent may be lower alkyl (e.g., $C_{1-6}$ alkyl such as methyl, ethyl, propyl, isopropyl, butyl, t-butyl, pentyl, hexyl or the like, etc.), aralkyl (e.g., $C_{7-10}$ aralkyl such as benzyl, phenethyl or the like, etc.), aromatic hydrocarbon group (e.g., $C_{6-10}$ aromatic hydrocarbon group such as phenyl, 1-naphthyl, 2-naphthyl or the like, etc.)), 1-pyrrolyl, 1-imidazolyl or the like, or the like.

The "carbamoyl which may be substituted" as a substituent for Cy may be exemplified by unsubstituted carbamoyl as well as N-monosubstituted carbamoyl, or N,N-disubstituted carbamoyl.

The "N-monosubstituted carbamoyl" may be exemplified by lower alkyl (e.g., $C_{1-6}$ alkyl such as methyl, ethyl, propyl, isopropyl, butyl, isobutyl, tert-butyl, pentyl, hexyl or the like, etc.), lower alkenyl (e.g., $C_{2-6}$ alkenyl such as vinyl, allyl, isopropenyl, propenyl, butenyl, pentenyl, hexenyl or the like, etc.), cycloalkyl (e.g., $C_{3-6}$ cycloalkyl such as cyclopropyl, cyclobutyl, cyclopentyl, cyclohexyl or the like, etc.), an aromatic hydrocarbon group (e.g., $C_{6-10}$ aromatic hydrocarbon group such as phenyl, 1-naphthyl, 2-naphthyl or the like, etc.), aralkyl (e.g., $C_{7-10}$ aralkyl such as benzyl, phenethyl or the like; preferably, phenyl-$C_{1-4}$ alkyl, etc.), arylalkenyl (e.g., $C_{8-10}$ arylalkenyl such as cinnamyl or the like; preferably, phenyl-$C_{2-4}$ alkenyl, etc.), a heterocyclic group (for example, the same group as the "heterocyclic group" of the "heterocyclic group which may be substituted" as the substituent for the above-mentioned "hydrocarbon group which may be substituted" as the substituent for Cy, etc.), amino which may be substituted with one to two of $C_{1-6}$ alkyl, or the like. The lower alkyl, lower alkenyl, cycloalkyl, aromatic hydrocarbon group, aralkyl, arylalkenyl, and heterocyclic group may be substituted, and the substituent may be exemplified by hydroxyl, amino which may be substituted [this amino may have one or two of substituents such as lower alkyl (e.g., $C_{1-6}$ alkyl such as methyl, ethyl, propyl, isopropyl, butyl, isobutyl, tert-butyl, pentyl, hexyl or the like, etc.), acyl (e.g., $C_{1-6}$ alkanoyl such as formyl, acetyl, propionyl, pivaloyl or the like, benzoyl, etc.), carboxyl, $C_{1-6}$ alkoxycarbonyl and the like], a halogen atom (for example, fluorine, chlorine, bromine, iodine, etc.), nitro, cyano, lower alkyl which may be substituted with 1 to 5 halogen atoms (for example, fluorine, chlorine, bromine, iodine, etc.), lower alkoxy which may be substituted with 1 to 5 halogen atoms (for example, fluorine, chlorine, bromine, iodine, etc.), or the like. The lower alkyl may be exemplified by $C_{1-6}$ alkyl such as methyl, ethyl, n-propyl, isopropyl, n-butyl, isobutyl, sec-butyl, tert-butyl, pentyl, hexyl, etc., or the like, and in particular, methyl, ethyl and the like are preferred. The lower alkoxy may be exemplified by $C_{1-6}$ alkoxy such as methoxy, ethoxy, n-propoxy, isopropoxy, n-butoxy, isobutoxy, sec-butoxy, tert-butoxy, etc., or the like, and in particular, methoxy, ethoxy and the like are preferred. It is preferable that one to three (preferably, one or two) of these substituents, which may be identical or different, are used for substitution.

The "N,N-disubstituted carbamoyl" means a carbamoyl group having two substituents on the nitrogen atom. Examples of one of the substituents include the same ones as the substituents for the above-mentioned "N-monosubstituted carbamoyl", while examples of the other substituent include lower alkyl (e.g., $C_{1-6}$ alkyl such as methyl, ethyl, propyl, isopropyl, butyl, tert-butyl, pentyl, hexyl or the like, etc.), $C_{3-6}$ cycloalkyl (e.g., cyclopropyl, cyclobutyl, cyclopentyl, cyclohexyl, etc.), $C_{7-10}$ aralkyl (e.g., benzyl, phenethyl, etc.; preferably, phenyl-$C_{1-4}$ alkyl, etc.), and the like. Further, two substituents may form cyclic amino together with the nitrogen, and the cyclic aminocarbamoyl in this case may be exemplified by cyclic aminocarbonyl of a 3- to 8-membered ring (preferably, 5- to 6-membered ring) 1-azetidinylcarbonyl, 1-pyrrolidinylcarbonyl, piperidinocarbonyl, morpholinocarbonyl, thiomorpholinocarbonyl (the sulfur atom may be oxidized), 1-piperazinylcarbonyl which may be substituted at the 4-position (the substituent is lower alkyl (e.g., $C_{1-6}$ alkyl such as methyl, ethyl, propyl, isopropyl, butyl, t-butyl, pentyl, hexyl or the like, etc.), aralkyl (e.g., $C_{7-10}$ aralkyl such as benzyl, phenethyl or the like, etc.), aromatic hydrocarbon group (e.g., $C_{6-10}$ aromatic hydrocarbon group such as phenyl, 1-naphthyl, 2-naphthyl or the like, etc.), etc.), or the like.

The substituent for the "thiocarbamoyl which may be substituted" and "sulfamoyl which may be substituted" as substituents for Cy, may be exemplified by the same ones as the substituents for the above-mentioned "carbamoyl which may be substituted", and the like.

The "carboxyl which may be esterified" as a substituent for Cy, may be exemplified by free carbonyl as well as lower alkoxycarbonyl, aryloxycarbonyl, aralkyloxycarbonyl or the like.

The "lower alkoxycarbonyl" may be exemplified by $C_{1-6}$ alkoxycarbonyl such as methoxycarbonyl, ethoxycarbonyl, proppoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, etc., or the like. Among them, $C_{1-3}$ alkoxycarbonyl such as methoxycarbonyl, ethoxycarbonyl, propoxycarbonyl and the like are preferred.

The "aryloxycarbonyl" is preferably, for example, $C_{7-12}$ aryloxycarbonyl such as phenoxycarbonyl, 1-naphthoxycarbonyl, 2-naphthoxycarbonyl, or the like.

The "aralkyloxycarbonyl" is preferably, for example, $C_{7-10}$ aralkyloxycarbonyl (preferably, $C_{6-10}$ aryl-$C_{1-4}$ alkoxycarbonyl, etc.) such as benzyloxycarbonyl, phenethyloxycarbonyl, or the like.

The "aryloxycarbonyl" and "aralkyloxycarbonyl" may be substituted, and for the substituent, the same ones of the same number as the substituents for the aromatic hydrocarbon group and aralkyl which have been mentioned as the exemplary substituents for the above-mentioned N-monosubstituted carbamoyl, are used.

The "acyl group" as a substituent for Cy may be exemplified by acyl derived from carboxylic acid, acyl derived from sulfinic acid, acyl derived sulfonic acid, acyl derived from phosphonic acid, and the like.

The "acyl derived from carboxylic acid" may be exemplified by one in which a hydrogen atom, or one substituent present on the nitrogen atom of the above-mentioned "N-monosubstituted carbamoyl" is bound to carbonyl (—C(O)—), for example, formyl; chain-like or cyclic $C_{2-8}$ alkanoyl which may be halogenated, such as acetyl, propionyl, butyryl, isobutyryl, valeryl, isovaleryl, pivaloyl, hexanoyl, cyclobutanecarbonyl, cyclopentanecarbonyl, cyclohexanecarbonyl, crotonyl, trifluoroacetyl or the like; benzyl, nicotinoyl, isonicotinoyl, and the like. Among these, $C_{2-5}$ alkanoyl such as acetyl, propionyl, butyryl, valeryl, pivaloyl or the like, and the like are preferred.

The "acyl derived sulfinic acid" may be exemplified by one in which one substituent present on the nitrogen atom of the above-mentioned "N-monosubstituted carbamoyl" is bound to sulfinyl (—S(O)—), for example, chain-like or cyclic $C_{1-6}$ alkylsulfinyl which may be halogenated, such as methanesulfinyl, ethanesulfinyl, propanesulfinyl, cyclopropanesulfinyl, cyclopentanesulfinyl, cyclohexanesulfinyl or the like, benzenesulfinyl, toluenesulfinyl and the like.

The "acyl derived from sulfonic acid" may be exemplified by one in which one substituent present on the nitrogen atom of the above-mentioned "N-monosubstituted carbamoyl" is bound to sulfonyl (—S(O)$_2$—), for example, chain-like or cyclic $C_{1-6}$ alkylsulfonyl which may be halogenated, such as methanesulfonyl, ethanesulfonyl, propanesulfonyl, cyclopropanesulfonyl, cyclopentanesulfonyl, cyclohexanesulfonyl or the like, benzenesulfonyl, toluenesulfonyl and the like.

The "acyl derived from phosphonic acid" may be exemplified by (mono- or di-$C_{1-4}$ alkyl)phosphono which may form a ring, such as dimethylphosphono, diethylphosphono, diisopropylphosphono, dibutylphosphono, 2-oxido-1,3,2-dioxaphosphinan-2-yl or the like, and the like.

Cy is preferably a phenyl group which may be substituted with a substituent selected from a halogen atom, $C_{1-6}$ alkyl, $C_{2-6}$ alkenyl, $C_{2-6}$ alkynyl, amino which may be substituted, nitro, cyano, amidino which may be substituted, and carboxyl which may be esterified or amidated; or a 5- to 6-membered aromatic monocyclic heterocyclic group (preferably, pyridyl) which may be substituted with a substituent selected from a halogen atom, $C_{1-6}$ alkyl, $C_{2-6}$ alkenyl, $C_{2-6}$ alkynyl, amino which may be substituted, nitro, cyano, amidino which may be substituted, and carboxyl which may be esterified or amidated.

Among these, phenyl which may be substituted with a halogen atom or $C_{2-4}$ alkenyl (preferably, a halogen atom) is preferred, and phenyl which may be substituted with a halogen atom is more preferred.

In the above-described formulas, $R^1$ is a hydrogen atom, or a hydrocarbon group which may be substituted.

The "hydrocarbon group" of the "hydrocarbon group which may be substituted" represented by $R^1$, may be exemplified by alkyl, alkenyl, alkynyl, aromatic hydrocarbon group, cycloalkyl, cycloalkenyl, aralkyl or the like.

The "alkyl" may be exemplified by $C_{1-6}$ alkyl such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 2-ethylpropyl, etc., or the like.

The "alkenyl" may be exemplified by $C_{2-6}$ alkenyl such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc., or the like.

The "alkynyl" may be exemplified by $C_{2-6}$ alkynyl such as ethynyl, 1-propinyl, 2-propinyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc., or the like.

The "aromatic hydrocarbon group" may be exemplified by a monocyclic or fused polycyclic aromatic hydrocarbon group, for example, a $C_{6-14}$ aromatic hydrocarbon group such as phenyl, naphthyl, anthryl, phenanthryl, acenaphthylenyl, etc., or the like.

The "cycloalkyl" may be exemplified by $C_{3-7}$ cycloalkyl such as cyclopropyl, cyclobutyl, cyclopentyl, cyclohexyl, cycloheptyl, etc., or the like.

The "cycloalkenyl" may be exemplified by $C_{3-6}$ cycloalkenyl such as cyclopropenyl, cyclobutenyl, cyclopentenyl, cyclohexenyl, etc., or the like.

The "aralkyl" may be exemplified by a $C_{7-16}$ aralkyl group, for example, a phenyl-$C_{1-6}$ alkyl group such as benzyl, phenethyl, 3-phenylpropyl, 4-phenylbutyl or the like, and a naphthyl-$C_{1-6}$ alkyl group such as (1-naphthyl)methyl, (2-naphthyl)methyl, 2-(1-naphthyl)ethyl, 2-(2-naphthyl)ethyl, etc., or the like.

The substituent which may be carried by the "hydrocarbon group" of the "hydrocarbon group which may be substituted" represented by $R^1$, may be exemplified by the same groups of the same number as the substituents for the above-mentioned Cy, as well as an oxo group, a thioxo group, or the like.

$R^1$ is preferably hydrogen atom, $C_{1-6}$ alkyl or the like, and among these, hydrogen atom is more preferred.

In the above-described formulas, V is —C(O)—, —S(O)— or —S(O)$_2$—.

V is preferably —C(O)—.

In the above-described formulas, W is —N($R^2$)—, —O— or a bond, and $R^2$ is a hydrogen atom, or a hydrocarbon group which may be substituted.

The hydrocarbon group of the "hydrocarbon group which may be substituted" represented by $R^2$, may be exemplified by the same group as the hydrocarbon group of the above-mentioned "hydrocarbon group which may be substituted" represented by $R^1$. The substituent which may be carried by the hydrocarbon group may be exemplified by the same groups of the same number as the substituents which may be carried by the hydrocarbon group of the above-mentioned "hydrocarbon group which may be substituted" represented by $R^1$, or the like.

W is preferably —N($R^2$)— or —O—, and among them, —N($R^2$)— is more preferred. $R^2$ is preferably hydrogen atom or $C_{1-4}$ alkyl, and among them, hydrogen atom is more preferred.

In the above-described formulas, X is alkylene which may be substituted. The alkylene may be exemplified by $C_{1-6}$ alkylene such as methylene, ethylene, trimethylene, tetramethylene or the like.

The substituent which may be carried by the alkylene may be exemplified by the same groups of the same number as the substituents which may be carried by the "aromatic hydrocarbon group" of the above-mentioned "aromatic hydrocarbon group which may be substituted" represented by Cy, as well as an oxo group, a thioxo group and the like.

X is preferably $C_{1-4}$ alkylene which may be substituted with a hydrocarbon group which may be substituted, an aromatic heterocyclic group which may be substituted, a hydroxyl group which may be substituted, amino which may be substituted, carbamoyl which may be substituted, or carboxyl which may be esterified, and among them, X is more preferably methylene which may be substituted with a hydrocarbon group which may be substituted, or an aromatic heterocyclic group which may be substituted. Among them, methylene which may be substituted with $C_{1-6}$ alkyl, $C_{2-6}$ alkenyl, $C_{2-6}$ alkynyl, phenyl, $C_{3-7}$ cycloalkyl, $C_{3-6}$ cycloalkenyl, $C_{7-16}$ aralkyl, or a 5- to 6-membered aromatic monocyclic heterocyclic group (these $C_{1-6}$ alkyl, $C_{2-6}$ alkenyl, $C_{2-6}$ alkynyl, phenyl, $C_{3-7}$ cycloalkyl, $C_{3-6}$ cycloalkenyl, $C_{7-16}$ aralkyl, and 5- to 6-membered aromatic monocyclic heterocyclic group may be respectively substituted with a hydroxyl group, a thiol group which may be substituted with $C_{1-6}$ alkyl, carboxyl, $C_{1-6}$ alkoxycarbonyl, acyl (e.g., $C_{1-6}$ alkanoyl such as formyl, acetyl, propionyl, pivaloyl or the like, benzoyl, $C_{1-6}$ alkylsulfinyl, $C_{1-6}$ alkylsulfonyl, etc.), amino which may be substituted [this amino may be substituted with one or two substituents of lower alkyl (e.g., $C_{1-6}$ alkyl such as methyl, ethyl, propyl, isopropyl, butyl, isobutyl, tert-butyl, pentyl, hexyl or the like, etc.), carboxyl, $C_{1-6}$ alkoxycarbonyl, acyl (e.g., $C_{1-6}$ alkanoyl such as formyl, acetyl, propionyl, pivaloyl or the like, benzoyl, etc.) or the like], a halogen atom (for example, fluorine, chlorine, bromine, iodine, etc.), carbamoyloxy, a nitro group, a cyano group, lower alkyl which may be substituted with 1 to 5 halogen atoms (for example, $C_{1-6}$ alkyl such as methyl, ethyl, n-propyl, isopropyl, n-butyl, isobutyl, sec-butyl, tert-butyl, pentyl, hexyl or the like), phenyl which may be substituted with 1 to 5 halogen atoms, lower alkoxy which may be substituted with phenyl or 1 to 5 halogen atoms (for example, $C_{1-6}$ alkoxy such as methoxy, ethoxy, n-propoxy, isopropoxy, n-butoxy, isobutoxy, sec-butoxy, tert-butoxy or the like, etc.), a 5- to 6-membered aromatic monocyclic heterocyclic group, oxo, thioxo, etc.), or the like, is particularly preferred.

In the above-described formulas, Y is —C(O)—, —S(O)— or —S(O)$_2$—.

Y is preferably —C(O)—.

In the above-described formulas, —W—X—Y— is preferably an amino acid residue.

The amino acid residue may be any divalent group that is obtained by eliminating one hydrogen atom and a hydroxyl radical from the amino group (unsubstituted amino group or N-monosubstituted amino group) and the carboxyl group, respectively, which constituted the amino acid.

The amino acid from which the amino acid residue originates may be exemplified by α-amino acid such as alanine, arginine, asparagines, aspartic acid, cystein, glutamine, glutamic acid, 2-aminomalonic acid, 2-aminoadipic acid, glycine, histidine, isoleucine, leucine, lysine, ornithine, 2,4-diaminobutyric acid, methionine, phenylalanine, proline, 4-hydroxyproline, thioproline, azetidine-2-carboxylic acid, pipecolinic acid (piperidine-2-carboxylic acid), indoline-2-carboxylic acid, tetrahydroisoquinoline-3-carboxylic acid, serine, threonine, tryptophan, 5-methyltryptophan, thyrosine, valine, alloisoleucine, norvaline, norleucine, tert-leucine, γ-methylleucine, phenylglycine, 2-aminobutyric acid, cysteic acid, homocysteic acid, 1-naphthylalanine, 2-naphthylalanine, 2-thienylglycine, 3-thienylglycine, 3-benzothienylalanine, 4-biphenylalanine, pentamethylphenylalanine, 1-aminocyclopropane-1-carboxylic acid, 1-aminocyclobutane-1-carboxylic acid, 1-aminocyclopentane-1-carboxylic acid, 1-aminocyclohexane-1-carboxylic acid, 1-aminocycloheptane-1-carboxylic acid or the like; and β-amino acid such as β-alanine, azetidine-3-carboxylic acid or the like.

When such amino acid has a functional group, for example, a hydroxyl group, a thiol group, an amino group, an imino group, a carboxyl group or the like, this functional group may be substituted with an appropriate substituent.

In this case, the substituted hydroxyl group may be exemplified by $C_{1-6}$ alkanoyloxy (for example, formyloxy, acetoxy, propionyloxy, etc.), $C_{4-9}$ aliphatic cyclic carbonyloxy (for example, cyclopentanecarbonyloxy, cyclohexanecarbonyloxy, etc.), $C_{7-15}$ arylcarbonyloxy (for example, benzoyloxy, 4-methylbenzoyloxy, etc.), $C_{8-16}$ aralkylcarbonyloxy (for example, phenylacetoxy, 2-phenylpropionyloxy, 3-phenylpropionyloxy, diphenylacetoxy, etc.), aromatic heterocyclic alkylcarbonyloxy (for example, indol-2-ylacetoxy, indol-3-ylacetoxy, etc.), $C_{1-6}$ alkoxy (for example, methoxy, ethoxy, n-propoxy, tert-butoxy, etc.), $C_{3-8}$ cycloalkoxy (for example, cyclopentyloxy, cyclohexyloxy, etc.), $C_{6-12}$ aryloxy (for example, phenyloxy, 4-methylphenyloxy, etc.), $C_{7-15}$ aralkyloxy (for example, benzyloxy, phenethyloxy, diphenylmethoxy, etc.), or the like. The α-amino acid having the substituted hydroxyl group may be exemplified by O-acetylserine, O-acetylthreonine, 4-acetoxyproline, O-benzoylserine, O-benzoylthreonine, 4-benzoyloxyproline, O-phenylacetylserine, O-phenylacetylthreonine, 4-phenylacetoxyproline, O-ethylserine, O-ethylthreonine, 4-ethoxyproline, O-cyclohexylserine, O-cyclohexylthreonine, 4-cyclohexyloxyproline, O-phenylserine, O-phenylthreonine, 4-phenoxyproline, O-benzylserine, O-benzylthreonine, 4-benzyloxyproline, O-diphenylmethylserine, O-diphenylmethylthreonine, 4-diphenylmethoxyproline, or the like.

The substituted thiol group may be exemplified by $C_{1-6}$ alkanoylthio (for example, formylthio, acetylthio, propionylthio, etc.), $C_{4-9}$ aliphatic cyclic carbonylthio (for example, cyclopentanecarbonylthio, cyclohexanecarbonylthio, etc.), $C_{7-15}$ arylcarbonylthio (for example, benzoylthio, 4-methylbenzoylthio, etc.), $C_{8-16}$ aralkylcarbonylthio (for example, phenylacetylthio, 2-phenylpropionylthio, 3-phenylpropionylthio, diphenylacetylthio, etc.), $C_{1-6}$ alkylthio (for example, methylthio, ethylthio, n-propylthio, tert-butylthio, etc.), $C_{3-8}$ cycloalkylthio (for example, cyclopentylthio, cyclohexylthio, etc.), $C_{6-12}$ arylthio (for example, phenylthio, 4-methylphenylthio, etc.), $C_{7-15}$ aralkylthio (for example, benzylthio, phenethylthio, diphenylmethylthio, etc.), or the like. The α-amino acid having the substituted thiol group may be exemplified by S-acetylcystein, S-benzoylcystein, S-phenylacetylcystein, S-ethylcystein, S-cyclohexylcystein, S-phenylcystein, S-benzylcystein or the like.

The substituted amino group may be exemplified by $C_{1-6}$ alkylamino (for example, N-methylamino, N-ethylamino, N-tert-butylamino, etc.), $C_{3-8}$ cycloalkylamino (for example, N-cyclopentylamino, N-cyclohexylamino, etc.), $C_{6-12}$ arylamino (for example, N-phenylamino, N-{4-methylphenyl}amino, etc.), $C_{7-15}$ aralkylamino (for example, N-benzylamino, N-phenethylamino, N-{2-chlorobenzyl}amino, N-{3-chlorobenzyl}amino, N-{4-chlorobenzyl}amino, N-{2-methylbenzyl}amino, N-{3-methylbenzyl}amino, N-{4-methylbenzyl}amino, N-{2-methoxybenzyl}amino, N-{3-methoxybenzyl}amino, N-{4-methoxybenzyl}amino, etc.), aromatic heterocyclic-$C_{1-6}$ alkylamino (for example, 2-furylmethylamino, 3-furylmethylamino, 2-thienylmethylamino, 3-thienylmethylamino, indol-2-ylmethylamino, indol-3-ylmethylamino); and the substituted amido group may be exemplified by $C_{1-6}$ aliphatic acylamido (for example, formamido, acetamido, propionamido, etc.), $C_{4-9}$ aliphatic cyclic acylamido (for example, cyclopentanecarbonylamido, cyclhexanecarbonylamido, etc.), $C_{7-15}$ arylacylamido (for example, benzamido, 3-methylbenzamido, etc.), $C_{8-16}$ aralkylacylamido (for example, phenylacetamido, 2-phenylpropionamido, 3-phenylpropionamido, diphenylacetamido, 1-naphthylacetamido, 2-naphthylacetamido, etc.), aromatic heterocyclic carboxamido (for example, indol-2-ylcarboxamido, indol-3-ylcarboxyamido, etc.), aromatic heterocyclic alkylcarboxamido (for example, indol-2-ylacetamido, indol-3-ylacetamido, etc.), sulfonylamido (for example, benzenesulfonylamido, para-toluenesulfonylamido, 4-methoxy-2,3,6-trimethylbenzenesulfonylamido, etc.) or the like.

The substituent for the substituted imino group may be exemplified by $C_{1-6}$ alkyl, $C_{3-8}$ cycloalkyl, $C_{6-12}$ aryl, $C_{7-15}$ aralkyl, aromatic heterocyclic-$C_{1-6}$ alkyl or the like, the same ones as the substituents for the above-mentioned substituted amino group or amido group.

The α-amino acid substituted with an amino group may be exemplified by N-methylglycine (sarcosine), N-ethylglycine, N-methylleucine, N-ethylleucine, N-methylphenylalanine, N-ethylphenylalanine, N(α)-methyltryptophan, N(α)-ethyltryptophan, N-cyclopentylglycine, N-cyclohexylglycine, N-phenylglycine, N-phenylleucine, N-benzylglycine, N-benzylleucine, N(π)-benzylhistidine, N(τ)-benzylhistidine, N(π)phenacylhistidine, N(π)-benzyloxymethylhistidine, $N^g$-benzenesulfonylarginine, $N^g$-para-toluenesulfonylarginine, $N^g$-(4-methoxy-2,3,6-trimethylbenzenesulfonyl)arginine, N(ε)-benzenesulfonyllysine, N(ε)-para-toluenesulfonyllysine, N(ε)-(4-methoxy-2,3,6-trimethylbenzenesulfonyl)lysine, $N^{in}$-methyltryptophan, $N^{in}$-ethyltryptophan, $N^{in}$-formyltryptophan, $N^{in}$-acetyltryptophan, N(ε)-benzyllysine, N(ε)-(2-furylmethyl)lysine, N(ε)-(2-theinylmethyl)lysine, N(ε)-(indol-3-ylmethyl)lysine, N(ε)-phenylacetyllysine, N(ε)-({2-furyl}acetyl)lysine, N(ε)-({2-thienyl}acetyl)lysine, N(ε)-({indol-3-yl}acetyl)lysine, N(ε)-benzoyllysine, N(δ)-(3-phenylpropionyl)lysine, N(δ)-benzylornithine, N(δ)-(2-furylmethyl)ornithine, N(δ)-(2-thienylmethyl)ornithine, N(δ)-(indol-3-ylmethyl)ornithine, N(δ)-benzoylornithine, N(δ)-phenylacetylornithine, N(δ)-(3-phenylpropionyl)ornithine, N(δ)-({2-methylphenyl}acetyl)ornithine, N(δ)-({3-methylphenyl}acetyl)ornithine, N(δ)-({4-methylphenyl}acetyl)ornithine, N(δ)-({2-chlorophenyl}acetyl)ornithine, N(δ)-({3-chlorophenyl}acetyl)ornithine, N(δ)-({4-chlorophenyl}acetyl)ornithine, N(δ)-({2-methoxyphenyl}acetyl)ornithine, N(δ)-({3-methoxyphenyl}acetyl)ornithine, N(δ)-({4-methoxyphenyl}acetyl)ornithine, N(δ)-(4-biphenylacetyl)ornithine, N(γ)-benzyl-2,4-diaminobutyric acid, N(γ)-(2-furylmethyl)-2,4-diaminobutyric acid, N(γ)-(2-thienylmethyl)-2,4-diaminobutyric acid, N(γ)-(indol-3-ylmethyl)-2,4-diaminobutyric acid, N(γ)-benzoyl-2,4-diaminobutyric acid, N(γ)-phenylacetyl-2,4-diaminobutyric acid, N(γ)-(3-phenylpropionyl)-2,4-diaminobutyric acid, N(γ)-(2-furylacetyl)-2,4-diaminobutyric acid, N(γ)-(2-thienylacetyl)-2,4-diaminobutyric acid, N(γ)-({indol-3-yl}acetyl)-2,4-diaminobutyric acid, or the like.

The substituted carboxyl group may be exemplified by carbamoyl group (—$CONH_2$), $C_{1-6}$ alkylcarbamoyl (for example, methylcarbamoyl, ethylcarbamoyl, n-propylcarbamoyl, tert-butylcarbamoyl, etc.), $C_{3-8}$ cycloalkylcarbamoyl (for example, cyclopentylcarbamoyl, cyclohexylcarbamoyl, etc.), $C_{6-12}$ arylcarbamoyl (for example, phenylcarbamoyl, {4-methylphenyl}carbamoyl, etc.), $C_{7-15}$ aralkylcarbamoyl (for example, benzylcarbamoyl, phenethylcarbamoyl, {1,2-diphenylethyl}carbamoyl, etc.), {aromatic heterocyclic-$C_{1-6}$ alkyl}carbamoyl (for example, [2-{indol-2-yl}ethyl]carbamoyl, [2-{indol-3-yl}ethyl]carbamoyl, etc.), piperidinocarbonyl, piperazinecarbonyl, $N^4$—$C_{1-6}$ alkylpiperazinecarbonyl (for example, $N^4$-methylpiperazinecarbonyl, $N^4$-ethylpiperazinecarbonyl, etc.), $N^4$—$C_{3-8}$ cycloalkylpiperazinecarbonyl (for example, $N^4$-cyclopentylpiperazinecarbonyl, $N^4$-cyclohexylpiperazinecarbonyl, etc.), $N^4$-5- to 7-membered heterocyclic piperazinecarbonyl (for example, $N^4$-pyridylpiperazinecarbonyl, $N^4$-furylpiperazinecarbonyl, $N^4$-thienylpiperazinecarbonyl, etc.), $N^4$—$C_{6-12}$ arylpiperazinecarbonyl (for example, $N^4$-phenylpiperazinecarbonyl, $N^4$-{4-methylphenyl}piperazinecarbonyl, etc.), $N^4$—$C_{7-15}$ aralkylpiperazinecarbonyl (for example, $N^4$-benzylpiperazinecarbonyl, $N^4$-phenethylpiperazinecarbonyl, $N^4$-{1,2-diphenylethyl}piperazinecarbonyl, etc.), $N^4$-{aromatic heterocyclic-$C_{1-6}$ alkyl}piperazinecarbonyl (for example, $N^4$-[2-{indol-2-yl}ethyl]piperazinecarbonyl, $N^4$-[2-{indol-3-yl}ethyl]piperazinecarbonyl, etc.), $N^4$—$C_{1-6}$ aliphatic acylpiperazinecarbonyl (for example, $N^4$-acetylpiperazinecarbonyl, $N^4$-propionylpiperazinecarbonyl, etc.), $N^4$—$C_{4-9}$ aliphatic cyclic acylpiperazinecarbonyl (for example, $N^4$-cyclopentanecarbonylpiperazinecarbonyl, $N^4$-cyclohexanecarbonylpiperazinecarbonyl, etc.), $N^4$—$C_{7-15}$ arylacylpiperazinecarbonyl (for example, $N^4$-benzoylpiperazinecarbonyl, $N^4$-{4-methylbenzoyl}piperazinecarbonyl, etc.), $N^4$—$C_{8-16}$ aralkylacylpiperazinecarbonyl (for example, $N^4$-phenylacetylpiperazinecarbonyl, $N^4$-{2-phenylpropion}piperazinecarbonyl, $N^4$-{3-phenylpropionyl}piperazinecarbonyl, $N^4$-diphenylacetylpiperazinecarbonyl, $N^4$-{1-naphthylacetyl}piperazinecarbonyl, $N^4$-{2-naphthylacetyl}piperazinecarbonyl, etc.), $N^4$-{aromatic heterocyclic carbonyl}piperazinecarbonyl (for example, $N^4$-{indol-2-ylcarbonyl}piperazinecarbonyl, $N^4$-{indol-3-ylcarbonyl}piperazineamide, etc.), $N^4$-{aromatic heterocyclic alkylcarbonyl}piperazinecarbonyl (for example, $N^4$-{indol-2-ylacetyl}piperazinecarbonyl, $N^4$-{indol-3-ylacetyl}piperazinecarbonyl, etc.), $C_{1-6}$ alkoxycarbonyl (for example, methoxycarbonyl, ethoxycarbonyl, n-propoxycarbonyl, etc.), $C_{3-8}$ cycloalkyloxycarbonyl (for example, cyclopentyloxycarbonyl, cyclohexyloxycarbonyl, etc.), $C_{7-15}$ aralkyloxycarbonyl (for example, benzyloxycarbonyl, phenethyloxycarbonyl, 1-phenylethoxycarbonyl, diphenylmethoxycarbonyl, etc.), or the like. The above-mentioned carbamoyl group also encompasses the amide of α-amino acids, or the amide of oligopeptides (for example, dipeptide, tripeptide, tetrapeptide, etc.).

The α-amino acid substituted with a carboxyl group may be exemplified by $N^4$-methylasparagine, $N^4$-phenylasparagine, $N^4$-benzylasparagine, $N^4$-phenethylasparagine, $N^4$-(2-{indol-3-yl}ethyl)asparagines, $N^5$-methylglutamine, $N^5$-phenylglutamine, $N^5$-benzylglutamine, $N^5$-phenethylglutamine, $N^5$-(2-{indol-3-yl}ethyl)glutamine, aspartic acid β-methyl ester, aspartic acid β-cyclopropyl ester, aspartic acid β-benzyl ester, aspartic acid β-phenethyl ester, aspartic acid β-$N^4$-phenylpiperazineamide, aspartic acid β-$N^4$-(2-methylphenyl)piperazineamide, aspartic acid β-$N^4$-(3-methylphenyl)piperazineamide, aspartic acid β-$N^4$-(4-methylphenyl)piperazineamide, aspartic acid β-$N^4$-(2-methoxyphenyl)piperazineamide, aspartic acid β-$N^4$-(3-methoxyphenyl)piperazineamide, aspartic acid β-$N^4$-(4-methoxyphenyl)piperazineamide, aspartic acid β-$N^4$-(2-chlorophenyl)piperazineamide, aspartic acid β-N-(3-chlorophenyl)piperazineamide, aspartic acid β-$N^4$-(4-chlorophenyl)piperazineamide, aspartic acid β-$N^4$-(4-nitrophenyl)piperazineamide, aspartic acid β-$N^4$-(4-fluorophenyl)piperazineamide, aspartic acid β-$N^4$-(3-trifluoromethylphenyl)piperazineamide, aspartic acid β-$N^4$-(2,3-dimethylphenyl)piperazineamide, aspartic acid β-$N^4$-(2-pyridyl)piperazineamide, aspartic acid β-$N^4$-(2-pyrimidyl)piperazineamide, glutamic acid γ-methyl ester, glutamic acid γ-cyclopropyl ester, glutamic acid γ-benzyl ester, glutamic acid γ-phenethyl ester, or the like.

When the amino acid from which the amino acid residue originates exists as optical isomers, any of the D-isomer, L-isomer and DL-isomer may be used.

In the above-described formulas, Z is a bond, a chain hydrocarbon group which may be substituted, or —N═.

The chain hydrocarbon group of the "chain hydrocarbon group which may be substituted" represented by Z, may be exemplified by a divalent chain hydrocarbon group, a trivalent chain hydrocarbon group, and a tetravalent chain hydrocarbon group.

The "divalent chain hydrocarbon group" may be exemplified by $C_{1-6}$ alkylene (for example, methylene, ethylene, trimethylene, tetramethylene, etc.), $C_{2-6}$ alkenylene (for example, vinylene, propylene, 1- or 2-butenylene, butadienylene, etc.), $C_{2-8}$ alkynylene (for example, ethynylene, 1- or 2-propynylene, 1- or 2-butynylene, etc.), and the like.

The "trivalent chain hydrocarbon group" may be exemplified by a trivalent group which is obtained by further eliminating one hydrogen atom from one terminal of a divalent chain hydrocarbon group selected from $C_{1-6}$ alkylene (for example, methylene, ethylene, trimethylene, tetramethylene, etc.), $C_{2-6}$ alkenylene (for example, vinylene, propylene, 1- or 2-butenylene, butadienylene, etc.), and $C_{2-8}$ alkynylene (for example, ethynylene, 1- or 2-propynylene, 1- or 2-butynylene, etc.), or the like.

The "tetravalent chain hydrocarbon group" may be exemplified by a tetravalent group which is obtained by further eliminating two hydrogen atoms from both terminals of a divalent chain hydrocarbon group selected from $C_{1-6}$ alkylene (for example, methylene, ethylene, trimethylene, tetramethylene, etc.), $C_{2-6}$ alkenylene (for example, vinylene, propylene, 1- or 2-butenylene, butadienylene, etc.), and $C_{2-8}$ alkynylene (for example, ethynylene, 1- or 2-propynylene, 1- or 2-butynylene, etc.), or the like.

The substituent which may be carried by the chain hydrocarbon group of the "chain hydrocarbon group which may be substituted" represented by Z, may be exemplified by the same groups of the same number as the above-mentioned substituents for Cy, as well as an oxo group, a thioxo group, or the like.

When Z is —N═, any of the bond with ring A or the bond with ring B may be a double bound, and it is preferable that the bond with ring B is a double bond.

Z is preferably a bond, or a $C_{1-6}$ alkylene group.

In the above-described formulas,

------, ----- are each independently a single bond or a double bond. Preferably,

-----and----- are both single bonds.

In the above-described formulas, ring A is a non-aromatic nitrogen-containing heterocyclic ring which may be substituted.

The "non-aromatic nitrogen-containing heterocyclic ring" may be exemplified by a 3- to 8-membered (preferably, 5- to 6-membered) saturated or unsaturated (preferably, saturated) non-aromatic monocyclic heterocyclic ring (aliphatic monocyclic heterocyclic ring) such as azetidine, pyrrolidine, piperidine, morpholine, thiomorpholine, piperazine, perhydroazepine or the like, and the like.

The substituent which may be carried by the "non-aromatic nitrogen-containing heterocyclic ring" of the "non-aromatic nitrogen-containing heterocyclic ring which may be substituted" represented by ring A, may be the same groups of the same number as the above-mentioned substituents for Cy, as well as an oxo group, a thioxo group or the like, and any of these substituents may be used for substitution at 1 to 5 (preferably, 1 to 3) substitutable positions. Among these, the substituent is preferably a $C_{1-6}$ alkyl group which may be substituted (the substituent may be exemplified by a $C_{1-6}$ alkylsulfinyl group, a $C_{1-6}$ alkylsulfonyl group, a hydroxyl group, or a carboxyl group which may be esterified or amidated), a hydroxyl group, a carboxyl group which may be esterified or amidated, and an oxo group.

Ring A is preferably a piperidine ring which may be substituted, or a piperazine ring which may be substituted, and inter alia, it is more preferable that the formula:

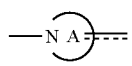

is the formula:

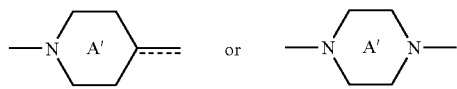

wherein ring A' may be substituted.

In the above-described formulas, ring B is a nitrogen-containing heterocyclic ring which may be substituted.

The "nitrogen-containing heterocyclic ring" of the "nitrogen-containing heterocyclic ring which may be substituted" represented by ring B, may be exemplified by an aromatic nitrogen-containing heterocyclic ring which contains at least one (preferably, 1 to 4, and more preferably 1 to 3) nitrogen atom, in addition to carbon atoms, and which may further contain one to three heteroatoms selected from oxygen atom, sulfur atom and the like, as the atoms constituting the ring system (ring atoms), and a saturated or unsaturated non-aromatic nitrogen-containing heterocyclic ring (aliphatic heterocyclic group).

The "aromatic nitrogen-containing heterocyclic ring" may be exemplified by an aromatic monocyclic nitrogen-containing heterocyclic ring such as pyrrole, oxazole, isoxazole, thiazole, isothiazole, imidazole (may be bound to Z at any of the 1-position, 2-position or 4-position), pyrazole, 1,2,3-oxadiazole, 1,2,4-oxadiazole, 1,3,4-oxadizole, furazane, 1,2,3-thiadiazole, 1,2,4-thiadiazole, 1,3,4-thiadiazole, 1,2,3-triazole, 1,2,4-triazole (may be bound to Z at any of the 1-position or 4-position), tetrazole, pyridine (may be bound to Z at any of the 2-position, 3-position or 4-position), pyridazine, pyrimidine, pyrazine, triazine or the like, and N-oxide products thereof, and for example, a 8- to 16-membered (preferably, 8- to 12-membered) aromatic fused nitrogen-containing heterocyclic ring such as indole, isoindole, 1H-indazole, benzimidazole, benzoxazole, 1,2-benzisoxazole, benzothiazole, 1,2-benzisothiazole, 1H-benzotriazole, quinoline, isoquinoline, 4H-quinolidine, cinnoline, quinazoline, quinoxaline, phthalazine, naphthyridine, purine, pteridine, carbazole, α-carboline, β-carboline, γ-carboline, acridine, phenoxazine, phenothiazine, phenazine, phenanthridine, phenanthroline, indolizine, pyrrolo[1,2-c]imidazole, pyrrolo[3,4-c]pyridine, pyrrolo[1,2-b]pyridazine, pyrazolo[1,5-a]pyridine, imidazo[1,5-b]pyrazole, pyrazolo[3,4-b]pyridine, pyrazolo[4,3-b]pyridine, imidazo[2,1-b]thiazole, imidazo[1,5-a]imidazole, imidazo[1,5-c]imidazole, imidazo[1,5-e]imidazole, imidazo[1,2-a]pyridine, imidazo[1,5-a]pyridine, imidazo[1,2-b]pyridazine, imidazo[1,2-a]pyrimidine, imidazo[1,2-a]pyrazine, imidazo[1,5-a]pyrazine, 1,2,4-trazolo[4,3-a]pyridine, 1,2,4-triazolo[4,3-b]pyridazine, 2,3,5,6-tetrahydroimidazo[2,1-b][1,3]thiazole, 5,6-dihydroimidazo[2,1-b][1,3]thiazole, 2,3,6,7-tetrahydro-5H-[1,3]thiazolo-[3,2-a]pyrimidine, 6,7-dihydro-5H-[1,3]thiazolo[3,2-a]pyrimidine or the like, and N-oxide products thereof.

The "non-aromatic nitrogen-containing heterocyclic ring" may be exemplified by aziridine, azetidine, pyrrolidine, piperidine (may be bound to Z at any of the 1-position, 2-position, 3-position or 4-position), morpholine, thiomorpholine, piperazine, homopiperazine and the like, in addition to partial reduction products of the above-mentioned "aromatic nitrogen-containing heterocyclic ring" (e.g., imidazoline, thiazoline, oxazoline, tetrahydropyrimidine, imidazoimidazoline, etc.).

Such nitrogen-containing heterocyclic ring may be bound to Z at any position capable of bonding.

The substituent which may be carried by the "nitrogen-containing heterocyclic ring" of the "nitrogen-containing heterocyclic ring which may be substituted" represented by ring B, may be exemplified by the same groups of the same number as the above-mentioned substituents for Cy, as well as an oxo group, an imino group which may be substituted (e.g., methylimino, ethylimino, propylimino, butylimino, isopropoxyimino, methoxycarbonylmethylimino, ethoxycarbonylmethylimino, etc.), or the like. Any of these substituents may be used for substitution at 1 to 3 (preferably, 1 to 2) substitutable positions. Further, the substituents of the "nitrogen-containing heterocyclic group" represented by ring B may be bonded to each other to form a ring (e.g., benzene, $C_{3-10}$ cycloalkene (for example, cyclobutene, cyclopentene, cyclohexene, cycloheptene, cyclooctene, etc.), $C_{3-10}$ cycloalkane (for example, cyclobutane, cyclopentane, cyclohexane, cycloheptane, cyclooctane), non-aromatic heterocyclic ring (for example, tetrahydropyridine, dihydropyridine, tetrahydropyrazine, tetrahydropyrimidine, tetrahydropyridazine, dihydropyrane, dihydropyrrole, dihydrothiophene, dihydrofuran, piperidine, piperazine, hexahydropyrimidine, hexahydropyridazine, tetrahydropyrane, morpholine, pyrrolidine, pyrazoline, imidazolidine, thiazoline, isothiazoline, oxazoline, isoxazoline, pyrazolidine, tetrahydrothiophene, tetrahydrofuran, tetrahydrothiazole, tetrahydroisothiazole, tetrahydrooxazole, tetrahydroisoxazole ring, etc.).

The substituent which may be carried by the "nitrogen-containing heterocyclic ring" of the "nitrogen-containing heterocyclic ring which may be substituted" is preferably a $C_{1-6}$ alkyl group, a hydroxyl group, an oxo group, an imino group, a methylimino group or the like.

Ring B is preferably a monocyclic nitrogen-containing heterocyclic ring which may be substituted, and inter alia, the monocyclic nitrogen-containing heterocyclic ring is preferably a piperidine ring, a piperazine ring, an imidazoline ring, a pyrrolidine ring, a pyridine ring, an imidazole ring, a thiazoline ring or the like.

Ring B is also preferably a fused nitrogen-containing heterocyclic ring which may be substituted, and inter alia, the fused nitrogen-containing heterocyclic ring is preferably a fused pyridine ring, a fused imidazole ring, a fused pyrazole ring, a fused thiazoline ring or the like, and in particular, a fused pyridine ring, a fused imidazole ring, a fused thiazoline ring or the like.

The fused pyridine ring may be exemplified by quinoline, isoquinoline, 4H-quinolidine, naphthyridine, pyrrolo[3,4-c]pyridine, imidazo[1,5-a]pyridine, 1,2,4-triazolo[4,3-a]pyridine, imidazo[1,2-a]pyridine and the like, and among these, imidazo[1,5-a]pyridine, imidazo[1,2,-a]pyridine and the like are preferred.

The fused imidazole ring may be exemplified by benzimidazole, purine, imidazo[1,5-a]pyridine, imidazo[1,2-a]pyridine, imidazo[1,2-a]pyrimidine, imidazo[1,2-b]pyridazine, imidazo[1,2-a]pyrazine, imidazo[1,5-a]pyrazine, pyrrolo[1,2-c]imidazole, imidazo[2,1-b]thiazole, imidazo[1,5-a]imidazole, imidazo[1,5-c]imidazole, imidazo[1,5-e]imidazole and the like, and among them, imidazo[1,5-c]imidazole, imidazo[1,5-a]imidazole and the like are preferred.

The fused pyrazole ring may be exemplified by 1H-indazole, imidazo[1,5-b]pyrazole, pyrazolo[3,4-b]pyridine, pyrazolo[4,3-b]pyridine and the like, and among these, imidazo[1,5-b]pyrazole and the like are preferred.

The fused thiazoline ring may be exemplified by 2,3,5,6-tetrahydroimidazo[2,1-b][1,3]thiazole, 5,6-dihydroimidazo[2,1-b][1,3]thiazole, 2,3,6,7-tetrahydro-5H-[1,3]thiazolo[3,2-a]pyrimidine, 6,7-dihydro-5H-[1,3]thiazolo[3,2-a]pyrimidine and the like, and among them, 5,6-dihydroimidazo[2,1-b][1,3]thiazole and the like are preferred.

In the above-described formulas, $R^1$ may be bound to $R^2$ to form a non-aromatic nitrogen-containing heterocyclic ring which may be substituted.

The "non-aromatic nitrogen-containing heterocyclic ring" may be exemplified by a 4- to 8-membered (preferably, 5- to 7-membered) saturated or unsaturated (preferably, saturated) non-aromatic monocyclic nitrogen-containing heterocyclic ring (aliphatic monocyclic nitrogen-containing heterocyclic ring) such as:

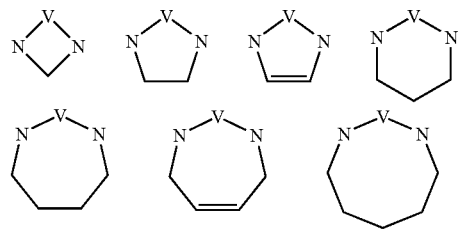

wherein the symbols have the same meaning as defined in the above, and the like.

The substituent which may be carried by the "non-aromatic nitrogen-containing heterocyclic ring" may be exemplified by the same groups of the same number as the above-mentioned substituents for Cy, as well as an oxo group, a thioxo group and the like, and any of these substituents may be used for substitution at 1 to 5 (preferably, 1 to 3) substitutable positions.

The "non-aromatic nitrogen-containing heterocyclic ring" may be a non-aromatic fused nitrogen-containing heterocyclic ring in which the above-mentioned non-aromatic monocyclic heterocyclic ring is fused with another ring such as a benzene ring or the like.

In the above-described formulas, $R^2$ may be bound to a substituent for X to form a non-aromatic nitrogen-containing heterocyclic ring which may be substituted.

The "non-aromatic nitrogen-containing heterocyclic ring" may be exemplified by a 3 to 8-membered (preferably, 5 to 6-membered) saturated or unsaturated (preferably, saturated) non-aromatic monocyclic nitrogen-containing heterocyclic ring (aliphatic monocyclic nitrogen-containing heterocyclic ring) such as aziridine, azetidine, pyrrolidine, piperidine, morpholine, thiomorpholine, perhydroazepine or the like.

The substituent which may be carried by the "non-aromatic nitrogen-containing heterocyclic ring" may be exemplified by the same groups of the same number as the above-mentioned substituents for Cy, as well as an oxo group, a thioxo group and the like, and any of these substituents may be used for substitution at 1 to 5 (preferably, 1 to 3) substitutable positions.

The "non-aromatic nitrogen-containing heterocyclic ring" may be a non-aromatic fused nitrogen-containing heterocyclic ring in which the above-mentioned non-aromatic monocyclic heterocyclic ring is fused with another ring such as a benzene ring or the like.

For the compound represented by Formula (I) according to the invention, N-(4-chlorophenyl)-N'-((1R)-2,2-dimethyl-1-((4-(5-methyl-3-oxo-1H-imidazo[1,5-c]imidazol-2(3H)-yl)-1-piperazinyl)carbonyl)propyl)urea, N-(4-chlorophenyl)-N'-(2-ethyl-2-hydroxy-1-((4-(5-methyl-3-oxo-1H-imidazo[1,5-c]imidazol-2(3H)-yl)-1-piperazinyl)carbonyl)butyl)urea, N-(4-chlorophenyl)-N'-((1S)-2-methyl-1-((4-(5-methyl-3-oxo-1H-imidazo[1,5-c]imidazol-2(3H)-yl)-1-piperazinyl) carbonyl)-2-(methylthio)propyl)urea, N-(4-chlorophenyl)-N'-(2-methoxy-2-methyl-1-((4-(5-methyl-3-oxo-1H-imidazo[1,5-c]imidazol-2(3H)-yl)-1-piperazinyl)carbonyl) propyl)urea and the like are particularly preferably used.

The salt for the compound represented by Formula (I) (hereinafter, may be simply referred to as Compound (1)) may be exemplified by pharmacologically acceptable salts and the like, for example, acid addition salts with acids such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid, etc.; for example, metal salts with sodium, potassium, magnesium, calcium and the like; for example, organic salts with trimethylamine, triethylamine, pyridine, picoline, N-methylpyrrolidine, N-methylpiperidine, N-methylmorpholine, etc.; or the like.

A prodrug of Compound (I) refers to a compound that is converted to Compound (I) by a reaction induced by enzyme, gastric acid or the like under the physiological conditions in vivo, that is, a compound that is converted to Compound (I) by enzymatic oxidation, reduction, hydrolysis or the like, or a compound that is converted to Compound (I) by gastric acid-induced hydrolysis. Examples of the prodrug of Compound (I) include a compound in which an amino group of Compound (I) is acylated, alkylated or phosphorylated (e.g., a compound in which an amino group of Compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, etc.); a compound in which a hydroxyl group of Compound (I) is acylated, alkylated, phosphorylated or borated (e.g., a compound in which a hydroxyl group of Compound (I) is acetylated, palmitoylated, propanoylated, pivaloylated, succinylated, fumarylated, alanylated, dimethylaminomethylcarbonylated, etc.); a compound in which a carboxyl group of Compound (I) is esterified or amidated (e.g., a compound in which a carboxyl group of Compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonyl ethyl esterified, methylamidated, etc.); and the like. Such compound can be prepared from Compound (I) by a method known per se.

Furthermore, the prodrug of Compound (I) may be also a compound which is converted to Compound (I) under physiological conditions, as described in "Development of Pharmaceutical Products", Vol. 7, Design of Molecules, Hirokawa Publisher, pp. 163-198 (1990).

Also, Compound (I) may be labeled with isotopes (for example, $^3H$, $^{14}C$, $^{35}S$, $^{125}I$, etc.).

Compound (I) or a salt thereof can be prepared by, for example, the following Methods A to C. Each of the compounds described in the following reaction schemes may be favorably in a salt form, provided that the reaction is not impeded by the form, and such salt may be exemplified by the salts of Compound (I).

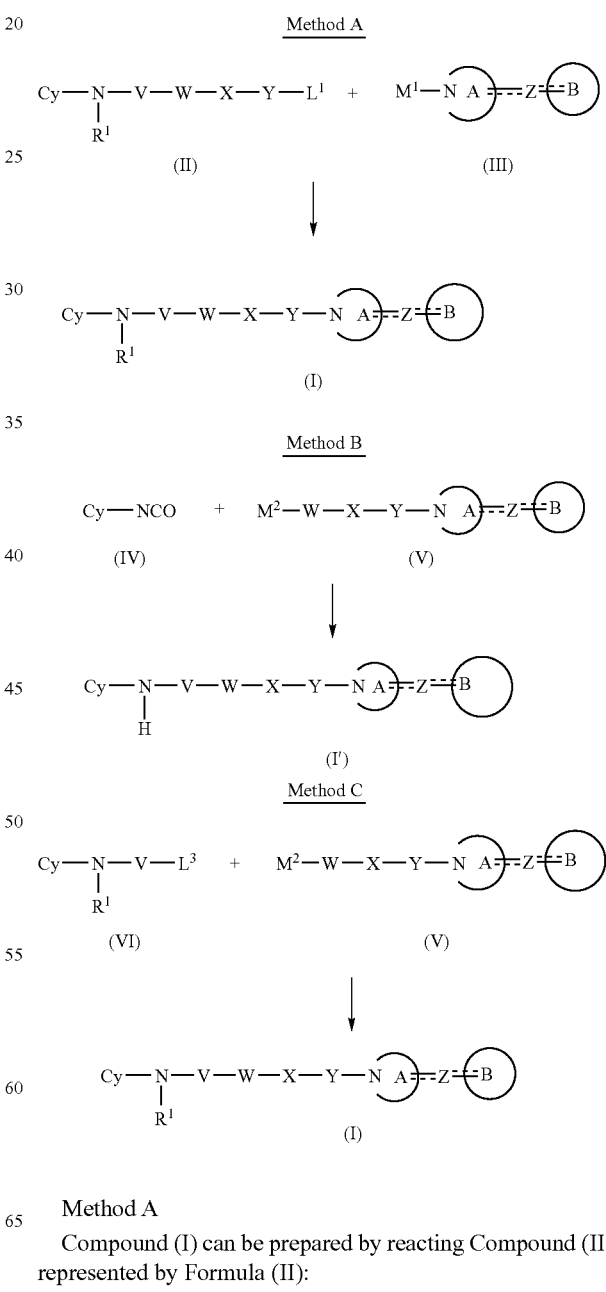

Method A

Compound (I) can be prepared by reacting Compound (II) represented by Formula (II):

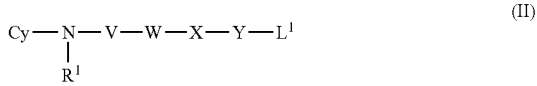

wherein $L^1$ is a leaving group [for example, a halogen atom (e.g., fluorine, chlorine, bromine, iodine, etc.), a $C_{1-6}$ alkylsulfonyloxy group which may be substituted with 1 to 3 halogen atoms (e.g., methanesulfonyloxy, ethanesulfonyloxy, trifluoromethanesulfonyloxy, etc.), an arylsulfonyloxy group which may be substituted (e.g., benzenesulfonyloxy, p-toluenesulfonyloxy, p-bromobenzenesulfonyloxy, etc.), a hydroxyl group or the like; this is a group forming free carboxylic acid, a salt thereof (inorganic salt, organic salt, etc.) or a reactive derivative thereof (e.g., acid halide, ester, acid azide, acid anhydride, mixed acid anhydride, active amide, active ester, active thioester, etc.) or the like]; and other symbols have the same meaning as defined in the above (in particular, Compound (II) wherein $L^1$ is a hydroxyl group is referred to as Free Acid (II')), with Compound (III) represented by Formula (III):

wherein $M^1$ is a hydrogen atom, an alkali metal (for example, lithium, sodium, potassium, cesium, etc.), an alkaline earth metal (for example, magnesium, calcium, etc.), or a leaving group (for example, a trimethylsilyl group, etc.); and other symbols have the same meaning as defined in the above.

The present method is also carried out by reacting Compound (III) or a salt thereof with Free Acid (II') or a salt thereof (inorganic salt, organic salt, etc.) or a reactive derivative thereof (for example, acid halide, ester, acid azide, acid anhydride, mixed acid anhydride, active amide, active ester, active thioester, etc.). The salt of Compound (III) may be exemplified by acid addition salts with the above-mentioned acids which form the acid addition salts of Compound (I).

The inorganic salt used for Compound (II) may be exemplified by an alkali metal salt (for example, lithium salt, sodium salt, potassium salt, cesium salt, etc.), an alkaline earth metal salt (for example, magnesium salt, calcium salt, etc.) or the like, while the organic salt may be exemplified by a trimethylamine salt, a triethylamine salt, a tert-butyldimethylamine salt, a dibenzylmethylamine salt, a benzyldimethylamine salt, an N,N-dimethylaniline salt, a pyridine salt, a quinoline salt or the like. The acid halide may be exemplified by acid chloride, acid bromide and the like; the ester may be exemplified by an ester of lower alkyl such as methyl, ethyl or the like, or the like; the mixed acid anhydride may be exemplified by mono-$C_{1-4}$ alkyl carbonate mixed acid anhydride (for example, mixed acid anhydride of Free Acid (II') with monomethyl carbonate, monoethyl carbonate, monoisopropyl carbonate, mono-isobutyl carbonate, mono-tert-butyl carbonate, monobenzyl carbonate, mono-(p-nitrobenzyl)carbonate, monoallyl carbonate or the like), $C_{1-6}$ aliphatic carboxylic acid mixed acid anhydride (for example, mixed acid anhydride of Free Acid (II') with acetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), $C_{7-11}$ aromatic carboxylic acid mixed acid anhydride (for example, mixed acid anhydride of Free Acid (II') with benzoic acid, p-toluic acid, p-chlorobenzoic acid, etc.), organic sulfonic acid mixed acid anhydride (for example, mixed acid anhydride with methanesulfonic acid, ethanesulfonic acid, benzenesulfonic acid, p-toluenesulfonic acid, etc.) or the like; the active amide may be exemplified by amide with a nitrogen-containing heterocyclic compound (for example, acid amide of Free Acid (II') with pyrazole, imidazole, benzotriazole, etc.; such a nitrogen-containing heterocyclic compound may be substituted with $C_{1-6}$ alkyl (for example, methyl, ethyl, propyl, isopropyl, butyl, isobutyl, sec-butyl, tert-butyl, etc.), $C_{1-6}$ alkoxy (for example, methoxy, ethoxy, propoxy, isopropoxy, butoxy, tert-butoxy, etc.), a halogen atom (for example, fluorine, chlorine, bromine, etc.), oxo, thioxo, $C_{1-6}$ alkylthio (for example, methylthio, ethylthio, propylthio, butylthio, etc.) etc.), or the like.

The active ester may be exemplified by an organic phosphoric acid ester (for example, diethoxyphosphate ester, diphenoxyphosphate ester, etc.), as well as p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyridone ester, or the like. The active thioester may be exemplified by an ester formed with aromatic heterocyclic thiol compound [such heterocyclic ring may be substituted with $C_{1-6}$ alkyl (for example, methyl, ethyl, propyl, isopropyl, butyl, isobutyl, sec-butyl, tert-butyl, etc.), $C_{1-6}$ alkoxy (for example, methoxy, ethoxy, propoxy, isopropoxy, butoxy, tert-butoxy, etc.), a halogen atom (for example, fluorine, chlorine, bromine, etc.), $C_{1-6}$ alkylthio (for example, methylthio, ethylthio, propylthio, butylthio, etc.) or the like] (e.g., 2-pyridylthiol ester, 2-benzothiazolylthiol ester), or the like.

The present reaction is in general carried out in a solvent, and if necessary, in the presence of base or a condensing agent (e.g., carbodiimides (N,N'-dicyclohexylcarbodiimide (DCC), water-soluble carbodiimide (WSC), N,N'-dicycloisopropylcarbodiimide (DIC), etc.), phosphoric acid derivatives (e.g., diethyl cyanophosphate, diphenylphosphonic azide (DPPA), bis(2-oxo-3-oxazolidinyl)phosphinic chloride (BOP-Cl), etc.), 4-(4,6-dimethoxy-1,3,5-triazin-2-yl)-4-methylmorpholinium chloride (DMTMM: Kunishima, et al., Tetrahydron, 1999, 55, 13159), etc.).

For the solvent, a solvent which does not impede the reaction is appropriately selected, and for example, ethers (e.g., dioxane, tetrahydrofuran, diethylether, tert-butylmethyl ether, diisopropyl ether, ethylene glycol-dimethyl ether, etc.), esters (e.g., ethyl formate, ethyl acetate, n-butyl acetate, etc.), halogenated hydrocarbons (e.g., dichloromethane, chloroform, carbon tetrachloride, trichloroethylene, 1,2-dichloroethane, chlorobenzene, etc.), hydrocarbons (e.g., n-hexane, benzene, toluene, etc.), amides (e.g., formamide, N,N-dimethylformamide, N,N-dimethylacetamide, etc.), ketones (e.g., acetone, methyl ethyl ketone, methyl isobutyl ketone, etc.), nitrites (e.g., acetonitrile, propionitrile, etc.), as well as sulfolane, hexamethylphosphoramide, water and the like are used individually or as mixed solvent.

For the base, inorganic bases such as, for example, lithium hydroxide, potassium hydroxide, sodium hydroxide, calcium hydroxide, sodium carbonate, potassium carbonate, sodium hydrogen carbonate, potassium hydrogen carbonate and the like; and tertiary amines such as, for example, triethylamine, tri(n-propyl)amine, tri(n-butyl)amine, diisopropylethylamine, cyclohexyldimethylamine, pyridine, lutidine, γ-coridine, N,N-dimethylaniline, N-methylpiperidine, N-methylpyrrolidine, N-methylmorpholine, diazabicycloundecane, diazabicycloundecene and the like are used.

For the present reaction, Compound (III) is used in an amount of 0.5 to 5 equivalents, preferably 0.8 to 2 equivalents, based on Compound (II).

The reaction temperature is −50 to 150° C., preferably −20 to 100° C.

The reaction time varies depending on the kind of Compound (II) or Compound (III), the kind of solvent and base, the reaction temperature or the like, but is usually about 1 minute to about 100 hours, preferably about 15 minutes to about 48 hours.

Method B

Compound (I'), which is Compound (I) with $R^1$ being a hydrogen atom, can be prepared by reacting Compound (IV) represented by Formula (IV):

wherein the symbols have the same meaning as defined above, or a salt thereof with Compound (V) represented by Formula (V):

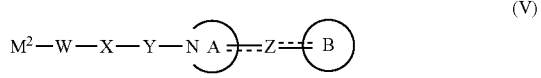

wherein $M^2$ is a hydrogen, an alkali metal (for example, lithium, sodium, potassium, cesium, etc.), or an alkaline earth metal (for example, magnesium, calcium, etc.); and other symbols have the same meaning as defined above, or a salt thereof. The salt of Compound (IV) or Compound (V) may be exemplified by acid addition salts with the above-mentioned acids which form acid addition salts with Compound (I), or the like.

The present reaction is in general carried out in a solvent, and a solvent which does not impede is appropriately selected. For the solvent and base used for the present reaction, the same ones as the above-mentioned solvents and bases described for Method A, and the like are used.

For the present reaction, Compound (IV) is used in an amount of 0.5 to 5 equivalents, preferably 0.8 to 2 equivalents, based on Compound (V).

The reaction temperature is −20 to 200° C., preferably −5 to 170° C.

The reaction time varies depending on the kind of Compound (IV) or Compound (V), the kind of solvent, reaction temperature and the like, but is usually about 1 minute to about 72 hours, preferably about 15 minutes to about 24 hours.

Method C

Compound (I) can be prepared by reacting Compound (VI) represented by Formula (VI):

wherein $L^3$ is a leaving group (for example, a halogen atom (e.g., fluorine, chlorine, bromine, iodine, etc.), an imidazolyl group which may be quaternized (e.g., an imidazolyl group, a 3-methylimidazoliumyl group, a phenoxy group which may be substituted (e.g., 4-nitrophenoxy group, etc.); and other symbols have the same meaning as defined above, or a salt thereof with Compound (V) represented by Formula (V):

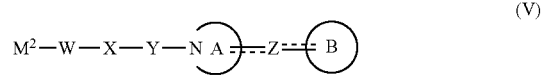

wherein the symbols have the same meaning as defined above, or a salt thereof. The salt of Compound (V) or Compound (VI) may be exemplified by acid addition salts of the above-mentioned acids which form the acid addition salts with Compound (I).

The present reaction is in general carried out in a solvent, and a solvent which does not impede the reaction is appropriately selected. For the solvent and base used for the present reaction, the same ones as the above-mentioned solvents and bases described for Method A, and the like are used.

For the present reaction, Compound (VI) is used in an amount of 0.5 to 10 equivalents, preferably 0.8 to 5 equivalents, based on Compound (V).

The reaction temperature is −20 to 200° C., preferably −5 to 170° C.

The reaction time varies depending on the kind of Compound (V) or Compound (VI), the kind of solvent, reaction temperature and the like, but is usually about 1 minute to about 100 hours, preferably about 15 minutes to about 72 hours.

The starting materials and intermediates used in the respective reactions are prepared by applying or adapting known methods, for example, methods described in reference examples or methods that are clearly chemically equivalent thereto, or according to the methods of the present invention.

Compound (I) thus obtained can be isolated and purified from the reaction mixture by means known per se, for example, means such as extraction, concentration, neutralization, filtration, recrystallization, column chromatography, thin layer chromatography or the like.

The salt of Compound (I) can be prepared according to means known per se, for example, by adding an inorganic acid or organic acid to Compound (I).

In case Compound (I) may possibly exist as optical isomers, the individual optical isomers and mixtures thereof are definitely included in the scope of the invention, and if desired, such isomers can be prepared by optical resolution or individually, according to means known per se. In particular, when —W—X—Y— is an amino acid residue, individual optical isomers of Compound (I) can be prepared easily at low costs, by using optically active amino acids as the starting materials.

Furthermore, Compound (I) or a salt thereof may be a hydrate, and such hydrates and non-hydrates are all included in the scope of the invention.

The Compound (I) of the invention or a salt thereof is safe due to low toxicity (for example, more excellent as medicine in the aspects of acute toxicity, chronic toxicity, genetic toxicity, regenerative toxicity, cardiac toxicity, drug interaction, carcinogenicity and the like), and inhibits FXa with anticoagulation action. Thus, the compound is useful for the prevention or treatment of various arterial and venous thrombosis in animals, particularly in mammals (for example, human, monkey, cat, pig, horse, cattle, mouse, rat, guinea pig, dog, rabbit, etc.), for example, myocardial infarction, cerebral infarction, deep vein thrombosis, pulmonary thromboembolism, arteriosclerosis obliterans, Economy Class Syndrome, intraoperative and/or post-operative thromboembolism and the following diseases, and inter alia, the compound is preferably used for the prevention or treatment of ischemic cerebral infarction (in particular, ischemic cerebral infarction caused by progress in cardiogenic cerebral embolism or arteriosclerosis by atrial fibrillation, or accentuation in the blood coagulation system), deep vein thrombosis, pulmonary thromboembolism and the like.

Brain:

Prevention and/or treatment of cerebral infarction, ischemic cerebrovascular disorder, cerebral embolism caused by atrial fibrillation or cardiac failure and valvular diseases, acute ischemic cerebral aploplexy, acute stage cerebral thrombosis, cerebrovascular spasm after subarachnoid hemorrhage, Alzheimer's disease, transient cerebral ischemic attack (TIA), mixed dementia, cerebrovascular dementia, asymptomatic/multiple cerebral infarction, lacunar infarction and the like, improvement in prognosis and/or prevention of secondary occurrence of cerebral infarction, prevention and/or treatment of thrombosis after bypass surgery in extracranial and intracranial arteries, combined use or supplementary use with thrombolytic agent for cerebral infarction (in particular, ischemic cerebrovascular disorder), combined therapy with antiplatelet drug such as aspirin in the critical prevention of cerebral infarction, etc.

Heart:

Prevention and/or treatment of acute coronary artery diseases such as acute myocardial infarction, myocardial infarction, ischemic coronary artery diseases, unstable angina pectoris, cardiomyopathy, acute cardiac failure, congestive chronic cardiac failure, valvular diseases and the like, improvement in prognosis and/or prevention of secondary occurrence of acute coronary artery diseases such as angina pectoris, prevention and/or treatment of thrombosis after artificial valve or artificial heart implantation surgery, prevention and/or treatment of vascular reocclusion and restenosis after coronary artery intervention such as placement of stent, percutaneous transluminal coronary angioplasty (PTCA), atherectomy or the like, prevention and/or treatment of vascular reocclusion and restenosis after coronary artery bypass operation, combined use or supplementary use with thrombolytic agent for acute coronary artery diseases, combined therapy with antiplatelet drug such as aspirin in the critical prevention of myocardial infarction, etc.

Periphery:

Prevention and/or treatment of deep vein thrombosis, chronic arterial occlusion, arteriosclerosis obliterans, peripheral circulatory failure such as Buerger's disease or the like, peripheral circulatory failure after frostbite, aneurysm, varicosity, adult respiratory distress syndrome, acute renal failure, chronic renal diseases (for example, diabetic renal failure, chronic glomerulonephritis, IgA renal failure, etc.), diabetic circulatory disorder, diabetic complications such as pain, neuropathy, diabetic retinopathy and the like, improvement in prognosis and/or prevention of secondary occurrence of deep vein thrombosis, prevention and/or treatment of deep vein thrombosis and/or pulmonary thromboembolism after joint surgery including total hip arthroplasty (THA) and total knee arthroplasty (TKA), prevention and/or treatment of deep vein thrombosis and or pulmonary thromboembolism after orthopedic surgery including spinal surgery, plastic surgery and/or general surgery, prevention and/or treatment of thrombosis after peripheral vascular bypass or placement of artificial blood vessel and/or vena caval filter, prevention and/or treatment of vascular reocclusion and restenosis after peripheral vascular intervention such as platement of stent, percutaneous transluminal angioplasty (PTA), atherectomy or the like, prevention and/or treatment of deep vein thrombosis and/or pulmonary thromboembolism associated to acute internal diseases, combined use or supplementary therapy with thrombolytic agent for deep vein thrombosis and pulmonary thromboembolism, combined therapy with antiplatelet drug such as aspirin in the treatment of peripheral circulatory failure such as arteriosclerosis obliterans or the like, etc.

Others:

Prevention and/or treatment of pulmonary embolism, acute pulmonary embolism, Economy Class Syndrome, reduction in platelets, accentuation of blood coagulation system, and/or complement activation due to dialysis, reduction in platelets during major surgery, thrombocytopenic purpura, progress of arteriosclerosis, metastasis, systemic inflammatory reaction syndrome (SIRS) or disseminated intravascular coagulation (DIC) occurring in patients suffering from pancreatitis, cancer, leukemia, major surgery, sepsis or the like, various organic disorders such as hepatic dysfunction due to avascularity, ischemia, blood congestion or the like, various organic failure (for example, pulmonary failure, hepatic failure, renal failure, cardiac failure, etc.) occurring due to shock or progress of DIC, systemic erythematosus, collagen disease, hyperthyroidism, parturient paralysis or the like, suppression of rejection during transplantation, organ protection or functional improvement during transplantation, prevention of perfusion blood coagulation during blood extracorporeal circulation, alternative therapeutic use during the occurrence of thrombocytopenia caused by heparin administration, acceleration of treatment of sore pressure or wound, suppression of accentuation of blood hypercoagulation during various hormone replacement therapy, alternative therapeutic use for patients having resistance or contraindication to coumarin drugs including Warfarin, suppression of accentuation of hypercoagulation during the administration of blood preparation or blood coagulation factor-containing preparation, etc.

The Compound (I) of the invention or a salt thereof can be administered orally or parenterally in its intact form or together with a pharmacologically acceptable carrier.

For the preparation of the invention containing Compound (I) or a salt thereof, the formulation to be orally administered may be exemplified by tablet (including sugar-coated tablet and film-coated tablet), pill, granule, powder, capsule (including soft capsule and microcapsule), syrup, emulsion, suspension and the like, while the formulation to be parenterally administered may be exemplified by injection, infusion, intravenous drip, suppository and the like. It is also effective to combine the preparation of the invention with an appropriate base (e.g., butyric polymer, glycolic acid polymer, butyric acid-glycolic acid copolymer, mixture of butyric polymer and glycolic polymer, polyglyerol aliphatic acid ester, etc.) to make a sustained release preparation.

The content of the Compound (I) or a salt thereof in the preparation of the invention may vary in accordance with the form of the preparation, but is usually 2 to 85% by weight, preferably 5 to 70% by weight, based on the entire preparation.

For the method for formulating the Compound (I) or a salt thereof into the above-mentioned formulations, known formulating methods that are generally used in the related art can be applied. In the case of formulating into the above-mentioned formulations, if necessary, those excipients, binding agents, disintegrants, lubricating agents, sweetening agents, surfactants, suspending agents, emulsifiers and the like that are conventionally used in the preparation field can be suitably mixed into the formulations in suitable amounts during formulating the formulations.

For example, in the case of formulating Compound (I) or a salt thereof into tablet, excipients, binding agents, disintegrants, lubricating agents and the like can be mixed into the formulation; and in the case of formulating into pill and granule, excipients, binding agents, disintegrants and the like can be mixed into the formulation. Further, in the case of formulating into powder and capsule, excipients can be mixed into the formulation; in the case of formulating into syrup, sweetening agents can be mixed into the formulation; and in the case of formulating into emulsion or suspension, suspending agents, surfactants, emulsifiers and the like can be mixed into the formulation.

Examples of the excipient include lactose, white sugar, glucose, starch, sucrose, microcrystalline cellulose, powdered glycyrrhizia, mannitol, sodium hydrogen carbonate, calcium phosphate, calcium sulfate and the like.

Examples of the binding agent include a solution containing 5 to 10% by weight of starch paste, a solution containing 10 to 20% by weight of gum arabic or gelatin, a solution containing 1 to 5% by weight of tragacanth, a carboxymethylcellulose solution, a sodium alginate solution, glycerin and the like.

Examples of the disintegrant include starch, calcium carbonate and the like.

Examples of the lubricating agent include magnesium stearate, stearic acid, calcium stearate, purified talc and the like.

Examples of the sweetening agent include glucose, fructose, invert sugar, sorbitol, xylytol, glycerin, simple syrup and the like.

Examples of the surfactant include sodium lauryl sulfate, polysorbate 80, sorbitan monofatty acid ester, polyoxyl stearate 40 and the like.

Examples of the suspending agent include gum arabic, sodium alginate, carboxymethylcellulose sodium, methylcellulose, bentonite and the like.

Examples of the emulsifying agent include gum arabic, tragacanth, gelatin, polysorbate 80 and the like.

Further, in the case of the Compound (I) or a salt thereof into the above-mentioned formulations, if desired, the coloring agents, preservatives, fragrant agent, flavoring agent, stabilizer, consistency agent and the like that are conventionally used in the purification field can be suitably added in suitable amounts.

The preparation of the invention containing Compound (I) or a salt thereof is stable and less toxic, and thus can be used safely. The daily dose varies depending on the condition or body weight of patient, the kind of compound, administration route and the like, but for example, in the case of orally administering to a patient to thrombosis, the daily dose for an adult (body weight about 60 kg) is about 1 to 2000 mg, preferably about 3 to 1000 mg, and more preferably about 10 to 500 mg, of the active ingredient (Compound (I) or a salt thereof), which amounts can be administered once, or in 2 to 3 divided portions.

When the Compound (I) of the invention or a salt thereof is administered parenterally, it is conventionally administered in the form of liquid (for example, injectable preparation). The daily dose varies depending on the subject of administration, subject organ, symptoms, administration mode and the like, but for example, the preparation is favorably administered intravenously in the form of injectable preparation, conventionally in an amount of about 0.01 mg to about 100 mg, preferably about 0.01 to about 50 mg, and more preferably about 0.01 to about 20 mg, per 1 kg of body weight. The injectable preparation includes intravenous injection, as well as subcutaneous injection, intradermal injection, intramuscular injection, drip injection and the like, and the sustained release preparation includes iontophoretic transdermal preparation and the like. Such injectable preparation is prepared by a method known per se, that is, by dissolving, suspending or emulsifying the Compound (I) of the invention or a salt thereof in a sterilized aqueous liquid or oily liquid. The aqueous liquid for injection may be exemplified by physiological saline, isotonic solution containing glucose or other pharmaceutical adjuvant (for example, D-sorbitol, D-mannitol, sodium chloride, etc.) and the like, and may be used in combination with a suitable dissolving aid, for example, alcohol (for example, ethanol), polyalcohol (for example, propylene glycol, polyethylene glycol), nonionic surfactant (for example, polysorbate 80, HCO-50) or the like. The oily liquid may be exemplified by sesame oil, soybean oil and the like, and may be used in combination with a dissolving aid such as benzyl benzoate, benzyl alcohol or the like. Buffering agents (for example, phosphate buffer, sodium acetate buffer), soothing agents (for example, benzalkonium chloride, procaine hydrochloride, etc.), stabilizers (for example, human serum albumin, polyethylene glycol, etc.), preservatives (for example, benzyl alcohol, phenol, etc.) and the like may be also mixed therein. The formulated injection solution is usually filled in ampoules.

The compound of the invention can be used in appropriate combination with a drug (hereinafter, simply referred to as combination drug) such as a thrombolytic agent (e.g., TPA, urokinase, etc.), a therapeutic drug for Alzheimer's disease (e.g., Calan, etc.), a cholesterol treating drug (e.g., HMG-CoA reductase inhibitor such as simvastatin, pravastatin or the like, etc.), a TG lowering drug (e.g., clofibrate, etc.), an AII antagonist (e.g., candesartan cilexetil, losartan, etc.), an antiplatelet drug (e.g., clopidogrel, abciximab, aspirin, etc.), a Ca antagonist (e.g., Calslot, amlodipin, etc.), an ACE inhibitor (e.g., enalapril, captopril, etc.), a β blocker (e.g., metoprolol, carvedilol, etc.), an anti-arrhythmic drug (e.g., procaine amide, etc.), or the like. This combination drug may be a low molecular weight compound, or may be a high molecular weight protein, polypeptide, antibody, or a vaccine. Here, the administration form of the compound of the invention and the combination drug is not particularly limited, and upon administration, the compound of the invention and the combination drug are favorably in combination. Such administration form may be exemplified by (1) administration of a single preparation which is obtained by simultaneously formulating the compound of the invention and a combination drug, (2) simultaneous administration by the same administration route, of two different preparations which are obtained by separately formulating the compound of the invention and a combination drug, (3) administration with a time interval by the same administration route, of two different preparations which are obtained by separately formulating the compound of the invention and a combination drug, (4) simultaneous administration by different administration routes, of two different preparations which are obtained by separately formulating the compound of the invention and a combination drug, (5)administration with a time interval by different administration routes, of two different preparations which are obtained by separately formulating the compound of the invention and a combination drug (for example, administration in an order of the compound of the invention and the combination drug, or administration in the reverse order), or the like. The amount of the combination drug to be administered can be appropriately selected based on the doses that are clinically used. Also, the mixing ratio of the compound of the invention and the combination drug can be appropriately selected based on the subject of administration, administration route, subject disease, symptoms, combination and the like. For example, when the subject of administration is human, the combination drug may be favorably used in an amount of 0.01 to 100 parts by weight relative to 1 part by weight of the compound of the invention.

The present invention is further described in detail by the following Examples, Preparation Examples and Experimental Examples, but these examples are merely illustrative, which are not intended to limit the present invention and may be varied without departing from the scope of the present invention.

The elution in column chromatography of Examples was carried out under observation by means of TLC (Thin Layer Chromatography). In the TLC observation, 60F$_{254}$ (manufactured by Merck & Co., Inc.) or NH (manufactured by Fuji Silysia Chemical, Ltd.) were adopted as a TLC plate, the solvent used for the elution in column chromatography was adopted as an eluent, a UV detector was adopted as the means for detection. As the silica gel for column, Kieselgel 60 (70 to 230 meshes) or Kieselgel 60 (230 to 400 meshes), which is likewise manufactured by Merck & Co., Inc.), was used. As the basic silica gel for column, basic silica NH-DM 1020 (manufactured by Fuji Silysia Chemical, Ltd.; 100 to 200 mesh) was used. NMR spectra were measured with a Varian Gemini 200 or 300 spectrometer by using tetramethylsilane as internal or external standard. The chemical shift was indicated by δ, and a coupling constant was indicated by Hz. IR spectra were measured with a Shimadzu FTZR-8200 spectrometer. The numeric value in parenthesis with regard to a mixed solvent is a volumetric mixing ratio of each solvent. Moreover, "%" in the solution represents the number of grams in 100 mL of a solution. In addition, symbols employed in Examples are described below:

s: singlet
d: doublet
t: triplet
q: quartet
dd: double doublet
m: multiplet
br: broad
brs: broad singlet
J: coupling constant
WSC: water soluble carbodiimide
THF: tetrahydrofuran
DMF: dimethylformamide
DMSO: dimethyl sulfoxide
HOBt: 1-hydroxybenzotriazole monohydrate
DBU: 1,8-diazabicyclo[5.4.0]-7-undecene
AcOEt: ethyl acetate
IPE: diisopropyl ether
Et$_2$O: diethyl ether

REFERENCE EXAMPLE 1

5-methyl-2-(4-piperidinyl)-1,2-dihydro-3H-imidazo[1,5-c]imidazol--one

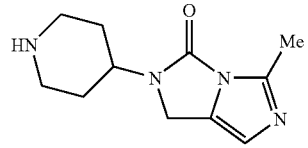

1a) 2-(1-benzyl-4-piperidinyl)-5-methyl-1,2-dihydro-3H-imidazo[1,5-c]imidazol-3-one To a solution of 2-methylimidazole-4-carbaldehyde (11.0 g), 4-amino-1-benzylpiperidine (19 g) and acetic acid (6.7 ml) in 1,2-dichloroethane (200 ml), under ice-cooling, was added sodium triacetoxyborohydride (32 g), and mixed at room temperature for 15 hours. The reaction solution was washed with an aqueous potassium carbonate solution and dried over anhydrous magnesium sulfate. The solvent was distilled off under reduced pressure, and then the residue was dissolved in THF (200 ml), N,N'-carbonyldiimidazole (18 g) and DBU (17 g) were added thereto, and mixed at room temperature for 15 hours. The reaction solution was concentrated, water was added thereto, and the reaction mixture was extracted with ethyl acetate. The extract was dried over anhydrous magnesium sulfate and the solvent was distilled off under reduced pressure. The residue was purified with silica gel column to obtain the title compound (19 g, 60%).

NMR (CDCl$_3$) δ: 1.74-1.85 (4H, m), 2.07-2.20 (2H, m), 2.61 (3H, s), 2.97-3.03 (2H, m), 3.53 (2H, s), 3.89-4.06 (1H, m), 4.30 (2H, s), 6.70 (1H, s), 7.32 (5H, m).

1b) 5-methyl-2-(4-piperidinyl)-1,2-dihydro-3H-imidazo[1,5-c]imidazol-3-one 2-(1-benzyl-4-piperidinyl)-5-methyl-1,2-dihydro-3H-imidazo[1,5-c]imidazol-3-one (18 g) obtained in Reference Example 1a) and 10% Pd/C (50% water content; 1.5 g) were added to methanol (300 ml), and then mixed under hydrogen atmosphere at room temperature for 2.5 days. The catalyst was filtered off, and then the filtrate was concentrated. The residue was recrystallized from ethyl acetate-hexane to obtain the title compound (11 g, 83%).

NMR (CDCl$_3$) δ: 1.56-1.89 (4H, m), 2.62 (3H, s), 2.75 (2H, m), 3.17-3.23 (2H, m), 3.97-4.13 (1H, m), 4.32 (2H, s), 6.71 (1H, s).

REFERENCE EXAMPLE 2

5-methyl-2-(1-piperazinyl)-1,2-dihydro-3H-imidazo[1,5-c]imidazol-3-one

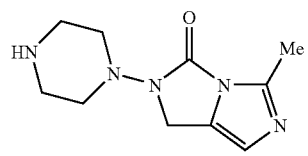

2a) 4-benzyl-N-((1E)-(2-methyl-1H-imidazol-4-yl)methylene)-1-piperazinamine

4-Benzyl-1-piperazinamine (K. L. Rinehart Jr et al. Bioorg. Chem., 6, 341 (1977); 10 g) and 2-methylimidazole-4-carbaldehyde (5.8 g) were suspended in methanol (200 ml), and the reaction mixture was heated under reflux for 3 hours. The reaction solution was cooled to room temperature, and then the solvent was distilled off under reduced pressure. To the residue was added diethyl ether, and the deposited precipitate was collected by filtration to obtain the title compound as a pale brown solid (13 g, 90%).
NMR (CDCl$_3$) δ: 2.40 (3H, s), 2.62 (4H, t, J=5.2), 3.09 (4H, t, J=5.2), 3.56 (2H, s), 6.97 (1H, s), 7.24-7.34 (5H, m), 7.43 (1H, s), 9.62 (1H, brs).

2b) 4-benzyl-N-((2-methyl-1H-imidazol-4-yl)methyl)-1-piperazinamine

To 4-benzyl-N-((1E)-(2-methyl-1H-imidazol-4-yl)methylene)-1-piperazinamine (13 g) obtained in Reference Example 2a), was added a solution of borane/THF complex in THF (1.0 M, 140 ml), and then mixed at room temperature for 15 hours. The solvent was distilled off under reduced pressure, and then to the residue was added 6 N hydrochloric acid (100 ml) under ice water, and mixed at 100° C. for 2 hours. Under ice-cooling, the reaction mixture was adjusted to pH 12 by adding sodium hydroxide and extracted with dichloromethane. The extract was dried over anhydrous magnesium sulfate, and then the solvent was distilled off under reduced pressure to obtain the title compound as a brown oil (15 g, quantitative).
NMR (CDCl$_3$) δ: 2.37 (3H, s), 2.53 (4H, brs), 2.75 (4H, brs), 3.52 (2H, s), 3.90 (2H, s), 6.76 (1H, s), 7.29-7.32 (5H, m).

2c) 2-(4-benzyl-1-piperazinyl)-5-methyl-1,2-dihydro-3H-imidazo[1,5-c]imidazol-3-one 4-Benzyl-N-((2-methyl-1H-imidazol-4-yl)methyl)-1-piperazinamine (15 g) obtained in Reference Example 2b) was dissolved in 1,2-dichloroethane (400 ml). DBU (11 ml) and N,N'-carbonyldiimidazole (15 g) were added to the solution, and then mixed at room temperature for 15 hours. The reaction mixture was diluted with water and chloroform, and the organic layer was collected by separation, and then dried over anhydrous magnesium sulfate. The solvent was distilled off under reduced pressure and the residue was purified with basic silica gel column (ethyl acetate) to obtain the title compound as a colorless solid (9.6 g, 65%).
NMR (CDCl$_3$) δ: 2.60-2.65 (7H, m), 3.14 (4H, t, J=4.6), 3.55 (2H, s), 4.43 (2H, s), 6.70 (1H, t, J=2.0), 7.25-7.34 (5H, m).

2d) 5-methyl-2-(1-piperazinyl)-1,2-dihydro-3H-imidazo[1,5-c]imidazol-3-one 2-(4-Benzyl-1-piperazinyl)-5-methyl-1,2-dihydro-3H-imidazo[1,5-c]imidazol-3-one (8.0 g) obtained in Reference Example 2c), ammonium formate (16 g) and 10% palladium carbon (1.6 g) were suspended in methanol (100 ml), and the mixture was heated under reflux for 6 hours. After cooling to room temperature, the precipitate was filtered off using Celite and the filtrate was concentrated under reduced pressure. To the residue was added a mixed solvent (ethyl acetate:diethyl ether=5:1), and the deposited precipitate was collected by filtration to obtain the title compound as a pale brown solid (5.3 g, 93%).

NMR (CDCl$_3$) δ: 2.61 (3H, s), 2.98-3.03 (4H, m), 3.10-3.15 (4H, m), 4.44 (2H, s), 6.70 (1H, s).

REFERENCE EXAMPLE 3

N-((2Z)-3-methyl-4-(1-piperazinyl)methyl-1,3-thiazol-2(3H)-ylidene)methanamine trihydrochloride

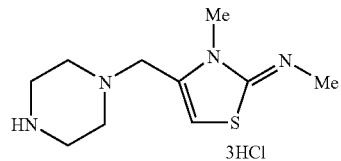

3a) tert-butyl 4-(((2Z)-3-methyl-2-methylimino-2,3-dihydro-1,3-thiazol-4-yl)methyl)-1-piperazinecarboxylate tert-Butyl 1-piperazinecarboxylate (2.5 g) was dissolved in acetonitrile (50 ml). Potassium carbonate (3.7 g) and 4-chloromethyl-3-methyl-1,3-thiazol-2(3H)-ylidene)-N-methanamine hydrochloride (3.2 g) were added thereto, and the mixture was refluxed for 4 hours. The solvent was distilled off under reduced pressure, and then to the residue was added an aqueous potassium hydrogen carbonate solution. The reaction mixture was extracted with chloroform and the extract was dried over anhydrous magnesium sulfate. The solvent was distilled off under reduced pressure, and then the residue was purified with basic silica gel column to obtain the title compound as a brown oil (4.3 g, 88%).
NMR (CDCl$_3$) δ: 1.43 (9H, s), 2.35-3.36 (3H, m), 2.97 (3H, s), 2.31 (2H, s), 3.33 (3H, s), 3.36-3.40 (4H, m), 5.69 (1H, s).

3b) N-((2Z)-3-methyl-4-(1-piperazinyl)methyl-1,3-thiazol-2(3H)-ylidene)methanamine trihydrochloride tert-Butyl 4-(((2Z)-3-methyl-2-methylimino-2,3-dihydro-1,3-thiazol-4-yl)methyl)-1-piperazinecarboxylate obtained in Reference Example 3a) (1.5 g) was dissolved in concentrated hydrochloric acid (5 ml), and then mixed at room temperature for 1 hour. The solvent was distilled off under reduced pressure, and then water was removed by azeotropy with ethanol. The residue was washed with ethanol to obtain the title compound (1.5 g, 97%) as pale brown powder. NMR (DMSO-d$_6$) δ: 2.86-3.33 (17H, m), 7.19 (1H, s), 9.43 (2H, br), 10.27-10.29 (1H, m).

REFERENCE EXAMPLE 4

2-methyl-5-(1-piperazinyl)imidazo[1,2-a]pyridine dihydrochloride

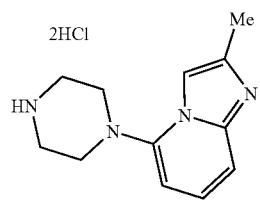

4a) tert-butyl 4-(2-methylimidazo[1,2-a]pyridin-5-yl)-1-piperazinecarboxylate 5-Chloro-2-methylimidazo[1,2-a]pyridine (5.0 g) and piperazine (26 g) were blended, and mixed at 125° C. under argon for 18 hours. After standing to cool to room temperature, to the reaction mixture were added water (200 ml) and chloroform (200 ml), the organic layer was collected by separation, washed with saturated brine, and then dried over anhydrous magnesium sulfate. The solvent was distilled off under reduced pressure, and the residue was dissolved in ethanol (100 ml). Di-tert-butyl dicarbonate (6.6 g) was added dropwise thereto at room temperature, and then the reaction solution was mixed at room temperature for 1 hour. The solvent was distilled off under reduced pressure, and the residue was diluted with water and ethyl acetate. The organic layer was collected by separation, washed with saturated brine and dried over anhydrous magnesium sulfate. Then, the solvent was distilled off under reduced pressure and the residue was purified with silica gel column (ethyl acetate/ethanol=10:1) to obtain the title compound as a pale yellow solid (8.5 g, 89%).

NMR (CDCl$_3$) δ 1.50 (9H, s), 2.48 (3H, s), 2.97-3.15 (4H, m), 3.58-3.78 (4H, m), 6.23 (1H, d, J=8.2), 7.13 (1H, dd, J=8.8, 7.0), 7.28-7.35 (2H, m).

4b) 2-methyl-5-(1-piperazinyl)imidazo[1,2-a]pyridine dihydrochloride tert-Butyl 4-(2-methylimidazo[1,2-a]pyridin-5-yl)-1-piperazinecarboxylate (8.5 g) obtained in Reference Example 4a) was dissolved in 12 N hydrochloric acid (22 ml), and then mixed at room temperature for 20 minutes. To the reaction mixture was added ethanol, followed by concentration under reduced pressure. The precipitated crystals were collected by filtration, and the crystals were washed with ethanol and diethyl ether to obtain the title compound as a pale yellow crystal (6.3 g, 81%).

NMR (D$_2$O) δ 2.59 (3H, s), 3.48-3.61 (4H, m), 3.61-3.72 (4H, m), 7.11 (1H, d, J=7.8), 7.61 (1H, d, J=9.0), 7.80 (1H, s), 7.91 (1H, dd, J=8.8, 7.8).

EXAMPLE 1

N-(1-benzyl-2-(4-(5-methyl-3-oxo-1H-imidazo[1,5-c]imidazol-2(3H)-yl)-1-piperidinyl)-2-oxoethyl)-N'-(4-chlorophenyl)urea

1a) methyl 2-(N'-(4-chlorophenyl)ureido)-3-phenyl-propanoate

To a solution of phenylalanine methyl ester hydrochloride (2.0 g) and DBU (1.4 ml) in acetonitrile (40 ml) was added 4-chlorophenyl isocyanate (1.4 g). The reaction mixture was mixed at room temperature for 1 hour, and then the reaction solution was concentrated under reduced pressure. The residue was dissolved in ethyl acetate, washed with water and saturated brine and dried over anhydrous sodium sulfate. The solvent was distilled off under reduced pressure to obtain the title compound as colorless powder (3.0 g, 97%).

NMR (CDCl$_3$) δ: 3.01-3.18 (2H, m), 3.74 (3H, s), 4.77-4.83 (1H, m), 5.34 (1H, d, J=7.8), 6.68 (1H, s), 7.08-7.30 (10H, m).

1b) 2-(N'-(4-chlorophenyl)ureido)-3-phenylpropanoic acid

A solution of methyl 2-(N'-(4-chlorophenyl)ureido)-3-phenylpropanoate (2.8 g) obtained in Example 1a) and 1 N sodium hydroxide (20 ml) in methanol (20 ml)-THF (10 ml) was mixed at room temperature for 15 hours, and the reaction solution was concentrated under reduced pressure. The solution was acidified by adding 1 N hydrochloric acid to the concentrated solution, and then extracted with ethyl acetate. The extract was washed with saturated brine and dried over anhydrous sodium sulfate. The solvent was distilled off under reduced pressure to obtain the title compound as colorless powder (2.6 g, 95%).

NMR (CDCl$_3$+CD$_3$OD) δ: 3.05-3.24 (2H, m), 4.72 (1H, t, J=6.0), 7.17-7.31 (10H, m).

1c) N-(1-benzyl-2-(4-(5-methyl-3-oxo-1H-imidazo[1,5-c]imidazol-2(3H)-yl)-1-piperidinyl)-2-oxoethyl)-N'-(4-chlorophenyl)urea To a solution of 2-(N'-(4-chlorophenyl)ureido)-3-phenylpropanoic acid (0.16 g) obtained in Example 1b) and HOBt (0.12 g) in DMF (10 ml) was added WSC (0.14 g), and the reaction mixture was mixed at room temperature for 15 minutes. Then, 5-methyl-2-(4-piperidinyl)-1,2-dihydro-3H-imidazo[1,5-c]imidazol-3-one (0.11 g) obtained in Reference Example 1 and N-methylmorpholine (0.08 ml) were added thereto. The reaction mixture was mixed at room temperature for 15 hours, and then the solvent was distilled off under reduced pressure. The residue was dissolved in ethyl acetate, washed with an aqueous sodium hydrogen carbonate solution and dried over anhydrous sodium sulfate. The solvent was distilled off under reduced pressure and the residue was purified with silica gel column (ethyl acetate to ethyl acetate/methanol=10/1). The product was washed with diethyl ether to obtain the title compound as colorless powder (0.13 g, 50%).

NMR (CDCl$_3$) δ: 1.49-1.90 (4H, m), 2.32-2.68 (1H, m), 2.59 (3H, s), 2.88-3.20 (3H, m), 3.91-4.18 (4H, m), 4.70-4.75 (1H, m), 5.15-5.30 (1H, m), 6.40-6.52 (1H, m), 6.68-6.75 (1H, m), 7.15-7.48 (10H, m).

Elemental analysis for C$_{27}$H$_{29}$ClN$_6$O$_3$.0.3AcOEt.H$_2$O
Calcd. (%): C, 59.90; H, 5.95; N, 14.86.
Found (%): C, 59.85; H, 5.91; N, 14.46.

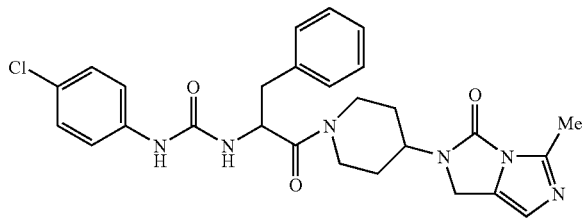

EXAMPLE 2

N-(1-benzyl-2-(4-(5-methyl-3-oxo-1H-imidazo[1,5-c]imidazol-2(3H)-yl)-1-piperazinyl)-2-oxoethyl)-N'-(4-chlorophenyl)urea

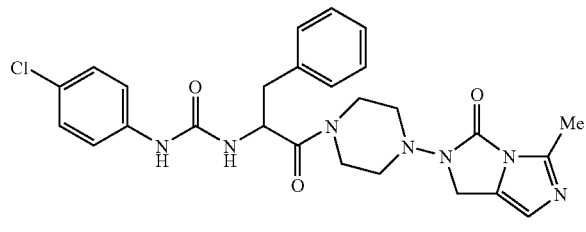

In the same manner as in Example 1c), the title compound as colorless powder (0.19 g, 73%) was obtained from 5-methyl-2-(1-piperazinyl)-1,2-dihydro-3H-imidazo[1,5-c]imidazol-3-one (0.11 g) obtained in Reference Example 2.

NMR (CDCl$_3$) δ: 2.45-2.47 (1H, m), 2.59 (3H, s), 2.94-3.25 (6H, m), 3.48-3.56 (1H, m), 3.72 (2H, m), 4.30 (2H, s), 5.12-5.20 (1H, m), 6.21 (1H, d, J=8.4), 6.71 (1H, s), 7.15-7.34 (10H, m).

Elemental analysis for $C_{26}H_{28}ClN_7O_3 \cdot 0.3AcOEt \cdot 0.5H_2O$
Calcd. (%): C, 58.61; H, 5.68; N, 17.59.
Found (%): C, 58.49; H, 5.75; N, 17.42.

EXAMPLE 3

2-(4-(5-methyl-3-oxo-1H-imidazo[1,5-c]imidazol-2(3H)-yl)-1-piperazinyl)-2-oxo-1-phenylethyl 4-chlorophenylcarbamate

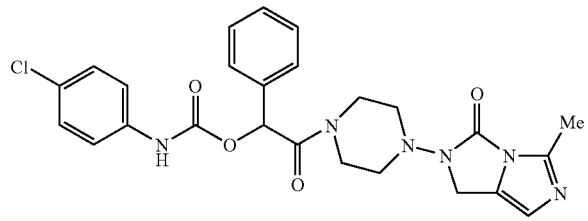

3a) methyl((((4-chlorophenyl)amino)carbonyl)oxy)(phenyl)acetate

To a solution of methyl mandelate (0.83 g) and triethylamine (0.51 g) in THF (40 ml) was added 4-chlorophenyl isocyanate (0.77 g). The reaction mixture was mixed at 60° C. for 3 hours, and then the reaction solution was concentrated under reduced pressure. The residue was dissolved in ethyl acetate, washed with water and saturated brine and dried over anhydrous sodium sulfate. The solvent was distilled off under reduced pressure, and the residue was purified with silica gel column (ethyl acetate/hexane=1/6 to 1/3) to obtain the title compound as a pale brown crystal (1.5 g, 91%).

NMR (CDCl$_3$) δ: 3.75 (3H, s), 6.02 (1H, s), 6.97 (1H, br), 7.24-7.51 (9H, m).

3b) ((((4-chlorophenyl)amino)carbonyl)oxy)(phenyl)acetic acid

Methyl((((4-chlorophenyl)amino)carbonyl)oxy)(phenyl)acetate (0.73 g) obtained in Example 3a) and 1 N sodium hydroxide (3.0 ml) were dissolved in methanol (10 ml) and THF (10 ml), and then mixed at room temperature for 15 hours. The reaction solution was then concentrated under reduced pressure, acidified by adding 1 N hydrochloric acid to the concentrated solution, and then the precipitate was collected by filtration and washed with water to obtain the title compound as pale brown powder (0.62 g, 89%).

NMR (CDCl$_3$+CD$_3$OD) δ: 6.02 (1H, s), 7.23-7.55 (10H, m).

3c) 2-(4-(5-methyl-3-oxo-1H-imidazo[1,5-c]imidazol-2(3H)-yl)-1-piperazinyl)-2-oxo-1-phenylethyl 4-chlorophenylcarbamate To a solution of ((((4-chlorophenyl)amino)carbonyl)oxy)(phenyl)acetic acid (0.31 g) obtained in Example 3b) and HOBt (0.23 g) in acetonitrile (10 ml) was added WSC (0.29 g), and the reaction mixture was mixed at room temperature for 15 minutes. Then, 5-methyl-2-(1-piperazinyl)-1,2-dihydro-3H-imidazo[1,5-c]imidazol-3-one (0.22 g) obtained in Reference Example 2 and triethylamine (0.30 g) were added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure and the residue was purified with silica gel column (ethyl acetate to ethyl acetate/methanol=5/1). The product was washed with diisopropyl ether to obtain the title compound as colorless powder (0.19 g, 37%).

NMR (CDCl$_3$) δ: 2.58 (3H, s), 2.69 (1H, br), 2.99-3.11 (3H, m), 3.49-3.89 (4H, m), 4.33 (2H, s), 6.33 (1H, s), 6.69 (1H, s), 7.22-7.49 (10H, m).

Elemental analysis for $C_{25}H_{25}ClN_6O_4 \cdot 0.1AcOEt \cdot 0.1H_2O$
Calcd. (%): C, 58.72; H, 5.04; N, 16.17.
Found (%): C, 58.66; H, 5.12; N, 15.94.

EXAMPLE 4

N-(4-chlorophenyl)-N'-(3-(4-(5-methyl-3-oxo-1H-imidazo[1,5-c]imidazol-2(3H)-yl)-1-piperazinyl)-3-oxo-2-phenylpropyl)urea

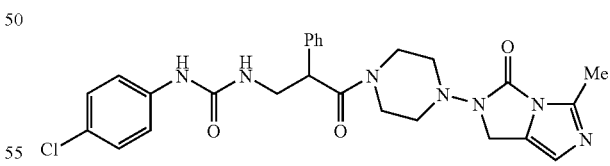

4a) ethyl 3-(N'-(4-chlorophenyl)ureido)-2-phenylpropanoate

In the same manner as in Example 1a), the title compound as pale brown powder (1.7 g, 75%) was obtained from ethyl 3-amino-2-phenylpropanoate hydrochloride (F. Leonard et al., J. Am. Chem. Soc., 26, 4062 (1961); 1.5 g).

NMR (CDCl$_3$) δ: 1.20 (3H, t, J=7.2), 3.64 (2H, d, J=7.1), 3.94 (1H, t, J=7.6), 4.09-4.20 (2H, m), 5.55 (1H, m), 7.19-7.37 (11H, m).

4b) 3-(N'-(4-chlorophenyl)ureido)-2-phenylpropanoic acid

A solution of ethyl 3-(N'-(4-chlorophenyl)ureido)-2-phenylpropanoate (1.5 g) obtained in Example 4a) and 1 N sodium hydroxide (10 ml) in ethanol (20 ml)-THF (20 ml) was mixed at room temperature for 15 hours, and then the reaction solution was concentrated under reduced pressure. The solution was acidified by adding 1 N hydrochloric acid to the concentrated solution, and then extracted with ethyl acetate. The extract was washed with saturated brine and dried over anhydrous sodium sulfate. The solvent was distilled off under reduced pressure to obtain the title compound as colorless powder (1.4 g, quantitative).

NMR (DMSO-$d_6$) δ: 3.41-3.56 (2H, m), 3.73-3.78 (1H, m), 6.29 (1H, m), 7.23-7.40 (10H, m).

4c) N-(4-chlorophenyl)-N'-(3-(4-(5-methyl-3-oxo-1H-imidazo[1,5-c]imidazol-2(3H)-yl)-1-piperazinyl)-3-oxo-2-phenylpropyl)urea In the same manner as in Example 3c), the title compound as colorless powder (0.34 g, 65%) was obtained from 3-(N'-(4-chlorophenyl)ureido)-2-phenylpropanoic acid (0.32 g) obtained in Example 4b).

NMR (CDCl$_3$) δ: 2.54-2.57 (1H, m), 2.56 (3H, s), 2.94-3.13 (3H, m), 3.36-3.88 (6H, m), 4.19-4.31 (3H, m), 5.78-5.83 (1H, m), 6.67 (1H, s), 7.23-7.40 (10H, m).

Elemental analysis for $C_{26}H_{28}ClN_7O_3 \cdot 0.3AcOEt \cdot 0.5H_2O$
Calcd. (%): C, 58.61; H, 5.68; N, 17.59.
Found (%): C, 58.36; H, 5.76; N, 17.32.

EXAMPLE 5

(3R)—N-(4-chlorophenyl)-3-cyclohexyl-4-(4-(5-methyl-3-oxo-1H-imidazo[1,5-c]imidazol-2(3H)-yl)-1-piperidinyl)-4-oxobutanamide

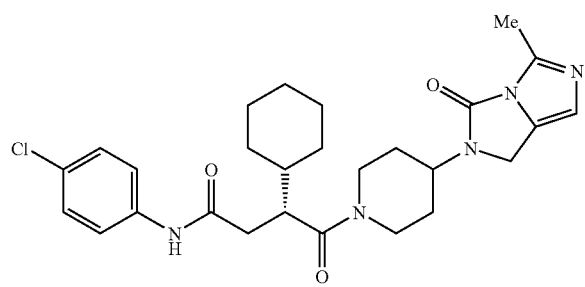

5a) methyl(2R)-4-((4-chlorophenyl)amino)-2-cyclohexyl-4-oxobutanoate

To a suspension of (3R)-3-cyclohexyl-4-methoxy-4-oxobutanoic acid (0.21 g), 4-chloroaniline (0.13 g) and HOBt (0.23 g) in acetonitrile (10 ml) were added WSC (0.29 g) and N-methylmorpholine (0.10 g), and mixed at room temperature for 15 hours. The reaction mixture was concentrated under reduced pressure, and the residue was dissolved in ethyl acetate. The ethyl acetate solution was washed sequentially with an aqueous sodium hydrogen carbonate solution, water, a 5% aqueous citric acid solution and saturated brine, and dried over anhydrous sodium sulfate. The solvent was distilled off under reduced pressure to obtain the title compound as a pale brown solid (0.30 g, 93%).

NMR (CDCl$_3$) δ: 1.02-1.26 (6H, m), 1.59-1.78 (5H, m), 2.47-2.53 (1H, m), 2.68-2.76 (1H, m), 2.85-2.90 (1H, m), 3.70 (3H, s), 7.24-7.26 (2H, m), 7.42-7.45 (2H, m), 7.54 (1H, br).

5b) (2R)-4-((4-chlorophenyl)amino)-2-cyclohexyl-4-oxobutanoic acid

Methyl(2R)-4-((4-chlorophenyl)amino)-2-cyclohexyl-4-oxobutanoate (0.29 g) obtained in Example 5a) and 1 N sodium hydroxide (1.0 ml) were dissolved in methanol (12 ml) and THF (3 ml), and mixed at room temperature for 1 hour. Then, the reaction solution was concentrated under reduced pressure, acidified by adding 1 N hydrochloric acid to the concentrated solution and extracted with ethyl acetate. The extract was dried over anhydrous sodium sulfate, and the solvent was distilled off under reduced pressure to obtain the title compound as pale brown powder (0.28 g, quantitative).

NMR (CDCl$_3$) δ: 0.96-1.30 (6H, m), 1.57-1.83 (5H, m), 2.47-2.86 (3H, m), 7.22-7.30 (2H, m), 7.43-7.53 (3H, m).

5c) (3R)—N-(4-chlorophenyl)-3-cyclohexyl-4-(4-(5-methyl-3-oxo-1H-imidazo[1,5-c]imidazol-2(3H)-yl)-1-piperidinyl)-4-oxobutanamide To a solution of (2R)-4-((4-chlorophenyl)amino)-2-cyclohexyl-4-oxobutanoic acid (0.27 g) obtained in Example 5b) and HOBt (0.20 g) in acetonitrile (10 ml) was added WSC (0.25 g), and the reaction mixture was mixed at room temperature for 15 minutes. Then, 5-methyl-2-(4-piperidinyl)-1,2-dihydro-3H-imidazo[1,5-c]imidazol-3-one dihydrochloride (0.26 g), DBU (0.27 g) and triethylamine (0.27 g) were added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, the residue was purified with silica gel column (ethyl acetate to ethyl acetate/methanol=10/1), and the product was washed with ethyl acetate-hexane to obtain the title compound as colorless powder (0.13 g, 29%).

NMR (CDCl$_3$) δ0.99-1.35 (6H, m), 1.58-1.85 (8H, m), 2.42-3.18 (8H, m), 3.77-4.26 (5H, m), 4.73-4.77 (1H, m), 6.72 (1H, m), 7.21-7.30 (2H, m), 7.45-7.54 (2H, m), 7.95-8.06 (1H, m).

Elemental analysis for $C_{27}H_{34}ClN_5O_3 \cdot 0.5H_2O$
Calcd. (%): C, 62.24; H, 6.77; N, 13.44.
Found (%): C, 62.51; H, 6.54; N, 13.17.

EXAMPLE 6

N-(4-chlorophenyl)-N'-(2-(4-(5-methyl-3-oxo-1H-imidazo[1,5-c]imidazol-2(3H)-yl)-1-piperidinyl)-2-oxoethyl)urea

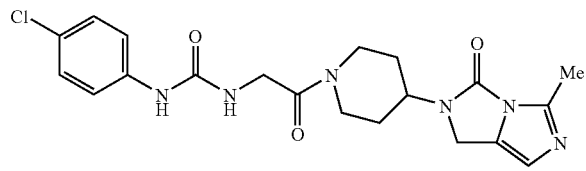

6a) tert-butyl 2-(4-(5-methyl-3-oxo-1H-imidazo[1,5-c]imidazol-2(3H)-yl)-1-piperidinyl)-2-oxoethylcarbamate To a solution of Boc-glycine (0.44 g) and HOBt (0.58 g) in acetonitrile (15 ml) was added WSC (0.72 g), and the reaction mixture was mixed at room temperature for 15 minutes. Then, a solution of 5-methyl-2-(4-piperidinyl)-1,2-dihydro-3H-imidazo[1,5-c]imidazol-3-one dihydrochloride (0.73 g), DBU (0.75 ml) and triethylamine (1.1 ml) in acetonitrile (5 ml) was added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure and the residue was purified with basic silica gel column (ethyl acetate to ethyl acetate/methanol=5/1) to obtain the title compound as a colorless solid (0.62 g, 66%).

NMR (CDCl$_3$) δ: 1.46 (9H, s), 1.63-1.72 (2H, m), 1.90-2.05 (2H, m), 2.61 (3H, s), 2.68-2.76 (1H, m), 3.13-3.20 (1H, m), 3.83-4.23 (4H, m), 4.27 (2H, s), 4.76-4.82 (1H, m), 5.49 (1H, br), 6.72 (1H, s).

6b) N-(4-chlorophenyl)-N'-(2-(4-(5-methyl-3-oxo-1H-imidazo[1,5-c]imidazol-2(3H)-yl)-1-piperidinyl)-2-oxoethyl)urea tert-Butyl 2-(4-(5-methyl-3-oxo-1H-imidazo[1,5-c]imidazol-2(3H)-yl)-1-piperidinyl)-2-oxoethylcarbamate (0.15 g) obtained in Example 6a) was dissolved in trifluoroacetic acid (3 ml), mixed at room temperature for 1 hour, and then concentrated under reduced pressure. After water was removed by azeotropy with toluene, the residue was dissolved in triethylamine (2 ml) and DMF (3 ml), 4-chlorophenyl isocyanate (61 mg) was added thereto, and mixed at room temperature for 15 hours. The solvent was distilled off under reduced pressure, and the residue was dissolved in chloroform, washed with a saturated aqueous sodium hydrogen carbonate solution and dried over anhydrous sodium sulfate. The solvent was distilled off under reduced pressure, and the residue was purified with silica gel column (ethyl acetate to ethyl acetate/methanol=5/1) to obtain the title compound as colorless powder (82 mg, 48%).

NMR (CDCl$_3$) δ: 1.62-1.75 (2H, m), 1.92-2.00 (2H, m), 2.61 (3H, s), 2.71-2.78 (1H, m), 3.15-3.24 (1H, m), 3.93-3.97 (1H, m), 4.04-4.30 (5H, m), 4.73-4.78 (1H, m), 6.21-6.24 (1H, m), 6.73 (1H, m), 7.20 (2H, dt, J=9.0, 2.0), 7.25 (2H, dt, J=9.0, 2.0), 7.46 (1H, s).

Elemental analysis for C$_{20}$H$_{23}$ClN$_6$O$_3$.0.1AcOEt.0.8H$_2$O
Calcd. (%): C, 53.96; H, 5.64; N, 18.51.
Found (%): C, 54.01; H, 5.48; N, 18.37.

EXAMPLE 7

N'-(4-chlorophenyl)-N-methyl-N-(2-(4-(5-methyl-3-oxo-1H-imidazo[1,5-c]imidazol-2(3H)-yl)-1-piperidinyl)-2-oxoethyl)urea

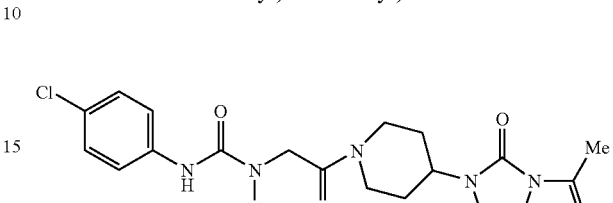

7a) tert-butyl methyl(2-(4-(5-methyl-3-oxo-1H-imidazo[1,5-c]imidazol-2(3H)-yl)-1-piperidinyl)-2-oxoethyl)carbamate In the same manner as in Example 6a), the title compound as a colorless oil (0.70 g, 72%) was obtained from Boc-sarcosine (0.47 g).

NMR (CDCl$_3$) δ: 1.48 (9H, s), 1.63-1.72 (2H, m), 1.91 (2H, m), 2.61 (3H, s), 2.68-2.71 (1H, m), 2.94 (3H, s), 3.13-3.20 (1H, m), 3.69-3.76 (1H, m), 3.90-3.96 (2H, m), 4.11-4.22 (2H, m), 4.27 (2H, s), 4.76-4.80 (1H, m), 6.72 (1H, m).

7b) N'-(4-chlorophenyl)-N-methyl-N-(2-(4-(5-methyl-3-oxo-1H-imidazo[1,5-c]imidazol-2(3H)-yl)-1-piperidinyl)-2-oxoethyl)urea In the same manner as in Example 6b), the title compound as colorless powder (0.12 g, 66%) was obtained from tert-butyl methyl(2-(4-(5-methyl-3-oxo-1H-imidazo[1,5-c]imidazol-2(3H)-yl)-1-piperidinyl)-2-oxoethyl)carbamate (0.16 g) obtained in Example 7a).

NMR (CDCl$_3$) δ: 1.68-1.75 (2H, m), 1.93-2.00 (2H, m), 2.61 (3H, s), 2.67-2.75 (1H, m), 3.13 (3H, s), 3.17-3.26 (1H, m), 3.94-4.04 (2H, m), 4.14-4.22 (1H, m), 4.29 (2H, s), 4.44-4.50 (1H, m), 4.73-4.79 (1H, m), 6.71 (1H, m), 7.25 (2H, d, J=9.0), 7.36 (2H, d, J=9.0), 7.46 (1H, s).

Elemental analysis for C$_{21}$H$_{25}$ClN$_6$O$_3$.0.1AcOEt 1.6H$_2$O
Calcd. (%): C, 53.26; H, 6.06; N, 17.42.
Found (%): C, 53.43; H, 5.82; N, 17.38.

EXAMPLE 8

N-(4-chlorophenyl)-N'-(3-(4-(5-methyl-3-oxo-1H-imidazo[1,5-c]imidazol-2(3H)-yl)-1-piperidinyl)-3-oxopropyl)urea

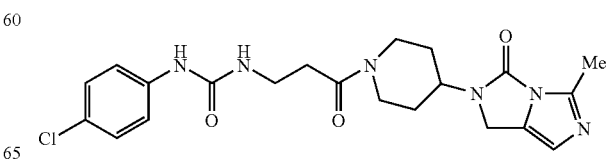

8a) tert-butyl 3-(4-(5-methyl-3-oxo-1H-imidazo[1,5-c]imidazol-2(3H)-yl)-1-piperidinyl)-3-oxopropylcarbamate In the same manner as in Example 6a), the title compound as a colorless oil (0.80 g, 82%) was obtained from Boc-β-alanine (0.47 g).

NMR (CDCl$_3$) δ: 1.44 (9H, s), 1.63-1.72 (2H, m), 1.89-1.94 (2H, m), 2.53-2.57 (2H, m), 2.61 (3H, s), 2.65-2.70 (1H, m), 3.10-3.20 (1H, m), 3.41-3.47 (2H, m), 3.94-3.98 (1H, m), 4.11-4.22 (1H, m), 4.27 (2H, s), 4.78-4.84 (1H, m), 5.27 (1H, m), 6.72 (1H, m).

8b) N-(4-chlorophenyl)-N'-(3-(4-(5-methyl-3-oxo-1H-imidazo[1,5-c]imidazol-2(3H)-yl)-1-piperidinyl)-3-oxopropyl)urea In the same manner as in Example 6b), the title compound as colorless powder (82 mg, 38%) was obtained from tert-butyl 3-(4-(5-methyl-3-oxo-1H-imidazo[1,5-c]imidazol-2(3H)-yl)-1-piperidinyl)-3-oxopropylcarbamate (0.19 g) obtained in Example 8a).

NMR (CDCl$_3$) δ: 1.62-1.71 (2H, m), 1.88-1.97 (2H, m), 2.60 (3H, s), 2.62-2.71 (3H, m), 3.12-3.21 (1H, m), 3.55-3.60 (2H, m), 3.96-4.19 (2H, m), 4.21 (2H, s), 4.74-4.78 (1H, m), 5.79 (1H, m), 6.70 (1H, s), 7.24 (2H, dt, J=2.6, 9.4), 7.31 (2H, dt, J=2.6, 9.4), 7.32 (1H, br).

Elemental analysis for C$_{21}$H$_{25}$ClN$_6$O$_3$.0.6H$_2$O
Calcd. (%): C, 55.35; H, 5.79; N, 18.44.
Found (%): C, 55.13; H, 5.80; N, 18.61.

EXAMPLE 9

N—((1R)-1-benzyl-2-(4-(5-methyl-3-oxo-1H-imidazo[1,5-c]imidazol-2(3H)-yl)-1-piperidinyl)-2-oxoethyl)—N'—(4-chlorophenyl)urea

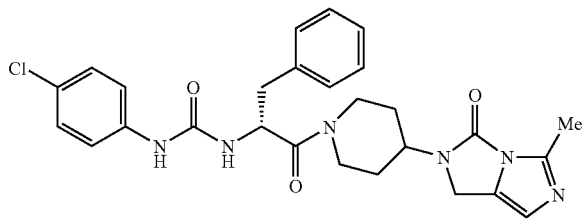

9a) tert-butyl(1R)-1-benzyl-2-(4-(5-methyl-3-oxo-1H-imidazo[1,5-c]imidazol-2(3H)-yl)-1-piperidinyl)-2-oxoethylcarbamate In the same manner as in Example 6a), the title compound as a colorless oil (0.48 g, quantitative) was obtained from Boc-D-phenylalanine (0.27 g).

NMR (CDCl$_3$) δ: 1.44 (9H, s), 1.63-1.92 (4H, m), 2.59 (3H, m), 2.51-2.59 (1H, m), 2.92-4.22 (7H, m), 4.72-4.91 (2H, m), 5.35-5.44 (1H, m), 6.70-6.74 (1H, m), 7.16-7.34 (5H, m).

9b) N—((1R)-1-benzyl-2-(4-(5-methyl-3-oxo-1H-imidazo[1,5-c]imidazol-2(3H)-yl)-1-piperidinyl)-2-oxoethyl)—N'—(4-chlorophenyl)urea In the same manner as in Example 6b), the title compound as colorless powder (0.23 g, 46%, >99.9% ee) was obtained from tert-butyl(1R)-1-benzyl-2-(4-(5-methyl-3-oxo-1H-imidazo[1,5-c]imidazol-2(3H)-yl)-1-piperidinyl)-2-oxoethylcarbamate (0.45 g) obtained in Example 9a).

NMR (CDCl$_3$) δ: 1.49-1.90 (4H, m), 2.32-2.68 (1H, m), 2.59 (3H, s), 2.88-3.20 (3H, m), 3.91-4.18 (4H, m), 4.70-4.75 (1H, m), 5.15-5.30 (1H, m), 6.40-6.52 (1H, m), 6.68-6.75 (1H, m), 7.15-7.58 (10H, m).

Elemental analysis for C$_{27}$H$_{29}$ClN$_6$O$_3$.0.1AcOEt.0.8H$_2$O
Calcd. (%): C, 60.47; H, 5.82; N, 15.44.
Found (%): C, 60.48; H, 5.99; N, 15.16.

EXAMPLE 10

N—((1R)-1-benzyl-2-(4-(5-methyl-3-oxo-1H-imidazo[1,5-c]imidazol-2(3H)-yl)-1-piperazinyl)-2-oxoethyl)—N'—(4-chlorophenyl)urea

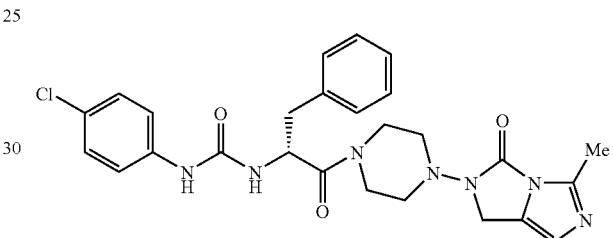

10a) tert-butyl(1R)-1-benzyl-2-(4-(5-methyl-3-oxo-1H-imidazo[1,5-c]imidazol-2(3H)-yl)-1-piperazinyl)-2-oxoethylcarbamate To a solution of Boc-D-phenylalanine (0.27 g) and HOBt (0.23 g) in acetonitrile (10 ml) was added WSC (0.29 g), and the reaction mixture was mixed at room temperature for 15 minutes. Then, 5-methyl-2-(1-piperazinyl)-1,2-dihydro-3H-imidazo[1,5-c]imidazol-3-one (0.22 g) obtained in Reference Example 2 and triethylamine (0.42 ml) were added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with basic silica gel column (ethyl acetate) to obtain the title compound as a colorless oil (0.48 g, quantitative).

NMR (CDCl$_3$) δ: 1.44 (9H, s), 2.30-2.36 (1H, m), 2.59 (3H, s), 2.87-3.14 (5H, m), 3.39-3.72 (4H, m), 4.29 (2H, s), 4.80-4.88 (1H, m), 5.40-5.43 (1H, m), 6.72 (1H, s), 7.21-7.36 (5H, m).

10b) N—((1R)-1-benzyl-2-(4-(5-methyl-3-oxo-1H-imidazo[1,5-c]imidazol-2(3H)-yl)-1-piperazinyl)-2-oxoethyl)—N'—(4-chlorophenyl)urea In the same manner as in Example 6b), the title compound as colorless powder (0.28 g, 56%) was obtained from tert-butyl(1R)-1-benzyl-2-(4-(5-methyl-3-oxo-1H-imidazo[1,5- c]imidazol-2(3H)-yl)-1-piperazinyl)-2-oxoethylcarbamate (0.45 g) obtained in Example 10a).

NMR (CDCl$_3$) δ: 2.45-2.47 (1H, m), 2.59 (3H, s), 2.94-3.25 (6H, m), 3.48-3.56 (1H, m), 3.72 (2H, m), 4.30 (2H, s), 5.12-5.20 (1H, m), 6.60 (1H, d, J=8.4), 6.72 (1H, s), 7.15-7.45 (10H, m).

Elemental analysis for $C_{26}H_{28}ClN_7O_3 \cdot 0.1AcOEt \cdot 0.8H_2O$
Calcd. (%): C, 58.16; H, 5.62; N, 17.98.
Found (%): C, 58.20; H, 5.71; N, 17.82.

EXAMPLE 11

N—(4-chlorophenyl)—N'—((1R)-2-(4-(5-methyl-3-oxo-1H-imidazo[1,5-c]imidazol-2(3H)-yl)-1-piperidinyl)-2-oxo-1-phenylethyl)urea and N—(4-chlorophenyl)—N'—((1S)-2-(4-(5-methyl-3-oxo-1H-imidazo[1,5-c]imidazol-2(3H)-yl)-1-piperidinyl)-2-oxo-1-phenylethyl)urea

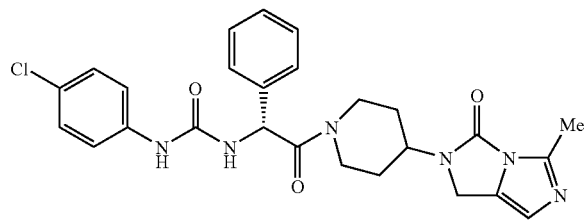

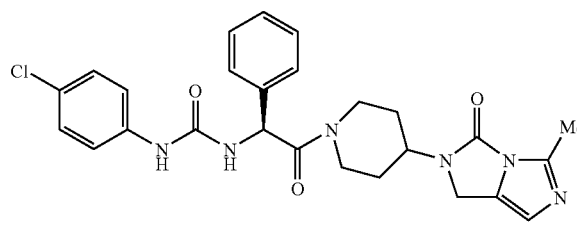

11a) tert-butyl 2-(4-(5-methyl-3-oxo-1H-imidazo[1,5-c]imidazol-2(3H)-yl)-1-piperidinyl)-2-oxo-1-phenylethylcarbamate To a solution of Boc-D-phenylglycine (1.3 g) and HOBt (1.2 g) in acetonitrile (30 ml) was added WSC (1.4 g), and the reaction mixture was mixed at room temperature for 15 minutes. Then, 5-methyl-2-(4-piperidinyl)-1,2-dihydro-3H-imidazo[1,5-c]imidazol-3-one (1.1 g) obtained in Reference Example 1 and triethylamine (2.1 ml) were added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with silica gel column (ethyl acetate to ethyl acetate/methanol=10/1) to obtain the title compound as colorless powder (2.1 g, 93%).

NMR (CDCl$_3$) δ: 1.41-1.42 (9H, m), 1.62-1.93 (2H, m), 2.56-2.59 (3H, m), 2.60-3.13 (2H, m), 3.77-4.27 (5H, m), 4.79-4.84 (1H, m), 5.55-5.61 (1H, m), 5.94-6.09 (1H, m), 6.65-6.71 (1H, m), 7.29-7.40 (5H, m).

11b) N—(4-chlorophenyl)—N'—((1R)-2-(4-(5-methyl-3-oxo-1H-imidazo[1,5-c]imidazol-2(3H)-yl)-1-piperidinyl)-2-oxo-1-phenylethyl)urea and N—(4-chlorophenyl)—N'—((1S)-2-(4-(5-methyl-3-oxo-1H-imidazo[1,5-c]imidazol-2(3H)-yl)-1-piperidinyl)-2-oxo-1-phenylethyl)urea tert-Butyl 2-(4-(5-methyl-3-oxo-1H-imidazo[1,5-c]imidazol-2(3H)-yl)-1-piperidinyl)-2-oxo-1-phenylethylcarbamate (0.45 g) obtained in Example 11a) was dissolved in trifluoroacetic acid (2 ml), mixed at room temperature for 1 hour, and then concentrated under reduced pressure. The residue was dissolved in water, and the reaction mixture was basified with potassium carbonate and extracted with chloroform. The extract was dried over anhydrous sodium sulfate and the solvent was distilled off under reduced pressure. The residue was dissolved in acetonitrile (20 ml), 4-chlorophenyl isocyanate (0.15 g) was added thereto, and mixed at room temperature for 2 hours. The solvent was distilled off under reduced pressure, and the residue was purified with basic silica gel column (ethyl acetate to ethyl acetate/methanol=20/1) and solidified with ethyl acetate-hexane to obtain a mixture (0.40 g, 79%) of two title compounds as colorless powder. The resulting mixture was subjected to optical resolution using high-performance liquid chromatography (CHIRALCEL OD) to obtain N—(4-chlorophenyl)—N'—((1R)-2-(4-(5-methyl-3-oxo-1H-imidazo[1,5-c]imidazol-2(3H)-yl)-1-piperidinyl)-2-oxo-1-phenylethyl)urea (0.16 g, >99.9% ee, as colorless powder) and N—(4-chlorophenyl)—N'—((1S)-2-(4-(5-methyl-3-oxo-1H-imidazo[1,5-c]imidazol-2(3H)-yl)-1-piperidinyl)-2-oxo-1-phenylethyl)urea (0.11 g, 99.0% ee, colorless powder), respectively.

N—(4-chlorophenyl)—N'—((1R)-2-(4-(5-methyl-3-oxo-1H-imidazo[1,5-c]imidazol-2(3H)-yl)-1-piperidinyl)-2-oxo-1-phenylethyl)urea NMR (CDCl$_3$) δ: 1.35-1.89 (4H, m), 2.56-2.60 (3H, m), 2.70-3.19 (2H, m), 3.79-4.26 (5H, m), 4.77-4.81 (1H, m), 5.87-5.96 (1H, m), 6.62-6.73 (2H, m), 7.15-7.38 (9H, m).

Elemental analysis for $C_{26}H_{27}ClN_6O_3 \cdot H_2O \cdot 0.7EtOH$
Calcd. (%): C, 59.06; H, 6.01; N, 15.08.
Found (%): C, 59.18; H, 5.78; N, 14.90.

N—(4-chlorophenyl)—N'—((1S)-2-(4-(5-methyl-3-oxo-1H-imidazo[1,5-c]imidazol-2(3H)-yl)-1-piperidinyl)-2-oxo-1-phenylethyl)urea NMR (CDCl$_3$) δ: 1.35-1.89 (4H, m), 2.56-2.60 (3H, m), 2.70-3.19 (2H, m), 3.79-4.26 (5H, m), 4.78-4.81 (1H, m), 5.88-5.96 (1H, m), 6.61-6.73 (2H, m), 7.15-7.38 (9H, m).

Elemental analysis for $C_{26}H_{27}ClN_6O_3 \cdot 0.5H_2O \cdot 0.8EtOH$
Calcd. (%): C, 59.96; H, 5.98; N, 15.20.
Found (%): C, 60.19; H, 5.71; N, 14.90.

EXAMPLE 12

N—(4-chlorophenyl)—N'—((1R)-2-(4-(5-methyl-3-oxo-1H-imidazo[1,5-c]imidazol-2(3H)-yl)-1-piperazinyl)-2-oxo-1-phenylethyl)urea and N—(4-chlorophenyl)—N'—((1S)-2-(4-(5-methyl-3-oxo-1H-imidazo[1,5-c]imidazol-2(3H)-yl)-1-piperazinyl)-2-oxo-1-phenylethyl)urea

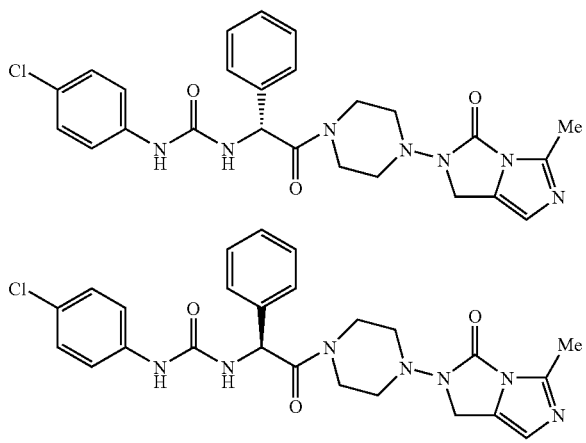

12a) tert-butyl 2-(4-(5-methyl-3-oxo-1H-imidazo[1,5-c]imidazol-2(3H)-yl)-1-piperazinyl)-2-oxo-1-phenylethylcarbamate In the same manner as in Example 10a), the title compound as a colorless oil (0.46 g, quantitative) was obtained from Boc-D-phenylglycine (0.25 g).

NMR (CDCl$_3$) δ: 1.44 (9H, s), 2.30-2.36 (1H, m), 2.58 (3H, s), 2.96-3.15 (4H, m), 3.39-3.90 (4H, m), 4.25-4.37 (2H, m), 5.58 (1H, d, J=7.5), 6.00 (1H, d, J=7.9), 6.69 (1H, t, J=1.7), 7.31-7.38 (5H, m).

12b) N—(4-chlorophenyl)—N'—((1R)-2-(4-(5-methyl-3-oxo-1H-imidazo[1,5-c]imidazol-2(3H)-yl)-1-piperazinyl)-2-oxo-1-phenylethyl)urea and N—(4-chlorophenyl)—N'—((1S)-2-(4-(5-methyl-3-oxo-1H-imidazo[1,5-c]imidazol-2(3H)-yl)-1-piperazinyl)-2-oxo-1-phenylethyl)urea In the same manner as in Example 11b), N—(4-chlorophenyl)—N'—((1R)-2-(4-(5-methyl-3-oxo-1H-imidazo[1,5-c]imidazol-2(3H)-yl)-1-piperazinyl)-2-oxo-1-phenylethyl)urea (0.40 g, 39%, >99.9% ee) as colorless powder and N—(4-chlorophenyl)—N'—((1S)-2-(4-(5-methyl-3-oxo-1H-imidazo[1,5-c]imidazol-2(3H)-yl)-1-piperazinyl)-2-oxo-1-phenylethyl)urea (0.29 g, 29%, >99.9% ee) as colorless powder were respectively obtained from tert-butyl 2-(4-(5-methyl-3-oxo-1H-imidazo[1,5-c]imidazol-2(3H)-yl)-1-piperazinyl)-2-oxo-1-phenylethylcarbamate (0.90 g) obtained in Example 12a).

N—(4-chlorophenyl)—N'—((1R)-2-(4-(5-methyl-3-oxo-1H-imidazo[1,5-c]imidazol-2(3H)-yl)-1-piperazinyl)-2-oxo-1-phenylethyl)urea NMR (CDCl$_3$) δ: 2.57 (3H, s), 2.60-2.68 (1H, m), 2.97-3.12 (3H, m), 3.48-3.71 (3H, m), 3.90-3.96 (1H, m), 4.26-4.37 (2H, m), 5.91-5.94 (1H, m), 6.69 (1H, s), 6.74-6.77 (1H, m), 7.11-7.57 (11H, m).
Elemental analysis for C$_{25}$H$_{26}$ClN$_7$O$_3$.0.3EtOH.0.8H$_2$O
Calcd. (%): C, 57.34; H, 5.53; N, 18.29.
Found (%): C, 57.49; H, 5.69; N, 18.04.

N—(4-chlorophenyl)—N'—((1S)-2-(4-(5-methyl-3-oxo-1H-imidazo[1,5-c]imidazol-2(3H)-yl)-1-piperazinyl)-2-oxo-1-phenylethyl)urea NMR (CDCl$_3$) δ: 2.57 (3H, s), 2.60-2.68 (1H, m), 2.97-3.13 (3H, m), 3.44-3.70 (3H, m), 3.90-3.96 (1H, m), 4.26-4.37 (2H, m), 5.89-5.92 (1H, m), 6.62-6.65 (1H, m), 6.69 (1H, s), 7.14-7.37 (10H, m).
Elemental analysis for C$_{25}$H$_{26}$ClN$_7$O$_3$.1.1H$_2$O
Calcd. (%): C, 56.89; H, 5.39; N, 18.58.
Found (%): C, 57.04; H, 5.42; N, 18.24.

EXAMPLE 13

N—(4-chlorophenyl)—N'—((1R)-1-methyl-2-(4-(5-methyl-3-oxo-1H-imidazo[1,5-c]imidazol-2(3H)-yl)-1-piperidinyl)-2-oxoethyl)urea

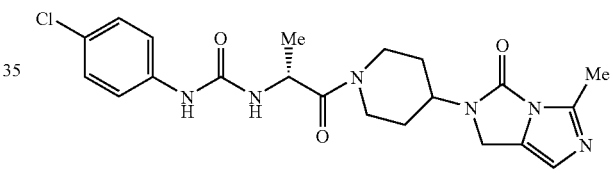

13a) tert-butyl(1R)-1-methyl-2-(4-(5-methyl-3-oxo-1H-imidazo[1,5-c]imidazol-2(3H)-yl)-1-piperidinyl)-2-oxoethylcarbamate In the same manner as in Example 6a), the title compound as a colorless oil (0.31 g, 79%) was obtained from Boc-D-alanine (0.19 g).

NMR (CDCl$_3$) δ: 1.29-1.35 (3H, m), 1.45 (9H, s), 1.63-1.93 (4H, m), 2.61 (3H, s), 2.66-2.74 (1H, m), 3.14-3.19 (1H, m), 4.09-4.23 (3H, m), 4.26-4.28 (2H, m), 4.64-4.81 (2H, m), 5.47-5.50 (1H, m), 6.72 (1H, s).

13b) N—(4-chlorophenyl)—N'—((1R)-1-methyl-2-(4-(5-methyl-3-oxo-1H-imidazo[1,5-c]imidazol-2(3H)-yl)-1-piperidinyl)-2-oxoethyl)urea tert-Butyl(1R)-1-methyl-2-(4-(5-methyl-3-oxo-1H-imidazo[1,5-c]imidazol-2(3H)-yl)-1-piperidinyl)-2-oxoethylcarbamate (0.31 g) obtained in Example 13a) was dissolved in concentrated hydrochloric acid (1.5 ml), mixed at room temperature for 10 minutes, and then concentrated under reduced pressure. Water was removed from the residue by azeotropy with ethanol, the residue was dissolved in DBU (0.24 g) and acetonitrile (10 ml), 4-chlorophenyl isocyanate (0.12 g) was added thereto, and mixed at room temperature for 2 hours. The solvent was distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the precipitated crystal was collected by filtration to obtain the title compound (0.24 g, 68%) as colorless powder.

NMR (CDCl$_3$) δ: 1.37-1.42 (3H, m), 1.63-2.05 (3H, m), 2.62 (3H, s), 2.77-2.81 (1H, m), 3.21-3.40 (1H, m), 4.11-4.31 (5H, m), 4.76-4.98 (2H, m), 6.48-6.52 (1H, m), 6.72-6.74 (1H, m), 7.11-7.15 (4H, m), 7.43-7.45 (1H, m).

Elemental analysis for $C_{21}H_{25}ClN_6O_3 \cdot 0.2H_2O$

Calcd. (%): C, 56.24; H, 5.71; N, 18.74.

Found (%): C, 56.49; H, 5.92; N, 18.46.

EXAMPLE 14

(2R)—N—(4-chlorophenyl)-2-((4-(5-methyl-3-oxo-1H-imidazo[1,5-c]imidazol-2(3H)-yl)-1-piperidinyl)carbonyl)-1-pyrrolidine carboxamide

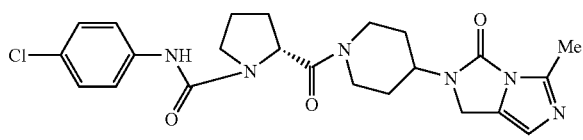

14a) tert-butyl(2R)-2-((4-(5-methyl-3-oxo-1H-imidazo[1,5-c]imidazol-2(3H)-yl)-1-piperidinyl)carbonyl)-1-pyrrolidinecarboxylate In the same manner as in Example 6a), the title compound as a yellow oil (0.25 g, 60%) was obtained from Boc-D-proline (0.22 g).

NMR (CDCl$_3$) δ: 1.47 (9H, s), 1.60-2.23 (6H, m), 2.61 (3H, s), 2.62-2.74 (2H, m), 3.14-3.58 (4H, m), 4.16 (1H, m), 4.28 (1H, s), 4.55-4.80 (3H, m), 6.72 (1H, s).

14b) (2R)—N—(4-chlorophenyl)-2-((4-(5-methyl-3-oxo-1H-imidazo[1,5-c]imidazol-2(3H)-yl)-1-piperidinyl)carbonyl)-1-pyrrolidine carboxamide In the same manner as in Example 13b), the title compound as colorless powder (0.16 g, 57%) was obtained from tert-butyl (2R)-2-((4-(5-methyl-3-oxo-1H-imidazo[1,5-c]imidazol-2(3H)-yl)-1-piperidinyl)carbonyl)-1-pyrrolidinecarboxylate (0.25 g) obtained in Example 14a).

NMR (CDCl$_3$) δ: 1.60-2.24 (8H, m), 2.61 (3H, m), 2.65-2.71 (1H, m), 3.10-3.30 (1H, m), 3.54 (1H, m), 3.69-3.72 (1H, m), 4.11-4.27 (4H, m), 4.74-4.80 (1H, m), 4.94-4.98 (1H, m), 6.41 (1H, s), 6.72 (1H, s), 7.22 (2H, d, J=9.0), 7.33 (2H, d, J=9.0).

Elemental analysis for $C_{23}H_{27}ClN_6O_3 \cdot 0.5H_2O \cdot 0.2AcOEt$

Calcd. (%): C, 57.45; H, 6.00; N, 16.89.

Found (%): C, 57.30; H, 6.05; N, 16.86.

EXAMPLE 15

N—(4-chlorophenyl)—N'—((1R)-2-methyl-1-((4-(5-methyl-3-oxo-1H-imidazo[1,5-c]imidazol-2(3H)-yl)-1-piperidinyl)carbonyl)propyl)urea

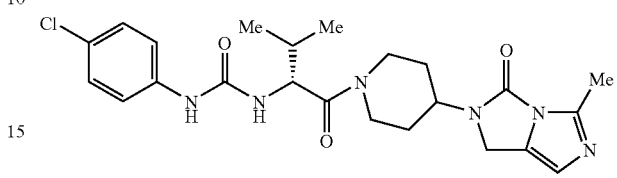

15a) tert-butyl(1R)-2-methyl-1-((4-(5-methyl-3-oxo-1H-imidazo[1,5-c]imidazol-2(3H)-yl)-1-piperidinyl)carbonyl)propylcarbamate In the same manner as in Example 6a), the title compound as a colorless oil (0.42 g, quantitative) was obtained from Boc-D-valine (0.22 g).

NMR (CDCl$_3$) δ: 0.90 (3H, t, J=6.2), 0.98 (3H, t, J=6.2), 1.45 (9H, s), 1.55-1.93 (6H, m), 2.61 (3H, s), 2.69-2.74 (1H, m), 3.14-3.19 (1H, m), 4.09-4.29 (3H, m), 4.29-4.51 (1H, m), 4.78-4.81 (1H, m), 5.29 (1H, m), 6.72 (1H, s).

15b) N—(4-chlorophenyl)—N'—((1R)-2-methyl-1-((4-(5-methyl-3-oxo-1H-imidazo[1,5-c]imidazol-2(3H)-yl)-1-piperidinyl)carbonyl)propyl)urea tert-Butyl(1R)-2-methyl-1-((4-(5-methyl-3-oxo-1H-imidazo[1,5-c]imidazol-2(3H)-yl)-1-piperidinyl)carbonyl)propylcarbamate (0.40 g) obtained in Example 15a) was dissolved in concentrated hydrochloric acid (1.5 ml), mixed at room temperature for 10 minutes, and then concentrated under reduced pressure. Water was removed from the residue by azeotropy with ethanol, then dissolved in DBU (0.29 g) and acetonitrile (10 ml), 4-chlorophenyl isocyanate (0.15 g) was added thereto, and mixed at room temperature for 2 hours. The solvent was distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with silica gel column (ethyl acetate to ethyl acetate/methanol=5/1) and solidified with ethyl acetate and diethyl ether to obtain the title compound (0.30 g, 67%, >99% ee) as colorless powder.

NMR (CDCl$_3$) δ: 0.99-1.19 (6H, m), 1.60-2.05 (5H, m), 2.61-2.62 (3H, m), 2.73-2.80 (1H, m), 3.26-3.31 (1H, m), 4.17-4.31 (4H, m), 4.78-4.83 (2H, m), 6.40-6.45 (1H, m), 6.72 (1H, s), 7.15-7.23 (4H, m), 7.57 (1H, s).

Elemental analysis for $C_{23}H_{29}ClN_6O_3 \cdot 0.5H_2O$

Calcd. (%): C, 57.32; H, 6.27; N, 17.44.

Found (%): C, 57.45; H, 6.20; N, 17.20.

EXAMPLE 16

N—(4-chlorophenyl)—N'—((1R)-2-methyl-1-((4-(5-methyl-3-oxo-1H-imidazo[1,5-c]imidazol-2(3H)-yl)-1-piperazinyl)carbonyl)propyl)urea

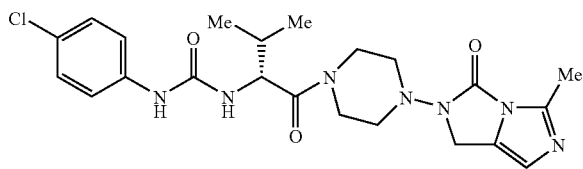

16a) tert-butyl(1R)-2-methyl-1-((4-(5-methyl-3-oxo-1H-imidazo[1,5-c]imidazol-2(3H)-yl)-1-piperazinyl)carbonyl)propylcarbamate In the same manner as in Example 10a), the title compound as colorless powder (0.63 g, quantitative) was obtained from Boc-D-valine (0.33 g).

NMR (CDCl$_3$) δ: 0.42-1.22 (6H, m), 1.44-1.46 (9H, m), 1.97 (1H, m), 2.60 (3H, s), 3.21-3.29 (4H, m), 3.55-3.80 (3H, m), 4.24-4.47 (4H, m), 5.38-5.41 (1H, m), 6.72 (1H, s).

16b) N—(4-chlorophenyl)—N'—((1R)-2-methyl-1-((4-(5-methyl-3-oxo-1H-imidazo[1,5-c]imidazol-2(3H)-yl)-1-piperazinyl)carbonyl)propyl)urea In the same manner as in Example 15b), the title compound as colorless powder (0.43 g, 60%) was obtained from tert-butyl(1R)-2-methyl-1-((4-(5-methyl-3-oxo-1H-imidazo[1,5-c]imidazol-2(3H)-yl)-1-piperazinyl)carbonyl)propylcarbamate (0.63 g) obtained in Example 16a).

NMR (CDCl$_3$) δ: 0.99 (3H, d, J=6.8), 1.05 (3H, d, J=6.8), 1.94-2.03 (1H, m), 2.60 (3H, s), 3.12-3.35 (4H, m), 3.82 (4H, br), 4.42 (2H, s), 4.75-4.80 (1H, m), 6.43 (1H, d, J=9.0), 6.73 (1H, s), 7.14-7.19 (4H, m), 7.59 (1H, s).

Elemental analysis for C$_{22}$H$_{28}$ClN$_7$O$_3$·0.7H$_2$O·0.3IPE
Calcd. (%): C, 55.27; H, 6.55; N, 18.96.
Found (%): C, 55.02; H, 6.29; N, 18.78.

EXAMPLE 17

N—((1S)-1-benzyl-2-(4-(5-methyl-3-oxo-1H-imidazo[1,5-c]imidazol-2(3H)-yl)-1-piperidinyl)-2-oxoethyl)—N'—(4-chlorophenyl)urea

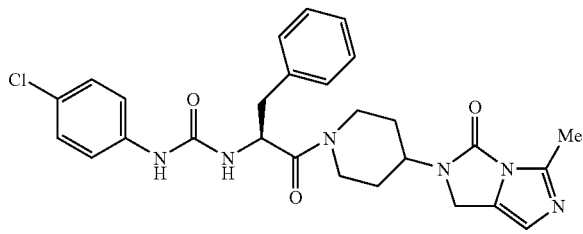

17a) tert-butyl (1S)-1-benzyl-2-(4-(5-methyl-3-oxo-1H-imidazo[1,5-c]imidazol-2(3H)-yl)-1-piperidinyl)-2-oxoethylcarbamate In the same manner as in Example 6a), the title compound as yellow powder (0.45 g, 96%) was obtained from Boc-L-phenylalanine (0.27 g).

NMR (CDCl$_3$) δ: 1.44 (9H, m), 1.63-1.92 (4H, m), 2.59 (3H, m), 2.51-2.59 (1H, m), 2.92-4.22 (7H, m), 4.72-4.910 (2H, m), 5.35-5.44 (1H, m), 6.70-6.74 (1H, m), 7.16-7.34 (5H, m).

17b) N—((1S)-1-benzyl-2-(4-(5-methyl-3-oxo-1H-imidazo[1,5-c]imidazol-2(3H)-yl)-1-piperidinyl)-2-oxoethyl)—N'—(4-chlorophenyl)urea In the same manner as in Example 15b), the title compound as colorless powder (0.35 g, 71%, 98% ee) was obtained from tert-butyl (1S)-1-benzyl-2-(4-(5-methyl-3-oxo-1H-imidazo[1,5-c]imidazol-2(3H)-yl)-1-piperidinyl)-2-oxoethylcarbamate (0.44 g) obtained in Example 17a).

NMR (CDCl$_3$) δ: 1.49-1.90 (4H, m), 2.32-2.68 (1H, m), 2.59 (3H, s), 2.88-3.20 (3H, m), 3.91-4.18 (4H, m), 4.70-4.75 (1H, m), 5.15-5.30 (1H, m), 6.40-6.52 (1H, m), 6.68-6.75 (1H, m), 7.15-7.58 (10H, m).

Elemental analysis for C$_{27}$H$_{29}$ClN$_6$O·0.5H$_2$O
Calcd. (%): C, 61.18; H, 5.71; N, 15.86.
Found (%): C, 61.48; H, 5.78; N, 15.76.

EXAMPLE 18

N—(4-chlorophenyl)—N'—((1R)-3-methyl-1-((4-(5-methyl-3-oxo-1H-imidazo[1,5-c]imidazol-2(3H)-yl)-1-piperidinyl)carbonyl)butyl)urea

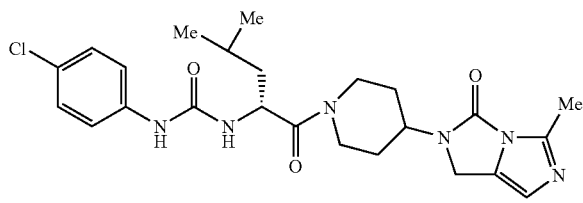

18a) tert-butyl(1R)-3-methyl-1-((4-(5-methyl-3-oxo-1H-imidazo[1,5-c]imidazol-2(3H)-yl)-1-piperidinyl)carbonyl)butylcarbamate In the same manner as in Example 6a), the title compound as a yellow oil (0.44 g, quantitative) was obtained from Boc-D-leucine (0.23 g).

NMR (CDCl$_3$) δ: 0.92-1.02 (6H, m), 1.45 (9H, s), 1.55-1.93 (8H, m), 2.62 (3H, s), 2.69-2.74 (1H, m), 3.14-3.19 (1H, m), 4.09-4.29 (3H, m), 4.29-4.51 (1H, m), 4.78-4.81 (1H, m), 6.72 (1H, s).

18b) N—(4-chlorophenyl)—N'—((1R)-3-methyl-1-((4-(5-methyl-3-oxo-1H-imidazo[1,5-c]imidazol-2(3H)-yl)-1-piperidinyl)carbonyl)butyl)urea In the same manner as in Example 15b), the title compound as colorless powder (0.25 g, 54%) was obtained from tert-butyl(1R)-3-methyl-1-((4-(5-methyl-3-oxo-1H-imidazo[1,5-c]imidazol-2(3H)-yl)-1-piperidinyl)carbonyl)butylcarbamate (0.41 g) obtained in Example 18a).

NMR (CDCl$_3$) δ: 0.96-1.04 (6H, m), 1.44-2.05 (7H, m), 2.62 (3H, m), 2.72-2.81 (1H, m), 3.26-3.31 (1H, m), 4.11-4.33 (4H, m), 4.77-4.99 (2H, m), 6.48-6.53 (1H, m), 6.74 (1H, m), 7.09-7.17 (4H, m), 7.50-7.53 (1H, m).

Elemental analysis for C$_{24}$H$_{31}$ClN$_6$O$_3$.0.4H$_2$O
Calcd. (%): C, 58.33; H, 6.49; N, 17.01.
Found (%): C, 58.55; H, 6.59; N, 16.77.

EXAMPLE 19

N—(4-chlorophenyl)—N'—((1R)-2,2-dimethyl-1-((4-(5-methyl-3-oxo-1H-imidazo[1,5-c]imidazol-2(3H)-yl)-1-piperidinyl)carbonyl)propyl)urea

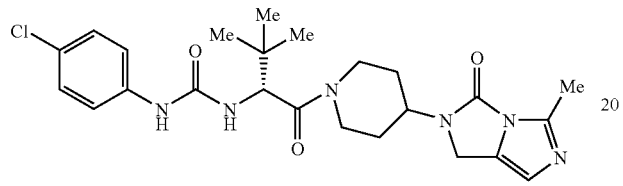

19a) tert-butyl(1R)-2,2-dimethyl-1-((4-(5-methyl-3-oxo-1H-imidazo[1,5-c]imidazol-2(3H)-yl)-1-piperidinyl)carbonyl)propylcarbamate To a solution of Boc-D-tert-leucine (0.23 g) and HOBt (0.23 g) in acetonitrile (5 ml) was added WSC (0.29 g), and the reaction mixture was mixed at room temperature for 15 minutes. Then, a solution of 5-methyl-2-(4-piperidinyl)-1,2-dihydro-3H-imidazo[1,5-c]imidazol-3-one dihydrochloride (0.29 g), DBU (0.30 g) and triethylamine (0.30 g) in acetonitrile (5 ml) was added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with basic silica gel column (ethyl acetate to ethyl acetate/methanol=5/1) to obtain the title compound as colorless powder (0.40 g, 92%).

NMR (CDCl$_3$) δ: 0.98-1.01 (9H, m), 1.43-1.45 (9H, m), 1.61-1.95 (4H, m), 2.59-2.72 (1H, m), 2.61 (3H, s), 3.14-3.22 (1H, m), 4.20-4.29 (4H, m), 4.51-4.55 (1H, m), 4.80-4.85 (1H, m), 5.31-5.34 (1H, m), 6.70-6.71 (1H, m).

19b) N—(4-chlorophenyl)—N'—((1R)-2,2-dimethyl-1-((4-(5-methyl-3-oxo-1H-imidazo[1,5-c]imidazol-2(3H)-yl)-1-piperidinyl)carbonyl)propyl)urea N—(4-chlorophenyl)—N'—((1R)-2,2-dimethyl-1-((4-(5-methyl-3-oxo-1H-imidazo[1,5-c]imidazol-2(3H)-yl)-1-piperidinyl)carbonyl)propyl)urea (0.40 g) obtained in Example 19a) was dissolved in concentrated hydrochloric acid (1.5 ml), mixed at room temperature for 10 minutes, and then concentrated under reduced pressure. Water was removed from the residue by azeotropy with ethanol, and then the residue was dissolved in DBU (0.29 g) and acetonitrile (10 ml). 4-Chlorophenyl isocyanate (0.15 g) was added thereto, and mixed at room temperature for 2 hours. The solvent was distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with silica gel column (ethyl acetate to ethyl acetate/methanol=5/1) and solidified with ethyl acetate and diethyl ether to obtain the title compound as colorless powder (0.26 g, 64%, 99.8% ee).

NMR (CDCl$_3$) δ: 1.03-1.07 (9H, m), 1.49-2.05 (4H, m), 2.61-2.62 (3H, m), 2.66-2.75 (1H, m), 3.16-3.25 (1H, m), 4.03-4.41 (4H, m), 4.80-4.91 (2H, m), 6.04-6.12 (1H, m), 6.72-6.74 (1H, m), 7.19-7.39 (5H, m).

Elemental analysis for C$_{24}$H$_{31}$ClN$_6$O$_3$.0.5H$_2$O.0.1Et$_2$O
Calcd. (%): C, 58.33; H, 6.62; N, 16.73.
Found (%): C, 58.40; H, 6.62; N, 16.46.

EXAMPLE 20

N—(4-chlorophenyl)—N'—((1R)-2,2-dimethyl-1-((4-(5-methyl-3-oxo-1H-imidazo[1,5-c]imidazol-2(3H)-yl)-1-piperazinyl)carbonyl)propyl)urea

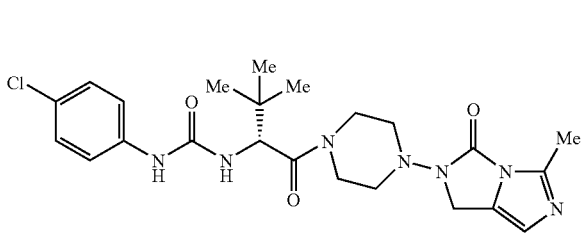

20a) tert-butyl(1R)-2,2-dimethyl-1-((4-(5-methyl-3-oxo-1H-imidazo[1,5-c]imidazol-2(3H)-yl)-1-piperazinyl)carbonyl)propylcarbamate In the same manner as in Example 10a), the title compound as a pale yellow oil (0.34 g, 78%) was obtained from Boc-D-tert-leucine (0.23 g).

NMR (CDCl$_3$) δ: 1.00 (9H, s), 1.44 (9H, s), 2.60 (3H, s), 3.15-3.23 (4H, m), 3.65-3.89 (4H, m), 4.43 (2H, s), 4.51 (1H, d, J=9.8), 5.33 (1H, d, J=9.5), 6.71-6.72 (1H, m).

20b) N—(4-chlorophenyl)—N'—((1R)-2,2-dimethyl-1-((4-(5-methyl-3-oxo-1H-imidazo[1,5-c]imidazol-2(3H)-yl)-1-piperazinyl)carbonyl)propyl)urea In the same manner as in Example 15b), the title compound as colorless powder (0.24 g, 63%, 96.5% ee) was obtained from tert-butyl(1R)-2,2-dimethyl-1-((4-(5-methyl-3-oxo-1H-imidazo[1,5-c]imidazol-2(3H)-yl)-1-piperazinyl)carbonyl)propylcarbamate (0.34 g) obtained in Example 20a).

NMR (CDCl$_3$) δ: 1.04 (9H, s), 2.60 (3H, s), 3.11-3.28 (4H, m), 3.65-3.91 (4H, m), 4.38 (2H, s), 4.86 (1H, d, J=9.4), 5.99 (1H, d, J=9.1), 6.72 (1H, s), 7.22-7.29 (5H, m).

Elemental analysis for C$_{23}$H$_{30}$ClN$_7$O$_3$.0.2AcOEt 0.6H$_2$O
Calcd. (%): C, 55.35; H, 6.40; N, 18.99.
Found (%): C, 55.21; H, 6.46; N, 18.85.

EXAMPLE 21

N—(4-chlorophenyl)—N'—((1R,2S)-2-methyl-1-((4-(5-methyl-3-oxo-1H-imidazo[1,5-c]imidazol-2(3H)-yl)-1-piperidinyl)carbonyl)butyl)urea

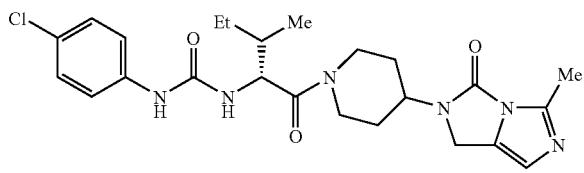

21a) tert-butyl (1R,2S)-2-methyl-1-((4-(5-methyl-3-oxo-1H-imidazo[1,5-c]imidazol-2(3H)-yl)-1-piperidinyl)carbonyl)butylcarbamate In the same manner as in Example 6a), the title compound as colorless powder (0.33 g, 76%) was obtained from Boc-D-isoleucine (0.23 g).

NMR (CDCl$_3$) δ: 0.88-0.96 (6H, m), 1.44 (9H, s), 1.43-1.46 (7H, m), 2.61 (3H, s), 2.69-2.73 (1H, m), 3.17-3.28 (2H, m), 4.20-4.29 (3H, m), 4.68-4.82 (2H, m), 5.23-5.26 (1H, m), 6.72 (1H, s).

21b) N—(4-chlorophenyl)—N'—((1R,2S)-2-methyl-1-((4-(5-methyl-3-oxo-1H-imidazo[1,5-c]imidazol-2(3H)-yl)-1-piperidinyl)carbonyl)butyl)urea In the same manner as in Example 15b), the title compound as colorless powder (0.12 g, 32%) was obtained from tert-butyl (1R,2S)-2-methyl-1-((4-(5-methyl-3-oxo-1H-imidazo[1,5-c]imidazol-2(3H)-yl)-1-piperidinyl)carbonyl)butylcarbamate (0.33 g) obtained in Example 21a).

NMR (CDCl$_3$) δ: 0.89-1.26 (8H, m), 1.58-2.11 (5H, m), 2.61 (3H, s), 2.75-2.82 (1H, m), 3.21-3.30 (1H, m), 4.13-4.41 (4H, m), 4.79-4.84 (2H, m), 6.38-6.41 (1H, m), 6.71-6.72 (1H, m), 7.14-7.20 (4H, m), 7.51 (1H, s).

Elemental analysis for C$_{24}$H$_{31}$ClN$_6$O$_3$.0.5H$_2$O
Calcd. (%): C, 58.12; H, 6.50; N, 16.94.
Found (%): C, 58.34; H, 6.67; N, 16.90.

EXAMPLE 22

N—(4-chlorophenyl)—N'—((1R,2S)-2-methyl-1-((4-(5-methyl-3-oxo-1H-imidazo[1,5-c]imidazol-2(3H)-yl)-1-piperazinyl)carbonyl)butyl)urea

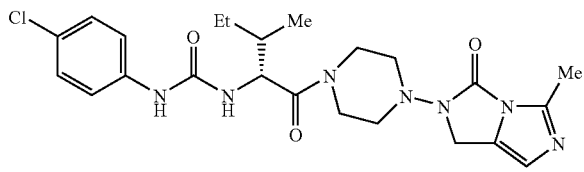

22a) tert-butyl (1R,2S)-2-methyl-1-((4-(5-methyl-3-oxo-1H-imidazo[1,5-c]imidazol-2(3H)-yl)-1-piperazinyl)carbonyl)butylcarbamate In the same manner as in Example 10a), the title compound as a colorless oil (0.38 g, 87%) was obtained from Boc-D-isoleucine (0.23 g).

NMR (CDCl$_3$) δ: 0.88-0.96 (6H, m), 1.44 (9H, s), 1.51-1.71 (3H, m), 2.60 (3H, s), 3.15-3.24 (4H, m), 3.71-3.85 (4H, m), 4.43-4.50 (3H, m), 5.22-5.25 (1H, m), 6.72 (1H, s).

22b) N—(4-chlorophenyl)—N'—((1R,2S)-2-methyl-1-((4-(5-methyl-3-oxo-1H-imidazo[1,5-c]imidazol-2(3H)-yl)-1-piperazinyl)carbonyl)butyl)urea In the same manner as in Example 15b), the title compound as colorless powder (67 mg, 16%) was obtained from tert-butyl (1R,2S)-2-methyl-1-((4-(5-methyl-3-oxo-1H-imidazo[1,5-c]imidazol-2(3H)-yl)-1-piperazinyl)carbonyl)butylcarbamate (0.38 g) obtained in Example 22a).

NMR (CDCl$_3$) δ: 0.91-1.28 (8H, m), 1.62-1.78 (2H, m), 2.60 (3H, s), 3.17-3.35 (4H, m), 3.83-3.88 (4H, m), 4.42 (2H, s), 4.75-4.81 (1H, m), 6.45 (1H, d, J=9.0), 6.72 (1H, s), 7.14-7.18 (4H, m), 7.54 (1H, s).

Elemental analysis for C$_{23}$H$_{30}$ClN$_7$O$_3$.0.8H$_2$O.0.2IPE
Calcd. (%): C, 55.59; H, 6.63; N, 18.75.
Found (%): C, 55.42; H, 6.64; N, 18.46.

EXAMPLE 23

N—(4-chlorophenyl)—N'—(1-cyclopropyl-2-(4-(5-methyl-3-oxo-1H-imidazo[1,5-c]imidazol-2(3H)-yl)-1-piperidinyl)-2-oxoethyl)urea

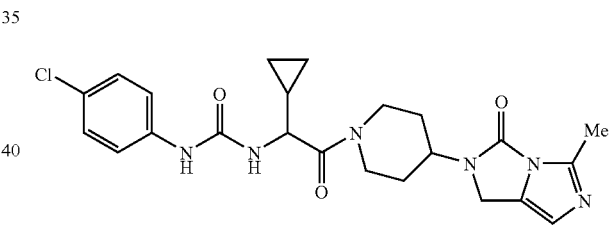

23a) tert-butyl 1-cyclopropyl-2-(4-(5-methyl-3-oxo-1H-imidazo[1,5-c]imidazol-2(3H)-yl)-1-piperidinyl)-2-oxoethylcarbamate In the same manner as in Example 6a), the title compound as a colorless oil (0.53 g, 64%) was obtained from ((tert-butoxycarbonyl)amino)(cyclopropyl)acetic acid (Y. K. Chen et al., J. Am. Chem. Soc., 124, 12225 (2002); 0.43 g).

NMR (CDCl$_3$) δ: 0.38-1.22 (5H, m), 1.44-1.46 (9H, m), 1.67-1.93 (4H, m), 2.62 (3H, s), 2.72-2.80 (1H, m), 3.17-3.21 (2H, m), 4.10-4.50 (4H, m), 4.78-4.82 (1H, m), 5.41 (1H, m), 6.72 (1H, s).

23b) N—(4-chlorophenyl)—N'—(1-cyclopropyl-2-(4-(5-methyl-3-oxo-1H-imidazo[1,5-c]imidazol-2(3H)-yl)-1-piperidinyl)-2-oxoethyl)urea In the same manner as in Example 15b), the title compound as colorless powder (0.29 g, 48%) was obtained from tert-butyl 1-cyclopropyl-2-(4-(5-methyl-3-oxo-1H-imidazo[1,5-c]imidazol-2(3H)-yl)-1-piperidinyl)-2-oxoethylcarbamate (0.53 g) obtained in Example 23a).

NMR (CDCl$_3$) δ: 0.41-0.61 (4H, m), 1.10-1.14 (1H, m), 1.63-1.97 (4H, m), 2.62 (3H, s), 2.80-2.84 (1H, m), 3.23-3.35 (1H, m), 4.23-4.32 (4H, m), 4.65-4.83 (2H, m), 6.43-6.45 (1H, m), 6.72 (1H, s), 7.16-7.21 (4H, m), 7.65-7.70 (1H, m).

Elemental analysis for C$_{23}$H$_{27}$ClN$_6$O$_3$.0.6H$_2$O.0.1IPE

Calcd. (%): C, 57.61; H, 6.06; N, 17.08.

Found (%): C, 57.77; H, 6.20; N, 16.81.

EXAMPLE 24

N—(4-chlorophenyl)—N'—(1-cyclopropyl-2-(4-(5-methyl-3-oxo-1H-imidazo[1,5-c]imidazol-2(3H)-yl)-1-piperazinyl)-2-oxoethyl)urea

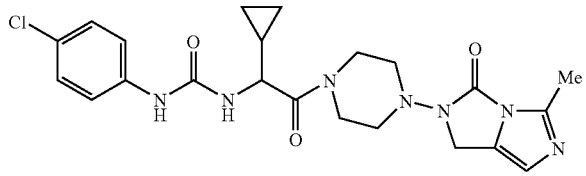

24a) tert-butyl 1-cyclopropyl-2-(4-(5-methyl-3-oxo-1H-imidazo[1,5-c]imidazol-2(3H)-yl)-1-piperazinyl)-2-oxoethylcarbamate In the same manner as in Example 10a), the title compound as a colorless oil (0.84 g, quantitative) was obtained from ((tert-butoxycarbonyl)amino)(cyclopropyl)acetic acid (0.43 g).

NMR (CDCl$_3$) δ: 0.42-1.22 (5H, m), 1.44-1.46 (9H, m), 2.60 (3H, s), 3.21-3.29 (4H, m), 3.55-3.80 (3H, m), 4.24-4.47 (4H, m), 5.38-5.41 (1H, m), 6.72 (1H, s).

24b) N—(4-chlorophenyl)—N'—(1-cyclopropyl-2-(4-(5-methyl-3-oxo-1H-imidazo[1,5-c]imidazol-2(3H)-yl)-1-piperazinyl)-2-oxoethyl)urea In the same manner as in Example 15b), the title compound as colorless powder (0.21 g, 22%) was obtained from tert-butyl 1-cyclopropyl-2-(4-(5-methyl-3-oxo-1H-imidazo[1,5-c]imidazol-2(3H)-yl)-1-piperazinyl)-2-oxoethylcarbamate (0.84 g) obtained in Example 24a).

NMR (CDCl$_3$) δ: 0.43-0.61 (4H, m), 1.13-1.16 (1H, m), 2.61 (3H, s), 3.19-3.35 (4H, m), 3.81-3.84 (4H, m), 4.44 (2H, s), 4.67 (1H, t, J=7.7), 6.37 (1H, d, J=7.9), 6.73 (1H, s), 7.17-7.29 (5H, m), 7.52 (1H, s).

Elemental analysis for C$_{22}$H$_{26}$ClN$_7$O$_3$.0.5H$_2$O.0.3IPE

Calcd. (%): C, 55.87; H, 6.15; N, 19.16.

Found (%): C, 56.07; H, 6.10; N, 18.99.

EXAMPLE 25

N—(4-chlorophenyl)—N'—(2-ethyl-1-((4-(5-methyl-3-oxo-1H-imidazo[1,5-c]imidazol-2(3H)-yl)-1-piperidinyl)carbonyl)butyl)urea

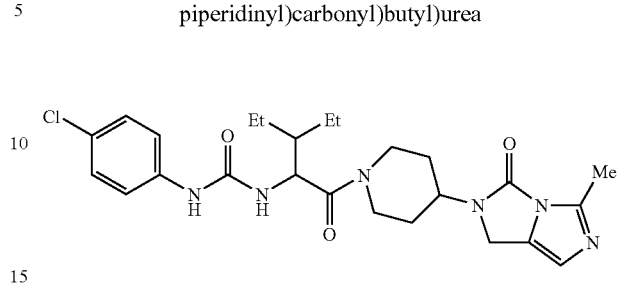

25a) tert-butyl 2-ethyl-1-((4-(5-methyl-3-oxo-1H-imidazo[1,5-c]imidazol-2(3H)-yl)-1-piperidinyl)carbonyl)butylcarbamate In the same manner as in Example 6a), the title compound as a colorless oil (0.41 g, 92%) was obtained from 2-((tert-butoxycarbonyl)amino)-3-ethylpentanoic acid (E. C. Jorgensen et al., J. Med. Chem., 14, 899 (1971); 0.25 g).

NMR (CDCl$_3$) δ: 0.84-1.04 (6H, m), 1.22-1.92 (9H, m), 1.43-1.46 (9H, m), 2.61 (3H, s), 2.69-2.73 (1H, m), 3.17-3.28 (2H, m), 4.20-4.29 (3H, m), 4.68-4.82 (2H, m), 5.23-5.26 (1H, m), 6.72 (1H, s).

25b) N—(4-chlorophenyl)—N'—(2-ethyl-1-((4-(5-methyl-3-oxo-1H-imidazo[1,5-c]imidazol-2(3H)-yl)-1-piperidinyl)carbonyl)butyl)urea In the same manner as in Example 15b), the title compound as colorless powder (0.36 g, 80%) was obtained from tert-butyl 2-ethyl-1-((4-(5-methyl-3-oxo-1H-imidazo[1,5-c]imidazol-2(3H)-yl)-1-piperidinyl)carbonyl)butylcarbamate (0.40 g) obtained in Example 25a).

NMR (CDCl$_3$) δ: 0.84-1.00 (6H, m), 1.25-1.52 (6H, m), 1.90-2.00 (4H, m), 2.61 (3H, s), 2.76-2.81 (1H, m), 3.21-3.34 (1H, m), 4.21-4.31 (3H, m), 4.79-4.84 (1H, m), 5.01-5.03 (1H, m), 6.25-6.28 (1H, m), 6.72 (1H, s), 7.17-7.27 (4H, m), 7.51-7.56 (1H, m).

Elemental analysis for C$_{25}$H$_{33}$ClN$_6$O$_3$.0.6H$_2$O.0.3AcOEt

Calcd. (%): C, 58.46; H, 6.85; N, 15.61.

Found (%): C, 58.60; H, 6.99; N, 15.34.

EXAMPLE 26

N—(4-chlorophenyl)—N'—(2-ethyl-1-((4-(5-methyl-3-oxo-1H-imidazo[1,5-c]imidazol-2(3H)-yl)-1-piperazinyl)carbonyl)butyl)urea

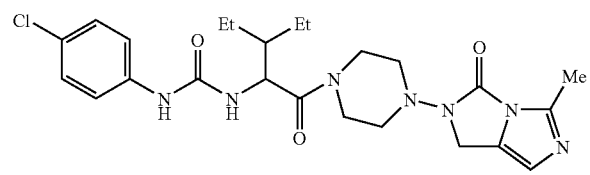

26a) tert-butyl 2-ethyl-1-((4-(5-methyl-3-oxo-1H-imidazo[1,5-c]imidazol-2(3H)-yl)-1-piperazinyl)carbonyl)butylcarbamate In the same manner as in Example 10a), the title compound as a colorless oil (0.44 g, 98%) was obtained from 2-((tert-butoxycarbonyl)amino)-3-ethylpentanoic acid (0.25 g).

NMR (CDCl$_3$) δ: 0.89 (3H, t, J=7.3), 0.99 (3H, t, J=7.3), 1.19-1.40 (4H, m), 1.44 (9H, s), 2.60 (3H, s), 3.14-3.27 (5H, m), 3.71-3.79 (4H, m), 4.43 (2H, s), 4.66-4.70 (1H, m), 5.23-5.26 (1H, m), 6.72 (1H, s).

26b) N—(4-chlorophenyl)—N'—(2-ethyl-1-((4-(5-methyl-3-oxo-1H-imidazo[1,5-c]imidazol-2(3H)-yl)-1-piperazinyl)carbonyl)butyl)urea In the same manner as in Example 15b), the title compound as colorless powder (0.35 g, 72%) was obtained from tert-butyl 2-ethyl-1-((4-(5-methyl-3-oxo-1H-imidazo[1,5-c]imidazol-2(3H)-yl)-1-piperazinyl)carbonyl)butylcarbamate (0.43 g) obtained in Example 26a).

NMR (CDCl$_3$) δ: 0.89 (3H, t, J=7.3), 0.98 (3H, t, J=7.3), 1.14-1.39 (5H, m), 2.61 (3H, s), 3.14-3.34 (4H, m), 3.83-3.84 (4H, m), 4.43 (2H, s), 4.96-5.01 (1H, m), 6.32 (1H, d, J=9.1), 6.73 (1H, s), 7.16-7.24 (4H, m), 7.60 (1H, s).

Elemental analysis for C$_{24}$H$_{32}$ClN$_7$O$_3$·0.5H$_2$O·0.1IPE
Calcd. (%): C, 56.69; H, 6.65; N, 18.81.
Found (%): C, 56.91; H, 6.80; N, 18.66.

EXAMPLE 27 methyl 3-(N'—(4-chlorophenyl)ureido)-4-(4-(5-methyl-3-oxo-1H-imidazo[1,5-c]imidazol-2(3H)-yl)-1-piperazinyl)-4-oxobutanoate

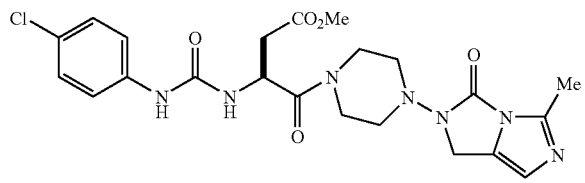

27a) methyl 3-((tert-butoxycarbonyl)amino)-4-(4-(5-methyl-3-oxo-1H-imidazo[1,5-c]imidazol-2(3H)-yl)-1-piperidinyl)-4-oxobutanoate In the same manner as in Example 10a), the title compound as colorless powder (0.68 g, 75%) obtained from 2-((tert-butoxycarbonyl)amino)-4-methoxy-4-oxobutanoic acid (0.50 g).

NMR (CDCl$_3$) δ: 1.44 (9H, s), 2.60 (3H, s), 2.65-2.80 (2H, m), 3.17-3.21 (4H, m), 3.71 (3H, s), 3.73-3.80 (5H, m), 4.43 (2H, m), 4.95-5.02 (1H, m), 5.44-5.47 (1H, m), 6.72 (1H, s).

27b) methyl 3-(N'—(4-chlorophenyl)ureido)-4-(4-(5-methyl-3-oxo-1H-imidazo[1,5-c]imidazol-2(3H)-yl)-1-piperazinyl)-4-oxobutanoate In the same manner as in Example 15b), the title compound as colorless powder (0.32 g, 42%) was obtained from methyl 3-((tert-butoxycarbonyl)amino)-4-(4-(5-methyl-3-oxo-1H-imidazo[1,5-c]imidazol-2(3H)-yl)-1-piperidinyl)-4-oxobutanoate (0.68 g) obtained in Example 27a).

NMR (CDCl$_3$) δ: 2.60 (3H, s), 2.69-2.88 (2H, m), 3.21-3.29 (4H, m), 3.70 (3H, s), 3.73-3.85 (4H, m), 4.43 (2H, s), 5.25-5.32 (1H, m), 6.27-6.30 (1H, m), 6.72 (1H, s), 7.21-7.42 (5H, m).

Elemental analysis for C$_{22}$H$_{26}$ClN$_7$O$_5$·0.5H$_2$O·0.2IPE
Calcd. (%): C, 52.24; H, 5.63; N, 18.38.
Found (%): C, 51.94; H, 5.69; N, 18.26.

EXAMPLE 28

N—(4-chlorophenyl)—N'—(1-(methoxymethyl)-2-(4-(5-methyl-3-oxo-1H-imidazo[1,5-c]imidazol-2(3H)-yl)-1-piperazinyl)-2-oxoethyl)urea

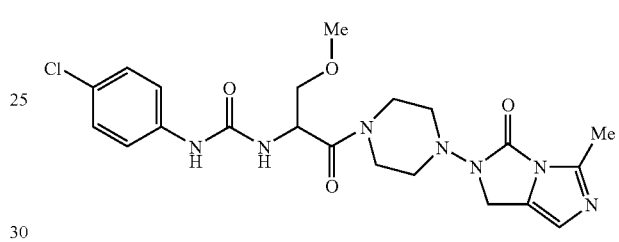

28a) tert-butyl 1-(methoxymethyl)-2-(4-(5-methyl-3-oxo-1H-imidazo[1,5-c]imidazol-2(3H)-yl)-1-piperazinyl)-2-oxoethylcarbamate In the same manner as in Example 10a), the title compound as colorless powder (0.56 g, 66%) was obtained from 2-((tert-butoxycarbonyl)amino)-3-methoxypropanoic acid (PCT Japanese Translation Patent Publication No. 10287669; 0.44 g).

NMR (CDCl$_3$) δ: 1.45 (9H, s), 2.60 (3H, s), 3.18 (4H, m), 3.36 (3H, s), 3.43-3.90 (6H, m), 4.43 (2H, s), 4.78-4.85 (1H, m), 5.44-5.47 (1H, m), 6.72 (1H, s).

28b) N—(4-chlorophenyl)—N'—(1-(methoxymethyl)-2-(4-(5-methyl-3-oxo-1H-imidazo[1,5-c]imidazol-2(3H)-yl)-1-piperazinyl)-2-oxoethyl)urea In the same manner as in Example 15b), the title compound as colorless powder (0.23 g, 34%) was obtained from tert-butyl 1-(methoxymethyl)-2-(4-(5-methyl-3-oxo-1H-imidazo[1,5-c]imidazol-2(3H)-yl)-1-piperazinyl)-2-oxoethylcarbamate (0.56 g) obtained in Example 28a).

NMR (CDCl$_3$) δ: 2.61 (3H, s), 3.17-3.98 (13H, m), 4.44 (2H, s), 5.14-5.21 (1H, m), 6.50-6.54 (1H, m), 6.72 (1H, s), 7.22-7.29 (4H, m), 7.70-7.73 (1H, m).

Elemental analysis for C$_{21}$H$_{26}$ClN$_7$O$_4$·0.5H$_2$O·0.2IPE
Calcd. (%): C, 52.76; H, 5.94; N, 19.40.
Found (%): C, 52.53; H, 5.94; N, 19.19.

EXAMPLE 29

N—(4-chlorophenyl)-3-((4-(5-methyl-3-oxo-1H-imidazo[1,5-c]imidazol-2(3H)-yl)-1-piperazinyl)carbonyl)-1-piperidinecarboxamide

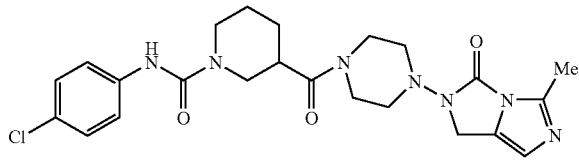

29a) tert-butyl 3-((4-(5-methyl-3-oxo-1H-imidazo[1,5-c]imidazol-2(3H)-yl)-1-piperazinyl)carbonyl)-1-piperidinecarboxylate In the same manner as in Example 10a), the title compound as colorless powder (0.37 g, 86%) was obtained from Boc-nipecotic acid (0.23 g).

NMR (CDCl$_3$) δ: 1.44 (9H, s), 1.70-1.87 (4H, m), 2.60 (3H, s), 2.62-3.27 (7H, m), 3.70-3.73 (4H, m), 4.09-4.16 (2H, m), 4.44 (2H, s), 6.72 (1H, s).

29b) N—(4-chlorophenyl)-3-((4-(5-methyl-3-oxo-1H-imidazo[1,5-c]imidazol-2(3H)-yl)-1-piperazinyl)carbonyl)-1-piperidinecarboxamide In the same manner as in Example 13b), the title compound as colorless powder (0.33 g, 79%) was obtained from tert-butyl 3-((4-(5-methyl-3-oxo-1H-imidazo[1,5-c]imidazol-2(3H)-yl)-1-piperazinyl)carbonyl)-1-piperidinecarboxylate (0.37 g) obtained in Example 29a).

NMR (CDCl$_3$) δ: 1.77-1.94 (4H, m), 2.60 (3H, s), 2.76 (1H, m), 3.17-3.27 (6H, m), 3.71-3.77 (5H, m), 3.99-4.04 (1H, m), 4.44 (2H, s), 6.72 (1H, s), 6.92 (1H, s), 7.23-7.33 (4H, m).

Elemental analysis for C$_{23}$H$_{28}$ClN$_7$O$_3$.0.5H$_2$O
Calcd. (%): C, 55.81; H, 5.91; N, 19.81.
Found (%): C, 56.16; H, 6.03; N, 19.53.

EXAMPLE 30

N—(4-chlorophenyl)—N'—(1-cyclopentyl-2-(4-(5-methyl-3-oxo-1H-imidazo[1,5-c]imidazol-2(3H)-yl)-1-piperazinyl)-2-oxoethyl)urea

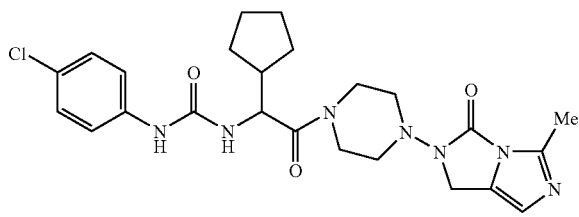

30a) tert-butyl 1-cyclopentyl-2-(4-(5-methyl-3-oxo-1H-imidazo[1,5-c]imidazol-2(3H)-yl)-1-piperazinyl)-2-oxoethylcarbamate In the same manner as in Example 10a), the title compound as colorless powder (0.38 g, 85%) was obtained from ((tert-butoxycarbonyl)amino)(cyclopentyl)acetic acid (0.24 g).

NMR (CDCl$_3$) δ: 1.44 (9H, s), 1.62-1.74 (8H, m), 2.12-2.20 (1H, m), 2.60 (3H, s), 3.15-3.27 (4H, m), 3.73-3.84 (4H, m), 4.43 (2H, s), 4.55-4.57 (1H, m), 5.26-5.29 (1H, m), 6.72 (1H, s).

30b) N—(4-chlorophenyl)—N'—(1-cyclopentyl-2-(4-(5-methyl-3-oxo-1H-imidazo[1,5-c]imidazol-2(3H)-yl)-1-piperazinyl)-2-oxoethyl)urea In the same manner as in Example 15b), the title compound as colorless powder (0.13 g, 30%) was obtained from tert-butyl 1-cyclopentyl-2-(4-(5-methyl-3-oxo-1H-imidazo[1,5-c]imidazol-2(3H)-yl)-1-piperazinyl)-2-oxoethylcarbamate (0.38 g) obtained in Example 30a).

NMR (CDCl$_3$) δ: 1.30-1.75 (8H, m), 2.18-2.23 (1H, m), 2.61 (3H, s), 3.18-3.33 (4H, m), 3.81-3.91 (4H, m), 4.42 (2H, s), 4.79-4.84 (1H, m), 6.49 (1H, d, J=8.6), 6.72 (1H, s), 7.14-7.24 (4H, m), 7.55 (1H, s).

Elemental analysis for C$_{24}$H$_{30}$ClN$_7$O$_3$.0.5H$_2$O.0.2IPE
Calcd. (%): C, 57.17; H, 6.43; N, 18.52.
Found (%): C, 57.00; H, 6.36; N, 18.36.

EXAMPLE 31

N—(4-chlorophenyl)—N'—(1-(ethoxymethyl)-2-(4-(5-methyl-3-oxo-1H-imidazo[1,5-c]imidazol-2(3H)-yl)-1-piperazinyl)-2-oxoethyl)urea

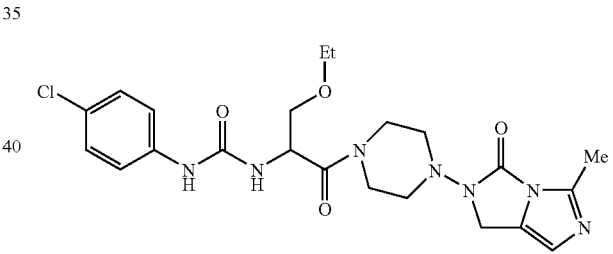

31a) tert-butyl 1-(ethoxymethyl)-2-(4-(5-methyl-3-oxo-1H-imidazo[1,5-c]imidazol-2(3H)-yl)-1-piperazinyl)-2-oxoethylcarbamate In the same manner as in Example 10a), the title compound as colorless powder (0.96 g, 88%) was obtained from 2-((tert-butoxycarbonyl)amino)-3-ethoxypropanoic acid (EP 266950; 0.58 g).

NMR (CDCl$_3$) δ: 1.18 (3H, t, J=7.0), 1.44 (9H, s), 2.60 (3H, s), 3.17 (4H, m), 3.47-3.53 (2H, m), 3.62-3.96 (6H, m), 4.42 (2H, s), 4.79-4.86 (1H, m), 5.43-5.46 (1H, m), 6.72 (1H, s).

31b) N—(4-chlorophenyl)—N'—(1-(ethoxymethyl)-2-(4-(5-methyl-3-oxo-1H-imidazo[1,5-c]imidazol-2(3H)-yl)-1-piperazinyl)-2-oxoethyl)urea In the same manner as in Example 15b), the title compound as colorless powder (0.54 g, 50%) was obtained from tert-butyl 1-(ethoxymethyl)-2-(4-(5-methyl-3-oxo-1H-imidazo[1,5-c]imidazol-2(3H)-yl)-1-piperazinyl)-2-oxoethylcarbamate (0.96 g) obtained in Example 31a).

NMR (CDCl₃) δ: 1.14-1.21 (3H, m), 2.61 (3H, s), 3.16-3.98 (12H, m), 4.43 (2H, s), 5.12-5.19 (1H, m), 6.43-6.45 (1H, m), 6.73 (1H, s), 7.19-7.30 (4H, m), 7.53 (1H, s).

Elemental analysis for C₂₂H₂₈ClN₇O₄·0.7H₂O·0.2IPE
Calcd. (%): C, 53.28; H, 6.21; N, 18.75.
Found (%): C, 53.04; H, 6.21; N, 18.79.

EXAMPLE 32

N'—(4-chlorophenyl)—N-methyl-N—((1R)-2-methyl-1-((4-(5-methyl-3-oxo-1H-imidazo[1,5-c]imidazol-2(3H)-yl)-1-piperazinyl)carbonyl)propyl)urea

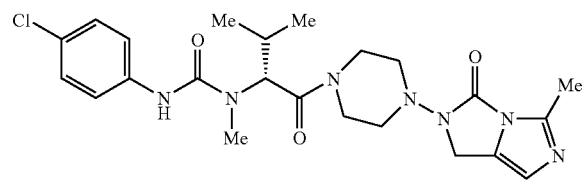

32a) tert-butyl methyl((1R)-2-methyl-1-((4-(5-methyl-3-oxo-1H-imidazo[1,5-c]imidazol-2(3H)-yl)-1-piperazinyl)carbonyl)propyl)carbamate In the same manner as in Example 10a), the title compound as a colorless oil (0.23 g, 53%) was obtained from Boc-N-methyl-D-valine (0.23 g).

NMR (CDCl₃) δ: 0.86-0.92 (6H, m), 1.44-1.47 (9H, m), 2.35-2.42 (1H, m), 2.60 (3H, s), 2.77 (3H, s), 3.10-3.18 (4H, m), 3.62-3.90 (5H, m), 4.42 (2H, s), 6.71 (1H, s).

32b) N'—(4-chlorophenyl)—N-methyl-N—((1R)-2-methyl-1-((4-(5-methyl-3-oxo-1H-imidazo[1,5-c]imidazol-2(3H)-yl)-1-piperazinyl)carbonyl)propyl)urea In the same manner as in Example 15b), the title compound as colorless powder (0.15 g, 59%) was obtained from tert-butyl methyl((1R)-2-methyl-1-((4-(5-methyl-3-oxo-1H-imidazo[1,5-c]imidazol-2(3H)-yl)-1-piperazinyl)carbonyl)propyl)carbamate (0.22 g) obtained in Example 32a).

NMR (CDCl₃) δ: 0.91-0.96 (6H, m), 2.37-2.41 (1H, m), 2.59 (3H, s), 3.04 (3H, s), 3.15-3.23 (4H, m), 3.58-3.96 (4H, m), 4.41 (2H, s), 4.89-4.93 (1H, m), 6.58 (1H, br), 6.70 (1H, s), 7.23-7.33 (4H, m).

Elemental analysis for C₂₃H₃₀ClN₇O₃·0.5H₂O·0.3AcOEt
Calcd. (%): C, 55.53; H, 6.43; N, 18.73.
Found (%): C, 55.66; H, 6.40; N, 18.66.

EXAMPLE 33

N—(4-chlorophenyl)—N'—(2-hydroxy-2-methyl-1-((4-(5-methyl-3-oxo-1H-imidazo[1,5-c]imidazol-2(3H)-yl)-1-piperidinyl)carbonyl)propyl)urea

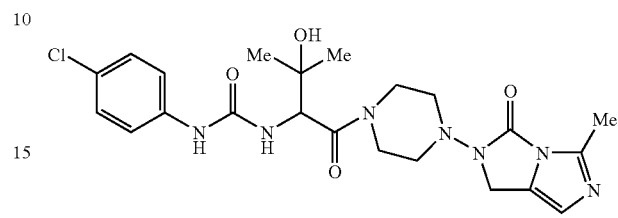

33a) tert-butyl 2-hydroxy-2-methyl-1-((4-(5-methyl-3-oxo-1H-imidazo[1,5-c]imidazol-2(3H)-yl)-1-piperidinyl)carbonyl)propylcarbamate In the same manner as in Example 6a), the title compound as colorless powder (0.15 g, 54%) was obtained from 2-((tert-butoxycarbonyl)amino)-3-hydroxy-3-methylbutanoic acid (U. Schmidt et al., J. Pept. Res., 52, 143 (1998); 0.15 g).

NMR (CDCl₃) δ: 1.22-1.35 (6H, m), 1.44-1.45 (9H, m), 1.65-1.95 (4H, m), 2.61 (3H, s), 2.70-2.73 (1H, m), 3.16-3.25 (1H, m), 4.23-4.61 (6H, m), 4.78-4.82 (1H, m), 5.47-5.56 (1H, m), 6.71-6.72 (1H, m).

33b) N—(4-chlorophenyl)—N'—(2-hydroxy-2-methyl-1-((4-(5-methyl-3-oxo-1H-imidazo[1,5-c]imidazol-2(3H)-yl)-1-piperidinyl)carbonyl)propyl)urea tert-Butyl 2-hydroxy-2-methyl-1-((4-(5-methyl-3-oxo-1H-imidazo[1,5-c]imidazol-2(3H)-yl)-1-piperidinyl)carbonyl)propylcarbamate (0.15 g) obtained in Example 33a) was dissolved in trifluoroacetic acid (1.5 ml), mixed at room temperature for 1 hour, and then concentrated under reduced pressure. The residue was dissolved in water, and the reaction mixture was basified with potassium carbonate and extracted with chloroform. The extract was dried over anhydrous sodium sulfate, and the solvent was distilled off under reduced pressure. The residue was dissolved in acetonitrile (10 ml), 4-chlorophenyl isocyanate (46 mg) was added thereto, and mixed at room temperature for 2 hours. The solvent was distilled off under reduced pressure, and the residue was purified with basic silica gel column (ethyl acetate to ethyl acetate/methanol=5/1) to obtain the title compound (65 mg, 39%) as colorless powder.

NMR (CDCl₃) δ: 1.14-1.39 (6H, m), 1.69-2.10 (4H, m), 2.60-2.62 (3H, m), 2.75-2.80 (1H, m), 3.20-3.24 (1H, m), 4.20-4.30 (3H, m), 4.60-4.83 (3H, m), 5.44-5.63 (1H, m), 6.24-6.31 (1H, m), 6.69-6.72 (1H, m), 7.22-7.34 (4H, m), 7.70-7.81 (1H, m).

Elemental analysis for C₂₃H₂₉ClN₆O₄·0.9H₂O·0.3AcOEt
Calcd. (%): C, 54.67; H, 6.29; N, 15.81.
Found (%): C, 54.93; H, 6.40; N, 15.84.

EXAMPLE 34

N—(4-chlorophenyl)—N'—(2-hydroxy-2-methyl-1-((4-(5-methyl-3-oxo-1H-imidazo[1,5-c]imidazol-2(3H)-yl)-1-piperazinyl)carbonyl)propyl)urea

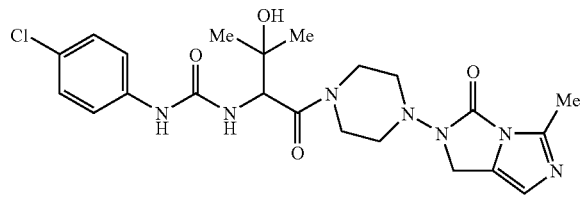

34a) tert-butyl 2-hydroxy-2-methyl-1-((4-(5-methyl-30-oxo-1H-imidazo[1,5-c]imidazol-2(3H)-yl)-1-piperazinyl)propylcarbamate In the same manner as in Example 10a), the title compound as colorless powder (0.82 g, 52%) was obtained from 2-((tert-butoxycarbonyl)amino)-3-hydroxy-3-methylbutanoic acid (0.85 g).

NMR (CDCl$_3$) δ: 1.21-1.27 (6H, m), 1.45 (9H, s), 2.60 (3H, s), 3.18-3.25 (4H, m), 3.72-3.91 (4H, m), 4.38-4.53 (3H, m), 5.52-5.55 (1H, m), 6.72 (1H, s).

34b) N—(4-chlorophenyl)—N'—(2-hydroxy-2-methyl-1-((4-(5-methyl-3-oxo-1H-imidazo[1,5-c]imidazol-2(3H)-yl)-1-piperazinyl)carbonyl)propyl)urea In the same manner as in Example 33b), the title compound as colorless powder (0.62 g, 69%) was obtained from tert-butyl 2-hydroxy-2-methyl-1-((4-(5-methyl-3-oxo-1H-imidazo[1,5-c]imidazol-2(3H)-yl)-1-piperazinyl)carbonyl)propylcarbamate (0.80 g) obtained in Example 34a).

NMR (CDCl$_3$) δ: 1.24 (3H, s), 1.29 (3H, s), 2.59 (3H, s), 3.19-3.39 (4H, m), 3.75-4.02 (4H, br), 4.45 (2H, s), 4.66-4.69 (1H, m), 6.35-6.68 (4H, m), 7.23 (2H, d, J=7.1), 7.34 (2H, d, J=6.8).

Elemental analysis for $C_{22}H_{28}ClN_7O_4 \cdot 0.5H_2O \cdot 0.3AcOEt$
Calcd. (%): C, 53.04; H, 6.02; N, 18.66.
Found (%): C, 53.10; H, 6.25; N, 18.44.

EXAMPLE 35

2-(N'—(4-chlorophenyl)ureido)-1,1-dimethyl-3-(4-(5-methyl-3-oxo-1H-imidazo[1,5-c]imidazol-2(3H)-yl)-1-piperazinyl)-3-oxopropyl carbamate

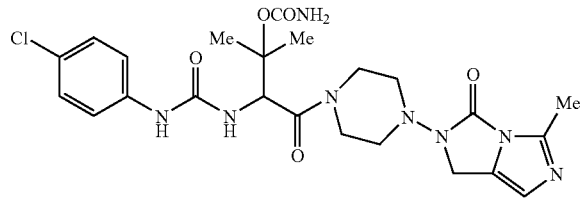

To a solution of N—(4-chlorophenyl)—N'—(2-hydroxy-2-methyl-1-((4-(5-methyl-3-oxo-1H-imidazo[1,5-c]imidazol-2(3H)-yl)-1-piperazinyl)carbonyl)propyl)urea (0.18 g) obtained in Example 34 in dichloromethane (15 ml) was added trichloroacetyl isocyanate (0.065 ml) at 0° C., and the temperature of the mixture was elevated to room temperature and mixed at room temperature for 6 hours. To the reaction mixture were added methanol (5 ml), water (5 ml) and potassium carbonate (0.15 g), and then mixed at room temperature for 15 hours. The reaction mixture was concentrated under reduced pressure, and then extracted with ethyl acetate. The extract was dried over anhydrous sodium sulfate, and the solvent was distilled off under reduced pressure. The residue was purified with basic silica gel column (ethyl acetate to ethyl acetate/methanol=10/1) to obtain the title compound as colorless powder (0.12 g, 62%).

NMR (CDCl$_3$) δ: 1.58-1.62 (6H, m), 2.59 (3H, s), 3.12-3.31 (4H, m), 3.78-3.92 (4H, m), 4.43 (2H, s), 5.20-5.30 (3H, m), 6.30-6.33 (1H, s), 6.71 (1H, s), 7.23 (2H, d, J=8.6), 7.34 (2H, d, J=9.0), 7.96 (1H, s).

Elemental analysis for $C_{23}H_{29}ClN_8O_5H_2O \cdot 0.3AcOEt$
Calcd. (%): C, 50.34; H, 5.83; N, 19.41.
Found (%): C, 50.10; H, 5.61; N, 19.27.

EXAMPLE 36

N—(4-chlorophenyl)—N'—(2-ethyl-2-hydroxy-1-((4-(5-methyl-3-oxo-1H-imidazo[1,5-c]imidazol-2(3H)-yl)-1-piperidinyl)carbonyl)butyl)urea

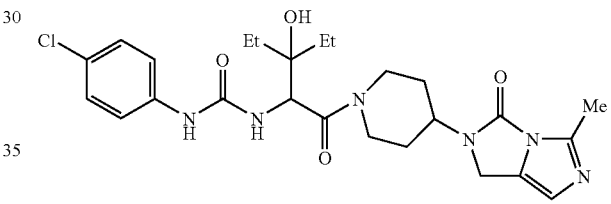

36a) tert-butyl 2-ethyl-2-hydroxy-1-(hydroxymethyl)butylcarbamate

Boc-serine methyl ester (6.30 g) was dissolved in diethyl ether (150 ml), and a solution of ethyl magnesium bromide (in 3 M diethyl ether, 57 ml) was added dropwise thereto while the mixture was cooled to −78° C. After addition by dropping, the temperature of the reaction mixture was elevated to room temperature, and mixed at room temperature for 2 hours. The reaction mixture was again cooled to 0° C., and a saturated aqueous ammonium chloride solution was added dropwise thereto. The organic layer was collected by separation, and the aqueous layer was extracted three times with ethyl acetate. The extracts were all mixed, washed with saturated brine and dried over anhydrous sodium sulfate. The solvent was distilled off under reduced pressure to obtain the title compound as a colorless oil (1.10 g, 79%).

NMR (CDCl$_3$) δ: 0.82-0.93 (6H, m), 1.46 (9H, s), 1.52-1.75 (3H, m), 2.38-2.42 (2H, m), 3.58-4.04 (4H, m), 5.38 (1H, m).

36b) 2-((tert-butoxycarbonyl)amino)-3-ethyl-3-hydroxypentanoic acid tert-Butyl 2-ethyl-2-hydroxy-1-(hydroxymethyl)butylcarbamate (5.80 g) obtained in Example 36a) and 2,2,6,6-tetramethyl-1-piperidinyloxy (0.73 g) were dissolved in phosphate buffer (pH 6.8, 100 ml) and acetonitrile (100 ml). While the mixture was warmed to 35° C., an aqueous sodium hypochlorite solution (1.3 ml) and an aqueous solution (20 ml) of sodium chlorite (6.4 g) were simultaneously added dropwise thereto over 2 hours, respectively. The reaction mixture was mixed at 35° C. overnight, and returned to room temperature. The solution was acidified by adding a 5% aqueous citric acid solution and extracted three times with ethyl acetate. The extracts were combined and dried over anhydrous sodium sulfate, and the solvent was distilled off under reduced pressure. The residue was purified with silica gel column (ethyl acetate/hexane=1/1 to 3/1) to obtain the title compound as colorless powder (0.28 g, 24%).

NMR (CDCl$_3$) δ: 0.89 (3H, t, J=7.5), 0.95 (3H, t, J=7.5), 1.45 (9H, s), 1.51-1.66 (3H, m), 3.80-4.33 (4H, m), 5.41 (1H, m).

36c) tert-butyl 2-ethyl-2-hydroxy-1-((4-(5-methyl-3-oxo-1H-imidazo[1,5-c]imidazol-2(3H)-yl)-1-piperidinyl)carbonyl)butylcarbamate In the same manner as in Example 6a), the title compound as colorless powder (0.18 g, 13%) was obtained from 2-((tert-butoxycarbonyl)amino)-3-ethyl-3-hydroxypentanoic acid (0.80 g) obtained in Example 36b).

NMR (CDCl$_3$) δ: 0.82-1.04 (6H, m), 1.46 (9H, s), 1.54-1.95 (8H, m), 2.61 (3H, s), 2.70-2.73 (1H, m), 3.16-3.25 (1H, m), 4.23-4.61 (6H, m), 4.78-4.82 (1H, m), 5.47-5.56 (1H, m), 6.71-6.72 (1H, m).

36d) N—(4-chlorophenyl)—N'—(2-ethyl-2-hydroxy-1-((4-(5-methyl-3-oxo-1H-imidazo[1,5-c]imidazol-2(3H)-yl)-1-piperidinyl)carbonyl)butyl)urea In the same manner as in Example 33b), the title compound as colorless powder (15 mg, 8%) was obtained from tert-butyl 2-ethyl-2-hydroxy-1-((4-(5-methyl-3-oxo-1H-imidazo[1,5-c]imidazol-2(3H)-yl)-1-piperidinyl)carbonyl)butylcarbamate (0.17 g) obtained in Example 36c).

NMR (CDCl$_3$) δ: 0.88-1.00 (6H, m), 1.43-2.04 (8H, m), 2.61-2.62 (3H, m), 2.75-2.80 (1H, m), 3.17-3.28 (1H, m), 4.19-4.30 (3H, m), 4.65-4.87 (3H, m), 6.35-6.43 (1H, m), 6.71-6.73 (2H, m), 7.21-7.32 (4H, m), 7.51-7.59 (1H, m).

Elemental analysis for $C_{25}H_{33}ClN_6O_4 \cdot 0.4H_2O \cdot 0.4IPE$
Calcd. (%): C, 58.24; H, 7.03; N, 14.87.
Found (%): C, 58.50; H, 7.23; N, 14.61.

EXAMPLE 37

N—(4-chlorophenyl)—N'—(2-ethyl-2-hydroxy-1-((4-(5-methyl-3-oxo-1H-imidazo[1,5-c]imidazol-2(3H)-yl)-1-piperazinyl)carbonyl)butyl)urea

37a) tert-butyl 2-ethyl-2-hydroxy-1-((4-(5-methyl-3-oxo-1H-imidazo[1,5-c]imidazol-2(3H)-yl)-1-piperazinyl)carbonyl)butylcarbamate To a solution of 2-((tert-butoxycarbonyl)amino)-3-ethyl-3-hydroxypentanoic acid (0.80 g) obtained in Example 36b) and HOBt (0.65 g) in acetonitrile (30 ml) was added WSC (0.83 g), and the reaction mixture was mixed at room temperature for 15 minutes. Then, 5-methyl-2-(1-piperazinyl)-1,2-dihydro-3H-imidazo[1,5-c]imidazol-3-one (0.63 g) obtained in Reference Example 2 and triethylamine (1.2 ml) were added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with basic silica gel column (ethyl acetate) to obtain the title compound as colorless powder (0.11 g, 8%).

NMR (CDCl$_3$) δ: 0.82-0.91 (6H, m), 1.44-1.46 (9H, m), 1.57-1.73 (4H, m), 2.60 (3H, s), 3.16-3.22 (4H, m), 3.72-3.96 (4H, m), 4.42-4.53 (3H, m), 5.51-5.54 (1H, m), 6.72 (1H, s).

37b) N—(4-chlorophenyl)—N'—(2-ethyl-2-hydroxy-1-((4-(5-methyl-3-oxo-1H-imidazo[1,5-c]imidazol-2(3H)-yl)-1-piperazinyl)carbonyl)butyl)urea tert-Butyl 2-ethyl-2-hydroxy-1-((4-(5-methyl-3-oxo-1H-imidazo[1,5-c]imidazol-2(3H)-yl)-1-piperazinyl)carbonyl)butylcarbamate (0.11 g) obtained in Example 37a) was dissolved in trifluoroacetic acid (1.5 ml), mixed at room temperature for 1 hour, and then concentrated under reduced pressure. The residue was dissolved in water, and the reaction mixture was basified with potassium carbonate and extracted with chloroform. The extract was dried over anhydrous sodium sulfate, and the solvent was distilled off under reduced pressure. The residue was dissolved in acetonitrile (10 ml), 4-chlorophenyl isocyanate (46 mg) was added, and mixed at room temperature for 2 hours. The solvent was distilled off under reduced pressure, and the residue was purified with basic silica gel column (ethyl acetate to ethyl acetate/methanol=5/1) to obtain the title compound as colorless powder (38 mg, 31%).

NMR (CDCl$_3$) δ: 0.88 (3H, t, J=7.5), 0.95 (3H, t, J=7.5), 1.51-1.69 (4H, m), 2.60 (3H, s), 3.17-3.27 (4H, m), 3.68-4.09 (4H, m), 4.42 (2H, s), 4.83 (1H, d, J=9.4), 5.21 (1H, br), 6.32 (1H, d, J=9.4), 6.71-6.72 (1H, m), 7.22-7.34 (4H, m), 7.53 (1H, m).

Elemental analysis for $C_{24}H_{32}ClN_7O_4 \cdot 0.2H_2O \cdot 0.2IPE$
Calcd. (%): C, 55.84; H, 6.55; N, 18.09.
Found (%): C, 55.98; H, 6.80; N, 17.89.

EXAMPLE 38

N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylthio)propyl)urea

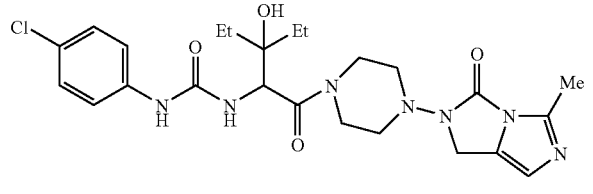

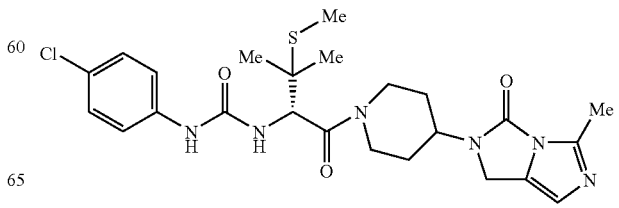

38a) tert-butyl (1S)-2-methyl-1-((4-(5-methyl-3-oxo-1H-imidazo[1,5-c]imidazol-2(3H)-yl)-1-piperidinyl)carbonyl)-2-(methylthio)propylcarbamate To a solution of (2S)-2-((tert-butoxycarbonyl)amino)-3-methyl-3-(methylthio)butanoic acid (T. Fukami et al., J. Med. Chem., 39, 2313 (1996); 1.3 g) and HOBt (1.14 g) in acetonitrile (30 ml) was added WSC (1.42 g), and the reaction mixture was mixed at room temperature for 15 minutes. Then, a solution of 5-methyl-2-(4-piperidinyl)-1,2-dihydro-3H-imidazo[1,5-c]imidazol-3-one dihydrochloride (1.43 g), DBU (1.47 ml) and triethylamine (2.2 ml) in acetonitrile (10 ml) was added thereto. The reaction mixture was mixed at room temperature for 15 hours, the solvent was then distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with basic silica gel column (ethyl acetate to ethyl acetate/methanol=5/1) to obtain the title compound as colorless powder (1.7 g, 71%).

NMR (CDCl$_3$) δ: 1.31-1.40 (6H, m), 1.44-1.45 (9H, m), 1.72-1.96 (4H, m), 2.05-2.09 (3H, m), 2.61 (3H, s), 2.65-2.74 (1H, m), 3.21-3.29 (1H, m), 4.16-4.38 (4H, m), 4.75-4.85 (2H, m), 5.40-5.49 (1H, m), 6.71 (1H, s).

38b) N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylthio)propyl)urea tert-Butyl(1S)-2-methyl-1-((4-(5-methyl-3-oxo-1H-imidazo[1,5-c]imidazol-2(3H)-yl)-1-piperidinyl)carbonyl)-2-(methylthio)propylcarbamate (1.7 g) obtained in Example 38a) was dissolved in trifluoroacetic acid (15 ml), mixed at room temperature for 1 hour, and then concentrated under reduced pressure. The residue was dissolved in water, and the reaction mixture was basified with potassium carbonate and extracted with chloroform. The extract was dried over anhydrous sodium sulfate, and the solvent was distilled off under reduced pressure. The residue was dissolved in acetonitrile (100 ml), 4-chlorophenyl isocyanate (460 mg) was added thereto, and mixed at room temperature for 2 hours. The solvent was distilled off under reduced pressure, and the residue was purified with basic silica gel column (ethyl acetate to ethyl acetate/methanol=5/1) to obtain the title compound as colorless powder (1.2 g, 65%).

NMR (CDCl$_3$) δ: 1.39-1.42 (6H, m), 1.60-2.00 (4H, m), 2.07-2.12 (3H, m), 2.60-2.62 (3H, m), 2.68-2.76 (1H, m), 3.24-3.31 (1H, m), 4.17-4.45 (4H, m), 4.46-4.82 (1H, m), 5.07-5.14 (1H, m), 6.01-6.06 (1H, m), 6.69-6.72 (1H, m), 7.20-7.30 (5H, m).

Elemental analysis for C$_{24}$H$_{31}$ClN$_6$O$_3$S
Calcd. (%): C, 55.53; H, 6.02; N, 16.19.
Found (%): C, 55.24; H, 6.17; N, 16.01.

EXAMPLE 39

N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylsulfinyl)propyl)urea

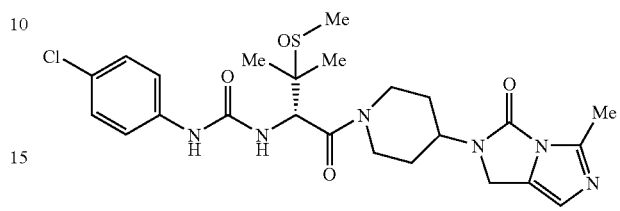

and

N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylsulfonyl)propyl)urea

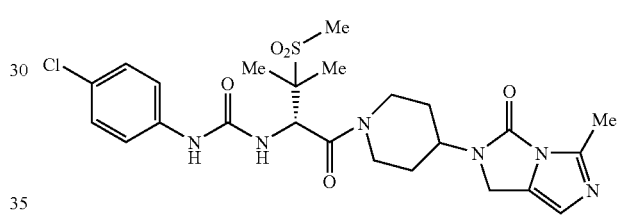

N—(4-Chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylthio)propyl)urea (0.52 g) obtained in Example 38 and methanesulfonic acid (0.06 ml) were dissolved in dichloromethane (20 ml). While the mixture was cooled to 0° C., 3-chloroperbenzoic acid (70%; 0.42 g) was added thereto, and mixed at 0° C. for 3 hours. To the reaction mixture was added an aqueous sodium sulfite solution, and mixed for 30 minutes. Then, an aqueous sodium hydrogen carbonate solution was added thereto, and the organic layer was collected by separation and dried over anhydrous sodium sulfate. The solvent was distilled off under reduced pressure, and the residue was purified with basic silica gel column (ethyl acetate/methanol=20/1 to 10/1) to obtain N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylsulfinyl)propyl)urea as colorless powder (0.12 g, 22%) and N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylsulfonyl)propyl)urea as colorless powder (0.12 g, 22%).

N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylsulfinyl)propyl)urea NMR (CDCl$_3$) δ: 1.39-1.41 (6H, m), 1.60-2.13 (4H, m), 2.45-2.47 (3H, m), 2.60-2.61 (3H, m), 2.68-2.76 (1H, m), 3.24-3.31 (1H, m), 3.42-3.46 (1H, m), 4.17-4.45 (4H, m), 4.78-4.82 (1H, m), 5.20-5.26 (1H, m), 6.67-6.69 (1H, m), 7.21-7.63 (5H, m).

Elemental analysis for $C_{24}H_{31}ClN_6O_4S \cdot 0.2H_2O$
Calcd. (%): C, 53.51; H, 5.88; N, 15.60.
Found (%): C, 53.54; H, 5.83; N, 15.31.

N—(4-chlorophenyl)—N'—((1S)-2-methyl-1-((4-(5-methyl-3-oxo-1H-imidazo[1,5-c]imidazol-2(3H)-yl)-1-piperidinyl)carbonyl)-2-(methylsulfonyl)propyl)urea NMR (CDCl$_3$) δ: 1.54-1.55 (6H, m), 1.83-1.96 (4H, m), 2.60-2.61 (3H, m), 2.65-2.80 (1H, m), 2.95-2.97 (3H, m), 3.22-3.31 (1H, m), 4.19-4.50 (4H, m), 4.71-4.75 (1H, m), 5.56-5.60 (1H, m), 6.02-6.15 (1H, m), 6.69-6.72 (1H, m), 7.23-7.34 (5H, m).

Elemental analysis for $C_{24}H_{31}ClN_6O_5S \cdot 0.6H_2O \cdot 0.3AcOEt$
Calcd. (%): C, 51.45; H, 5.93; N, 14.29.
Found (%): C, 51.23; H, 5.95; N, 14.23.

EXAMPLE 40

N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylthio)propyl)urea

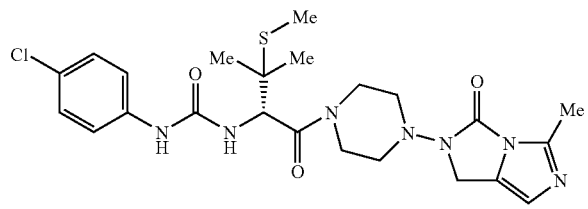

40a) tert-butyl (1S)-2-methyl-1-((4-(5-methyl-3-oxo-1H-imidazo[1,5-c]imidazol-2(3H)-yl)-1-piperazinyl)carbonyl)-2-(methylthio)propylcarbamate In the same manner as in Example 10a), the title compound as yellow green powder (1.8 g, 64%) was obtained from (2S)-2-((tert-butoxycarbonyl)amino)-3-methyl-3-(methylthio)butanoic acid (1.6 g).

NMR (CDCl$_3$) δ: 1.35 (6H, m), 1.45 (9H, m), 2.07 (3H, s), 2.60 (3H, s), 3.16-3.31 (4H, m), 3.80-3.88 (4H, m), 4.43 (2H, s), 4.73-4.77 (1H, m), 5.42-5.46 (1H, m), 6.71 (1H, s).

40b) N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylthio)propyl)urea In the same manner as in Example 33b), the title compound as colorless powder (1.2 g, 63%) was obtained from tert-butyl (1S)-2-methyl-1-((4-(5-methyl-3-oxo-1H-imidazo[1,5-c]imidazol-2(3H)-yl)-1-piperazinyl)carbonyl)-2-(methylthio)propylcarbamate (1.7 g) obtained in Example 40a).

NMR (CDCl$_3$) δ: 1.40 (6H, s), 2.09 (3H, m), 2.60 (3H, s), 3.14-3.36 (4H, m), 3.75-3.90 (4H, m), 4.42 (2H, s), 5.08 (1H, d, J=9.1), 5.99 (1H, d, J=9.1), 6.72 (1H, s), 7.13-7.30 (5H, m).

Elemental analysis for $C_{23}H_{30}ClN_7O_3S$
Calcd. (%): C, 53.12; H, 5.81; N, 18.85.
Found (%): C, 52.93; H, 5.93; N, 18.85.

EXAMPLE 41

N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylsulfinyl)propyl)urea

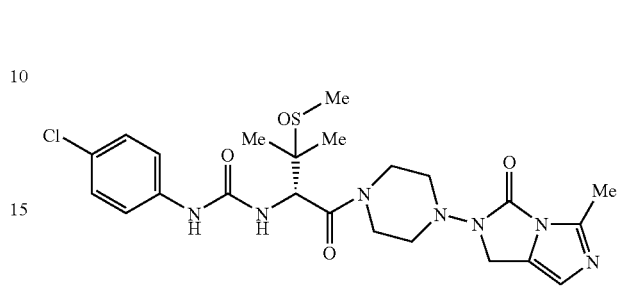

and

N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylsulfonyl)propyl)urea

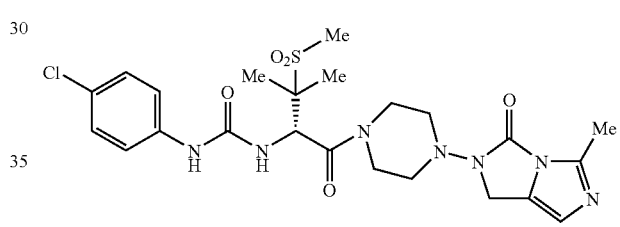

In the same manner as in Example 39, N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylsulfinyl)propyl)urea as colorless powder (70 mg, 12%) and N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylsulfonyl)propyl)urea as colorless powder (0.23 g, 39%) were obtained from N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylthio)propyl)urea (0.56 g) obtained in Example 40, respectively.

N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylsulfinyl)propyl)urea NMR (CDCl$_3$) δ: 1.24-1.26 (3H, m), 1.41-1.44 (3H, m), 2.47-2.55 (3H, m), 2.59 (3H, s), 3.13-3.34 (4H, m), 3.77-3.88 (4H, m), 4.40-4.42 (2H, m), 5.20-5.32 (1H, m), 6.32-6.66 (1H, m), 6.71 (1H, s), 7.21-7.35 (4H, m), 7.71-7.81 (1H, m).

Elemental analysis for $C_{23}H_{30}ClN_7O_4S \cdot H_2O$
Calcd. (%): C, 49.86; H, 5.82; N, 17.70.
Found (%): C, 49.81; H, 5.89; N, 17.72.

N—(4-chlorophenyl)—N'—((1S)-2-methyl-1-((4-(5-methyl-3-oxo-1H-imidazo[1,5-c]imidazol-2(3H)-yl)-1-piperazinyl)carbonyl)-2-(methylsulfonyl)propyl)urea NMR (CDCl₃) δ: 1.50 (3H, s), 1.56 (3H, s), 2.59 (3H, s), 2.97 (3H, s), 3.18-3.35 (4H, m), 3.71-3.90 (4H, m), 4.42 (2H, s), 5.58 (1H, d, J=9.8), 6.27 (1H, d, J=9.4), 6.72 (1H, s), 7.22-7.35 (4H, m), 7.65 (1H, s).

Elemental analysis for $C_{23}H_{30}ClN_7O_5S \cdot 0.8H_2O \cdot 0.2AcOEt$

Calcd. (%): C, 48.94; H, 5.73; N, 16.79.
Found (%): C, 48.97; H, 5.90; N, 16.50.

EXAMPLE 42

N—(4-chlorophenyl)—N'—((1S)-2-((2-methoxyethyl)thio)-2-methyl-1-((4-(5-methyl-3-oxo-1H-imidazo[1,5-c]imidazol-2(3H)-yl)-1-piperazinyl)carbonyl)propyl)urea

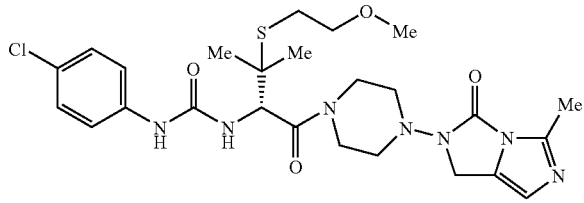

42a) (2S)-2-((tert-butoxycarbonyl)amino)-3-((2-methoxyethyl)thio)-3-methylbutanoic acid To a solution of D-penicillamine (2.98 g) and a 1 N aqueous sodium hydroxide solution (21 ml) in ethanol (20 ml) was added dropwise 2-methoxyethyl bromide (2.0 ml) while cooling to 0° C. The temperature of the mixture was elevated to room temperature, and mixed at room temperature for 15 hours. To the reaction mixture were added dropwise di-tert-butyl dicarbonate (5.1 ml) and a 1 N aqueous sodium hydroxide solution (22 ml), and mixed at room temperature for 15 hours. Ethanol was distilled off under reduced pressure, and then washed with diethyl ether. The aqueous layer was acidified with a 5% aqueous citric acid solution, and then extracted with ethyl acetate. The extract was washed with saturated brine and dried over anhydrous sodium sulfate. The solvent was distilled off under reduced pressure to obtain the title compound as a brown oil (6.3 g, quantitative).

NMR (CDCl₃) δ: 1.22-1.29 (6H, m), 1.45-1.46 (9H, s), 2.81-2.85 (1H, m), 3.41 (3H, m), 3.54-3.63 (2H, m), 4.34-4.38 (1H, m), 5.50-5.54 (1H, m), 6.34 (1H, s).

42b) tert-butyl (1S)-2-((2-methoxyethyl)thio)-2-methyl-1-((4-(5-methyl-3-oxo-1H-imidazo[1,5-c]imidazol-2(3H)-yl)-1-piperazinyl)carbonyl)propylcarbamate In the same manner as in Example 10a), the title compound as a colorless oil (0.36 g, 70%) was obtained from (2S)-2-((tert-butoxycarbonyl)amino)-3-((2-methoxyethyl)thio)-3-methylbutanoic acid (0.31 g) obtained in Example 42a).

NMR (CDCl₃) δ: 1.37-1.39 (6H, m), 1.45 (9H, s), 2.60 (3H, s), 2.74-2.81 (1H, m), 3.12-3.60 (8H, m), 3.36 (3H, s), 3.73-3.86 (4H, m), 4.43 (2H, s), 4.67-4.77 (1H, m), 5.44-5.59 (1H, m), 6.71 (1H, s).

42c) N—(4-chlorophenyl)—N'—((1S)-2-((2-methoxyethyl)thio)-2-methyl-1-((4-(5-methyl-3-oxo-1H-imidazo[1,5-c]imidazol-2(3H)-yl)-1-piperazinyl)carbonyl)propyl)urea In the same manner as in Example 33b), the title compound as colorless powder (0.12 g, 29%) was obtained from tert-butyl(1S)-2-((2-methoxyethyl)thio)-2-methyl-1-((4-(5-methyl-3-oxo-1H-imidazo[1,5-c]imidazol-2(3H)-yl)-1-piperazinyl)carbonyl)propylcarbamate (0.37 g) obtained in Example 42b).

NMR (CDCl₃) δ: 1.42 (6H, m), 2.60 (3H, s), 2.77-2.82 (2H, m), 3.13-3.70 (6H, m), 3.37 (3H, s), 3.87-3.89 (4H, m), 4.41 (2H, s), 5.07 (1H, d, J=9.4), 6.15 (1H, d, J=9.4), 6.72 (1H, s), 7.20-7.30 (5H, m).

Elemental analysis for $C_{25}H_{34}ClN_7O_4S \cdot 0.5H_2O \cdot 0.1AcOEt$

Calcd. (%): C, 52.43; H, 6.20; N, 16.85.
Found (%): C, 52.35; H, 6.28; N, 16.55.

EXAMPLE 43

N—(4-chlorophenyl)—N'—(1-methyl-3-(4-(5-methyl-3-oxo-1H-imidazo[1,5-c]imidazol-2(3H)-yl)-1-piperidinyl)-3-oxopropyl)urea

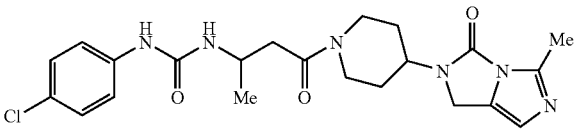

43a) tert-butyl 1-methyl-3-(4-(5-methyl-3-oxo-1H-imidazo[1,5-c]imidazol-2(3H)-yl)-1-piperidinyl)-3-oxopropylcarbamate In the same manner as in Example 6a), the title compound as colorless powder (0.37 g, 91%) was obtained from 3-((tert-butoxycarbonyl)amino)butanoic acid (0.20 g).

NMR (CDCl₃) δ: 1.20-1.28 (3H, m), 1.44 (9H, s), 1.89-1.93 (3H, m), 2.54-2.71 (3H, m), 2.61 (3H, s), 3.13-3.24 (1H, m), 3.98-4.22 (4H, m), 4.28-4.29 (2H, m), 4.77-4.82 (1H, m), 5.08 (1H, m), 6.71 (1H, s).

43b) N—(4-chlorophenyl)—N'—(1-methyl-3-(4-(5-methyl-3-oxo-1H-imidazo[1,5-c]imidazol-2(3H)-yl)-1-piperidinyl)-3-oxopropyl)urea In the same manner as in Example 33b), the title compound as colorless powder (65 mg, 20%) was obtained from tert-butyl 1-methyl-3-(4-(5-methyl-3-oxo-1H-imidazo[1,5-c]imidazol-2(3H)-yl)-1-piperidinyl)-3-oxopropylcarbamate (0.37 g) obtained in Example 43a).

NMR (CDCl₃) δ: 1.29-1.35 (3H, m), 1.77-1.97 (3H, m), 2.38-2.84 (3H, m), 2.59-2.60 (3H, m), 3.22-3.27 (1H, m), 3.95-4.33 (6H, m), 4.70-4.80 (1H, m), 5.31-5.56 (1H, m), 6.63-6.69 (1H, m), 7.20-7.34 (5H, m).

Elemental analysis for $C_{22}H_{27}ClN_6O_3 \cdot 0.5H_2O$

Calcd. (%): C, 56.47; H, 6.03; N, 17.96.
Found (%): C, 56.64; H, 5.89; N, 18.09.

EXAMPLE 44

N—(4-chlorophenyl)—N'—(2-methyl-3-(4-(5-methyl-3-oxo-1H-imidazo[1,5-c]imidazol-2(3H)-yl)-1-piperidinyl)-3-oxopropyl)urea

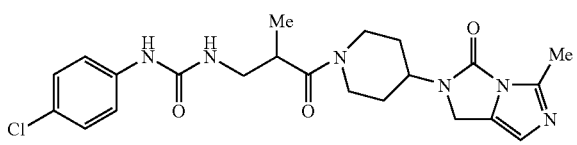

44a) tert-butyl 2-methyl-3-(4-(5-methyl-3-oxo-1H-imidazo[1,5-c]imidazol-2(3H)-yl)-1-piperidinyl)-3-oxopropylcarbamate In the same manner as in Example 6a), the title compound as a colorless oil (0.40 g, 99%) was obtained from 3-((tert-butoxycarbonyl)amino)-2-methylpropanoic acid (WO 0166530; 0.20 g).

NMR (CDCl$_3$) δ: 1.09-1.13 (3H, m), 1.43 (9H, s), 1.89-1.94 (3H, m), 2.61 (3H, s), 2.65-2.69 (1H, m), 3.03-3.26 (6H, m), 4.09-4.18 (2H, m), 4.28 (2H, s), 4.80-4.85 (1H, m), 5.08 (1H, m), 6.71 (1H, s).

44b) N—(4-chlorophenyl)—N'—(2-methyl-3-(4-(5-methyl-3-oxo-1H-imidazo[1,5-c]imidazol-2(3H)-yl)-1-piperidinyl)-3-oxopropyl)urea In the same manner as in Example 33b), the title compound as colorless powder (0.18 g, 51%) was obtained from tert-butyl 2-methyl-3-(4-(5-methyl-3-oxo-1H-imidazo[1,5-c]imidazol-2(3H)-yl)-1-piperidinyl)-3-oxopropylcarbamate (0.40 g) obtained in Example 44a).

NMR (CDCl$_3$) δ: 1.12-1.17 (3H, m), 1.48-2.03 (2H, m), 2.57-2.61 (3H, m), 2.61-2.71 (1H, m), 3.14-3.59 (5H, m), 3.89-4.77 (6H, m), 5.84-5.98 (1H, m), 6.60-6.71 (1H, m), 7.20-7.96 (5H, m).

Elemental analysis for C$_{22}$H$_{27}$ClN$_6$O$_3$.0.8H$_2$O$_3$.0.2AcOEt
Calcd. (%): C, 55.78; H, 6.20; N, 17.12.
Found (%): C, 55.99; H, 6.41; N, 16.88.

EXAMPLE 45

N—(4-chlorophenyl)—N'—(3-(4-(5-methyl-3-oxo-1H-imidazo[1,5-c]imidazol-2(3H)-yl)-1-piperidinyl)-3-oxo-1-phenylpropyl)urea

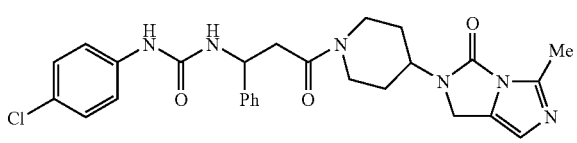

45a) tert-butyl 3-(4-(5-methyl-3-oxo-1H-imidazo[1,5-c]imidazol-2(3H)-yl)-1-piperidinyl)-3-oxo-1-phenylpropylcarbamate In the same manner as in Example 6a), the title compound as a colorless oil (0.47 g, quantitative) was obtained from 3-((tert-butoxycarbonyl)amino)-3-phenylpropanoic acid (A. R. Minter et al., J. Am. Chem. Soc., 125, 6846 (2003); 0.27 g).

NMR (CDCl$_3$) δ: 1.42 (9H, s), 1.57-1.83 (2H, m), 2.51-3.04 (6H, m), 2.59-2.60 (3H, m), 3.72-4.23 (4H, m), 4.72-4.77 (1H, m), 5.06-5.08 (1H, m), 5.83-6.52 (1H, m), 6.70-6.73 (1H, m), 7.23-7.39 (5H, m).

45b) N—(4-chlorophenyl)—N'—(3-(4-(5-methyl-3-oxo-1H-imidazo[1,5-c]imidazol-2(3H)-yl)-1-piperidinyl)-3-oxo-1-phenylpropyl)urea In the same manner as in Example 33b), the title compound as colorless powder (0.26 g, 52%) was obtained from tert-butyl 3-(4-(5-methyl-3-oxo-1H-imidazo[1,5-c]imidazol-2(3H)-yl)-1-piperidinyl)-3-oxo-1-phenylpropylcarbamate (0.47 g) obtained in Example 45a).

NMR (CDCl$_3$) δ: 1.37-2.08 (4H, m), 2.58 (3H, s), 2.67-3.40 (5H, m), 3.98-4.32 (4H, m), 4.69-4.73 (1H, m), 5.24-5.34 (1H, m), 6.63-6.71 (1H, m), 7.19-7.38 (10H, m).

Elemental analysis for C$_{27}$H$_{29}$ClN$_6$O$_3$.0.3H$_2$O
Calcd. (%): C, 61.60; H, 5.67; N, 15.96.
Found (%): C, 61.88; H, 5.60; N, 16.10.

EXAMPLE 46

N—(4-chlorophenyl)—N'—(3-(4-(5-methyl-3-oxo-1H-imidazo[1,5-c]imidazol-2(3H)-yl)-1-piperazinyl)-3-oxo-1-phenylpropyl)urea

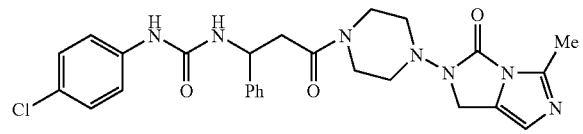

46a) tert-butyl 3-(4-(5-methyl-3-oxo-1H-imidazo[1,5-c]imidazol-2(3H)-yl)-1-piperazinyl)-3-oxo-1-phenylpropylcarbamate In the same manner as in Example 10a), the title compound as colorless powder (0.39 g, 83%) was obtained from 3-((tert-butoxycarbonyl)amino)-3-phenylpropanoic acid (0.27 g).

NMR (CDCl$_3$) δ: 1.42 (9H, s), 2.59 (3H, s), 2.60-2.74 (1H, m), 2.94-3.04 (4H, m), 3.36-3.75 (5H, m), 4.33 (2H, s), 5.05 (1H, m), 6.14 (1H, m), 6.72 (1H, s), 7.25-7.36 (5H, m).

46b) N—(4-chlorophenyl)—N'—(3-(4-(5-methyl-3-oxo-1H-imidazo[1,5-c]imidazol-2(3H)-yl)-1-piperazinyl)-3-oxo-1-phenylpropyl)urea In the same manner as in Example 33b), the title compound as colorless powder (0.18 g, 41%) was obtained from tert-butyl 3-(4-(5-methyl-3-oxo-1H-imidazo[1,5-c]imidazol-2(3H)-yl)-1-piperazinyl)-3-oxo-1-phenylpropylcarbamate (0.39 g) obtained in Example 46a).

NMR (CDCl$_3$+CD$_3$OD) δ: 2.59 (3H, s), 2.79-3.11 (6H, m), 3.47-3.73 (5H, m), 4.25-4.40 (2H, m), 5.25-5.29 (1H, m), 6.70 (1H, m), 7.19-7.40 (10H, m).

Elemental analysis for C$_{26}$H$_{28}$ClN$_7$O$_3$
Calcd. (%): C, 59.82; H, 5.41; N, 18.78.
Found (%): C, 59.62; H, 5.26; N, 18.65.

EXAMPLE 47

N—(4-chlorophenyl)—N'—(2,2-dimethyl-1-(2-(4-(5-methyl-3-oxo-1H-imidazo[1,5-c]imidazol-2(3H)-yl)-1-piperazinyl)-2-oxoethyl)propyl)urea

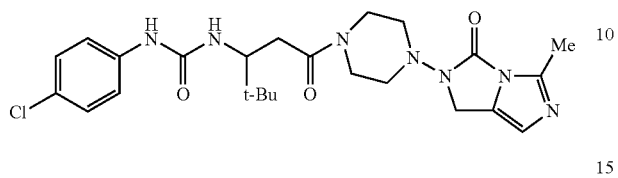

47a) 3-((tert-butoxycarbonyl)amino)-4,4-dimethyl-pentanoic acid 3-amino-4,4-dimethylpentanoic acid (0.51 g) and triethylamine (0.78 g) were dissolved in THF (10 ml) and water (10 ml), di-tert-butyl dicarbonate (0.71 g) was added thereto, and mixed at room temperature for 15 hours. The reaction mixture was concentrated under reduced pressure, washed with diethyl ether, acidified with a 5% aqueous citric acid solution, and then extracted with ethyl acetate. The extract was dried over anhydrous sodium sulfate and the solvent was distilled off under reduced pressure to obtain the title compound as colorless powder (0.65 g, 85%).

NMR (CDCl$_3$) δ: 0.93 (9H, s), 1.43 (9H, s), 2.60-2.67 (2H, m), 4.69-4.72 (1H, m), 5.54-5.56 (1H, m).

47b) tert-butyl 2,2-dimethyl-1-(2-(4-(5-methyl-3-oxo-1H-imidazo[1,5-c]imidazol-2(3H)-yl)-1-piperazinyl)-2-oxoethyl)propylcarbamate In the same manner as in Example 10a), the title compound as colorless powder (0.32 g, 71%) was obtained from 3-((tert-butoxycarbonyl)amino)-4,4-dimethylpentanoic acid (0.25 g) obtained in Example 47a).

NMR (CDCl$_3$) δ: 0.94 (9H, s), 1.44 (9H, s), 2.24-2.38 (2H, m), 2.61 (3H, s), 2.77-2.82 (1H, m), 2.98-3.33 (3H, m), 3.61-3.95 (5H, m), 4.38-4.53 (2H, m), 4.73-4.76 (1H, m), 6.72 (1H, s).

47c) N—(4-chlorophenyl)—N'—(2,2-dimethyl-1-(2-(4-(5-methyl-3-oxo-1H-imidazo[1,5-c]imidazol-2(3H)-yl)-1-piperazinyl)-2-oxoethyl)propyl)urea In the same manner as in Example 33b), the title compound as colorless powder (0.20 g, 60%) was obtained from tert-butyl 2,2-dimethyl-1-(2-(4-(5-methyl-3-oxo-1H-imidazo[1,5-c]imidazol-2(3H)-yl)-1-piperazinyl)-2-oxoethyl)propylcarbamate (0.30 g) obtained in Example 47b).

NMR (CDCl$_3$) δ: 0.99 (9H, s), 1.97 (1H, m), 2.28-2.37 (1H, m), 2.60 (3H, s), 2.82-3.14 (4H, m), 3.38-4.45 (8H, m), 5.69 (1H, br), 6.69 (1H, s), 7.17 (2H, d, J=8.7), 7.32 (2H, d, J=9.0).

Elemental analysis for C$_{24}$H$_{32}$ClN$_7$O$_3$
Calcd. (%): C, 57.42; H, 6.43; N, 19.53.
Found (%): C, 57.14; H, 6.46; N, 19.42.

EXAMPLE 48

N—(4-chlorophenyl)-3-((4-(5-methyl-3-oxo-1H-imidazo[1,5-c]imidazol-2(3H)-yl)-1-piperazinyl)carbonyl)-1-pyrrolidine carboxamide

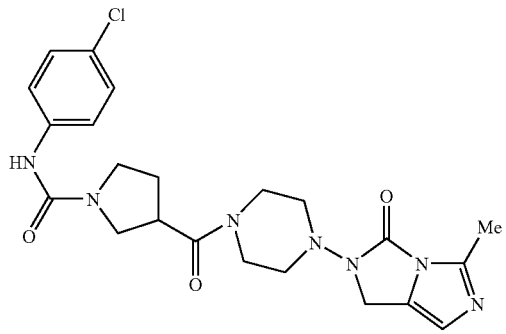

48a) tert-butyl 3-((4-(5-methyl-3-oxo-1H-imidazo[1,5-c]imidazol-2(3H)-yl)-1-piperazinyl)carbonyl)-1-pyrrolidinecarboxylate In the same manner as in Example 10a), the title compound as a colorless oil (0.31 g, 84%) was obtained from Boc-3-pyrrolidinecarboxylic acid (EP 307142; 0.19 g).

NMR (CDCl$_3$) δ: 1.46 (9H, s), 2.60 (3H, s), 3.21-3.79 (15H, m), 4.44 (2H, s), 6.72 (1H, s).

48b) N—(4-chlorophenyl)-3-((4-(5-methyl-3-oxo-1H-imidazo[1,5-c]imidazol-2(3H)-yl)-1-piperazinyl)carbonyl)-1-pyrrolidine carboxamide In the same manner as in Example 33b), the title compound as colorless powder (0.24 g, 71%) was obtained from tert-butyl 3-((4-(5-methyl-3-oxo-1H-imidazo[1,5-c]imidazol-2(3H)-yl)-1-piperazinyl)carbonyl)-1-pyrrolidinecarboxylate (0.30 g) obtained in Example 48a).

NMR (CDCl$_3$+CD$_3$OD) δ: 2.17-2.34 (2H, m), 2.61 (3H, s), 3.22-3.32 (4H, m), 3.45-3.53 (1H, m), 3.63-3.80 (8H, m), 4.45 (2H, s), 6.24 (1H, s), 6.71-6.73 (1H, m), 7.23-7.38 (4H, m).

Elemental analysis for C$_{22}$H$_{26}$ClN$_7$O$_3$.0.5H$_2$O.0.2AcOEt
Calcd. (%): C, 54.93; H, 5.78; N, 19.67.
Found (%): C, 54.84; H, 5.82; N, 19.53.

EXAMPLE 49

N—(4-chlorophenyl)-1-(2-(4-(5-methyl-3-oxo-1H-imidazo[1,5-c]imidazol-2(3H)-yl)-1-piperazinyl)-2-oxoethyl)-3,4-dihydro-2(1H)-isoquinoline carboxamide

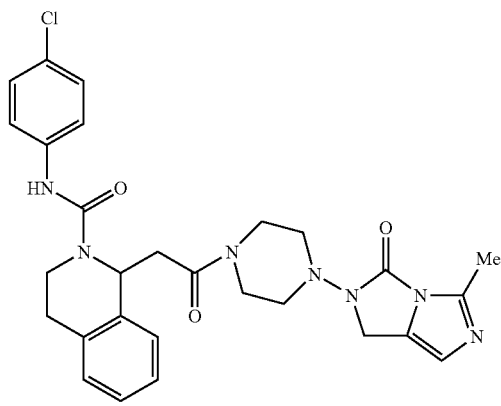

49a) tert-butyl 1-(2-(4-(5-methyl-3-oxo-1H-imidazo[1,5-c]imidazol-2(3H)-yl)-1-piperazinyl)-2-oxoethyl)-3,4-dihydro-2(1H)-isoquinolinecarboxylate In the same manner as in Example 10a), the title compound as colorless powder (0.40 g, 81%) was obtained from (2-(tert-butoxycarbonyl)-1,2,3,4-tetrahydro-1-isoquinolinyl)acetic acid (WO 0351869; 0.29 g).
NMR (CDCl$_3$) δ: 1.48 (9H, s), 2.61 (3H, s), 2.78-3.56 (10H, m), 3.74-4.00 (4H, m), 4.39-4.44 (2H, m), 5.52-5.58 (1H, m), 6.72 (1H, s), 7.14-7.22 (4H, m).

49b) N—(4-chlorophenyl)-1-(2-(4-(5-methyl-3-oxo-1H-imidazo[1,5-c]imidazol-2(3H)-yl)-1-piperazinyl)-2-oxoethyl)-3,4-dihydro-2(1H)-isoquinoline carboxamide In the same manner as in Example 33b), the title compound as colorless powder (0.22 g, 50%) was obtained from tert-butyl 1-(2-(4-(5-methyl-3-oxo-1H-imidazo[1,5-c]imidazol-2(3H)-yl)-1-piperazinyl)-2-oxoethyl)-3,4-dihydro-2(1H)-isoquinolinecarboxylate (0.39 g) obtained in Example 49a).
NMR (CDCl$_3$) δ: 2.60 (3H, s), 2.67-4.09 (13H, m), 4.40 (1H, m), 4.43 (2H, s), 5.57-5.60 (1H, m), 6.72 (1H, s), 7.10-7.43 (8H, m), 9.67 (1H, s).
Elemental analysis for C$_{28}$H$_{30}$ClN$_7$O$_3$.H$_2$O.0.3AcOEt
Calcd. (%): C, 59.19; H, 5.85; N, 16.55.
Found (%): C, 59.24; H, 5.73; N, 16.38.

EXAMPLE 50

N—(4-chlorophenyl)—N'—(2-(4-(5-methyl-3-oxo-1H-imidazo[1,5-c]imidazol-2(3H)-yl)-1-piperidinyl)-2-oxo-1-phenylethyl)urea

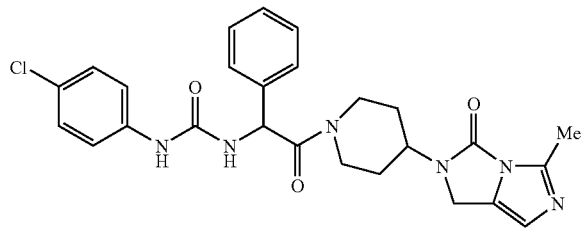

50a) tert-butyl 2-(4-(5-methyl-3-oxo-1H-imidazo[1,5-c]imidazol-2(3H)-yl)-1-piperidinyl)-2-oxo-1-phenylethylcarbamate Boc-phenylglycine (0.25 g) was dissolved in acetonitrile (10 ml). HOBt (0.23 g), WSC (0.29 g), triethylamine (0.2 ml) and 5-methyl-2-(4-piperidinyl)-1,2-dihydro-3H-imidazo[1,5-c]imidazol-3-one dihydrochloride (0.29 g) were added thereto, and mixed at room temperature for 15 hours. The solvent was distilled off under reduced pressure, and the residue was dissolved in ethyl acetate. The ethyl acetate solution was washed with a saturated aqueous sodium hydrogen carbonate solution and dried over anhydrous magnesium sulfate. The solvent was distilled off under reduced pressure to obtain the title compound as a green oil (0.43 g, 95%).
NMR (CDCl$_3$) δ: 1.41-1.42 (9H, m), 1.67-2.01 (2H, m), 2.55-3.13 (5H, m), 3.77-4.28 (6H, m), 4.82 (1H, d, J=11.7), 5.56-5.62 (1H, m), 5.96-6.11 (1H, m), 6.66-6.73 (1H, m), 7.22-7.43 (5H, m).

50b) 2-(1-(2-amino-2-phenylacetyl)-4-piperidinyl)-5-methyl-1,2-dihydro-3H-imidazo[1,5-c]imidazol-3-one tert-Butyl 2-(4-(5-methyl-3-oxo-1H-imidazo[1,5-c]imidazol-2(3H)-yl)-1-piperidinyl)-2-oxo-1-phenylethylcarbamate (0.43 g) obtained in Example 50a) was dissolved in concentrated hydrochloric acid (1.5 ml), and mixed at room temperature for 5 minutes. Ethyl acetate was added thereto, and the reaction mixture was washed with an aqueous sodium hydrogen carbonate solution and dried over anhydrous magnesium sulfate. The solvent was distilled off under reduced pressure to obtain the title compound as colorless powder (0.10 g, 31%).
NMR (CDCl$_3$) δ: 1.39-2.05 (7H, m), 2.56-3.05 (5H, m), 3.79-4.26 (4H, m), 4.75 (1H, s), 4.84-4.89 (1H, m), 6.65-6.71 (1H, m), 7.25-7.38 (5H, m).

50c) N—(4-chlorophenyl)—N'—(2-(4-(5-methyl-3-oxo-1H-imidazo[1,5-c]imidazol-2(3H)-yl)-1-piperidinyl)-2-oxo-1-phenylethyl)urea 2-(1-(2-Amino-2-phenylacetyl)-4-piperidinyl)-5-methyl-1,2-dihydro-3H-imidazo[1,5-c]imidazol-3-one (0.10 g) obtained in Example 50b) was dissolved in DMF (3.0 ml), 4-chlorophenyl isocyanate (0.05 g) was added thereto, and mixed at room temperature for 1 hour. The reaction mixture was dissolved in ethyl acetate, washed with an aqueous sodium hydrogen carbonate solution and dried over anhydrous magnesium sulfate. The solvent was distilled off under reduced pressure, and the residue was purified with basic silica gel column (ethyl acetate to methanol/ethyl acetate=1/10). The product was crystallized from ethyl acetate-diethyl ether to obtain the title compound as colorless powder (0.09 g, 59%).
NMR (CDCl$_3$) δ: 1.43-1.79 (3H, m), 2.43-2.46 (3H, m), 2.68-3.24 (3H, m), 3.88-4.57 (5H, m), 5.75-5.82 (1H, m), 6.69-6.73 (1H, m), 7.01-7.11 (1H, m), 7.23-7.50 (9H, m), 8.96-8.99 (1H, m).
Elemental analysis for C$_{26}$H$_{27}$ClN$_6$O$_3$.H$_2$O
Calcd. (%): C, 59.48; H, 5.57; N, 16.01.
Found (%): C, 59.83; H, 5.61; N, 15.71.

EXAMPLE 51

N—(4-chlorophenyl)—N'—(2-(4-(5-methyl-3-oxo-1H-imidazo[1,5-c]imidazol-2(3H)-yl)-1-piperidinyl)-2-oxo-1-(2-thienyl)ethyl)urea

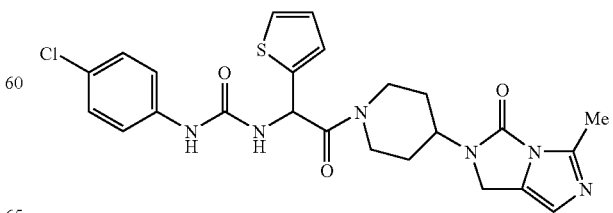

51a) ((tert-butoxycarbonyl)amino)(2-thienyl)acetic acid

Amino(2-thienyl)acetic acid (1.0 g) was dissolved in THF (6 ml) and water (6 ml). Triethylamine (1.3 ml) and di-tert-butyl dicarbonate (1.6 ml) were added thereto, and mixed at room temperature for 15 hours. The solvent was distilled off under reduced pressure, and the residue was dissolved in water and washed with ethyl acetate. Then, the aqueous layer was concentrated to obtain the title compound as a dark brown oil (1.67 g, quantitative).

NMR (CDCl$_3$) δ: 1.42 (9H, s), 5.34 (1H, d, J=6.6), 6.00 (1H, s), 6.88-6.92 (1H, m), 7.07-7.27 (2H, m).

51b) tert-butyl (2-(4-(5-methyl-3-oxo-1H-imidazo[1,5-c]imidazol-2(3H)-yl)-1-piperidinyl)-2-oxo-1-(2-thienyl)ethyl)carbamate In the same manner as in Example 50a), the title compound as pale brown powder (0.32 g, 34%) was obtained from ((tert-butoxycarbonyl)amino)(2-thienyl)acetic acid (0.52 g) obtained in Example 51a).

NMR (CDCl$_3$) δ: 1.43-1.45 (9H, m), 1.50-1.97 (5H, m), 2.58-2.60 (3H, m), 2.68-2.77 (1H, m), 2.91-3.22 (1H, m), 3.92-4.02 (2H, m), 4.21-4.28 (1H, m), 4.80-4.85 (1H, m), 5.86-6.05 (2H, m), 6.67-6.72 (1H, m), 6.95-7.12 (2H, m), 7.26-7.31 (1H, m).

51c) N—(4-chlorophenyl)—N'—(2-(4-(5-methyl-3-oxo-1H-imidazo[1,5-c]imidazol-2(3H)-yl)-1-piperidinyl)-2-oxo-1-(2-thienyl)ethyl)urea To tert-butyl(2-(4-(5-methyl-3-oxo-1H-imidazo[1,5-c]imidazol-2(3H)-yl)-1-piperidinyl)-2-oxo-1-(2-thienyl)ethyl)carbamate (0.32 g) obtained in Example Sib) was added a 4 N solution of hydrogen chloride in ethyl acetate (2.6 ml), mixed at room temperature for 5 minutes, and then concentrated under reduced pressure. The residue was dissolved in acetonitrile (5 ml), triethylamine (0.14 ml) and 4-chlorophenyl isocyanate (0.08 g) were added thereto, and mixed at room temperature for 3 hours. The solvent was distilled off under reduced pressure, and the residue was dissolved in ethyl acetate. The ethyl acetate solution was washed with an aqueous sodium hydrogen carbonate solution and dried over anhydrous magnesium sulfate. The solvent was distilled off under reduced pressure, and the residue was purified with basic silica gel column (ethyl acetate to ethyl acetate/methanol=10/1). The product was crystallized from ethyl acetate-diethyl ether to obtain the title compound as colorless powder (0.11 g, 42%).

NMR (CDCl$_3$) δ: 1.45-1.91 (5H, m), 2.58-2.60 (3H, m), 2.70-3.28 (2H, m), 4.01-4.25 (4H, m), 4.75-4.82 (1H, m), 6.18-6.22 (1H, m), 6.68-6.73 (2H, m), 6.92-7.60 (7H, m).

Elemental analysis for C$_{24}$H$_{25}$ClN$_6$O$_3$S.0.5H$_2$O

Calcd. (%): C, 55.22; H, 5.02; N, 16.10.

Found (%): C, 54.89; H, 4.73; N, 15.72.

EXAMPLE 52

N—(4-chlorophenyl)—N'—(2-(4-(5-methyl-3-oxo-1H-imidazo[1,5-c]imidazol-2(3H)-yl)-1-piperazinyl)-2-oxo-1-(2-thienyl)ethyl)urea

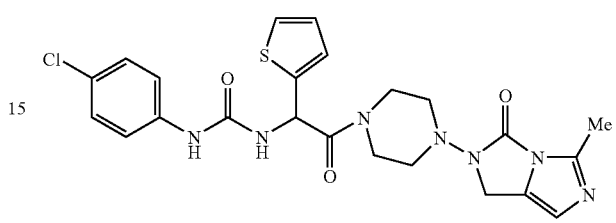

52a) tert-butyl (2-(4-(5-methyl-3-oxo-1H-imidazo[1,5-c]imidazol-2(3H)-yl)-1-piperazinyl)-2-oxo-1-(2-thienyl)ethyl)carbamate ((tert-butoxycarbonyl)amino)(2-thienyl)acetic acid (0.26 g) obtained in Example 51a) was dissolved in acetonitrile (10 ml). HOBt (0.23 g), WSC (0.29 g), triethylamine (0.14 ml) and 5-methyl-2-(1-piperazinyl)-1,2-dihydro-3H-imidazo[1,5-c]imidazol-3-one (0.26 g) obtained in Reference Example 2 were added thereto, and mixed at room temperature for 15 hours. The solvent was distilled off under reduced pressure, and the residue was dissolved in ethyl acetate. The ethyl acetate solution was washed with a saturated aqueous sodium hydrogen carbonate solution and dried over anhydrous magnesium sulfate. Then, the solvent was distilled off under reduced pressure to obtain the title compound as a brown oil (0.24 g, 52%).

NMR (CDCl$_3$) δ: 1.44-1.45 (9H, m), 2.59 (3H, s), 2.76-3.18 (3H, m), 3.53-3.67 (1H, m), 3.78-3.94 (3H, m), 4.36 (2H, s), 5.50-5.62 (1H, m), 5.84-5.99 (1H, m), 6.70 (1H, s), 6.96-6.99 (1H, m), 7.03-7.06 (1H, m), 7.25-7.30 (2H, m).

52b) N—(4-chlorophenyl)—N'—(2-(4-(5-methyl-3-oxo-1H-imidazo[1,5-c]imidazol-2(3H)-yl)-1-piperazinyl)-2-oxo-1-(2-thienyl)ethyl)urea In the same manner as in Example 51c), the title compound as pale brown powder (0.05 g, 20%) was obtained from tert-butyl (2-(4-(5-methyl-3-oxo-1H-imidazo[1,5-c]imidazol-2(3H)-yl)-1-piperazinyl)-2-oxo-1-(2-thienyl)ethyl)carbamate (0.24 g) obtained in Example 52a).

NMR (CDCl$_3$) δ: 2.58 (3H, s), 2.89-2.92 (1H, m), 3.07-3.20 (3H, m), 3.63-3.72 (3H, m), 3.91-3.98 (1H, m), 4.36 (2H, s), 6.16-6.18 (1H, m), 6.70-6.72 (2H, m), 6.94-6.99 (2H, m), 7.15-7.23 (4H, m), 7.28-7.30 (1H, m), 7.48 (1H, s).

Elemental analysis for C$_{23}$H$_{24}$ClN$_7$O$_3$S.0.5H$_2$O

Calcd. (%): C, 52.82; H, 4.82; N, 18.75.

Found (%): C, 52.77; H, 4.66; N, 18.49.

EXAMPLE 53

N—(4-chlorophenyl)—N'—((1R)-1-(4-cyanobenzyl)-2-(4-(5-methyl-3-oxo-1H-imidazo[1,5-c]imidazol-2(3H)-yl)-1-piperidinyl)-2-oxoethyl)urea

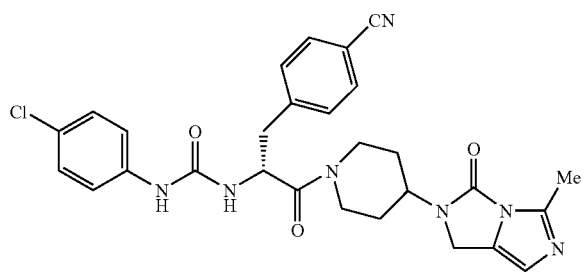

53a) (2R)-2-((tert-butoxycarbonyl)amino)-3-(4-cyanophenyl)propanoic acid

In the same manner as in Example 51a), the title compound as a green oil (1.5 g, quantitative) was obtained from (2R)-2-amino-3-(4-cyanophenyl)propanoic acid (1.0 g).

NMR (CDCl$_3$) δ: 1.41 (9H, s), 3.07-3.30 (2H, m), 4.35-4.37 (1H, m), 5.44 (1H, d, J=6.2), 7.33 (2H, d, J=8.0), 7.52 (2H, d, J=8.0).

53b) tert-butyl(1R)-1-(4-cyanobenzyl)-2-(4-(5-methyl-3-oxo-1H-imidazo[1,5-c]imidazol-2(3H)-yl)-1-piperidinyl)-2-oxoethylcarbamate In the same manner as in Example 50a), the title compound as colorless powder (0.47 g, 48%) was obtained from (2R)-2-((tert-butoxycarbonyl)amino)-3-(4-cyanophenyl)propanoic acid (0.58 g) obtained in Example 53a).

NMR (CDCl$_3$) δ: 1.41 (9H, s), 1.64-1.88 (5H, m), 2.60 (3H, s), 2.81-3.15 (3H, m), 3.97-4.23 (3H, m), 4.68-4.78 (1H, m), 4.85-4.91 (1H, m), 5.30-5.41 (1H, m), 6.71-6.76 (1H, m), 7.28-7.31 (2H, m), 7.39-7.42 (1H, m), 7.58-7.66 (2H, m).

53c) N—(4-chlorophenyl)—N'—((1R)-1-(4-cyanobenzyl)-2-(4-(5-methyl-3-oxo-1H-imidazo[1,5-c]imidazol-2(3H)-yl)-1-piperidinyl)-2-oxoethyl)urea In the same manner as in Example 51c), the title compound as colorless powder (0.11 g, 40%) was obtained from tert-butyl(1R)-1-(4-cyanobenzyl)-2-(4-(5-methyl-3-oxo-1H-imidazo[1,5-c]imidazol-2(3H)-yl)-1-piperidinyl)-2-oxoethylcarbamate (0.47 g) obtained in Example 53b).

NMR (CDCl$_3$) δ: 1.59-1.90 (3H, m), 2.60 (3H, s), 2.67-2.88 (2H, m), 3.02-3.19 (3H, m), 4.00-4.24 (4H, m), 4.67-4.77 (1H, m), 5.19-5.30 (1H, m), 6.36-6.47 (1H, m), 6.70-6.77 (1H, m), 7.20-7.21 (4H, m), 7.28-7.43 (2H, m), 7.53-7.67 (3H, m).

Elemental analysis for C$_{28}$H$_{28}$ClN$_7$O$_3$.0.5H$_2$O
Calcd. (%): C, 60.59; H, 5.27; N, 17.67.
Found (%): C, 60.27; H, 5.17; N, 17.55.

EXAMPLE 54

N—((1R)-1-(4-(benzyloxy)benzyl)-2-(4-(5-methyl-3-oxo-1H-imidazo[1,5-c]imidazol-2(3H)-yl)-1-piperidinyl)-2-oxoethyl)—N'—(4-chlorophenyl)urea

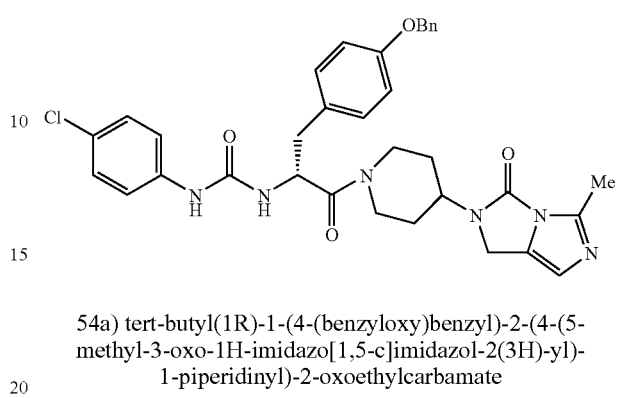

54a) tert-butyl(1R)-1-(4-(benzyloxy)benzyl)-2-(4-(5-methyl-3-oxo-1H-imidazo[1,5-c]imidazol-2(3H)-yl)-1-piperidinyl)-2-oxoethylcarbamate In the same manner as in Example 50a), the title compound as colorless powder (0.57 g, 99%) was obtained from (2R)-3-(4-(benzyloxy)phenyl)-2-((tert-butoxycarbonyl)amino)propanoic acid (0.37 g).

NMR (CDCl$_3$) δ: 1.43-1.44 (9H, m), 1.53-1.74 (2H, m), 2.49-2.60 (4H, m), 2.81-3.16 (4H, m), 3.89-4.20 (4H, m), 4.69-5.07 (4H, m), 5.42-5.50 (1H, m), 6.28-6.69 (1H, m), 6.83-7.10 (3H, m), 7.22-7.45 (7H, m).

54b) N—((1R)-1-(4-(benzyloxy)benzyl)-2-(4-(5-methyl-3-oxo-1H-imidazo[1,5-c]imidazol-2(3H)-yl)-1-piperidinyl)-2-oxoethyl)—N'—(4-chlorophenyl)urea In the same manner as in Example 51c), the title compound as colorless powder (0.31 g, 50%) was obtained from tert-butyl(1R)-1-(4-(benzyloxy)benzyl)-2-(4-(5-methyl-3-oxo-1H-imidazo[1,5-c]imidazol-2(3H)-yl)-1-piperidinyl)-2-oxoethylcarbamate (0.57 g) obtained in Example 54a).

NMR (CDCl$_3$) δ: 1.15-1.28 (1H, m), 1.49-1.85 (3H, m), 2.49-2.70 (4H, m), 2.90-3.17 (3H, m), 3.93-4.24 (5H, m), 4.69-4.72 (1H, m), 5.01-5.15 (3H, m), 6.32 (1H, s), 6.86-7.42 (13H, m), 8.01-8.21 (1H, m).

Elemental analysis for C$_{33}$H$_{34}$ClN$_7$O$_4$.H$_2$O
Calcd. (%): C, 63.30; H, 5.78; N, 13.03.
Found (%): C, 63.08; H, 5.63; N, 12.97.

EXAMPLE 55

N—(4-chlorophenyl)—N'—((1R)-1-(4-hydroxybenzyl)-2-(4-(5-methyl-3-oxo-1H-imidazo[1,5-c]imidazol-2(3H)-yl)-1-piperidinyl)-2-oxoethyl)urea trifluoroacetate

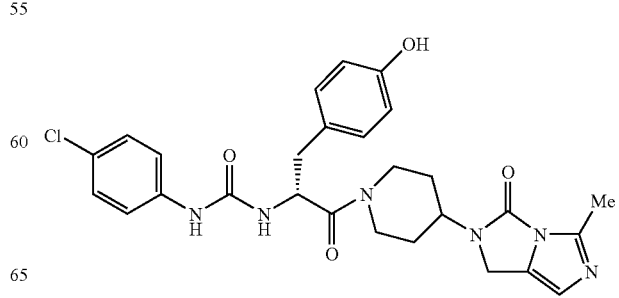

N—((1R)-1-(4-(benzyloxy)benzyl)-2-(4-(5-methyl-3-oxo-1H-imidazo[1,5-c]imidazol-2(3H)-yl)-1-piperidinyl)-2-oxoethyl)—N'—(4-chlorophenyl)urea (0.10 g) obtained in Example 54 was dissolved in THF (5 ml). Palladium hydroxide (0.05 g) was added thereto, and mixed under hydrogen atmosphere at room temperature for 1 week. Palladium hydroxide was filtered off, and the filtrate was distilled off under reduced pressure. The residue was purified with preparative high-performance liquid chromatography to obtain the title compound as colorless powder (0.03 g, 33%).

NMR (DMSO-d$_6$) δ: 1.15-1.23 (1H, m), 1.60-1.91 (2H, m), 2.50 (3H, s), 2.66 (2H, s), 2.72-3.14 (3H, m), 3.92-4.04 (2H, m), 4.22-4.53 (4H, m), 4.84-4.92 (1H, m), 6.51-6.76 (3H, m), 6.95-7.07 (2H, m), 7.23-7.41 (5H, m), 8.83-8.92 (1H, m).

Elemental analysis for C$_{27}$H$_{29}$ClN$_6$O$_4$.CF$_3$COOH.2H$_2$O
Calcd. (%): C, 50.70; H, 4.99; N, 12.23.
Found (%): C, 50.43; H, 4.89; N, 11.94.

EXAMPLE 56

N—(4-chlorophenyl)—N'—((1R)-2-(4-(5-methyl-3-oxo-1H-imidazo[1,5-c]imidazol-2(3H)-yl)-1-piperidinyl)-2-oxo-1-(3-pyridinyl)methylethyl)urea

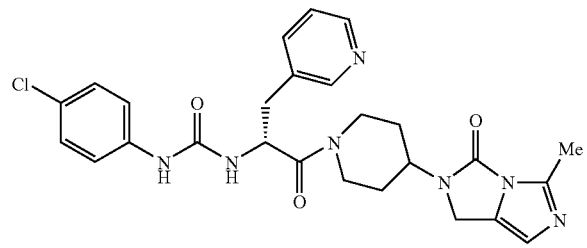

56a) tert-butyl(1R)-2-(4-(5-methyl-3-oxo-1H-imidazo[1,5-c]imidazol-2(3H)-yl)-1-piperidinyl)-2-oxo-1-(3-pyridinyl)methylethylcarbamate In the same manner as in Example 50a), the title compound as a colorless oil (0.26 g, 72%) was obtained from (2R)-2-((tert-butoxycarbonyl)amino)-3-(3-pyridinyl)propanoic acid (0.21 g).

NMR (CDCl$_3$) δ: 1.42-1.43 (9H, m), 1.54-1.87 (4H, m), 2.59-2.60 (3H, m), 2.97-3.10 (3H, m), 4.03-4.23 (4H, m), 4.73-4.88 (2H, m), 5.42-5.47 (1H, m), 6.70-6.72 (1H, m), 7.21-7.34 (1H, m), 7.50-7.52 (1H, m), 7.61-7.67 (1H, m), 8.42-8.54 (2H, m).

56b) N—(4-chlorophenyl)—N'—((1R)-2-(4-(5-methyl-3-oxo-1H-imidazo[1,5-c]imidazol-2(3H)-yl)-1-piperidinyl)-2-oxo-1-(3-pyridinyl)methylethyl)urea In the same manner as in Example 51c), the title compound as colorless powder (0.01 g, 2%) was obtained from tert-butyl(1R)-2-(4-(5-methyl-3-oxo-1H-imidazo[1,5-c]imidazol-2(3H)-yl)-1-piperidinyl)-2-oxo-1-(3-pyridinyl)methylethylcarbamate (0.26 g) obtained in Example 56a).

NMR (CDCl$_3$) δ: 1.64-2.05 (4H, m), 2.06 (3H, s), 2.67-3.14 (4H, m), 4.07-4.24 (4H, m), 4.07-4.77 (1H, m), 5.19-5.22 (1H, m), 6.45-6.57 (1H, m), 6.70-6.74 (1H, m), 7.19-7.32 (5H, m), 7.52-7.68 (2H, m), 8.44-8.56 (2H, m).

EXAMPLE 57

N—(4-chlorophenyl)—N'—((1R)-2-(4-(5-methyl-3-oxo-1H-imidazo[1,5-c]imidazol-2(3H)-yl)-1-piperazinyl)-2-oxo-1-(4-pyridinyl)methylethyl)urea

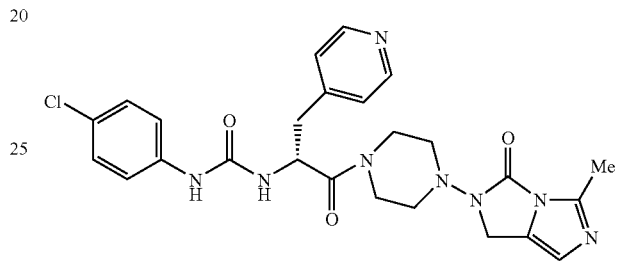

57a) tert-butyl(1R)-2-(4-(5-methyl-3-oxo-1H-imidazo[1,5-c]imidazol-2(3H)-yl)-1-piperazinyl)-2-oxo-1-(4-pyridinyl)methylethylcarbamate In the same manner as in Example 52a), the title compound as colorless powder (0.32 g, 68%) was obtained from (2R)-2-((tert-butoxycarbonyl)amino)-3-(4-pyridinyl)propanoic acid (0.27 g).

NMR (CDCl$_3$) δ: 1.42 (9H, s), 2.59 (3H, s), 2.98-3.72 (7H, m), 3.30-3.72 (3H, m), 2.23 (2H, s), 4.83-4.91 (1H, m), 5.40-5.43 (1H, m), 6.71 (1H, s), 7.12-7.19 (2H, m), 8.53-8.57 (2H, m).

57b) N—(4-chlorophenyl)—N'—((1R)-2-(4-(5-methyl-3-oxo-1H-imidazo[1,5-c]imidazol-2(3H)-yl)-1-piperazinyl)-2-oxo-1-(4-pyridinyl)methylethyl)urea tritrifluoroacetate In the same manner as in Example 51c), the title compound as pale yellow powder (0.13 g, 21%) was obtained from tert-butyl(1R)-2-(4-(5-methyl-3-oxo-1H-imidazo[1,5-c]imidazol-2(3H)-yl)-1-piperazinyl)-2-oxo-1-(4-pyridinyl)methylethylcarbamate (0.32 g) obtained in Example 57a).

NMR (CDCl$_3$) δ: 2.80 (3H, s), 2.99-3.93 (6H, m), 3.61-3.83 (6H, m), 4.58 (2H, s), 5.16 (1H, t, J=6.6), 7.11 (1H, s), 7.18-7.28 (4H, m), 7.86 (2H, d, J=6.2), 8.67 (2H, d, J=6.2).

Elemental analysis for C$_{25}$H$_{27}$ClN$_8$O$_3$.3CF$_3$COOH
Calcd. (%): C, 43.04; H, 3.50; N, 12.95.
Found (%): C, 43.08; H, 3.81; N, 12.93.

EXAMPLE 58

N—(4-chlorophenyl)—N'—((1R)-2-(4-(5-methyl-3-oxo-1H-imidazo[1,5-c]imidazol-2(3H)-yl)-1-piperidinyl)-2-oxo-1-(2-thienyl)methylethyl)urea trifluoroacetate

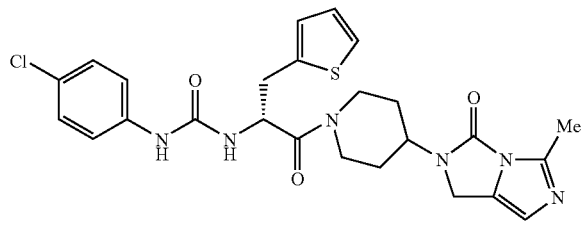

58a) tert-butyl (2R)-3-(4-(5-methyl-3-oxo-1H-imidazo[1,5-c]imidazol-2(3H)-yl)-1-piperidinyl)-3-oxo-2-(2-thienyl)methylpropanoate In the same manner as in Example 50a), the title compound as a colorless oil (0.43 g, 91%) was obtained from (2R)-2-((tert-butoxycarbonyl)amino)-3-(2-thienyl)propanoic acid (0.27 g).

NMR (CDCl$_3$) δ: 1.44 (9H, s), 1.55-1.83 (4H, m), 2.43-2.75 (5H, m), 3.04-3.43 (3H, m), 4.01-4.23 (3H, m), 4.73-4.95 (2H, m), 5.42-5.53 (1H, m), 6.70-6.73 (1H, m), 6.82-7.00 (2H, m), 7.13-7.22 (1H, m).

58b) N—(4-chlorophenyl)—N'—((1R)-2-(4-(5-methyl-3-oxo-1H-imidazo[1,5-c]imidazol-2(3H)-yl)-1-piperidinyl)-2-oxo-1-(2-thienyl)methylethyl)urea trifluoroacetate In the same manner as in Example 51c), the title compound as colorless powder (0.20 g, 41%) was obtained from tert-butyl (2R)-3-(4-(5-methyl-3-oxo-1H-imidazo[1,5-c]imidazol-2(3H)-yl)-1-piperidinyl)-3-oxo-2-(2-thienyl)methylpropanoate (0.43 g) obtained in Example 58a).

NMR (CDCl$_3$) δ: 1.36-1.92 (3H, m), 2.45-2.73 (4H, m), 3.00-3.55 (4H, m), 4.01 (2H, s), 4.22-4.35 (2H, m), 4.46-4.50 (1H, m), 4.92-4.97 (1H, m), 6.65-6.69 (2H, m), 6.86-7.03 (2H, m), 7.25-7.51 (5H, m), 8.92-9.16 (1H, m).

Elemental analysis for C$_{25}$H$_{27}$ClN$_6$O$_3$S.CF$_3$COOH.1.5H$_2$O
Calcd. (%): C, 48.54; H, 4.68; N, 12.58.
Found (%): C, 48.41; H, 4.67; N, 12.18.

EXAMPLE 59

N—(4-chlorophenyl)—N'—((1R)-1-((4-(5-methyl-3-oxo-1H-imidazo[1,5-c]imidazol-2(3H)-yl)-1-piperidinyl)carbonyl)propyl)urea

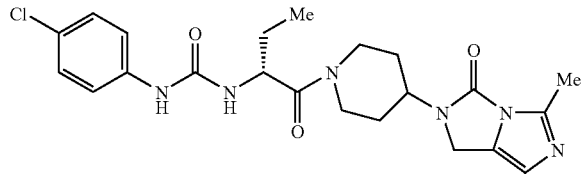

59a) tert-butyl(1R)-1-((4-(5-methyl-3-oxo-1H-imidazo[1,5-c]imidazol-2(3H)-yl)-1-piperidinyl)carbonyl)propylcarbamate In the same manner as in Example 50a), the title compound as a pale yellow oil (0.41 g, quantitative) was obtained from (2R)-2-((tert-butoxycarbonyl)amino)butanoic acid (0.23 g).

NMR (CDCl$_3$) δ: 0.91-0.99 (3H, m), 1.44-1.45 (9H, m), 1.50-2.05 (6H, m), 2.61 (3H, s), 2.65-2.74 (1H, m), 3.14-3.26 (1H, m), 4.07-4.29 (4H, m), 4.54-4.61 (1H, m), 4.77-4.81 (1H, m), 5.41-5.44 (1H, m), 6.71 (1H, s).

59b) N—(4-chlorophenyl)—N'—((1R)-1-((4-(5-methyl-3-oxo-1H-imidazo[1,5-c]imidazol-2(3H)-yl)-1-piperidinyl)carbonyl)propyl)urea In the same manner as in Example 51c), the title compound as colorless powder (0.24 g, 51%) was obtained from tert-butyl(1R)-1-((4-(5-methyl-3-oxo-1H-imidazo[1,5-c]imidazol-2(3H)-yl)-1-piperidinyl)carbonyl)propylcarbamate (0.44 g) obtained in Example 59a).

NMR (CDCl$_3$) δ: 1.01-1.08 (3H, m), 1.64-2.10 (5H, m), 2.66-2.67 (3H, m), 2.71-3.36 (3H, m), 4.09-4.33 (3H, m), 4.79-4.83 (2H, m), 6.59-6.68 (1H, m), 6.82-6.96 (1H, m), 7.12-7.29 (5H, m), 7.81-7.98 (1H, m).

Elemental analysis for C$_{22}$H$_{27}$ClN$_6$O$_3$.H$_2$O.0.1AcOEt
Calcd. (%): C, 55.38; H, 6.18; N, 17.30.
Found (%): C, 55.72; H, 6.10; N, 17.44.

EXAMPLE 60

N—(4-chlorophenyl)—N'—((1R)-1-((4-(5-methyl-3-oxo-1H-imidazo[1,5-c]imidazol-2(3H)-yl)-1-piperidinyl)carbonyl)butyl)urea trifluoroacetate

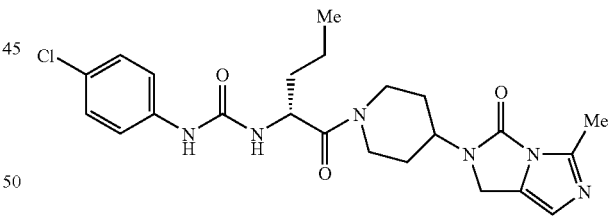

60a) tert-butyl(1R)-1-((4-(5-methyl-3-oxo-1H-imidazo[1,5-c]imidazol-2(3H)-yl)-1-piperidinyl)carbonyl)butylcarbamate In the same manner as in Example 50a), the title compound as a colorless oil (0.41 g, 97%) was obtained from (2R)-2-((tert-butoxycarbonyl)amino)pentanoic acid (0.22 g).

NMR (CDCl$_3$) δ: 0.94-0.96 (3H, m), 1.44 (9H, s), 1.62-1.83 (4H, m), 2.61-2.73 (5H, m), 3.19-3.49 (2H, m), 4.09-4.29 (6H, m), 4.61-4.76 (2H, m), 5.36-5.38 (1H, m), 6.71 (1H, s).

60b) N—(4-chlorophenyl)—N'—((1R)-1-((4-(5-methyl-3-oxo-1H-imidazo[1,5-c]imidazol-2(3H)-yl)-1-piperidinyl)carbonyl)butyl)urea trifluoroacetate In the same manner as in Example 51c), the title compound as colorless powder (0.20 g, 43%) was obtained from tert-butyl(1R)-1-((4-(5-methyl-3-oxo-1H-imidazo[1,5-c]imidazol-2(3H)-yl)-1-piperidinyl)carbonyl)butylcarbamate (0.41 g) obtained in Example 60a).

NMR (DMSO-d$_6$) δ: 0.89-0.91 (3H, m), 1.32-1.84 (8H, m), 2.67-2.76 (1H, m), 3.18-3.55 (4H, m), 4.04-4.08 (2H, m), 4.39-4.54 (3H, m), 4.70-4.78 (1H, m), 6.52 (1H, s), 6.73 (1H, s), 7.25-7.49 (4H, m), 8.86-8.97 (1H, m).

Elemental analysis for C$_{23}$H$_{29}$ClN$_6$O$_3$.1.5CF$_3$COOH.H$_2$O
Calcd. (%): C, 47.17; H, 4.95; N, 12.69.
Found (%): C, 47.38; H, 4.98; N, 12.59.

EXAMPLE 61

N—(4-chlorophenyl)—N'—((1R)-1-((4-(5-methyl-3-oxo-1H-imidazo[1,5-c]imidazol-2(3H)-yl)-1-piperidinyl)carbonyl)pentyl)urea hydrochloride

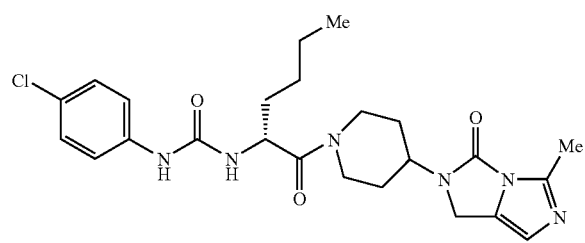

61a) tert-butyl(1R)-1-((4-(5-methyl-3-oxo-1H-imidazo[1,5-c]imidazol-2(3H)-yl)-1-piperidinyl)carbonyl)pentylcarbamate In the same manner as in Example 50a), the title compound as pale yellow powder (0.43 g, 98%) was obtained from (2R)-2-((tert-butoxycarbonyl)amino)hexanoic acid (0.25 g).

NMR (CDCl$_3$) δ: 0.88-0.91 (3H, m), 1.30-1.37 (5H, m), 1.44-1.45 (9H, m), 1.56-2.05 (5H, m), 2.61-2.74 (4H, m), 3.14-3.26 (1H, m), 4.07-4.28 (4H, m), 4.57-4.64 (1H, m), 4.76-4.81 (1H, m), 5.35-5.38 (1H, m), 6.72 (1H, s).

61b) N—(4-chlorophenyl)—N'—((1R)-1-((4-(5-methyl-3-oxo-1H-imidazo[1,5-c]imidazol-2(3H)-yl)-1-piperidinyl)carbonyl)pentyl)urea hydrochloride In the same manner as in Example 51c), the title compound as colorless powder (0.30 g, 59%) %) was obtained from tert-butyl(1R)-1-((4-(5-methyl-3-oxo-1H-imidazo[1,5-c]imidazol-2(3H)-yl)-1-piperidinyl)carbonyl)pentylcarbamate (0.43 g) obtained in Example 61a).

NMR (DMSO-d$_6$) δ: 0.84-0.89 (3H, m), 1.26-1.90 (10H, m), 2.74-2.75 (3H, m), 3.21 (1H, t, J=12.4), 4.00-4.09 (2H, m), 4.48-4.68 (5H, m), 6.60-6.70 (1, m), 7.25 (2H, d, J=8.7), 7.38-7.42 (2H, m), 7.52 (1H, s), 9.15-9.26 (1H, m).

Elemental analysis for C$_{24}$H$_{31}$ClN$_6$O$_3$.HCl.1.5H$_2$O
Calcd. (%): C, 52.36; H, 6.32; N, 15.27.
Found (%): C, 52.41; H, 6.46; N, 15.15.

EXAMPLE 62

N—((1R)-2,2-dimethyl-1-((4-(5-methyl-3-oxo-1H-imidazo[1,5-c]imidazol-2(3H)-yl)-1-piperazinyl)carbonyl)propyl)—N'—(4-methylphenyl)urea

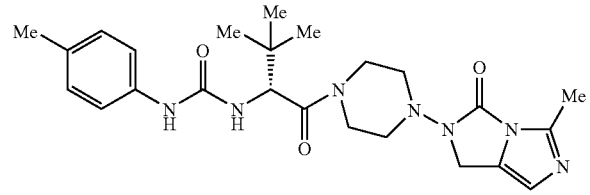

To tert-butyl(1R)-2,2-dimethyl-1-((4-(5-methyl-3-oxo-1H-imidazo[1,5-c]imidazol-2(3H)-yl)-1-piperazinyl)carbonyl)propylcarbamate (0.44 g) obtained in Example 20a) was added a 4 N solution of hydrogen chloride in ethyl acetate (4.0 ml), and mixed at room temperature for 5 minutes. Then, the solvent was distilled off under reduced pressure, and the residue was dissolved in acetonitrile (10 ml). Triethylamine (0.28 ml) and 4-tolyl isocyanate (0.13 ml) were added thereto, and mixed at room temperature for 3 hours. The solvent was distilled off under reduced pressure and the residue was dissolved in ethyl acetate. The ethyl acetate solution was washed with an aqueous sodium hydrogen carbonate solution and dried over anhydrous magnesium sulfate. The solvent was distilled off under reduced pressure, and the residue was purified with basic silica gel column (ethyl acetate to ethyl acetate/methanol=10/1). The product was crystallized from ethyl acetate-ether to obtain the title compound as colorless powder (0.25 g, 52%).

NMR (CDCl$_3$) δ: 1.04 (9H, s), 2.27 (3H, s), 2.59 (3H, s), 2.96-3.01 (1H, m), 3.08-3.19 (3H, m), 3.56-3.65 (1H, m), 3.73-3.79 (1H, m), 3.93-3.97 (2H, m), 4.26 (1H, d, J=15.9), 4.33 (1H, d, J=15.9), 4.89 (1H, d, J=9.3), 6.17 (1H, d, J=9.3), 6.69 (1H, s), 7.08 (2H, d, J=8.4), 7.13 (2H, J=8.4), 7.45 (1H, s).

Elemental analysis for C$_{24}$H$_{33}$N$_7$O$_3$.H$_2$O
Calcd. (%): C, 59.36; H, 7.27; N, 20.19.
Found (%): C, 59.12; H, 7.15; N, 19.80.

EXAMPLE 63

N—(4-chlorophenyl)—N'—((1R)-1-cyclohexyl-2-(4-(5-methyl-3-oxo-1H-imidazo[1,5-c]imidazol-2(3H)-yl)-1-piperidinyl)-2-oxoethyl)urea

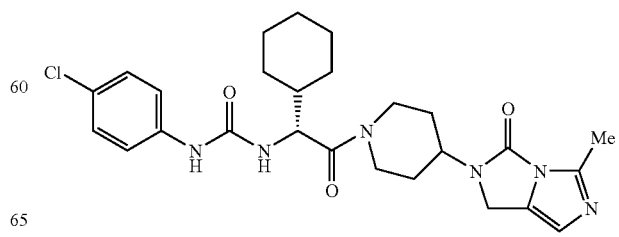

63a) tert-butyl((1R)-1-cyclohexyl-2-(4-(5-methyl-3-oxo-1H-imidazo[1,5-c]imidazol-2(3H)-yl)-1-piperidinyl)-2-oxoethyl)carbamate In the same manner as in Example 50a), the title compound as colorless powder (0.46 g, quantitative) was obtained from (2R)-((tert-butoxycarbonyl)amino)(cyclohexyl)acetic acid (0.26 g).

NMR (CDCl$_3$) δ: 1.14-1.34 (4H, m), 1.43-1.44 (9H, m), 1.53-1.82 (8H, m), 2.61-2.73 (3H, m), 3.14-3.49 (2H, m), 4.09-4.29 (4H, m), 4.47-4.50 (1H, m), 4.78-4.82 (1H, m), 5.27-5.30 (1H, m), 6.71 (1H, s).

63b) N—(4-chlorophenyl)—N'—((1R)-1-cyclohexyl-2-(4-(5-methyl-3-oxo-1H-imidazo[1,5-c]imidazol-2(3H)-yl)-1-piperidinyl)-2-oxoethyl)urea In the same manner as in Example 51c), the title compound as colorless powder (0.15 g, 27%) was obtained from tert-butyl((1R)-1-cyclohexyl-2-(4-(5-methyl-3-oxo-1H-imidazo[1,5-c]imidazol-2(3H)-yl)-1-piperidinyl)-2-oxoethyl)carbamate (0.46 g) obtained in Example 63a).

NMR (CDCl$_3$) δ: 1.14-1.21 (5H, m), 1.59-1.99 (11H, m), 2.73 (3H, s), 3.23-3.30 (1H, m), 4.01-4.12 (2H, m), 4.50-4.63 (4H, m), 6.56-6.61 (1H, m), 7.23-7.50 (5H, m), 9.08-9.17 (1H, m).

Elemental analysis for C$_{26}$H$_{33}$ClN$_6$O$_3$.0.6H$_2$O
Calcd. (%): C, 55.73; H, 6.33; N, 15.00.
Found (%): C, 55.68; H, 6.52; N, 14.63.

EXAMPLE 64

N—(4-chlorophenyl)—N'—((1R)-1-cyclohexyl-2-(4-(5-methyl-3-oxo-1H-imidazo[1,5-c]imidazol-2(3H)-yl)-1-piperazinyl)-2-oxoethyl)urea

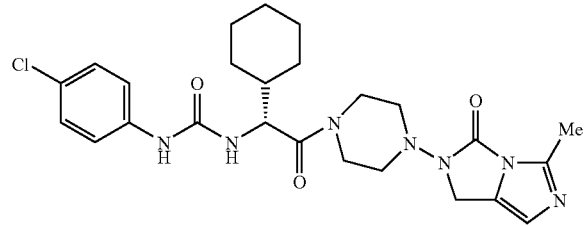

64a) tert-butyl(1R)-1-cyclohexyl-2-(4-(5-methyl-3-oxo-1H-imidazo[1,5-c]imidazol-2(3H)-yl)-1-piperazinyl)-2-oxoethylcarbamate In the same manner as in Example 52a), the title compound as a colorless oil (0.46 g, quantitative) was obtained from (2R)-((tert-butoxycarbonyl)amino)(cyclohexyl)acetic acid (0.28 g).

NMR (CDCl$_3$) δ: 1.01-1.18 (4H, m), 1.44 (9H, s), 1.56-1.83 (6H, m), 2.60 (3H, s), 3.17-3.23 (5H, m), 3.65-3.90 (4H, m), 4.44-4.48 (3H, m), 5.31 (1H, d, J=9.2), 6.72 (1H, s).

64b) N—(4-chlorophenyl)—N'—((1R)-1-cyclohexyl-2-(4-(5-methyl-3-oxo-1H-imidazo[1,5-c]imidazol-2(3H)-yl)-1-piperazinyl)-2-oxoethyl)urea In the same manner as in Example 51c), the title compound as colorless powder (0.36 g, 70%) was obtained from tert-butyl(1R)-1-cyclohexyl-2-(4-(5-methyl-3-oxo-1H-imidazo[1,5-c]imidazol-2(3H)-yl)-1-piperazinyl)-2-oxoethylcarbamate (0.46 g) obtained in Example 64a).

NMR (CDCl$_3$) δ: 1.05-1.24 (5H, m), 1.79-1.84 (8H, m), 2.61 (3H, s), 3.13-3.31 (3H, m), 3.76-3.89 (4H, m), 4.42 (2H, s), 4.77 (1H, t, J=8.1), 6.61 (1H, d, J=8.9), 6.73 (1H, s), 7.13-7.21 (4H, m), 7.72 (1H, s).

Elemental analysis for C$_{25}$H$_{32}$ClN$_7$O$_3$.0.5H$_2$O
Calcd. (%): C, 57.41; H, 6.36; N, 18.75.
Found (%): C, 57.54; H, 6.72; N, 18.46.

EXAMPLE 65

N—(4-chlorophenyl)—N'—((1R)-1-((4-(5-methyl-3-oxo-1H-imidazo[1,5-c]imidazol-2(3H)-yl)-1-piperidinyl)carbonyl)-3-(methylthio)propyl)urea

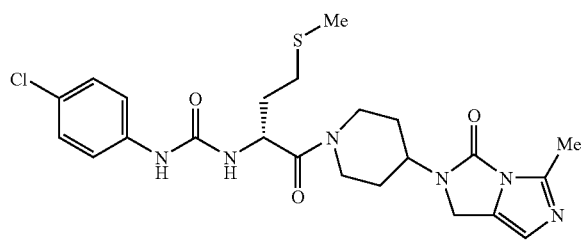

65a) tert-butyl(1R)-1-((4-(5-methyl-3-oxo-1H-imidazo[1,5-c]imidazol-2(3H)-yl)-1-piperidinyl)carbonyl)-3-(methylthio)propylcarbamate In the same manner as in Example 50a), the title compound as colorless powder (1.8 g, 99%) was obtained from (2R)-2-((tert-butoxycarbonyl)amino)-4-(methylthio)butanoic acid (1.0 g).

NMR (CDCl$_3$) δ: 1.44-1.45 (9H, m), 1.60-2.13 (11H, m), 2.53-2.70 (4H, m), 3.15-3.30 (1H, m), 4.09-4.29 (4H, m), 4.75-4.80 (2H, m), 5.38 (1H, d, J=8.7), 6.72 (1H, s).

65b) N—(4-chlorophenyl)—N'—((1R)-1-((4-(5-methyl-3-oxo-1H-imidazo[1,5-c]imidazol-2(3H)-yl)-1-piperidinyl)carbonyl)-3-(methylthio)propyl)urea In the same manner as in Example 51c), the title compound as colorless powder (1.2 g, 62%) was obtained from tert-butyl(1R)-1-((4-(5-methyl-3-oxo-1H-imidazo[1,5-c]imidazol-2(3H)-yl)-1-piperidinyl)carbonyl)-3-(methylthio)propylcarbamate (1.8 g) obtained in Example 65a).

NMR (CDCl$_3$) δ: 1.59-2.14 (6H, m), 2.18 (3H, s), 2.56-2.68 (5H, m), 2.77 (1H, t, J=12.0), 3.21-3.35 (1H, m), 4.11-4.31 (4H, m), 4.76 (1H, d, J=13.0), 5.08-5.19 (1H, m), 6.63 (1H, t, J=7.8), 6.73 (1H, s), 7.13 (2H, d, J=9.0), 7.19 (2H, d, J=9.0), 7.79 (1H, d, J=2.8).

Elemental analysis for C$_{23}$H$_{29}$ClN$_6$O$_3$S.0.2H$_2$O
Calcd. (%): C, 54.31; H, 5.83; N, 16.52.
Found (%): C, 54.27; H, 5.97; N, 16.24.

EXAMPLE 66

N—(4-chlorophenyl)—N'—((1R)-1-((4-(5-methyl-3-oxo-1H-imidazo[1,5-c]imidazol-2(3H)-yl)-1-piperazinyl)carbonyl)-3-(methylthio)propyl)urea

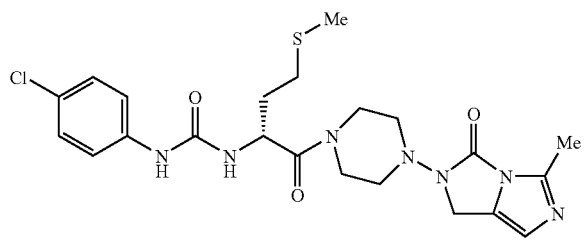

66a) tert-butyl(1R)-1-((4-(5-methyl-3-oxo-1H-imidazo[1,5-c]imidazol-2(3H)-yl)-1-piperazinyl)carbonyl)-3-(methylthio)propylcarbamate In the same manner as in Example 52a), the title compound as a colorless oil (0.42 g, 92%) was obtained from (2R)-2-((tert-butoxycarbonyl)amino)-4-(methylthio)butanoic acid (0.25 g).

NMR (CDCl$_3$) δ: 1.45 (9H, s), 1.76-2.00 (2H, m), 2.12 (3H, s), 2.51-2.60 (5H, m), 3.17-3.28 (4H, m), 3.74-3.79 (4H, m), 4.44 (2H, s), 4.77-4.85 (1H, m), 5.39 (1H, d, J=8.7), 6.72 (1H, t, J=1.4).

66b) N—(4-chlorophenyl)—N'—((1R)-1-((4-(5-methyl-3-oxo-1H-imidazo[1,5-c]imidazol-2(3H)-yl)-1-piperazinyl)carbonyl)-3-(methylthio)propyl)urea In the same manner as in Example 51c), the title compound as colorless powder (0.28 g, 60%) was obtained from tert-butyl(1R)-1-((4-(5-methyl-3-oxo-1H-imidazo[1,5-c]imidazol-2(3H)-yl)-1-piperazinyl)carbonyl)-3-(methylthio)propylcarbamate (0.42 g) obtained in Example 66a).

NMR (CDCl$_3$) δ: 1.83-2.00 (2H, m), 2.13 (3H, s), 2.60 (3H, s), 2.64 (2H, t, J=6.8), 3.15-3.21 (1H, m), 3.25-3.35 (3H, m), 3.72-3.87 (4H, m), 4.44 (2H, s), 5.12 (1H, td, J=4.6, 8.4), 6.56 (1H, d, J=8.5), 6.73 (1H, s), 7.12-7.19 (4H, m), 7.58 (1H, s).

Elemental analysis for $C_{22}H_{28}ClN_7O_3S \cdot 0.5H_2O$
Calcd. (%): C, 51.31; H, 5.68; N, 19.04.
Found (%): C, 51.45; H, 5.65; N, 18.92.

EXAMPLE 67

N—(4-chlorophenyl)—N'—((1R)-1-((4-(5-methyl-3-oxo-1H-imidazo[1,5-c]imidazol-2(3H)-yl)-1-piperidinyl)carbonyl)-3-(methylsulfinyl)propyl)urea

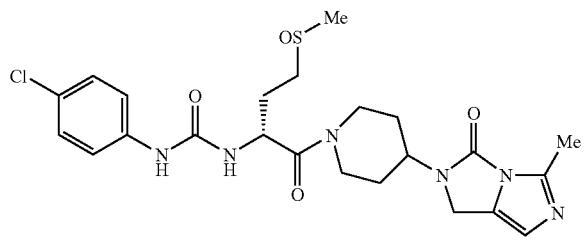

To a solution of N—(4-chlorophenyl)—N'—((1R)-1-((4-(5-methyl-3-oxo-1H-imidazo[1,5-c]imidazol-2(3H)-yl)-1-piperidinyl)carbonyl)-3-(methylthio)propyl)urea (0.21 g) obtained in Example 65 in dichloromethane (15 ml) was added 3-chloroperbenzoic acid (0.10 g), and mixed at 0° C. for 20 minutes. The reaction mixture was diluted with dichloromethane, washed with a saturated aqueous sodium hydrogen carbonate solution and saturated brine and dried over anhydrous magnesium sulfate. The solvent was distilled off under reduced pressure, and the residue was purified with basic silica gel column (ethyl acetate to ethyl acetate/methanol=10/1). The product was recrystallized from ethanol-diethyl ether to obtain the title compound as colorless powder (0.12 g, 54%).

NMR (CDCl$_3$) δ: 1.63-1.98 (3H, m), 2.05-2.30 (3H, m), 2.61-2.64 (6H, m), 2.69-2.94 (2H, m), 3.20-3.29 (1H, m), 4.09-4.30 (4H, m), 4.72 (1H, d, J=13.0), 5.06-5.10 (1H, m), 6.47-6.57 (1H, m), 6.71 (1H, s), 7.19-7.33 (5H, m), 7.79-7.93 (1H, m).

Elemental analysis for $C_{23}H_{29}ClN_6O_4S \cdot 0.25Et_2O \cdot 0.5H_2O$
Calcd. (%): C, 52.79; H, 6.00; N, 15.39.
Found (%): C, 52.47; H, 5.97; N, 15.06.

EXAMPLE 68

N—(4-chlorophenyl)—N'—((1R)-1-((4-(5-methyl-3-oxo-1H-imidazo[1,5-c]imidazol-2(3H)-yl)-1-piperidinyl)carbonyl)-3-(methylsulfonyl)propyl)urea

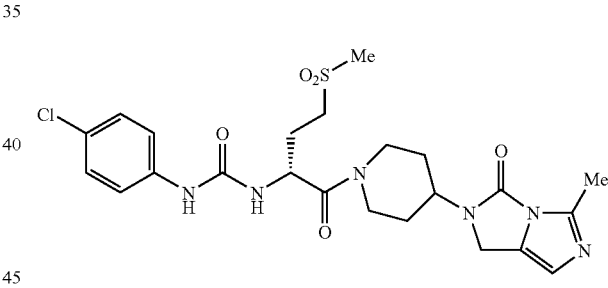

To a solution of N—(4-chlorophenyl)—N'—((1R)-1-((4-(5-methyl-3-oxo-1H-imidazo[1,5-c]imidazol-2(3H)-yl)-1-piperidinyl)carbonyl)-3-(methylthio)propyl)urea (0.30 g) obtained in Example 65 in dichloromethane (15 ml) was added 3-chloroperbenzoic acid (0.30 g), and mixed at 0° C. for 20 minutes. The reaction mixture was diluted with dichloromethane, washed with a saturated aqueous sodium hydrogen carbonate solution and saturated brine and dried over anhydrous magnesium sulfate. The solvent was distilled off under reduced pressure, and the residue was purified with basic silica gel column (ethyl acetate to ethyl acetate/methanol=10/1). The product was recrystallized from ethanol-diethyl ether to obtain the title compound as colorless powder (0.12 g, 36%).

NMR (CDCl$_3$) δ: 1.66-2.05 (5H, m), 2.25-2.45 (1H, m), 2.61 (3H, s), 2.77-2.85 (1H, m), 2.97 (3H, s), 3.10-3.32 (4H, m), 4.21-4.24 (2H, m), 4.30 (1H, d, J=5.0), 4.74-4.69 (1H, m), 5.12-5.14 (1H, m), 6.44-6.51 (qH, m), 6.70-6.71 (1H, m), 7.18-7.24 (4H, m), 7.61-7.64 (1H, m).

Elemental analysis for $C_{23}H_{29}ClN_6O_5S\cdot0.5H_2O$.
Calcd. (%): C, 50.59; H, 5.54; N, 15.39.
Found (%): C, 50.97; H, 5.57; N, 15.00.

EXAMPLE 69

N-(2-(benzyloxy)-1-((1R)-4-(5-methyl-3-oxo-1H-imidazo[1,5-c]imidazol-2(3H)-yl)-1-piperidinyl)carbonyl)propyl)-N'-(4-chlorophenyl)urea

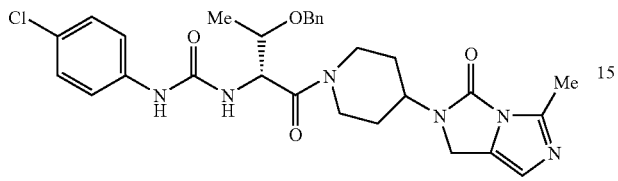

69a) tert-butyl (2-(benzyloxy)-1-((1R)-4-(5-methyl-3-oxo-1H-imidazo[1,5-c]imidazol-2(3H)-yl)-1-piperidinyl)carbonyl)propyl)carbamate In the same manner as in Example 50a), the title compound as colorless powder (0.49 g, 95%) was obtained from (2R)—O-benzyl-N-(tert-butoxycarbonyl)threonine (0.31 g).

NMR (CDCl$_3$) δ: 1.44-1.45 (9H, m), 1.63-1.91 (2H, m), 2.54-2.66 (4H, m), 2.71-3.11 (2H, m), 3.66-4.90 (12H, m), 5.63-5.88 (1H, m), 6.62-6.71 (1H, m), 7.24-7.37 (5H, m), 7.60-7.87 (1H, m).

69b) N-(2-(benzyloxy)-1-((1R)-4-(5-methyl-3-oxo-1H-imidazo[1,5-c]imidazol-2(3H)-yl)-1-piperidinyl)carbonyl)propyl)-N'-(4-chlorophenyl)urea In the same manner as in Example 51c), the title compound as colorless powder (0.23 g, 43%) was obtained from tert-butyl (2-(benzyloxy)-1-((1R)-4-(5-methyl-3-oxo-1H-imidazo[1,5-c]imidazol-2(3H)-yl)-1-piperidinyl)carbonyl)propyl)carbamate (0.49 g) obtained in Example 69a).

NMR (CDCl$_3$) δ: 1.27-1.88 (6H, m), 2.55-2.70 (4H, m), 2.86-3.16 (3H, m), 3.68-4.26 (4H, m), 4.40-4.77 (3H, m), 4.97-5.22 (1H, m), 6.51-6.58 (1H, m), 6.88-6.96 (1H, m), 7.16-7.33 (9H, m), 7.84-8.02 (1H, m).

Elemental analysis for $C_{29}H_{33}ClN_6O_4\cdot1.5H_2O$.
Calcd. (%): C, 58.83; H, 14.19; N, 6.13.
Found (%): C, 58.66; H, 14.03; N, 5.84.

EXAMPLE 70

N-(4-chlorophenyl)-N'-(2-hydroxy-1-((1R)-4-(5-methyl-3-oxo-1H-imidazo[1,5-c]imidazol-2(3H)-yl)-1-piperidinyl)carbonyl)propyl)urea

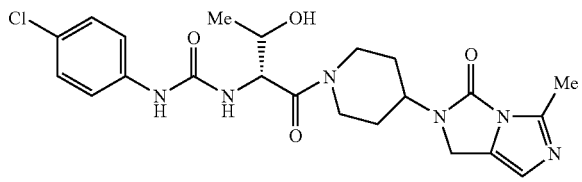

In the same manner as in Example 55, the title compound as a colorless needle-like crystal (0.01 g, 11%) was obtained from N-(2-(benzyloxy)-1-((1R)-4-(5-methyl-3-oxo-1H-imidazo[1,5-c]imidazol-2(3H)-yl)-1-piperidinyl)carbonyl)propyl)-N'-(4-chlorophenyl)urea (0.06 g) obtained in Example 69.

NMR (DMSO-d$_6$) δ: 1.10 (3H, s), 1.61-1.85 (4H, m), 2.63 (3H, s), 2.80-4.09 (7H, m), 4.52-4.87 (4H, m), 6.42-6.52 (1H, m), 7.17-7.43 (4H, m), 8.89-9.08 (1H, m).

EXAMPLE 71

N-(4-chlorophenyl)-N'-(2-(4-(5-methyl-3-oxo-1H-imidazo[1,5-c]imidazol-2(3H)-yl)-1-piperazinyl)-2-oxo-1-tetrahydro-2H-pyran-4-ylethyl)urea

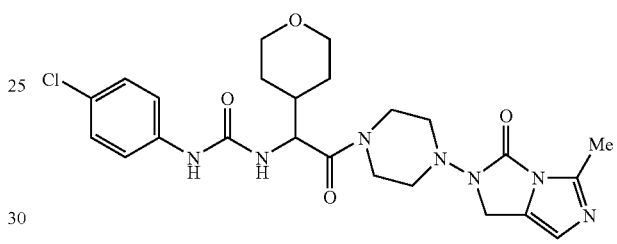

To a solution of ethyl (formylamino)(tetrahydro-2H-pyran-4-yl)acetate (M. J. Burk et al., J. Am. Chem. Soc., 117, 9375-9376 (1995); 0.30 g) in ethanol (7 ml) was added a 1 N aqueous sodium hydroxide solution (2.8 ml), and mixed at 80° C. for 40 minutes. The reaction mixture was neutralized by adding 1 N hydrochloric acid, and then water was removed by azeotropy with toluene to obtain (formylamino)(tetrahydro-2H-pyran-4-yl)acetic acid as a crude product. In the same manner as in Example 50a), 2-(4-(5-methyl-3-oxo-1H-imidazo[1,5-c]imidazol-2(3H)-yl)-1-piperazinyl)-2-oxo-1-tetrahydro-2H-pyran-4-ylethylformamide was obtained from this carboxylic acid as a crude product. The product was dissolved in methanol (7 ml) and diethyl ether(14 ml). A 4 N solution of hydrogen chloride in ethyl acetate (3.5 ml) was added and mixed at room temperature for 4 hours, and the solvent was distilled off under reduced pressure. The residue was dissolved in acetonitrile (14 ml), triethylamine (0.39 ml) and 4-chlorophenyl isocyanate (0.21 g) were added thereto, and mixed at room temperature for 15 hours. The solvent was distilled off under reduced pressure, and the residue was dissolved in ethyl acetate. The ethyl acetate solution was washed with an aqueous sodium hydrogen carbonate solution and dried over anhydrous magnesium sulfate. The solvent was distilled off under reduced pressure, and the residue was purified with basic silica gel column (ethyl acetate to ethyl acetate/methanol=10/1) to obtain the title compound as colorless powder (0.03 g, 5%).

NMR (CDCl$_3$) δ: 1.42-2.05 (7H, m), 2.60 (3H, s), 3.24-3.32 (5H, m), 3.66-3.95 (5H, m), 4.44 (2H, s), 4.80-4.88 (1H, m), 6.14-6.19 (1H, m), 6.73 (1H, m), 7.23-7.32 (5H, m).

Elemental analysis for C$_{24}$H$_{30}$ClN$_7$O$_4$·H$_2$O.
Calcd. (%): C, 53.98; H, 6.04; N, 18.36.
Found (%): C, 54.17; H, 6.25; N, 18.15.

EXAMPLE 72

N-(4-chlorophenyl)-N'-(1-(1-hydroxycyclohexyl)-2-(4-(5-methyl-3-oxo-1H-imidazo[1,5-c]imidazol-2(3H)-yl)-1-piperidinyl)-2-oxoethyl)urea

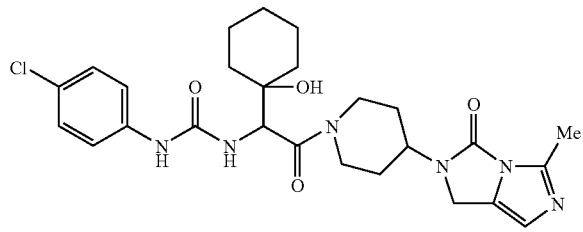

72a) tert-butyl 1-(1-hydroxycyclohexyl)-2-(4-(5-methyl-3-oxo-1H-imidazo[1,5-c]imidazol-2(3H)-yl)-1-piperidinyl)-2-oxoethylcarbamate In the same manner as in Example 50a), the title compound as a pale yellow oil (1.5 g, 47%) was obtained from ((tert-butoxycarbonyl)amino)(1-hydroxycyclohexyl)acetic acid (U.S. Pat. No. 4,638,060; 1.8 g).

NMR (CDCl$_3$) δ: 1.44 (9H, s), 1.45-2.04 (14H, m), 2.61 (3H, s), 2.68-2.72 (1H, m), 3.24-3.15 (1H, m), 4.22-4.37 (4H, m), 4.53-4.62 (2H, m), 4.76-4.80 (1H, m), 5.47-5.57 (1H, m), 6.70 81H, s).

72b) N-(4-chlorophenyl)-N'-(1-(1-hydroxycyclohexyl)-2-(4-(5-methyl-3-oxo-1H-imidazo[1,5-c]imidazol-2(3H)-yl)-1-piperidinyl)-2-oxoethyl)urea In the same manner as in Example 51c), the title compound as colorless powder (0.01 g, 4%) was obtained from tert-butyl 1-(1-hydroxycyclohexyl)-2-(4-(5-methyl-3-oxo-1H-imidazo[1,5-c]imidazol-2(3H)-yl)-1-piperidinyl)-2-oxoethylcarbamate (0.24 g) obtained in Example 72a).

NMR (CDCl$_3$) δ: 1.46-2.10 (16H, m), 2.60-2.61 (2H, m), 2.73 (1H, t, J=12.0), 3.20-3.28 (1H, m), 4.13-4.29 (2H, m), 4.64 (1H, d, J=14.1), 4.80-4.84 (2H, m), 5.17 (1H, s), 6.53 (1H, s), 6.17-6.68 (1H, m), 7.21 (2H, d, J=8.7), 7.29 (2H, d, J=8.7), 7.86 (1H, s).

EXAMPLE 73

N-(4-chlorophenyl)-N'-(2-methoxy-2-methyl-1-((4-(5-methyl-3-oxo-1H-imidazo[1,5-c]imidazol-2(3H)-yl)-1-piperidinyl)carbonyl)propyl)urea

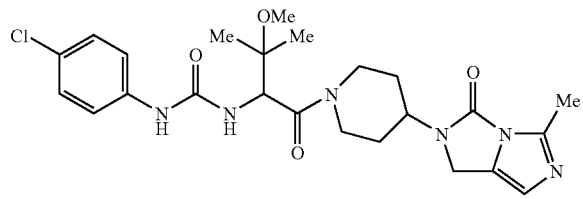

73a) tert-butyl 4-(1-methoxy-1-methylethyl)-2,2-dimethyl-1,3-oxazolidine-3-carboxylate tert-Butyl 4-(1-hydroxy-1-methylethyl)-2,2-dimethyl-1,3-oxazolidine-3-carboxylate (Y. Yonezaw et al., Synthesis, 634-636 (2000); 2.6 g) and methyl iodide (1.2 ml) were dissolved in dimethylformamide (20 ml). Sodium hydride (0.59 g) and n-tetrabutyl iodide ammonium (0.72 g) were added thereto at 0° C., and mixed at room temperature for 2.5 days. To the reaction mixture was added water, and extracted with diethyl ether. The extract was dried over anhydrous magnesium sulfate, and the solvent was distilled off under reduced pressure to obtain the title compound as a pale yellow oil (2.5 g, 95%).

NMR (CDCl$_3$) δ: 1.14-1.67 (21H, m), 3.32 (3H, s), 3.74-4.17 (3H, m).

73b) tert-butyl 1-(hydroxymethyl)-2-methoxy-2-methylpropylcarbamate tert-Butyl 4-(1-methoxy-1-methylethyl)-2,2-dimethyl-1,3-oxazolidine-3-carboxylate (2.5 g) obtained in Example 73a) was dissolved in methanol (45 ml), p-toluenesulfonic acid monohydrate (0.18 g) was added thereto, and mixed at room temperature for 20 minutes. The solvent was distilled off under reduced pressure, and the residue was diluted with ethyl acetate, washed with a saturated aqueous sodium hydrogen carbonate solution and dried over anhydrous magnesium sulfate. The solvent was distilled off under reduced pressure to obtain the title compound as a colorless solid (2.1 g, 95%).

NMR (CDCl$_3$) δ: 1.23 (3H, s), 1.28 (3H, s), 1.45 (9H, s), 3.21 (3H, s), 3.52-3.55 (1H, m), 3.63-3.70 (1H, m), 3.96 (1H, dd, J=2.8, 12.1), 5.32 (1H, d, J=9.1).

73c) 2-((tert-butoxycarbonyl)amino)-3-methoxy-3-methylbutanoic acid tert-Butyl 1-(hydroxymethyl)-2-methoxy-2-methylpropylcarbamate (0.23 g) obtained in Example 73b) was dissolved in acetone (8 ml) and a 5% aqueous sodium hydrogen carbonate solution (2.7 ml). Potassium bromide (0.01 g), 2,2,6,6-tetramethyl-1-piperidinyloxy (0.17 g) and an aqueous sodium hypochlorite solution (1.7 ml) were added thereto, and mixed at 0° C. for 50 minutes. Acetone was distilled off under reduced pressure, and the residue was diluted with water, washed with diethyl ether, acidified with 1 N hydrochloric acid and extracted with ethyl acetate. The extract was dried over anhydrous magnesium sulfate, and the solvent was distilled off under reduced pressure to obtain the title compound as a pale yellow oil (0.20 g, 82%).

NMR (CDCl$_3$) δ: 1.22 (3H, s), 1.26 (3H, s), 1.45 (9H, s), 3.33 (3H, s), 4.33 (1H, d, J=12.1), 5.31 (1H, s).

73d) tert-butyl 2-methoxy-2-methyl-1-((4-(5-methyl-3-oxo-1H-imidazo[1,5-c]imidazol-2(3H)-yl)-1-piperidinyl)carbonyl)propylcarbamate 2-((tert-butoxycarbonyl)amino)-3-methoxy-3-methylbutanoic acid (0.20 g) obtained in Example 73c) was dissolved in acetonitrile (10 ml). HOBt (0.19 g), WSC (0.24 g), triethylamine (0.16 ml) and 5-methyl-2-(4-piperidinyl)-1,2-dihydro-3H-imidazo[1,5-c]imidazol-3-one dihydrochloride (0.24 g) were added thereto, and mixed at room temperature for 15 hours. The solvent was distilled off under reduced pressure, and the residue was dissolved in ethyl acetate. The ethyl acetate solution was washed with a saturated aqueous sodium hydrogen carbonate solution and dried over anhydrous magnesium sulfate. The solvent was distilled off under reduced pressure to obtain the title compound as a colorless oil (0.36 g, 96%).

NMR (CDCl$_3$) δ: 1.14-1.29 (6H, m), 1.43-1.45 (9H, m), 1.56-1.94 (5H, m), 2.61 (3H, s), 2.65-2.71 (1H, m), 3.08-3.13 (1H, m), 3.20-3.24 (3H, m), 4.23 (2H, s), 4.36 (1H, s), 4.69 (1H, d, J=8.9), 4.82 (1H, s), 5.55 (1H, d, J=8.9), 6.70 (1H, s).

73e) N-(4-chlorophenyl)-N'-(2-methoxy-2-methyl-1-((4-(5-methyl-3-oxo-1H-imidazo[1,5-c]imidazol-2(3H)-yl)-1-piperidinyl)carbonyl)propyl)urea tert-Butyl 2-methoxy-2-methyl-1-((4-(5-methyl-3-oxo-1H-imidazo[1,5-c]imidazol-2(3H)-yl)-1-piperidinyl)carbonyl)propylcarbamate (0.36 g) obtained in Example 73d) was added a 4 N solution of hydrogen chloride in ethyl acetate (2.6 ml), mixed at room temperature for 5 minutes, and then concentrated under reduced pressure. The residue was dissolved in acetonitrile (5 ml), triethylamine (0.14 ml) and 4-chlorophenyl isocyanate (0.08 g) were added thereto, and mixed at room temperature for 3 hours. The solvent was distilled off under reduced pressure, and the residue was dissolved in ethyl acetate. The ethyl acetate solution was washed with an aqueous sodium hydrogen carbonate solution and dried over anhydrous magnesium sulfate. The solvent was distilled off under reduced pressure, and the residue was purified with basic silica gel column (ethyl acetate to ethyl acetate/methanol=10/1). The product was crystallized from ethyl acetate-diethyl ether to obtain the title compound as colorless powder (0.28 g, 71%).

NMR (CDCl$_3$) δ: 1.23 (3H, s), 1.32-1.34 (3H, m), 1.52-1.93 (4H, m), 2.60-2.62 (3H, m), 2.65-2.76 (1H, m), 3.16-3.18 (1H, m), 3.22-3.27 (3H, m), 4.11-4.23 (2H, m), 4.30-4.80 (3H, m), 4.91-5.27 (1H, m), 6.41-6.48 (1H, m), 6.70-6.73 (1H, m), 7.18-7.30 (4H, m), 7.79-7.88 (1H, m).

Elemental analysis for C$_{24}$H$_{31}$ClN$_6$O$_4$.0.25AcOEt.0.5H$_2$O.
Calcd. (%): C, 56.32; H, 6.42; N, 15.74.
Found (%): C, 56.20; H, 6.38; N, 15.90.

EXAMPLE 74

N-(4-chlorophenyl)-N'-(2-methoxy-2-methyl-1-((4-(5-methyl-3-oxo-1H-imidazo[1,5-c]imidazol-2(3H)-yl)-1-piperazinyl)carbonyl)propyl)urea

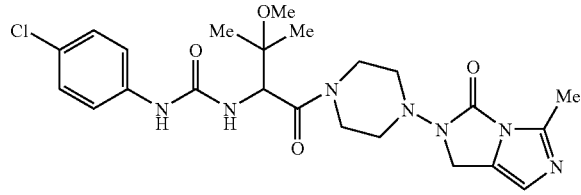

74a) tert-butyl 2-methoxy-2-methyl-1-((4-(5-methyl-3-oxo-1H-imidazo[1,5-c]imidazol-2(3H)-yl)-1-piperazinyl)carbonyl)propylcarbamate In the same manner as in Example 52a), the title compound as a pale yellow oil (0.77 g, quantitative) was obtained from 2-((tert-butoxycarbonyl)amino)-3-methoxy-3-methylbutanoic acid (0.42 g) obtained in Example 73d).

NMR (CDCl$_3$) δ: 1.14-1.28 (6H, m), 1.44 (9H, s), 2.60 (3H, s), 3.08-3.29 (7H, m), 3.55-3.74 (2H, m), 3.86-4.03 (2H, m), 4.43 (2H, s), 4.66 (1H, d, J=8.8), 5.55 (1H, d, J=8.8), 6.70 (1H, t, J=1.7).

74b) N-(4-chlorophenyl)-N'-(2-methoxy-2-methyl-1-((4-(5-methyl-3-oxo-1H-imidazo[1,5-c]imidazol-2(3H)-yl)-1-piperazinyl)carbonyl)propyl)urea In the same manner as in Example 51c), the title compound as colorless powder (0.51 g, 59%) was obtained from tert-butyl 2-methoxy-2-methyl-1-((4-(5-methyl-3-oxo-1H-imidazo[1,5-c]imidazol-2(3H)-yl)-1-piperazinyl)carbonyl)propylcarbamate (0.77 g) obtained in Example 74a).

NMR (CDCl$_3$) δ: 1.22 (3H, s), 1.33 (3H, s), 2.61 (3H, s), 3.10-3.19 (3H, m), 3.26 (3H, s), 3.25 (1H, t, J=7.4), 3.56-3.65 (1H, m), 3.68-3.81 (1H, m), 3.95-3.99 (2H, m), 4.41 (2H, s), 5.06 (1H, d, J=8.9), 6.51 (1H, d, J=8.9), 6.72 (1H, s), 7.20 (2H, d, J=9.2), 7.26 (2H, d, J=9.2), 7.90 (1H, s).

Elemental analysis for C$_{23}$H$_{30}$ClN$_7$O$_4$.0.5H$_2$O.
Calcd. (%): C, 53.85; H, 6.09; N, 19.11.
Found (%): C, 53.80; H, 6.04; N, 18.80.

EXAMPLE 75

N-(4-chlorophenyl)-N'-(2-ethoxy-2-methyl-1-((4-(5-methyl-3-oxo-1H-imidazo[1,5-c]imidazol-2(3H)-yl)-1-piperidinyl)carbonyl)propyl)urea

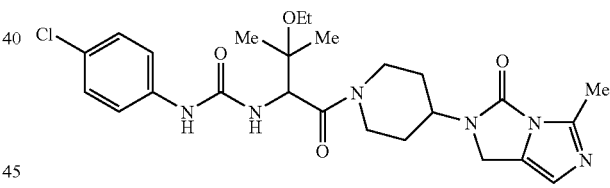

75a) tert-butyl 4-(1-ethoxy-1-methylethyl)-2,2-dimethyl-1,3-oxazolidine-3-carboxylate In the same manner as in Example 73a), the title compound as a colorless oil (0.26 g, 30%) was obtained from tert-butyl 4-(1-hydroxy-1-methylethyl)-2,2-dimethyl-1,3-oxazolidine-3-carboxylate (0.78 g) and ethyl iodide (0.48 ml).

NMR (CDCl$_3$) δ: 1.10-1.20 (9H, m), 1.46-1.68 (15H, m), 3.36-3.46 (2H, m), 3.84-4.20 (3H, m).

75b) tert-butyl 2-ethoxy-1-(hydroxymethyl)-2-methylpropylcarbamate

In the same manner as in Example 73b), the title compound as a pale yellow oil (0.21 g, 93%) was obtained from tert-butyl 4-(1-ethoxy-1-methylethyl)-2,2-dimethyl-1,3-oxazolidine-3-carboxylate (0.26 g) obtained in Example 75a).

NMR (CDCl$_3$) δ: 1.16 (3H, t, J=6.4), 1.24 (3H, s), 1.30 (3H, s), 1.46 (9H, s), 3.40-3.54 (3H, m), 3.61-3.69 (1H, m), 3.98-4.03 (1H, m), 5.38 (1H, d, J=8.9).

75c) 2-((tert-butoxycarbonyl)amino)-3-ethoxy-3-methylbutanoic acid

In the same manner as in Example 73c), the title compound as a colorless oil (0.17 g, 78%) was obtained from tert-butyl 2-ethoxy-1-(hydroxymethyl)-2-methylpropylcarbamate (0.21 g) obtained in Example 75b).

NMR (CDCl$_3$) δ: 1.21 (3H, s), 1.23 (3H, t, J=7.2), 1.33 (3H, s), 1.45 (9H, s), 3.52-3.62 (2H, m), 4.36 (1H, d, J=7.2), 5.33 (1H, d, J=6.8).

75d) tert-butyl 2-ethoxy-2-methyl-1-((4-(5-methyl-3-oxo-1H-imidazo[1,5-c]imidazol-2(3H)-yl)-1-piperidinyl)carbonyl)propylcarbamate In the same manner as in Example 50a), the title compound as a colorless oil (0.31 g, quantitative) was obtained from 2-((tert-butoxycarbonyl)amino)-3-ethoxy-3-methylbutanoic acid (0.17 g) obtained in Example 75c).

NMR (CDCl$_3$) δ: 1.09-1.28 (9H, m), 1.43-1.45 (9H, m), 1.58-1.91 (5H, m), 2.61 (3H, s), 2.63-2.72 (1H, m), 3.05-3.14 (1H, m), 3.34-3.51 (3H, m), 4.26 (2H, s), 4.34-4.44 (1H, m), 4.71 (1H, d, J=8.8), 4.80-4.85 (1H, m), 5.53 (1H, d, J=8.8), 6.71 (1H, s).

75e) N-(4-chlorophenyl)-N'-(2-ethoxy-2-methyl-1-((4-(5-methyl-3-oxo-1H-imidazo[1,5-c]imidazol-2(3H)-yl)-1-piperidinyl)carbonyl)propyl)urea In the same manner as in Example 51c), the title compound as colorless powder (0.21 g, 60%) was obtained from tert-butyl 2-ethoxy-2-methyl-1-((4-(5-methyl-3-oxo-1H-imidazo[1,5-c]imidazol-2(3H)-yl)-1-piperidinyl)carbonyl)propylcarbamate (0.31 g) obtained in Example 75d).

NMR (CDCl$_3$) δ: 1.11-1.28 (6H, m), 1.32-1.33 (3H, m), 1.49-1.91 (4H, m), 2.61-2.62 (3H, m), 2.69-2.77 (1H, m), 3.10-3.24 (1H, m), 3.35-3.58 (2H, m), 4.14-4.27 (3H, m), 4.50 (1H, t, J=11.7), 4.80 (1H, d, J=14.6), 5.09 (1H, d, J=8.8), 6.39-6.46 (1H, m), 6.71-6.74 (1H, m), 7.20 (2H, d, J=9.2), 7.26 (2H, d, J=9.2), 7.83 (1H, s).

Elemental analysis for C$_{25}$H$_{33}$ClN$_6$O$_4$·0.25AcOEt·0.5H$_2$O.

Calcd. (%): C, 56.98; H, 6.62; N, 15.23.

Found (%): C, 57.17; H, 6.57; N, 15.51.

EXAMPLE 76

N-(4-chlorophenyl)-N'-(2-ethoxy-2-methyl-1-((4-(5-methyl-3-oxo-1H-imidazo[1,5-c]imidazol-2(3H)-yl)-1-piperazinyl)carbonyl)propyl)urea

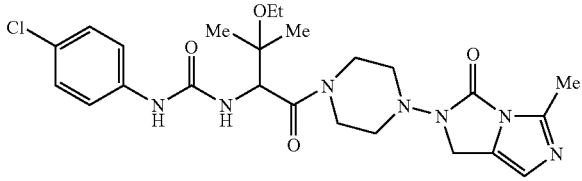

76a) tert-butyl 2-ethoxy-2-methyl-1-((4-(5-methyl-3-oxo-1H-imidazo[1,5-c]imidazol-2(3H)-yl)-1-piperazinyl)carbonyl)propylcarbamate In the same manner as in Example 52a), the title compound as a pale yellow oil (0.36 g, 94%) was obtained from 2-((tert-butoxycarbonyl)amino)-3-ethoxy-3-methylbutanoic acid (0.21 g) obtained in Example 75c).

NMR (CDCl$_3$) δ: 1.13-1.28 (9H, m), 1.44 (9H, m), 2.61 (3H, s), 3.15-3.23 (4H, m), 3.42-3.48 (2H, m), 3.70-3.88 (4H, m), 4.43 (2H, s), 4.68 (1H, d, J=8.6), 5.53 (1H, d, J=8.6), 6.72 (1H, s).

76b) N-(4-chlorophenyl)-N'-(2-ethoxy-2-methyl-1-((4-(5-methyl-3-oxo-1H-imidazo[1,5-c]imidazol-2(3H)-yl)-1-piperazinyl)carbonyl)propyl)urea In the same manner as in Example 51c), the title compound as colorless powder (0.19 g, 48%) was obtained from tert-butyl 2-ethoxy-2-methyl-1-((4-(5-methyl-3-oxo-1H-imidazo[1,5-c]imidazol-2(3H)-yl)-1-piperazinyl)carbonyl)propylcarbamate (0.36 g) obtained in Example 76a).

NMR (CDCl$_3$) δ: 1.10 (3H, t, J=7.4), 1.14 (3H, s), 1.18 (3H, s), 2.44 (3H, s), 3.04-3.33 (4H, m), 3.40-3.72 (4H, m), 4.51 (2H, s), 4.85 (1H, d, J=8.6), 6.63 (1H, d, J=8.6), 6.68 (1H, s), 7.26 (2H, d, J=9.2), 7.40 (2H, d, J=9), 8.94 (1H, s).

Elemental analysis for C$_{24}$H$_{32}$ClN$_7$O$_4$.

Calcd. (%): C, 55.65; H, 6.23; N, 18.93.

Found (%): C, 55.39; H, 6.35; N, 18.70.

EXAMPLE 77

N-(4-chlorophenyl)-N'-(3-methoxy-2,2-dimethyl-1-((4-(5-methyl-3-oxo-1H-imidazo[1,5-c]imidazol-2(3H)-yl)-1-piperazinyl)carbonyl)propyl)urea

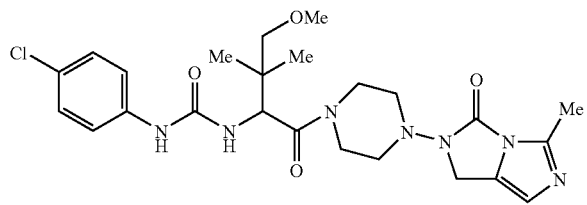

77a) 2-amino-4-methoxy-3,3-dimethylbutanenitrile

Ammonium chloride (2.9 g) and potassium cyanide (3.3 g) were dissolved in water (20 ml), a solution of 3-methoxy-2,2-dimethylpropanal (F. Effenberger et al., Tetrahedron: Asymmetry, 6, 271-282 (1995); 5.7 g) in aqueous ammonia (5 ml) was added dropwise at 0° C., and mixed at room temperature for 3 days. The reaction mixture was concentrated under reduced pressure, and the residue was diluted with diluted hydrochloric acid. The aqueous solution was washed with diethyl ether, alkalified with a 1 N aqueous sodium hydroxide solution and extracted with dichloromethane. The extract was dried over anhydrous magnesium sulfate, and the solvent was distilled off under reduced pressure to obtain the title compound as a pale yellow oil (0.57 g, 8%).

NMR (CDCl$_3$) δ: 1.03 (3H, s), 1.16 (3H, s), 3.28 (1H, d, J=9.2), 3.40 (3H, s), 3.64 (1H, d, J=9.2), 4.12 (1H, d, J=8.4), 4.23 (1H, d, J=8.4).

77b) 2-amino-4-methoxy-3,3-dimethylbutanoic acid

2-Amino-4-methoxy-3,3-dimethylbutanenitrile (0.57 g) obtained in Example 77a) was dissolved in 6 N hydrochloric acid (2.8 ml), and mixed at 100° C. for 15 hours. The mixture was cooled to room temperature, and water was removed by azeotropy with toluene. The residue was solidified by adding diethyl ether, and the precipitated solid was collected by filtration to obtain the title compound as colorless powder (0.65 g, quantitative).

NMR (CDCl$_3$) δ: 1.18 (6H, s), 3.37 (1H, d, J=4.3), 3.40 (3H, s), 3.42 (1H, d, J=4.3), 4.55 (1H, s).

77c) 2-((tert-butoxycarbonyl)amino)-4-methoxy-3,3-dimethylbutanoic acid

2-Amino-4-methoxy-3,3-dimethylbutanoic acid (0.65 g) obtained in Example 77b) was dissolved in THF (6 ml) and water (6 ml). Triethylamine (0.8 ml) and di-tert-butyl dicarbonate (1.0 ml) were added thereto, and mixed at room temperature for 15 hours. The solvent was distilled off under reduced pressure, and the residue was dissolved in water and extracted with ethyl acetate. The extract was dried over anhydrous magnesium sulfate, and the solvent was distilled off under reduced pressure to obtain the title compound as a colorless oil (1.0 g, 97%).

NMR (CDCl$_3$) δ: 1.04 (3H, s), 1.09 (3H, s), 1.53 (9H, s), 3.16 (1H, d, J=10.1), 3.37 (3H, s), 4.49 (1H, d, J=10.1), 5.52 (1H, d, J=9.6), 5.68 (1H, d, J=9.6).

77d) tert-butyl 3-methoxy-2,2-dimethyl-1-((4-(5-methyl-3-oxo-1H-imidazo[1,5-c]imidazol-2(3H)-yl)-1-piperazinyl)carbonyl)propylcarbamate In the same manner as in Example 52a), the title compound as a colorless oil (0.19 g, 41%) was obtained from 2-((tert-butoxycarbonyl)amino)-4-methoxy-3,3-dimethylbutanoic acid (0.26 g) obtained in Example 77c).

NMR (CDCl$_3$) δ: 0.94-1.13 (6H, m), 1.21-1.30 (2H, m), 1.44-1.47 (12H, m), 1.56-1.86 (3H, m), 2.61-2.70 (1H, m), 3.99-4.28 (3H, m), 4.48-4.52 (1H, m), 5.69-5.72 (1H, m), 6.70-6.71 (1H, m).

77e) N-(4-chlorophenyl)-N'-(3-methoxy-2,2-dimethyl-1-((4-(5-methyl-3-oxo-1H-imidazo[1,5-c]imidazol-2(3H)-yl)-1-piperazinyl)carbonyl)propyl)urea In the same manner as in Example 51c), the title compound as colorless powder (0.03 g, 9%) was obtained from tert-butyl 3-methoxy-2,2-dimethyl-1-((4-(5-methyl-3-oxo-1H-imidazo[1,5-c]imidazol-2(3H)-yl)-1-piperazinyl)carbonyl)propylcarbamate (0.30 g) obtained in Example 77d).

NMR (CDCl$_3$) δ: 0.97-1.06 (6H, m), 1.44 (2H, s), 2.60 (3H, s), 3.01-3.25 (4H, m), 3.32-3.37 (4H, m), 3.63-3.96 (3H, m), 4.40 (2H, s), 5.05 (1H, d, J=9.4), 6.62 (1H, d, J=9.4), 6.72 (1H, s), 7.19-7.31 (4H, m), 7.75 (1H, s).

Elemental analysis for C$_{24}$H$_{32}$ClN$_7$O$_4$.0.5AcOEt.3H$_2$O.
Calcd. (%): C, 50.69; H, 6.87; N, 15.91.
Found (%): C, 50.41; H, 6.46; N, 15.64.

EXAMPLE 78

N-(4-chlorophenyl)-N'-(1-((4-(5-methyl-3-oxo-1H-imidazo[1,5-c]imidazol-2(3H)-yl)-1-piperidinyl)carbonyl)cyclopentyl)urea

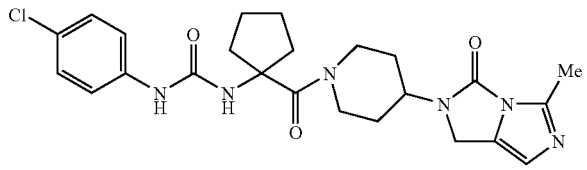

78a) tert-butyl 1-((4-(5-methyl-3-oxo-1H-imidazo[1,5-c]imidazol-2(3H)-yl)-1-piperidinyl)carbonyl)cyclopentylcarbamate In the same manner as in Example 50a), the title compound as colorless powder (0.43 g, 99%) was obtained from 1-((tert-butoxycarbonyl)amino)cyclopentane carboxylic acid (0.23 g).

NMR (CDCl$_3$) δ: 1.44 (9H, m), 1.60-1.91 (10H, m), 2.05-2.44 (6H, m), 2.61 (3H, s), 4.22 (2H, s), 4.46-4.78 (2H, m), 6.70 (1H, s).

78b) N-(4-chlorophenyl)-N'-(1-((4-(5-methyl-3-oxo-1H-imidazo[1,5-c]imidazol-2(3H)-yl)-1-piperidinyl)carbonyl)cyclopentyl)urea In the same manner as in Example 51c), the title compound as colorless powder (0.10 g, 21%) was obtained from tert-butyl 1-((4-(5-methyl-3-oxo-1H-imidazo[1,5-c]imidazol-2(3H)-yl)-1-piperidinyl)carbonyl)cyclopentylcarbamate (0.43 g) obtained in Example 78a).

NMR (CDCl$_3$) δ: 1.44-1.87 (10H, m), 2.41-2.51 (6H, m), 2.62-3.01 (2H, m), 3.75-4.02 (3H, m), 4.42 (2H, s), 6.52 (1H, s), 7.25-7.46 (4H, m), 9.06 (1H, s).

Elemental analysis for C$_{24}$H$_{29}$ClN$_6$O$_3$.H$_2$O.0.35CHCl$_3$.
Calcd. (%): C, 53.68; H, 5.80; N, 15.43.
Found (%): C, 53.36; H, 5.43; N, 15.67.

EXAMPLE 79

N-(1-benzyl-1-methyl-2-(4-(5-methyl-3-oxo-1H-imidazo[1,5-c]imidazol-2(3H)-yl)-1-piperidinyl)-2-oxoethyl)-N'-(4-chlorophenyl)urea

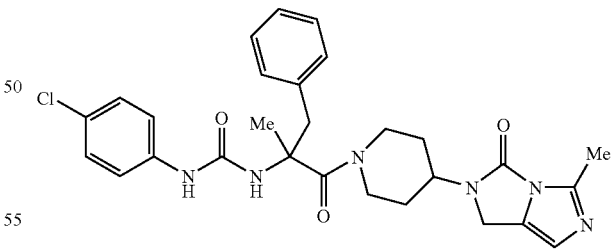

79a) tert-butyl 1-benzyl-1-methyl-2-(4-(5-methyl-3-oxo-1H-imidazo[1,5-c]imidazol-2(3H)-yl)-1-piperidinyl)-2-oxoethylcarbamate In the same manner as in Example 50a), the title compound as colorless powder (0.34 g, 84%) was obtained from 2-((tert-butoxycarbonyl)amino)-2-methyl-3-phenylpropanoic acid (0.24 g).

NMR (CDCl$_3$) δ: 1.34-1.38 (2H, m), 1.49 (9H, s), 1.60-1.93 (5H, m), 2.61 (3H, s), 3.14-3.40 (4H, m), 4.23-4.26 (3H, m), 4.58-4.86 (3H, m), 6.70 (1H, s), 7.11-7.18 (2H, m), 7.33-7.35 (3H, m).

79b) N-(1-benzyl-1-methyl-2-(4-(5-methyl-3-oxo-1H-imidazo[1,5-c]imidazol-2(3H)-yl)-1-piperidinyl)-2-oxoethyl)-N'-(4-chlorophenyl)urea In the same manner as in Example 51c), the title compound as colorless powder (0.03 g, 7%) was obtained from tert-butyl 1-benzyl-1-methyl-2-(4-(5-methyl-3-oxo-1H-imidazo[1,5-c]imidazol-2(3H)-yl)-1-piperidinyl)-2-oxoethylcarbamate (0.41 g) obtained in Example 79a).

NMR (CDCl$_3$) δ: 1.42 (3H, s), 1.46-1.71 (3H, m), 2.17 (2H, s), 2.53 (3H, s), 3.13-3.43 (3H, m), 3.81-3.87 (2H, m), 4.03-4.16 (1H, m), 4.65-4.79 (2H, m), 5.71 (1H, s), 6.61 (1H, s), 7.05-7.07 (2H, m), 7.14-7.29 (7H, m), 7.43-7.49 (1H, m).

Elemental analysis for C$_{28}$H$_{31}$ClN$_6$O$_3$·0.25AcOEt·0.5H$_2$O.

Calcd. (%): C, 61.53; H, 6.05; N, 14.85.
Found (%): C, 61.78; H, 5.96; N, 14.93.

EXAMPLE 80

N-(4-chlorophenyl)-N'-(1-((4-(5-methyl-3-oxo-1H-imidazo[1,5-c]imidazol-2(3H)-yl)-1-piperidinyl)carbonyl)pentyl)urea

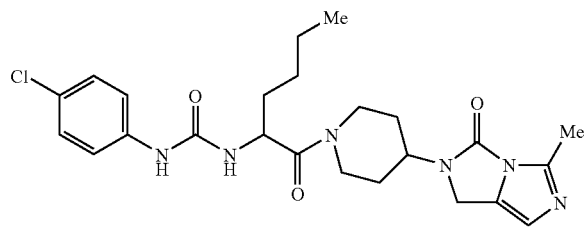

80a) 2-((tert-butoxycarbonyl)amino)hexanoic acid

To a solution of 2-aminohexanoic acid (2.5 g) and triethylamine (2.9 g) in THF-H$_2$O (50 ml/50 ml) was added dropwise di-tert-butyl dicarbonate (4.6 g) under ice-cooling. After 10 minutes, the reaction mixture was returned to room temperature, and mixed for 15 hours. THF was distilled off under reduced pressure and extracted with dichloromethane. The extract was washed with saturated brine and dried over anhydrous magnesium sulfate. The solvent was distilled off under reduced pressure to obtain the title compound as colorless powder (4.5 g, quantitative).

NMR (CDCl$_3$) δ: 0.86-0.89 (3H, m), 1.23-1.52 (6H, m), 1.43 (9H, s), 3.15 (1H, m).

80b) tert-butyl 1-((4-(5-methyl-3-oxo-1H-imidazo[1,5-c]imidazol-2(3H)-yl)-1-piperidinyl)carbonyl)pentylcarbamate To a solution of 2-((tert-butoxycarbonyl)amino)hexanoic acid (0.46 g) obtained in Example 80a), HOBt (0.46 g) and WSC (0.58 g) in acetonitrile (20 ml) was added a solution of 5-methyl-2-(4-piperidinyl)-1,2-dihydro-3H-imidazo[1,5-c]imidazol-3-one dihydrochloride (0.6 g), DBU (0.6 ml) and triethylamine (0.61 ml) in acetonitrile (20 ml), and mixed for 15 hours. The solvent was distilled off under reduced pressure, and the residue was dissolved in dichloromethane. The dichloromethane solution was washed with an aqueous sodium hydrogen carbonate solution and dried over anhydrous magnesium sulfate. The solvent was distilled off under reduced pressure, and the residue was purified with basic silica gel column (ethyl acetate/methanol=10/1) to obtain the title compound as colorless powder (0.7 g, 75%).

NMR (CDCl$_3$) δ: 0.90 (3H, t, J=7.5), 1.33-1.95 (10H, m), 1.45 (9H, s), 2.61 (3H, s), 2.64-2.74 (1H, m), 3.15-3.26 (1H, m), 4.01-4.28 (2H, m), 4.26 (2H, s), 4.59-4.64 (1H, m), 4.74-4.80 (1H, m), 5.34 (1H, d, J=10.1), 6.72 (1H, s).

80c) N-(4-chlorophenyl)-N'-(1-((4-(5-methyl-3-oxo-1H-imidazo[1,5-c]imidazol-2(3H)-yl)-1-piperidinyl)carbonyl)pentyl)urea To tert-butyl 1-((4-(5-methyl-3-oxo-1H-imidazo[1,5-c]imidazol-2(3H)-yl)-1-piperidinyl)carbonyl)pentylcarbamate (0.65 g) obtained in Example 80b) was added concentrated hydrochloric acid (5 ml), and mixed for 15 minutes. To the reaction solution was added ethanol, and then concentrated under reduced pressure. The residue and DBU (0.69 g) were dissolved in acetonitrile (15 ml), and a solution of 4-chlorophenyl isocyanate (0.25 g) in acetonitrile (15 ml) was added dropwise thereto. After reacting for 15 hours, the solvent was distilled off under reduced pressure, and the residue was purified with silica gel column (ethyl acetate to ethyl acetate/methanol=5/1). The product was recrystallized from ethyl acetate-diisopropyl ether to obtain the title compound as colorless powder (0.37 g, 51%).

NMR (CDCl$_3$) δ: 0.89 (3H, t, J=6.0), 1.28-1.42 (4H, m), 1.60-2.01 (6H, m), 2.62 (3H, s), 2.70-2.83 (1H, m), 3.21-3.35 (1H, m), 4.17-4.30 (2H, s), 4.75-4.82 (1H, m), 4.89-4.96 (1H, m), 6.43-6.53 (1H, m), 6.73 (1H, s), 7.15 (2H, d, J=9.0), 7.22 (2H, d, J=9.0), 7.73-7.81 (1H, m).

Elemental analysis for C$_{24}$H$_{31}$ClN$_6$O$_3$·0.25H$_2$O.
Calcd. (%): C, 58.65; H, 6.46; N, 17.10.
Found (%): C, 58.69; H, 6.45; N, 17.09.

EXAMPLE 81

N-(4-chlorophenyl)-N'-(2-methyl-1-((4-(5-methyl-3-oxo-1H-imidazo[1,5-c]imidazol-2(3H)-yl)-1-piperidinyl)carbonyl)propyl)urea

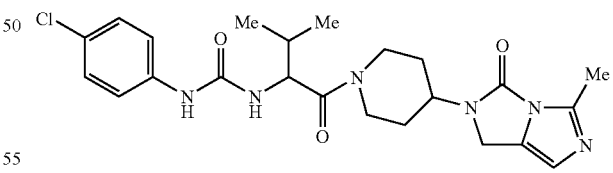

81a) tert-butyl 2-methyl-1-((4-(5-methyl-3-oxo-1H-imidazo[1,5-c]imidazol-2(3H)-yl)-1-piperidinyl)carbonyl)propylcarbamate In the same manner as in Example 80b), the title compound as colorless powder (0.30 g, 72%) was obtained from Boc-valine (0.29 g).

NMR (CDCl$_3$) δ: 0.91 (3H, t, J=6.6), 0.98 (3H, t, J=6.6), 1.45 (9H, s), 1.60-1.82 (1H, m), 1.88-2.00 (2H, m), 2.61 (3H, s), 2.62-2.70 (1H, m), 3.17-3.40 (1H, m), 4.06-4.20 (6H, m), 4.43-4.56 (1H, m), 4.70-4.84 (1H, m), 5.38 (1H, d, J=9.6), 6.71 (1H, s).

81b) N-(4-chlorophenyl)-N'-(2-methyl-1-((4-(5-methyl-3-oxo-1H-imidazo[1,5-c]imidazol-2(3H)-yl)-1-piperidinyl)carbonyl)propyl)urea In the same manner as in Example 80c), the title compound as colorless powder (0.19 g, 58%) was obtained from tert-butyl 2-methyl-1-((4-(5-methyl-3-oxo-1H-imidazo[1,5-c]imidazol-2(3H)-yl)-1-piperidinyl)carbonyl)propylcarbamate (0.3 g) obtained in Example 81a).

NMR (CDCl$_3$) δ: 0.94-1.05 (6H, m), 1.80-2.04 (5H, m), 2.61 (3H, s), 2.72-2.80 (1H, m), 3.19-3.31 (1H, m), 4.20-4.36 (4H, m), 4.74-4.85 (2H, m), 6.34 (1H, d, J=6.0), 6.72 (1H, s), 7.18-7.27 (4H, m), 7.61 (1H, d, J=6.0).

Elemental analysis for C$_{23}$H$_{29}$ClN$_6$O$_3$·0.25H$_2$·0.25AcOEt.
Calcd. (%): C, 57.71; H, 6.36; N, 16.82.
Found (%): C, 57.72; H, 6.40; N, 16.76.

EXAMPLE 82

N-(4-chlorophenyl)-N'-(2,2-dimethyl-1-((4-(5-methyl-3-oxo-1H-imidazo[1,5-c]imidazol-2(3H)-yl)-1-piperazinyl)carbonyl)propyl)urea

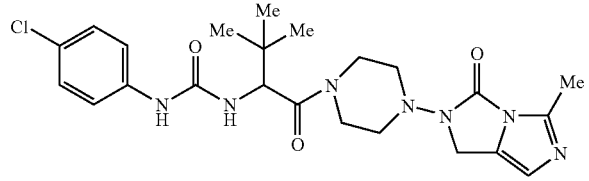

82a) tert-butyl 2,2-dimethyl-1-((4-(5-methyl-3-oxo-1H-imidazo[1,5-c]imidazol-2(3H)-yl)-1-piperazinyl)carbonyl)propylcarbamate In the same manner as in Example 10a), the title compound as colorless powder (0.37 g, 85%) was obtained from Boc-tert-leucine (0.23 g).

NMR (CDCl$_3$) δ: 1.00 (9H, s), 1.44 (9H, s), 2.60 (3H, s), 3.15-3.27 (4H, m), 3.65-3.90 (4H, m), 4.43 (2H, s), 4.51 (1H, d, J=9.9), 5.33 (1H, d, J=9.9), 6.72 (1H, s).

82b) N-(4-chlorophenyl)-N'-(2,2-dimethyl-1-((4-(5-methyl-3-oxo-1H-imidazo[1,5-c]imidazol-2(3H)-yl)-1-piperazinyl)carbonyl)propyl)urea In the same manner as in Example 80c), the title compound as colorless powder (0.18 g, 52%) was obtained from tert-butyl 2,2-dimethyl-1-((4-(5-methyl-3-oxo-1H-imidazo[1,5-c]imidazol-2(3H)-yl)-1-piperazinyl)carbonyl)propylcarbamate (0.32 g) obtained in Example 82a).

NMR (CDCl$_3$) δ: 1.03 (9H, s), 2.60 (3H, s), 3.10-3.30 (4H, m), 3.75-3.95 (4H, m), 4.42 (2H, s), 4.86 (1H, d, J=9.0), 6.05 (1H, d, J=9.0), 6.72 (1H, s), 7.24 (2H, d, J=9.0), 7.27 (2H, d, J=9.0).

Elemental analysis for C$_{23}$H$_{30}$ClN$_7$O$_3$·0.5AcOEt.
Calcd. (%): C, 56.44; H, 6.44; N, 18.43.
Found (%): C, 56.40; H, 6.48; N, 18.22.

EXAMPLE 83

N-(4-chlorophenyl)-N'-((1R)-1-((4-(5-(hydroxymethyl)-3-oxo-1H-imidazo[1,5-c]imidazol-2(3H)-yl)-1-piperidinyl)carbonyl-2,2-dimethylpropyl)urea

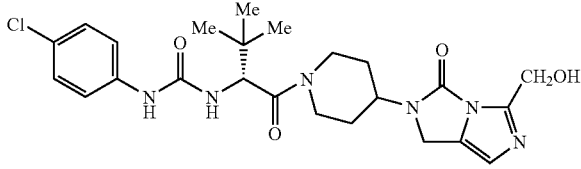

83a) 1-benzyl-N-((1H-imidazol-4-yl)methyl)-4-piperidinamine

To a solution of 1-benzyl-4-piperidinamine (3.4 g), imidazole-4-carbaldehyde (1.4 g) and acetic acid (1.7 ml) in 1,2-dichloroethane (100 ml) was added sodium triacetoxyborohydride (4.7 g), and mixed at room temperature for 15 hours. A 1 N aqueous sodium hydroxide solution was added to the reaction solution and pH of the aqueous layer was adjusted to about 12, and then extracted with chloroform (100 ml). The extract was dried over anhydrous magnesium sulfate, and then the solvent was distilled off under reduced pressure to obtain the title compound as a yellow oil (3.4 g).

NMR (CDCl$_3$) δ: 1.36-1.53 (2H, m), 1.75-2.08 (6H, m), 2.50-2.65 (1H, m), 2.66-2.86 (2H, m), 3.49 (2H, s), 4.31 (1H, brs), 6.86 (1H, s), 7.23-7.31 (5H, m), 7.51 (1H, s).

83b) tert-butyl (1-benzyl-4-piperidinyl)((1H-imidazol-4-yl)methyl)carbamate To a solution of 1-benzyl-N-((1H-imidazol-4-yl)methyl)-4-piperidinamine (3.4 g, 12 mmol) obtained in Example 83a) in ethanol (50 ml) was added di-tert-butyl dicarbonate (6.3 ml), and mixed at room temperature for 5 hours. Hydrazine hydrate (10 ml) was added, and mixed at room temperature for 18 hours. The solvent was distilled off under reduced pressure, and then the residue was diluted with ethyl acetate and water. The organic layer was collected by separation, washed with saturated brine and dried over anhydrous magnesium sulfate. The solvent was distilled off under reduced pressure, and then the residue was purified with basic silica gel column (ethyl acetate:ethanol=10:1) to obtain the title compound as a colorless oil (2.3 g, 42%).

NMR (CDCl$_3$) δ: 1.42-1.61 (12H, m), 1.66-1.84 (2H, m), 1.93-2.04 (2H, m), 2.92 (2H, d, J=7.6), 3.47 (2H, s), 3.70 (1H, brs), 4.29 (2H, s), 6.86 (1H, s), 7.24-7.33 (5H, m), 7.49 (1H, s).

83c) tert-butyl (1-benzyl-4-piperidinyl)((1-((2-(trimethylsilyl)ethoxy)methyl)-1H-imidazol-4-yl)methyl)carbamate To a solution of tert-butyl (1-benzyl-4-piperidinyl)((1H-imidazol-4-yl)methyl)carbamate (1.3 g) obtained in Example 83b) in DMF (30 ml) was added sodium hydride (0.22 g) under ice-cooling, and mixed at room temperature for 1 hour. Subsequently, 2-(trimethylsilyl)ethoxymethyl chloride (1.3 ml) was added under ice-cooling, and then mixed at room temperature for 2 hours. The reaction solution was diluted with ethyl acetate and water, and the organic layer was collected by separation. The organic layer was washed with saturated brine and dried over anhydrous magnesium sulfate, and then the solvent was distilled off under reduced pressure. The residue was purified with basic silica gel column (ethyl acetate:hexane=1:1) to obtain the title compound as a pale yellow oil (4.9 g, 24%).

NMR (CDCl$_3$) δ: 0.05 (9H, s), 0.91 (2H, t, J=8.1), 1.47 (9H, s), 1.62-1.66 (2H, m), 1.84-1.90 (3H, m), 2.03-2.09 (2H, m), 2.91-2.95 (2H, m), 3.41-3.54 (4H, m), 4.35 (2H, s), 5.22 (2H, s), 6.90 (1H, brs), 7.24-7.43 (5H, m), 7.48 (1H, s).

83d) tert-butyl (1-benzyl-4-piperidinyl)((2-formyl-1-((2-(trimethylsilyl)ethoxy)methyl)-1H-imidazol-4-yl)methyl)carbamate A solution of n-butyllithium in hexane (1.5 M, 5.7 ml) was added dropwise a solution of tert-butyl (1-benzyl-4-piperidinyl)((1-((2-(trimethylsilyl)ethoxy)methyl)-1H-imidazol-4-yl)methyl)carbamate (3.9 g) obtained in Example 83c) in THF (50 ml) at −40° C. under argon atmosphere. The reaction solution was mixed at −40° C. for 15 minutes, and then DMF (72 ml) was mixed, and mixed at room temperature for 15 hours. To the reaction solution was added a saturated aqueous ammonium chloride solution and extracted with ethyl acetate. The extract was washed with saturated brine and dried over anhydrous magnesium sulfate, and then the solvent was distilled off under reduced pressure. The residue was purified with silica gel column (ethyl acetate:ethanol=10:1) to obtain the title compound as a pale yellow oil (2.5 g, 61%).

NMR (CDCl$_3$) δ: −0.04 (9H, s), 0.90 (2H, t, J=8.2), 1.45 (9H, s), 1.63-1.77 (5H, m), 1.99-2.05 (2H, m), 2.91 (2H, d, J=11.1), 3.47 (2H, s), 3.53 (2H, t, J=8.2), 4.37 (2H, s), 5.71 (2H, s), 7.20-7.35 (5H, m), 9.74 (1H, s).

83e) tert-butyl(1-benzyl-4-piperidinyl)((2-(hydroxymethyl)-1-((2-(trimethylsilyl)ethoxy)methyl)-1H-imidazol-4-yl)methyl)carbamate To a solution of tert-butyl (1-benzyl-4-piperidinyl)((2-formyl-1-((2-(trimethylsilyl)ethoxy)methyl)-1H-imidazol-4-yl)methyl)carbamate (1.3 g) obtained in Example 83d) in ethanol (10 ml) was added sodium borohydride (95 mg) at 0° C., and mixed at room temperature for 1 hour. Water (1 ml) was added thereto, the solvent was then distilled off under reduced pressure, and the residue was diluted with ethyl acetate and water. The organic layer was collected by separation, washed with saturated brine and dried over anhydrous magnesium sulfate. Then, the solvent was distilled off under reduced pressure to obtain the title compound as a colorless oil (1.3 g, 98%).

NMR (CDCl$_3$) δ: −0.05 (9H, s), 0.88 (2H, t, J=8.4), 1.43 (9H, s), 1.57-1.60 (2H, m), 1.75-1.76 (1H, m), 1.98-1.99 (2H, m), 2.87 (2H, d, J=12.0), 3.44-3.49 (4H, m), 4.28 (2H, s), 4.66 (2H, s), 5.26 (2H, s), 6.75 (1H, brs), 7.19-7.29 (5H, m).

83f) (4-(((1-benzyl-4-piperidinyl)amino)methyl)-1H-imidazol-2-yl)methanol tert-Butyl(1-benzyl-4-piperidinyl)((2-(hydroxymethyl)-1-((2-(trimethylsilyl)ethoxy)methyl)-1H-imidazol-4-yl)methyl)carbamate (0.48 g) obtained in Example 83e) was dissolved in a mixed solution (TFA:water=1:1, 2 ml), and mixed at 80° C. for 3 hours. After cooling to room temperature, the mixture was neutralized with a saturated aqueous sodium hydrogen carbonate solution and extracted with chloroform. The extract was washed with saturated brine and dried over anhydrous magnesium sulfate, and then the solvent was distilled off under reduced pressure to obtain the title compound as a yellow oil (0.28 g, quantitative).

NMR (CDCl$_3$) δ: 1.48-1.55 (2H, m), 1.63-1.75 (2H, m), 1.87-2.02 (2H, m), 2.64-2.65 (1H, m), 2.84-2.88 (2H, m), 3.47 (2H, s), 3.74 (2H, s), 4.46 (2H, s), 5.42 (1H, brs), 6.76 (1H, s), 7.19-7.34 (5H, m).

83g) 1-benzyl-N-((2-(((tert-butyldimethylsilyl)oxy)methyl)-1H-imidazol-4-yl)methyl)-4-piperidinamine To a solution of (4-(((1-benzyl-4-piperidinyl)amino)methyl)-1H-imidazol-2-yl)methanol (0.28 g) obtained in Example 83f) and triethylamine (0.26 ml) in dichloromethane (5 ml) was added tert-butyl dimethylchlorosilane (0.17 g), and mixed at room temperature for 3 hours. The reaction solution was diluted with chloroform and water. The organic layer was collected by separation, washed with saturated brine and dried over anhydrous magnesium sulfate. The solvent was distilled off under reduced pressure, and the residue was purified with basic silica gel column (ethyl acetate:ethanol=10:1) to obtain the title compound as a pale yellow oil (0.20 g, 52%).

NMR (CDCl$_3$) δ: 0.10 (6H, s), 0.92 (9H, s), 1.41-1.44 (2H, m), 1.84-1.88 (2H, m), 1.97-2.04 (2H, m), 2.50-2.51 (1H, m), 2.82-2.86 (2H, m), 3.49 (2H, s), 3.75 (2H, s), 4.77 (2H, s), 6.81 (1H, s), 7.18-7.36 (5H, m).

83h) 2-(1-benzyl-4-piperidinyl)-5-(((tert-butyldimethylsilyl)oxy)methyl)-1,2-dihydro-3H-imidazo[1,5-c]imidazol-3-one To a solution of 1-benzyl-N-((2-(((tert-butyldimethylsilyl)oxy)methyl)-1H-imidazol-4-yl)methyl)-4-piperidinamine (0.20 g) obtained in Example 83g) and DBU (0.14 ml) in 1,2-dichloroethane (3 ml) was added N,N'-carbonyldiimidazole (94 mg), and mixed at 60° C. for 30 minutes. After cooling to room temperature, the reaction solution was diluted with chloroform and water. The organic layer was collected by separation, washed with saturated brine and dried over anhydrous magnesium sulfate. The solvent was distilled off under reduced pressure, and the residue was purified with silica gel column (ethyl acetate:ethanol=5:1) to obtain the title compound as a pale yellow oil (0.18 g, 85%).

NMR (CDCl$_3$) δ: 0.13 (6H, s), 0.91 (9H, s), 1.72-1.83 (4H, m), 2.08-2.17 (2H, m), 2.99 (2H, d, J=11.4), 3.52 (2H, s), 3.95-4.02 (1H, m), 4.30-4.31 (2H, m), 4.92 (2H, s), 6.79-6.80 (1H, m), 7.24-7.37 (5H, m).

83i) 5-(((tert-butyldimethylsilyl)oxy)methyl)-2-(4-piperidinyl)-1,2-dihydro-3H-imidazo[1,5-c]imidazol-3-one 2-(1-Benzyl-4-piperidinyl)-5-(((tert-butyldimethylsilyl)oxy)methyl)-1,2-dihydro-3H-imidazo[1,5-c]imidazol-3-one (0.18 g) obtained in Example 83h) and 10% palladium carbon (36 mg) were suspended in methanol (3 ml), and mixed under hydrogen atmosphere at room temperature for 18 hours. The reaction solution was filtered using Celite, and the filtrate was concentrated under reduced pressure to obtain the title compound as a colorless solid (0.16 g, quantitative).

NMR (CDCl$_3$) δ: 0.14 (6H, s), 0.92 (9H, s), 1.61-1.74 (2H, m), 1.85-1.88 (2H, m), 2.71-2.79 (2H, m), 3.20 (2H, d, J=11.7), 4.02-4.10 (1H, m), 4.32-4.33 (2H, m), 4.93 (2H, s), 6.80-6.81 (1H, m).

83j) benzyl(1R)-1-((4-(5-(((tert-butyldimethylsilyl)oxy)methyl)-3-oxo-1H-imidazo[1,5-c]imidazol-2(3H)-yl)-1-piperidinyl)carbonyl)-2,2-dimethylpropylcarbamate Z-D-tert-leucine (P. S. Dragovich et al., J. Med. Chem., 42, 1203 (1999); 0.25 g) was suspended in acetonitrile (10 ml). HOBt (0.17 g) and WSC (0.21 mg) were sequentially added thereto, and mixed at room temperature for 20 minutes. To the reaction solution was added a solution of 5-(((tert-butyldimethylsilyl)oxy)methyl)-2-(4-piperidinyl)-1,2-dihydro-3H-imidazo[1,5-c]imidazol-3-one (0.30 g) obtained in Example 83i) and triethylamine (0.18 ml) in acetonitrile (5 ml), and mixed at room temperature for 15 hours. Acetonitrile was distilled off under reduced pressure, and then to the residue was added ethyl acetate and water. The organic layer was collected by separation, washed with saturated brine and dried over anhydrous magnesium sulfate, and then the solvent was distilled off under reduced pressure. The residue was purified with silica gel column (ethyl acetate:hexane=1:1 to ethyl acetate) to obtain the title compound as a colorless oil (0.44 g, 86%).

NMR (CDCl$_3$) δ: 0.14 (6H, s), 0.92 (9H, s), 0.99 (9H, s), 1.59-1.71 (2H, m), 1.82-1.89 (2H, m), 2.62-2.65 (1H, m), 3.17-3.21 (1H, m), 4.16-4.31 (3H, m), 4.57-4.60 (1H, m), 4.78-4.87 (1H, m), 4.92 (2H, s), 5.08-5.11 (2H, m), 5.55-5.56 (1H, m), 6.81 (1H, s), 7.35-7.37 (5H, m).

83k) 2-(1-((2R)-2-amino-3,3-dimethylbutanoyl)-4-piperidinyl)-5-(((tert-butyldimethylsilyl)oxy)methyl)-1,2-dihydro-3H-imidazo[1,5-c]imidazol-3-one Benzyl(1R)-1-((4-(5-(((tert-butyldimethylsilyl)oxy)methyl)-3-oxo-1H-imidazo[1,5-c]imidazol-2(3H)-yl)-1-piperidinyl)carbonyl)-2,2-dimethylpropylcarbamate (0.44 g) obtained in Example 83j) and 10% palladium carbon (44 mg) were suspended in methanol (10 ml), and mixed under hydrogen atmosphere at room temperature for 1 hour. The reaction solution was filtered using Celite, and the filtrate was concentrated under reduced pressure to obtain the title compound as a colorless solid (0.33 g, 96%).

NMR (CDCl$_3$) δ: 0.14 (6H, s), 0.92 (9H, s), 0.97 (9H, s), 1.64-1.74 (2H, m), 1.93-1.94 (2H, m), 2.60-2.69 (1H, m), 3.10-3.19 (1H, m), 3.57 (1H, d, J=13.5), 4.17-4.31 (4H, m), 4.90-4.92 (3H, m), 6.81 (1H, d, J=4.5).

83l) N-((1R)-1-((4-(5-(((tert-butyldimethylsilyl)oxy)methyl)-3-oxo-1H-imidazo[1,5-c]imidazol-2(3H)-yl)-1-piperidinyl)carbonyl)-2,2-dimethylpropyl)-N'-(4-chlorophenyl)urea To a solution of 2-(1-((2R)-2-amino-3,3-dimethylbutanoyl)-4-piperidinyl)-5-(((tert-butyldimethylsilyl)oxy)methyl)-1,2-dihydro-3H-imidazo[1,5-c]imidazol-3-one (0.33 g) obtained in Example 83k) in acetonitrile was added 4-chlorophenyl isocyanate (0.11 g), and then mixed at room temperature for 1 hour. Acetonitrile was distilled off under reduced pressure, and then the residue was purified with silica gel column (ethyl acetate) to obtain the title compound as a colorless solid (0.38 g, 85%).

NMR (CDCl$_3$) δ: 0.91 (9H, s), 1.03-1.07 (9H, m), 1.44-2.05 (4H, m), 2.62-2.74 (1H, m), 3.16-3.26 (1H, m), 4.03-4.26 (2H, m), 4.32-4.40 (2H, m), 4.80-4.93 (4H, m), 6.09-6.15 (1H, m), 6.80-6.83 (1H, m), 7.20-7.28 (4H, m), 7.37-7.41 (1H, m).

83m) N-(4-chlorophenyl)-N'-((1R)-1-((4-(5-(hydroxymethyl)-3-oxo-1H-imidazo[1,5-c]imidazol-2(3H)-yl)-1-piperidinyl)carbonyl)-2,2-dimethylpropyl)urea N-((1R)-1-((4-(5-(((tert-butyldimethylsilyl)oxy)methyl)-3-oxo-1H-imidazo[1,5-c]imidazol-2(3H)-yl)-1-piperidinyl)carbonyl)-2,2-dimethylpropyl)-N'-(4-chlorophenyl)urea (0.31 g) obtained in Example 83l) was dissolved in a solution (acetic acid:water:THF=4:1:1, 6 ml), and mixed at 60° C. for 4 hours. The solvent was distilled off under reduced pressure, and then to the residue were added ethyl acetate and a saturated aqueous sodium hydrogen carbonate solution. The organic layer was collected by separation, washed with saturated brine and dried over anhydrous magnesium sulfate, and then the solvent was distilled off under reduced pressure. The residue was purified with basic silica gel column (ethyl acetate to ethyl acetate:ethanol=10:1) to obtain the title compound as a colorless solid (0.21 g, 85%).

NMR (CDCl$_3$) δ: 1.03-1.06 (9H, s), 1.56-2.12 (4H, m), 2.64-2.76 (1H, m), 3.16-3.26 (1H, m), 4.14-4.23 (2H, m), 4.35-4.40 (2H, m), 4.82-4.87 (4H, m), 5.95-6.07 (1H, m), 6.78-6.79 (1H, m), 7.18-7.34 (5H, m).

Elemental analysis for $C_{24}H_{31}ClN_6O_4 \cdot 0.5H_2O \cdot 0.2Et_2O$.
Calcd. (%): C, 56.54; H, 6.50; N, 15.95.
Found (%): C, 56.31; H, 6.58; N, 15.69.

EXAMPLE 84

N-(4-chlorophenyl)-N-methyl-N'-(2-(4-(5-methyl-3-oxo-1H-imidazo[1,5-c]imidazol-2(3H)-yl)-1-piperidinyl)-2-oxo-1-phenylethyl)urea

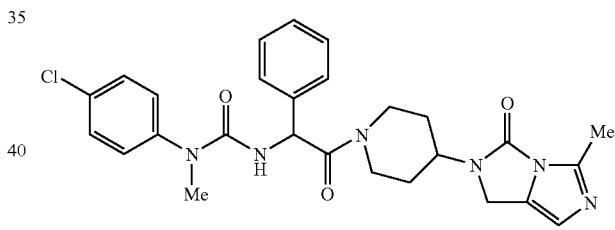

A solution of N,N'-carbonyldiimidazole (0.36 g) and 4-chloro-N-methylaniline (0.28 g) in THF (10 ml) was heated under reflux for 24 hours. The solvent was distilled off under reduced pressure, and then the residue was dissolved in ethyl acetate. The ethyl acetate solution was washed twice with water and dried over anhydrous sodium sulfate, and the solvent was distilled off under reduced pressure. The residue was dissolved in acetonitrile (10 ml), methyl iodide (0.50 ml) was added thereto, and mixed at room temperature for 15 hours and at 40° C. for 5 hours. The solvent was distilled off under reduced pressure, and the residue was dissolved in acetonitrile (5 ml). Then, a solution of 2-(1-(2-amino-2-phenylacetyl)-4-piperidinyl)-5-methyl-1,2-dihydro-3H-imidazo[1,5-c]imidazol-3-one (0.71 g) obtained in Example 50b) and DBU (0.61 g) in acetonitrile (5 ml) was added thereto, and the reaction mixture was mixed at room temperature for 48 hours. The reaction mixture was concentrated under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure, and the residue was purified with silica gel column (ethyl acetate to ethyl acetate/methanol=5/1 and ethyl acetate/ methanol=10/1) and solidified with diisopropyl ether to obtain the title compound (52 mg, 5%) as pale yellow powder.

NMR (CDCl$_3$) δ: 1.26-1.38 (2H, m), 1.78-1.91 (2H, m), 2.56-2.60 (3H, m), 2.67-3.12 (2H, m), 3.23-3.25 (3H, m), 3.79-4.27 (4H, m), 4.72-4.76 (1H, m), 5.74-6.01 (1H, m), 6.65-6.72 (2H, m), 7.20-7.40 (9H, m).

Elemental analysis for C$_{27}$H$_{29}$ClN$_6$O$_3$.1.3H$_2$O.
Calcd. (%): C, 59.56; H, 5.85; N, 15.44.
Found (%): C, 59.76; H, 5.92; N, 15.38.

EXAMPLE 85

N-(4-chlorophenyl)-N'-((1R)-2,2-dimethyl-1-((4-((5-methyl-3-oxo-1H-imidazo[1,5-c]imidazol-2(3H)-yl)methyl)-1-piperidinyl)carbonyl)propyl)urea

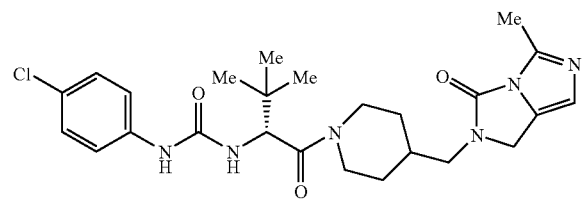

85a) tert-butyl 4-((5-methyl-3-oxo-1H-imidazo[1,5-c]imidazol-2(3H)-yl)methyl)-1-piperidinecarboxylate To a solution of tert-butyl 4-(aminomethyl)-1-piperidinecarboxylate (K. Ito et al., Eur. J. Med. Chem., 34, 977 (1999); 3.7 g), 2-methylimidazole-4-carbaldehyde (1.9 g) and acetic acid (1 ml) in 1,2-dichloroethane (100 ml) was added sodium triacetoxyborohydride (5.6 g), and mixed at room temperature for 15 hours. pH of the aqueous layer was adjusted to about 12 by adding a 1 N aqueous sodium hydroxide solution to the reaction solution, and then extracted with chloroform. The extract was dried over anhydrous magnesium sulfate, and then the solvent was distilled off under reduced pressure. The resulting yellow oil was dissolved in dichloromethane (100 ml), DBU (2.6 ml) and N,N'-carbonyldiimidazole (2.8 g) were added thereto, and mixed at room temperature for 15 hours. The reaction mixture was diluted with water and chloroform and the organic layer was collected by separation, and then dried over anhydrous magnesium sulfate. The solvent was distilled off under reduced pressure, and the residue was purified with silica gel column (ethyl acetate:ethanol=5:1) to obtain the title compound as a yellow oil (3.5 g, 59%).

NMR (CDCl$_3$) δ: 1.16-1.30 (2H, m), 1.45 (9H, s), 1.69 (2H, d, J=12.6), 1.83-1.91 (1H, m), 2.61 (3H, s), 2.70 (2H, t, J=11.9), 3.34 (2H, d, J=7.2), 4.08-4.15 (2H, m), 4.35 (2H, s), 6.69 (1H, s).

85b) tert-butyl(1R)-2,2-dimethyl-1-((4-((5-methyl-3-oxo-1H-imidazo[1,5-c]imidazol-2(3H)-yl)methyl)-1-piperidinyl)carbonyl)propylcarbamate To tert-butyl 4-((5-methyl-3-oxo-1H-imidazo[1,5-c]imidazol-2(3H)-yl)methyl)-1-piperidinecarboxylate (3.5 g) obtained in Example 85a) was added concentrated hydrochloric acid (10 ml), and mixed for 10 minutes. To the reaction mixture was added ethanol, and the solvent was distilled off under reduced pressure. To the residue was further added ethanol, and the solvent was distilled off under reduced pressure. To the residue was added isopropyl alcohol, and the precipitate was collected by filtration. The precipitate was washed sequentially with isopropyl alcohol and diethyl ether and dried under reduced pressure to obtain 5-methyl-2-(4-piperidinyl)methyl-1,2-dihydro-3H-imidazo[1,5-c]imidazol-3-one dihydrochloride as a colorless solid (2.5 g, 78%).

To a solution of Boc-D-tert-leucine (0.69 g), HOBt (0.69 g) and WSC (0.86 g) in acetonitrile (20 ml) was added a solution of 5-methyl-2-(4-piperidinylmethyl)-1,2-dihydro-3H-imidazo[1,5-c]imidazol-3-one dihydrochloride (0.91 g) as described above, DBU (0.6 ml) and triethylamine (0.61 ml) in acetonitrile (20 ml), and mixed for 15 hours. The solvent was distilled off under reduced pressure, and the residue was dissolved in dichloromethane. The dichloromethane solution was washed with an aqueous sodium hydrogen carbonate solution and dried over anhydrous magnesium sulfate. The solvent was distilled off under reduced pressure, and the residue was purified with basic silica gel column (ethyl acetate/methanol=10/1) to obtain the title compound as colorless powder (1.2 g, 66%).

NMR (CDCl$_3$) δ: 0.96 (9H, s), 1.42 (9H, s), 1.60-2.00 (4H, m), 2.50-2.70 (1H, m), 2.60 (3H, s), 3.00-3.10 (1H, m), 3.29-3.44 (3H, m), 4.11-4.18 (1H, m), 4.35 (2H, s), 4.50-4.72 (2H, m), 5.35 (1H, J=9.0), 6.70 (1H, s).

85c) N-(4-chlorophenyl)-N'-((1R)-2,2-dimethyl-1-((4-((5-methyl-3-oxo-1H-imidazo[1,5-c]imidazol-2(3H)-yl)methyl)-1-piperidinyl)carbonyl)propyl)urea In the same manner as in Example 15b), the title compound as colorless powder (recrystallization from ethyl acetate-hexane: 0.33 g, 48%) was obtained from tert-butyl (1R)-2,2-dimethyl-1-((4-((5-methyl-3-oxo-1H-imidazo[1,5-c]imidazol-2(3H)-yl)methyl)-1-piperidinyl)carbonyl)propylcarbamate (0.62 g) obtained in Example 85a).

NMR (CDCl$_3$) δ: 1.02-1.05 (9H, m), 1.58-2.04 (4H, m), 2.60-2.62 (3H, m), 3.05-3.78 (4H, m), 4.18-4.36 (4H, m), 4.51-4.72 (1H, m), 4.83-5.00 (1H, m), 6.20 (1H, d, J=9.0), 6.69-6.73 (1H, m), 7.16-7.23 (4H, m), 7.60 (1H, s).

Elemental analysis for C$_{25}$H$_{33}$ClN$_6$O$_3$.0.5H$_2$O.0.5Et$_2$O.
Calcd. (%): C, 59.23; H, 7.19; N, 15.36.
Found (%): C, 59.11; H, 6.84; N, 15.60.

EXAMPLE 86

N-(4-chlorophenyl)-N'-((1R)-2,2-dimethyl-1-((3-(5-methyl-3-oxo-1H-imidazo[1,5-c]imidazol-2(3H)-yl)-1-pyrrolidinyl)carbonyl)propyl)urea

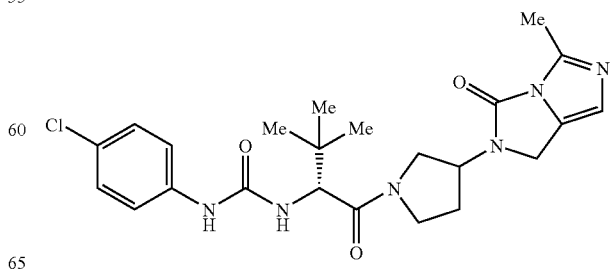

86a) 2-(1-benzyl-3-pyrrolidinyl)-5-methyl-1,2-dihydro-3H-imidazo[1,5-c]imidazol-3-one In the same manner as in Reference Example 1a), the title compound as a yellow oil (31 g, 80%) was obtained from 1-benzyl-3-pyrrolidinamine (23 g).

NMR (CDCl$_3$) δ: 1.81-1.89 (1H, m), 2.23-2.34 (2H, m), 2.51 (1H, dd, J=10.2, 6.9), 2.58 (3H, s), 2.78 (1H, dd, J=10.2, 2.4), 2.96-3.02 (1H, m), 3.54 (1H, d, J=12.8), 3.67 (1H, d, J=12.8), 4.41 (2H, s), 4.71-4.77 (1H, m), 6.68 (1H, t, J=1.5), 7.23-7.35 (5H, m).

86b) 5-methyl-2-(3-pyrrolidinyl)-1,2-dihydro-3H-imidazo[1,5-c]imidazol-3-one dihydrochloride 2-(1-Benzyl-3-pyrrolidinyl)-5-methyl-1,2-dihydro-3H-imidazo[1,5-c]imidazol-3-one (31 g) obtained in Example 86a), ammonium formate (40 g) and 10% palladium carbon (6.2 g) were suspended in methanol (300 ml), and heated under reflux for 2 hours. After cooling to room temperature, the precipitate was filtered using Celite, and then the filtrate was concentrated under reduced pressure. To the residue was added a mixed solvent (ethyl acetate:chloroform=5:1), and the precipitate was filtered off. To the filtrate was added a 4 N solution of hydrogen chloride in ethyl acetate (30 ml), mixed for 15 minutes, and then concentrated under reduced pressure. To the residue was added a mixed solvent (ethyl acetate:ethanol=5:1), and mixed at room temperature for 1 hour. The precipitate was collected by filtration to obtain the title compound as a pale brown solid (28 g, 91%).

NMR (DMSO-d$_6$) δ: 2.21-2.29 (2H, m), 2.76 (3H, s), 3.18-3.27 (1H, m), 3.33-3.47 (3H, m), 4.70-4.85 (3H, m), 7.55 (1H, s), 9.83 (1H, brs), 10.11 (1H, brs).

86c) tert-butyl(1R)-2,2-dimethyl-1-((3-(5-methyl-3-oxo-1H-imidazo[1,5-c]imidazol-2(3H)-yl)-1-pyrrolidinyl)carbonyl)propylcarbamate In the same manner as in Example 19a), the title compound as colorless powder (1.3 g, 79%) was obtained from 5-methyl-2-(3-pyrrolidinyl)-1,2-dihydro-3H-imidazo[1,5-c]imidazol-3-one dihydrochloride (1.1 g).

NMR (CD$_3$OD) δ: 1.00 (9H, s), 1.44 (9H, s), 2.08-2.37 (2H, m), 2.61 (3H, s), 3.49-3.68 (1H, m), 3.70-4.00 (1H, m), 4.11-4.85 (5H, m), 5.21 (1H, m), 6.62 (1H, s), 6.72 (1H, s).

86d) N-(4-chlorophenyl)-N'-((1R)-2,2-dimethyl-1-((3-(5-methyl-3-oxo-1H-imidazo[1,5-c]imidazol-2(3H)-yl)-1-pyrrolidinyl)carbonyl)propyl)urea In the same manner as in Example 15b), the title compound as colorless powder (0.40 g, 50%) was obtained from tert-butyl(1R)-2,2-dimethyl-1-((3-(5-methyl-3-oxo-1H-imidazo[1,5-c]imidazol-2(3H)-yl)-1-pyrrolidinyl)carbonyl)propylcarbamate (0.70 g) obtained in Example 86c).

NMR (CDCl$_3$) δ: 1.06 (9H, s), 2.05-2.38 (2H, m), 3.43-4.88 (8H, m), 5.95-6.05 (1H, m), 6.59-6.74 (1H, m), 7.17-7.26 (4H, m), 7.48-7.63 (1H, m).

Elemental analysis for $C_{23}H_{29}ClN_6O_3 \cdot 0.5H_2O \cdot 0.5Et_2O$.

Calcd. (%): C, 57.85; H, 6.80; N, 16.19.

Found (%): C, 58.18; H, 6.79; N, 16.32.

EXAMPLE 87

N-(4-chlorophenyl)-N'-((1R)-2,2-dimethyl-1-((3-(3-oxo-1H-imidazo[1,5-a]imidazol-2(3H)-yl)-1-pyrrolidinyl)carbonyl)propyl)urea

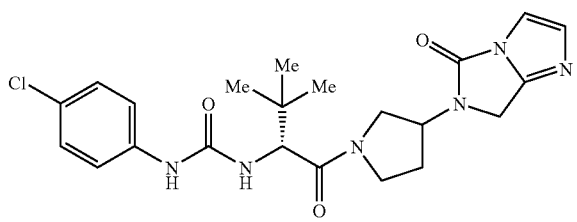

87a) 6-(1-benzyl-3-pyrrolidinyl)-1,2-dihydro-3H-imidazo[1,5-a]imidazol-3-one In the same manner as in Reference Example 1a), the title compound as a yellow oil (2.7 g, 12%) was obtained from 1-benzyl-3-pyrrolidinamine (14 g) and imidazole-2-carbaldehyde (7.7 g).

NMR (CDCl$_3$) δ: 1.79-1.90 (1H, m), 2.24-2.41 (2H, m), 2.45-2.51 (1H, m), 2.80 (1H, d, J=10.5), 3.02-3.09 (1H, m), 3.51 (1H, d, J=12.6), 3.70 (1H, d, J=12.6), 4.49 (2H, s), 4.79-4.86 (1H, m), 7.16 (1H, d, J=1.5), 7.22-7.35 (6H, m).

87b) 6-(3-pyrrolidinyl)-1,2-dihydro-3H-imidazo[1,5-a]imidazol-3-one 6-(1-Benzyl-3-pyrrolidinyl)-1,2-dihydro-3H-imidazo[1,5-a]imidazol-3-one (2.7 g) obtained in Example 87a), ammonium formate (1.8 g) and 10% palladium carbon (0.54 g) suspended in methanol (100 ml), and heated under reflux for 2 hours. After cooling to room temperature, the precipitate was filtered using Celite, and then the filtrate was concentrated under reduced pressure. To the residue was added a mixed solvent (ethyl acetate:chloroform=5:1), the precipitate was filtered off, and then the filtrate was further concentrated to obtain the title compound as a pale yellow solid (1.4 g, 78%).

NMR (CDCl$_3$) δ: 1.85-1.96 (1H, m), 2.18-2.30 (1H, m), 2.96-3.07 (2H, m), 3.15-3.28 (2H, m), 4.42 (1H, d, J=16.8), 4.49 (1H, d, J=16.8), 4.65-4.74 (1H, m), 7.19 (1H, d, J=1.2), 7.30 (1H, d, J=1.2).

87c) tert-butyl(1R)-2,2-dimethyl-1-((3-(3-oxo-1H-imidazo[1,5-a]imidazol-2(3H)-yl)-1-pyrrolidinyl)carbonyl)propylcarbamate In the same manner as in Example 11a), the title compound as colorless powder (1.3 g, 93%) was obtained from 6-(3-pyrrolidinyl)-1,2-dihydro-3H-imidazo[1,5-a]imidazol-3-one (0.65 g) obtained in Example 87b).

NMR (CDCl$_3$) δ: major diastereomer 1.02 (9H, s), 1.45 (9H, s), 2.11-2.43 (2H, m), 3.44-4.60 (6H, m), 4.75-4.93 (1H, m), 5.18-5.24 (1H, m), 7.19 (1H, s), 7.31 (1H, s).

87d) N-(4-chlorophenyl)-N'-((1R)-2,2-dimethyl-1-((3-(3-oxo-1H-imidazo[1,5-a]imidazol-2(3H)-yl)-1-pyrrolidinyl)carbonyl)propyl)urea In the same manner as in Example 15b), the title compound as colorless powder (recrystallization from diethyl ether-diisopropyl ether: 0.46 g, 71%) was obtained from tert-butyl (1R)-2,2-dimethyl-1-((3-(3-oxo-1H-imidazo[1,5-a]imidazol-2(3H)-yl)-1-pyrrolidinyl)carbonyl)propylcarbamate (0.57 g) obtained in Example 87c).

NMR (CDCl$_3$) δ: 0.94-1.04 (9H, m), 2.14-2.34 (2H, m), 2.35-4.68 (7H, m), 4.83-4.93 (1H, m), 6.07-6.16 (1H, m), 7.07-7.36 (4H, m), 7.76-7.96 (1H, m), 8.52 (1H, s).

Elemental analysis for C$_{22}$H$_{27}$ClN$_6$O$_3$.0.25H$_2$O.0.25Et$_2$O.

Calcd. (%): C, 57.32; H, 6.27; N, 17.44.
Found (%): C, 57.40; H, 6.32; N, 17.18.

EXAMPLE 88

N-(4-chlorophenyl)-N'-((1R)-1-((4-(5,7-dimethyl-3-oxo-1H-imidazo[1,5-c]imidazol-2(3H)-yl)-1-piperidinyl)carbonyl)-2,2-dimethylpropyl)urea

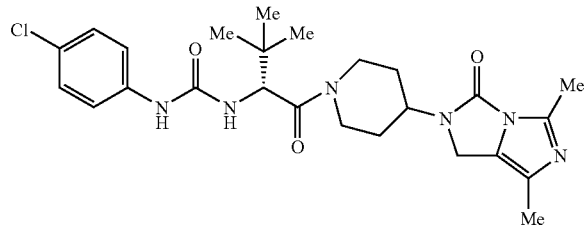

88a) tert-butyl 4-(((2,5-dimethyl-1H-imidazol-4-yl)methyl)amino)-1-piperidinecarboxylate N-(tert-butoxycarbonyl-4-piperidinyl)amine (4.8 g), 2,5-dimethylimidazole-4-carbaldehyde (3.0 g) and acetic acid (1.7 ml) were dissolved in 1,2-dichloroethane (50 ml), under ice-cooling, sodium triacetoxyborohydride (7.7 g) was added thereto, and mixed at room temperature for 15 hours. The reaction solution was poured into an aqueous potassium carbonate solution, and extracted with chloroform. The extract was dried over anhydrous magnesium sulfate, the solvent was distilled off under reduced pressure, and then the residue was purified with silica gel column to obtain a pale yellow oily title compound (8.0 g, quantitative).

NMR (CDCl$_3$) δ: 1.27-1.40 (2H, m), 1.45 (9H, s), 1.85-1.90 (2H, m), 2.15 (3H, s), 2.31 (3H, s), 2.66-2.80 (3H, m), 3.71 (2H, s), 4.00-4.18 (2H, m), 6.06 (2H, brs).

88b) tert-butyl 4-(5,7-dimethyl-3-oxo-1H-imidazo[1,5-c]imidazol-2(3H)-yl)-1-piperidinecarboxylate tert-Butyl 4-(((2,5-dimethyl-1H-imidazol-4-yl)methyl)amino)-1-piperidinecarboxylate (8.0 g) obtained in Example 88a) was dissolved in dichloromethane (100 ml), DBU (3.6 ml) and N,N'-carbonyldiimidazole (3.9 g) were added thereto. The reaction solution was mixed for 15 hours, and then the reaction solution was poured into an aqueous potassium carbonate solution and extracted with chloroform. The extract was dried over anhydrous magnesium sulfate, the solvent was distilled off under reduced pressure, and then the residue was purified with silica gel column to obtain a pale yellow oily title compound (7.8 g, 97%).

NMR (CDCl$_3$) δ: 1.47 (9H, s), 1.57-1.72 (2H, m), 1.77-1.92 (2H, m), 2.15 (3H, s), 2.57 (3H, s), 2.77-2.88 (2H, m), 4.03-4.15 (2H, m), 4.20 (2H, s), 4.29 (1H, brs).

88c) tert-butyl(1R)-1-((4-(5,7-dimethyl-3-oxo-1H-imidazo[1,5-c]imidazol-2(3H)-yl)-1-piperidinyl)carbonyl)-2,2-dimethylpropylcarbamate In the same manner as in Example 85b), the title compound as colorless powder (1.5 g, 79%) was obtained from tert-butyl 4-(5,7-dimethyl-3-oxo-1H-imidazo[1,5-c]imidazol-2(3H)-yl)-1-piperidinecarboxylate (1.0 g) obtained in Example 88b).

NMR (CDCl$_3$) δ: 0.98-1.02 (9H, m), 1.43-1.45 (9H, m), 1.57-2.06 (4H, m), 2.14 (3H, s), 2.56 (3H, s), 2.62-2.71 (1H, m), 3.13-3.26 (1H, m), 4.15-4.28 (4H, m), 4.52 (1H, d, J=10.5), 4.78-4.83 (1H, m), 5.31 (1H, d, J=10.5).

88d) N-(4-chlorophenyl)-N'-((1R)-1-((4-(5,7-dimethyl-3-oxo-1H-imidazo[1,5-c]imidazol-2(3H)-yl)-1-piperidinyl)carbonyl)-2,2-dimethylpropyl)urea In the same manner as in Example 15b), the title compound as a colorless solid (recrystallization from diethyl ether: 0.76 g, 50%) was obtained from tert-butyl (1R)-1-((4-(5,7-dimethyl-3-oxo-1H-imidazo[1,5-c]imidazol-2(3H)-yl)-1-piperidinyl)carbonyl)-2,2-dimethylpropylcarbamate (1.4 g) obtained in Example 88c).

NMR (CDCl$_3$) δ: 1.03 (9H, s), 1.42-1.97 (4H, m), 2.11 (3H, s), 2.55 (3H, s), 2.61-2.74 (1H, m), 3.16-3.30 (1H, m), 3.94 (1H, d, J=15.5), 4.05 (1H, d, J=15.5), 4.13-4.22 (1H, m), 4.36-4.41 (1H, m), 4.76-4.92 (2H, m), 6.26 (1H, d, J=9.3), 7.09-7.23 (4H, m), 7.55 (1H, s).

Elemental analysis for C$_{24}$H$_{31}$ClN$_6$O$_3$.0.5H$_2$O 0.25AcOEt.

Calcd. (%): C, 58.69; H, 6.82; N, 15.80.
Found (%): C, 58.61; H, 7.03; N, 15.85.

EXAMPLE 89

N-(4-chlorophenyl)-N'-((1R)-2,2-dimethyl-1-((4-(2-methyl-5-oxo-5H-imidazo[1,5-a]imidazol-6(7H)-yl)-1-piperidinyl)carbonyl)propyl)urea

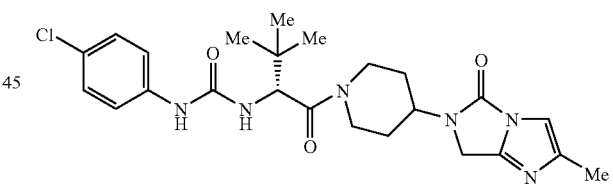

89a) tert-butyl 4-(((4-methyl-1H-imidazol-2-yl)methyl)amino)-1-piperidinecarboxylate In the same manner as in Example 88a), the title compound as a yellow oil (6.3 g, 68%) was obtained from 4-methylimidazole-2-carbaldehyde (N. J. Curtis et al., J. Org. Chem., 45, 4038 (1980); 3.4 g).

NMR (CDCl$_3$) δ: 1.16-1.29 (2H, m), 1.45 (9H, s), 1.84 (2H, d), 2.22 (3H, s), 2.59-2.66 (1H, m), 2.76 (2H, t), 3.89 (2H, s), 4.00 (2H, brs), 6.63 (1H, s).

89b) tert-butyl 4-(2-methyl-5-oxo-5H-imidazo[1,5-a]imidazol-6(7H)-yl)-1-piperidinecarboxylate In the same manner as in Example 88b), the title compound (1.2 g, 46%) as a yellow oil was obtained from tert-butyl 4-(((4-methyl-1H-imidazol-2-yl)methyl)amino)-1-piperidinecarboxylate (2.4 g) obtained in Example 89a).

NMR (CDCl$_3$) δ: 1.47 (9H, s), 1.56-1.70 (2H, m), 1.85 (2H, d), 2.28 (3H, s), 2.82 (2H, t), 4.10-4.24 (3H, m), 4.27 (2H, s), 7.00 (1H, s).

89c) tert-butyl(1R)-2,2-dimethyl-1-((4-(2-methyl-5-oxo-5H-imidazo[1,5-a]imidazol-6(7H)-yl)-1-piperidinyl)carbonyl)propylcarbamate In the same manner as in Example 85b), the title compound as colorless powder (0.18 g, 42%) was obtained from tert-butyl 4-(2-methyl-5-oxo-5H-imidazo[1,5-a]imidazol-6(7H)-yl)-1-piperidinecarboxylate (0.30 g) obtained in Example 89b).

NMR (CDCl$_3$) δ: 0.98 (9H, s), 1.44 (9H, s), 1.60-1.97 (4H, m), 2.28 (3H, s), 2.60-2.73 (1H, m), 3.11-3.24 (1H, m), 4.24 (2H, s), 4.25-4.35 (3H, m), 4.40-4.55 (1H, m), 4.78-4.86 (1H, m), 5.29-5.34 (1H, m), 7.01 (1H, s).

89d) N-(4-chlorophenyl)-N'-((1R)-2,2-dimethyl-1-((4-(2-methyl-5-oxo-5H-imidazo[1,5-a]imidazol-6(7H)-yl)-1-piperidinyl)carbonyl)propyl)urea To tert-butyl(1R)-2,2-dimethyl-1-((4-(2-methyl-5-oxo-5H-imidazo[1,5-a]imidazol-6(7H)-yl)-1-piperidinyl)carbonyl)propylcarbamate (0.17 g) obtained in Example 89c) was added a 40% solution of hydrogen chloride in ethanol (10 ml), and mixed for 1 hour. The reaction solution was concentrated under reduced pressure. The residue and triethylamine (0.16 ml) were dissolved in acetonitrile (15 ml) and a solution of 4-chlorophenyl isocyanate (72 mg) in acetonitrile (15 ml) was added dropwise thereto. The reaction mixture was mixed for 15 hours, then the solvent was distilled off under reduced pressure, and the residue was purified with silica gel column (ethyl acetate to ethyl acetate/methanol=5/1). The product was recrystallized from diethyl ether to obtain the title compound as colorless powder (0.17 g, 53%).

NMR (CDCl$_3$) δ: 0.95-1.05 (9H, two s), 1.40-2.09 (2H, m), 2.29-2.32 (3H, two s), 2.58-2.72 (1H, m), 3.10-3.25 (1H, m), 4.11-4.48 (5H, m), 4.71-4.81 (1H, m), 4.84-4.88 (1H, m), 5.70-6.05 (1H, m), 6.82-7.15 (2H, m), 7.15-7.35 (4H, m), 8.20 (1H, s).

Elemental analysis for $C_{24}H_{31}ClN_6O_3 \cdot H_2O$.
Calcd. (%): C, 57.08; H, 6.59; N, 16.64.
Found (%): C, 56.96; H, 6.66; N, 16.42.

EXAMPLE 90

N-(4-chlorophenyl)-N'-((1R)-1-((4-(5,7-dimethyl-3-oxo-1H-imidazo[1,5-c]imidazol-2(3H)-yl)-1-piperazinyl)carbonyl)-2,2-dimethylpropyl)urea

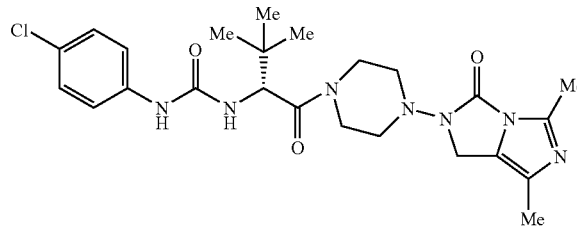

90a) 4-benzyl-N-((1E)-(2,5-dimethylimidazol-4-yl)methylene)-1-piperazinamine In the same manner as in Reference Example 2a), the title compound as pale yellow liquid (6.0 g, 84%) was obtained from 2,5-dimethylimidazole-4-carbaldehyde (3.0 g).

NMR (CDCl$_3$) δ: 2.23 (3H, s), 2.32 (3H, s), 2.62 (4H, t, J=4.8), 3.08 (3H, t, J=4.8), 3.55 (2H, s), 7.22-7.33 (5H, m), 7.48 (1H, s).

90b) 2-(4-benzyl-1-piperazinyl)-5,7-dimethyl-1,2-dihydro-3H-imidazo[1,5-c]imidazol-3-one The reactions was sequentially carried out in the same manner as in Reference Examples 2b) and 2c), the title compound as yellow liquid (2.7 g, 40%) was obtained from 4-benzyl-N-((1E)-(2,5-dimethylimidazol-4-yl)methylene)-1-piperazinamine (6.0 g) obtained in Example 90a).

NMR (CDCl$_3$) δ: 2.14 (3H, s), 2.52 (2H, t. J=5.0), 2.57 (3H, s), 2.63 (2H, t, J=5.0), 3.12 (2H, t, J=5.0), 3.56 (2H, s), 3.62 (2H, t, J=5.0), 4.36 (2H, s), 7.20-7.34 (5H, m).

90c) 5,7-dimethyl-2-(1-piperazinyl)-1,2-dihydro-3H-imidazo[1,5-c]imidazol-3-one In the same manner as in Reference Example 2d), the title compound as a colorless solid (1.2 g, 62%) was obtained from 2-(4-benzyl-1-piperazinyl)-5,7-dimethyl-1,2-dihydro-3H-imidazo[1,5-c]imidazol-3-one (2.7 g) obtained in Example 90b).

NMR (CDCl$_3$) δ: 2.16 (3H, s), 2.57 (3H, s), 2.82-3.04 (4H, m), 3.10-3.15 (4H, m), 4.38 (2H, s).

90d) tert-butyl(1R)-1-((4-(5,7-dimethyl-3-oxo-1H-imidazo[1,5-c]imidazol-2(3H)-yl)-1-piperazinyl)carbonyl)-2,2-dimethylpropylcarbamate In the same manner as in Example 10a), the title compound as colorless powder (1.4 g, 71%) was obtained from 5,7-dimethyl-2-(1-piperazinyl)-1,2-dihydro-3H-imidazo[1,5-c]imidazol-3-one (1.0 g) obtained in Example 90c) and Boc-D-tert-leucine (0.98 g).

NMR (CDCl$_3$) δ: 0.99 (9H, s), 1.44 (9H, s), 2.05 (3H, s), 2.56 (3H, s), 3.14-3.23 (4H, m), 3.70-3.84 (4H, m), 4.35 (2H, s), 4.51 (1H, d, J=9.0), 5.33 (1H, d, J=9.0).

90e) N-(4-chlorophenyl)-N'-((1R)-1-((4-(5,7-dimethyl-3-oxo-1H-imidazo[1,5-c]imidazol-2(3H)-yl)-1-piperazinyl)carbonyl)-2,2-dimethylpropyl)urea In the same manner as in Example 15b), the title compound as colorless powder (recrystallization from ethyl acetate-hexane: 0.50 g, 64%) was obtained from tert-butyl (1R)-1-((4-(5,7-dimethyl-3-oxo-1H-imidazo[1,5-c]imidazol-2(3H)-yl)-1-piperazinyl)carbonyl)-2,2-dimethylpropylcarbamate (0.70 g) obtained in Example 90d).

NMR (CDCl$_3$) δ: 1.05 (9H, s), 2.14 (3H, s), 2.56 (3H, s), 3.01-3.24 (4H, m), 3.63-3.98 (4H, m), 4.28 (2H, s), 4.89 (1H, d, J=9.0), 6.23 (1H, d, J=9.0), 7.13-7.24 (4H, m), 7.65 (1H, s).

Elemental analysis for $C_{24}H_{32}ClN_7O_3$.
Calcd. (%): C, 57.42; H, 6.43; N, 19.53.
Found (%): C, 57.12; H, 6.56; N, 19.42.

EXAMPLE 91

N-(4-chlorophenyl)-N'-((1R)-2,2-dimethyl-1-((4-(3-methyl-8-oxo-5,6-dihydroimidazo[1,5-a]pyrazin-7(8H)-yl)-1-piperidinyl)carbonyl)propyl)urea

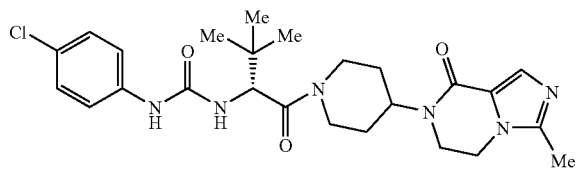

91a) tert-butyl 4-(2-hydroxyethyl)amino-1-piperidinecarboxylate

A solution of tert-butyl 4-oxo-1-piperidinecarboxylate (15 g), 2-aminoethanol (14 ml), acetic acid (6.6 ml) in 1,2-dichloroethane (300 ml) was mixed at room temperature for 1 hour, and then sodium triacetoxyborohydride (49 g) was added thereto, followed by mixing at room temperature for 15 hours. pH of the aqueous layer was adjusted to about 12 by adding a 1 N aqueous sodium hydroxide solution to the reaction mixture, and then extracted with chloroform. The extract was dried over anhydrous magnesium sulfate, and then the solvent was distilled off under reduced pressure to obtain the title compound as a colorless oil (18 g, 89%).

NMR (CDCl$_3$) δ: 1.17-1.37 (2H, m), 1.46 (9H, s), 1.88 (2H, m), 2.57-2.85 (5H, m), 3.66 (2H, m), 4.06 (2H, m).

91b) tert-butyl 4-((2-hydroxyethyl)((2-methyl-1H-imidazol-4-yl)carbonyl)amino)-1-piperidinecarboxylate 2-Methylimidazole-4-carboxylic acid (2.0 g) was suspended in acetonitrile (150 ml). HOBt (3.7 g) and WSC (4.6 g) were sequentially added thereto, and then mixed at room temperature for 20 minutes. To the reaction solution was added a solution of tert-butyl 4-(2-hydroxyethyl)amino-1-piperidinecarboxylate (4.7 g) obtained in Example 91a) and triethylamine (8.0 ml) in acetonitrile (50 ml), and mixed at room temperature for 15 hours. Acetonitrile was distilled off under reduced pressure, and then to the residue were added chloroform and water. The organic layer was collected by separation and dried over anhydrous magnesium sulfate, and then the solvent was distilled off under reduced pressure. The residue was purified with basic silica gel column (ethyl acetate:ethanol=5:1) to obtain the title compound as a colorless oil (1.0 g, 18%).

NMR (CDCl$_3$) δ: 1.47 (9H, s), 1.84 (4H, brs), 2.37 (2H, brs), 2.78 (2H, brs), 3.82 (4H, brs), 4.27 (3H, brs), 7.31 (1H, brs).

91c) tert-butyl 4-(3-methyl-8-oxo-5,6-dihydroimidazo[1,5-a]pyrazin-7(8H)-yl)-1-piperidinecarboxylate tert-Butyl 4-((2-hydroxyethyl)((2-methyl-1H-imidazol-5-yl)carbonyl)amino)-1-piperidinecarboxylate (0.94 g) obtained in Example 91b) and triethylamine (0.72 ml) were dissolved in THF (30 ml). Methanesulfonic acid chloride (0.24 ml) was added dropwise under ice-cooling, and then mixed at room temperature for 3 hours. To the reaction solution were added chloroform and water, and the organic layer was collected by separation and dried over anhydrous magnesium sulfate. Then, the solvent was distilled off under reduced pressure, and the residue was purified with basic silica gel column (ethyl acetate:ethanol=5:1) to obtain the title compound as a colorless solid (0.39 g, 44%).

NMR (CDCl$_3$) δ: 1.47 (9H, s), 1.52-1.72 (4H, s), 2.41 (3H, s), 2.85 (2H, m), 3.57 (2H, m), 4.04 (2H, m), 4.23 (2H, brs), 4.73-4.81 (1H, m), 7.62 (1H, s).

91d) tert-butyl(1R)-2,2-dimethyl-1-((4-(3-methyl-8-oxo-5,6-dihydroimidazo[1,5-a]pyrazin-7(8H)-yl)-1-piperidinyl)carbonyl)propylcarbamate In the same manner as in Example 85b), the title compound as colorless powder (0.82 g, 59%) was obtained from tert-butyl 4-(3-methyl-8-oxo-5,6-dihydroimidazo[1,5-a]pyrazin-7(8H)-yl)-1-piperidinecarboxylate (0.96 g) obtained in Example 91c).

NMR (CDCl$_3$) δ: 0.99 (9H, s), 1.45 (9H, s), 1.56-1.83 (4H, m), 2.41 (3H, s), 2.70 (1H, dt, J=12.6, 3.3), 3.24 (1H, dt, J=12.6, 3.3), 3.53 (2H, t, J=6.0), 4.01 (2H, t, J=6.0), 4.20-4.26 (1H, m), 4.50-4.55 (1H, m), 4.78-4.87 (1H, m), 4.88-4.93 (1H, m), 5.30-5.36 (1H, m), 7.64 (1H, s).

91e) N-(4-chlorophenyl)-N'-((1R)-2,2-dimethyl-1-((4-(3-methyl-8-oxo-5,6-dihydroimidazo[1,5-a]pyrazin-7(8H)-yl)-1-piperidinyl)carbonyl)propyl)urea In the same manner as in Example 15b), the title compound as colorless powder (recrystallization from ethyl acetate-hexane: 0.59 g, 64%) was obtained from tert-butyl (1R)-2,2-dimethyl-1-((4-(3-methyl-8-oxo-5,6-dihydroimidazo[1,5-a]pyrazin-7(8H)-yl)-1-piperidinyl)carbonyl)propylcarbamate (0.82 g) obtained in Example 91d).

NMR (CDCl$_3$) δ: 1.05-1.06 (9H, m), 1.60-2.00 (4H, m), 2.38-2.42 (3H, m), 2.73 (1H, t, J=12.9), 3.11-3.27 (3H, m), 3.78 (2H, t, J=5.7), 4.38-4.40 (1H, m), 4.75-4.87 (2H, m), 4.95 (1H, d, J=9.1), 6.25-6.45 (1H, m), 7.09-7.19 (4H, m), 7.58-7.64 (1H, m), 7.77-7.88 (1H, m).

Elemental analysis for C$_{25}$H$_{33}$ClN$_6$O$_3$.0.25AcOEt.0.75H$_2$O.

Calcd. (%): C, 58.20; H, 6.86; N, 15.66.

Found (%): C, 58.08; H, 7.14; N, 15.61.

EXAMPLE 92

N-(4-chlorophenyl)-N'-((1R)-2,2-dimethyl-1-((4-(1-methyl-8-oxo-5,6-dihydroimidazo[1,5-a]pyrazin-7(8H)-yl)-1-piperidinyl)carbonyl)propyl)urea

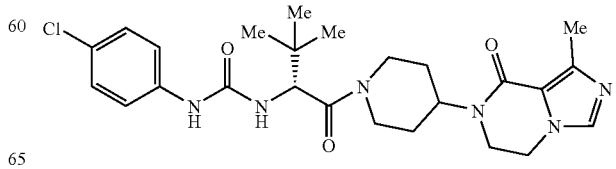

92a) tert-butyl 4-((2-hydroxyethyl)((5-methyl-1H-imidazol-4-yl)carbonyl)amino)-1-piperidinecarboxylate 5-Methylimidazole-4-carboxylic acid hydrochloride (G. Wellman et al., Synthesis, 356 (1984); 1.6 g) was suspended in acetonitrile (100 ml). HOBt (2.8 g) and WSC (3.5 g) were sequentially added thereto, and mixed at room temperature for 20 minutes (the reaction solution A). In a separate flask were dissolved tert-butyl 4-(2-hydroxyethyl)amino-1-piperidinecarboxylate (3.0 g) obtained in Example 91a), N-trimethylsilylacetamide (8.1 g) and triethylamine (5.0 ml) in acetonitrile (50 ml), and mixed at room temperature for 20 minutes (the reaction solution B). The reaction solution B was added to the reaction solution A, and mixed at room temperature for 15 hours. Acetonitrile was distilled off under reduced pressure, and then to the residue were added chloroform and water. The organic layer was collected by separation and dried over anhydrous magnesium sulfate, and then the solvent was distilled off under reduced pressure. The residue was purified with basic silica gel column (ethyl acetate:ethanol=5:1) to obtain the title compound as a colorless oil (2.0 g, 59%).

NMR (CDCl$_3$) δ: 1.46 (9H, s), 1.84 (4H, brs), 2.27 (3H, s), 2.77 (2H, brs), 3.68 (2H, brs), 3.79-3.82 (2H, m), 4.20-4.33 (3H, m), 7.32 (1H, s).

92b) tert-butyl 4-(1-methyl-8-oxo-5,6-dihydroimidazo[1,5-a]pyrazin-7(8H)-yl)-1-piperidinecarboxylate In the same manner as in Example 91c), the title compound as a colorless solid (0.56 g, 30%) was obtained from tert-butyl 4-((2-hydroxyethyl)((5-methyl-1H-imidazol-4-yl)carbonyl)amino)-1-piperidinecarboxylate obtained in Example 92a).

NMR (CDCl$_3$) δ: 1.47 (9H, s), 1.55-1.71 (4H, m), 2.54 (3H, s), 2.84 (2H, m), 3.55 (2H, m), 4.13 (2H, m), 4.22 (2H, brs), 4.74-4.83 (1H, m), 7.39 (1H, s).

92c) tert-butyl(1R)-2,2-dimethyl-1-((4-(1-methyl-8-oxo-5,6-dihydroimidazo[1,5-a]pyrazin-7(8H)-yl)-1-piperidinyl)carbonyl)propylcarbamate In the same manner as in Example 85b), the title compound as colorless powder (0.88 g, 94%) was obtained from tert-butyl 4-(1-methyl-8-oxo-5,6-dihydroimidazo[1,5-a]pyrazin-7(8H)-yl)-1-piperidinecarboxylate (0.65 g) obtained in Example 92b).

NMR (CDCl$_3$) δ: 0.96 (9H, s), 1.42 (9H, s), 1.60-2.00 (4H, m), 2.50-2.70 (1H, m), 2.60 (3H, s), 3.00-3.10 (1H, m), 3.29-3.44 (3H, m), 4.11-4.18 (1H, m), 4.35 (2H, s), 4.50-4.72 (2H, m), 5.35 (1H, d, J=9.0), 6.70 (1H, s).

92d) N-(4-chlorophenyl)-N'-((1R)-2,2-dimethyl-1-((4-(1-methyl-8-oxo-5,6-dihydroimidazo[1,5-a]pyrazin-7(8H)-yl)-1-piperidinyl)carbonyl)propyl)urea In the same manner as in Example 15b), the title compound as colorless powder (recrystallization from ethyl acetate-hexane: 0.16 g, 31%) was obtained from tert-butyl (1R)-2,2-dimethyl-1-((4-(1-methyl-8-oxo-5,6-dihydroimidazo[1,5-a]pyrazin-7(8H)-yl)-1-piperidinyl)carbonyl)propylcarbamate (0.45 g) obtained in Example 92c).

NMR (CDCl$_3$) δ: 1.04-1.06 (9H, m), 1.61-1.88 (4H, m), 2.54-2.56 (3H, m), 2.68-2.74 (1H, m), 3.20-3.36 (2H, m), 3.61-3.75 (1H, m), 3.99-4.03 (2H, m), 4.16-4.41 (1H, m), 4.75-4.95 (3H, m), 5.99-6.17 (1H, m), 7.15-7.21 (4H, m), 7.33 (1H, s), 7.40-7.44 (1H, m).

Elemental analysis for C$_{25}$H$_{33}$ClN$_6$O$_3$.0.5AcOEt.
Calcd. (%): C, 59.49; H, 6.84; N, 15.42.
Found (%): C, 59.12; H, 7.03; N, 15.29.

EXAMPLE 93

N-(4-chlorophenyl)-N'-((1R)-2,2-dimethyl-1-((4-(5-oxo-7,8-dihydroimidazo[1,5-c]pyrimidin-6(5H)-yl)-1-piperidinyl)carbonyl)propyl)urea

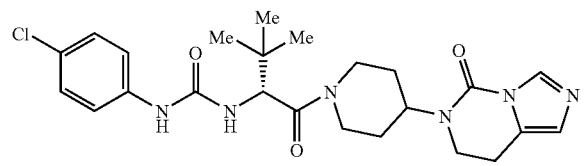

93a) tert-butyl 4-(5-oxo-7,8-dihydroimidazo[1,5-c]pyrimidin-6(5H)-yl)-1-piperidinecarboxylate To a solution of tert-butyl 4-oxo-1-piperidinecarboxylate (11 g) and histamine dihydrochloride (10 g) in 1,2-dichloroethane (300 ml) was added sodium triacetoxyborohydride (17 g), and mixed at room temperature for 15 hours. pH of the aqueous layer was adjusted to about 12 by adding a 1 N aqueous sodium hydroxide solution to the reaction solution, and then extracted with chloroform. The extract was dried over anhydrous magnesium sulfate, and then the solvent was distilled off under reduced pressure. The resulting yellow oil was dissolved in dichloromethane (300 ml), DBU (13 ml) and N,N'-carbonyldiimidazole (7.6 g) were added to the reaction solution, and mixed at room temperature for 15 hours. The reaction mixture was diluted with water and chloroform, and the organic layer was collected by separation, and then dried over anhydrous magnesium sulfate. The solvent was distilled off under reduced pressure, and the residue was purified with silica gel column (ethyl acetate:ethanol=5:1) to obtain the title compound as a colorless oil (13 g, 77%).

NMR (CDCl$_3$) δ: 1.49 (9H, s), 1.54-1.79 (4H, m), 2.78-2.99 (4H, m), 3.43 (2H, t, J=6.4), 4.26 (2H, d, J=12.4), 4.48-4.64 (1H, m), 6.81 (1H, d, J=1.1), 8.14 (1H, d, J=1.1).

93b) tert-butyl(1R)-2,2-dimethyl-1-((4-(5-oxo-7,8-dihydroimidazo[1,5-c]pyrimidin-6(5H)-yl)-1-piperidinyl)carbonyl)propylcarbamate In the same manner as in Example 85b), the title compound as colorless powder (0.93 g, 64%) was obtained from tert-butyl 4-(5-oxo-7,8-dihydroimidazo[1,5-c]pyrimidin-6(5H)-yl)-1-piperidinecarboxylate (0.98 g) obtained in Example 93a).

NMR (CDCl$_3$) δ: 0.98 (9H, s), 1.44 (9H, s), 1.58-1.90 (4H, m), 2.62-2.73 (1H, m), 2.94-2.98 (1H, m), 3.18-3.26 (1H, m), 3.35-3.45 (2H, t, J=7.5), 4.18-4.30 (1H, m), 4.53 (1H, d, J=9.0), 4.64-4.83 (2H, m), 5.32 (1H, d, J=9.0), 6.80 (1H, s), 8.14 (1H, s).

93c) N-(4-chlorophenyl)-N'-((1R)-2,2-dimethyl-1-((4-(5-oxo-7,8-dihydroimidazo[1,5-c]pyrimidin-6(5H)-yl)-1-piperidinyl)carbonyl)propyl)urea In the same manner as in Example 15b), the title compound as colorless powder (recrystallization from ethyl acetate-hexane: 0.24 g, 52%) was obtained from tert-butyl (1R)-2,2-dimethyl-1-((4-(5-oxo-7,8-dihydroimidazo[1,5-c]pyrimidin-6(5H)-yl)-1-piperidinyl)carbonyl)propylcarbamate (0.41 g) obtained in Example 93b).

NMR (CDCl$_3$) δ: 1.04-1.14 (9H, m), 1.73-1.95 (4H, m), 2.68-2.76 (1H, m), 2.81-3.01 (2H, m), 3.13-3.45 (3H, m), 4.32-4.40 (1H, m), 4.53-4.72 (1H, m), 4.75-4.92 (2H, m), 6.15-6.28 (1H, m), 6.81-6.84 (1H, m), 7.14-7.21 (4H, m), 7.56 (1H, s), 8.13-8.16 (1H, m).

Elemental analysis for $C_{24}H_{31}ClN_6O_3 \cdot 0.5H_2O$.
Calcd. (%): C, 58.12; H, 6.50; N, 16.94.
Found (%): C, 58.36; H, 6.70; N, 16.62.

EXAMPLE 94

N-(4-chlorophenyl)-N'-((1R)-1-((4-(2-(5,7-dimethyl-3-oxo-1H-imidazo[1,5-c]imidazol-2(3H)-yl)ethyl)-1-piperidinyl)carbonyl)-2,2-dimethylpropyl)urea

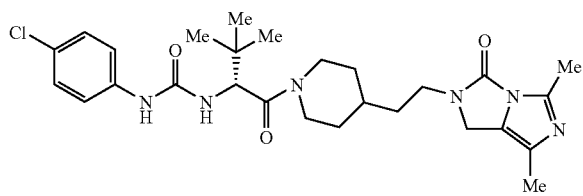

94a) 2-(2-(1-benzyl-4-piperidinyl)ethyl)-5,7-dimethyl-1,2-dihydro-3H-imidazo[1,5-c]imidazol-3-one To a solution of 2-(1-benzyl-4-piperidinyl)ethanamine (2.2 g), 2,5-dimethylimidazole-4-carbaldehyde (1.2 g) and acetic acid (0.3 ml) in 1,2-dichloroethane (25 ml) was added sodium triacetoxyborohydride (8.1 g) under ice-cooling. The reaction mixture was mixed at room temperature for 2 days, and then the reaction solution was washed with an aqueous potassium carbonate solution and dried over anhydrous magnesium sulfate. The solvent was distilled off under reduced pressure, and the residue was dissolved in THF (50 ml). To the reaction solution were added N,N'-carbonyldiimidazole (1.6 g) and DBU (1.6 ml), and mixed at room temperature for 15 hours. The solvent was distilled off under reduced pressure, and the residue was dissolved in chloroform. The reaction mixture was then washed with saturated brine, dried over anhydrous magnesium sulfate, and then concentrated under reduced pressure. The residue was purified with basic silica gel column (ethyl acetate/methanol=10/1). The product was recrystallized from ethyl acetate-hexane to obtain the title compound as colorless powder (1.3 g, 32%).

NMR (CDCl$_3$) δ: 1.26-1.35 (2H, m), 1.53-1.59 (2H, m), 1.67-1.74 (2H, m), 1.88-1.97 (1H, m), 1.97 (2H, t, J=10.5), 2.15 (3H, s), 2.56 (3H, s), 2.84-2.90 (2H, m), 3.44-3.49 (2H, m), 3.48 (2H, s), 4.21 (2H, s), 7.20-7.30 (5H, m).

94b) 5,7-dimethyl-2-(2-(4-piperidinyl)ethyl)-1,2-dihydro-3H-imidazo[1,5-c]imidazol-3-one 2-(2-(1-Benzyl-4-piperidinyl)ethyl)-5,7-dimethyl-1,2-dihydro-3H-imidazo[1,5-c]imidazol-3-one (1.1 g) obtained in Example 94a), 10% palladium carbon (0.22 g) and ammonium formate (2.0 g) were added to methanol (30 ml), and mixed at room temperature for 2 days. The catalyst was filtered off, and the filtrate was concentrated under reduced pressure. The residue was dissolved in chloroform, the precipitate was filtered off, and the filtrate was concentrated under reduced pressure to obtain the title compound as colorless powder (0.8 g, quantitative).

NMR (CDCl$_3$) δ: 1.55-1.80 (5H, m), 1.90-1.98 (2H, m), 2.16 (1H, s), 2.57 (3H, s), 2.82 (2H, m), 3.40 (2H, m), 3.50 (2H, t, J=6.0), 4.24 (2H, s).

94c) tert-butyl(1R)-1-((4-(2-(5,7-dimethyl-3-oxo-1H-imidazo[1,5-c]imidazol-2(3H)-yl)ethyl)-1-piperidinyl)carbonyl)-2,2-dimethylpropylcarbamate In the same manner as in Example 11a), the title compound as colorless powder (0.64 g, 75%) was obtained from 5,7-dimethyl-2-(2-(4-piperidinyl)ethyl)-1,2-dihydro-3H-imidazo[1,5-c]imidazol-3-one (0.42 g) obtained in Example 94b) and Boc-D-tert-leucine (0.60 g).

NMR (CDCl$_3$) δ: 0.96-0.99 (9H, m), 1.10-1.55 (2H, m), 1.42-1.43 (9H, two s), 1.53-1.60 (3H, m), 1.78-1.88 (2H, m), 2.15 (3H, s), 2.52-2.63 (1H, m), 2.57 (3H, s), 2.98-3.14 (1H, m), 3.45-3.55 (2H, m), 4.09-4.16 (1H, m), 4.24 (2H, s), 4.50-4.55 (1H, m), 4.60-4.68 (1H, m), 5.33-5.38 (1H, m).

94d) N-(4-chlorophenyl)-N'-((1R)-1-((4-(2-(5,7-dimethyl-3-oxo-1H-imidazo[1,5-c]imidazol-2(3H)-yl)ethyl)-1-piperidinyl)carbonyl)-2,2-dimethylpropyl)urea In the same manner as in Example 15b), the title compound as colorless powder (recrystallization from ethyl acetate-hexane: 0.50 g, 75%) was obtained from tert-butyl (1R)-1-((4-(2-(5,7-dimethyl-3-oxo-1H-imidazo[1,5-c]imidazol-2(3H)-yl)ethyl)-1-piperidinyl)carbonyl)-2,2-dimethylpropylcarbamate (0.60 g) obtained in Example 94c).

NMR (CDCl$_3$) δ: 1.02-1.05 (9H, m), 1.23-1.32 (2H, m), 1.48-1.87 (5H, m), 2.15 (3H, s), 2.53-2.65 (1H, m), 2.56 (3H, s), 3.03-3.17 (1H, m), 3.44-3.55 (2H, m), 4.18-4.25 (1H, m), 4.57-4.67 (1H, m), 4.90 (1H, t, J=9.3), 6.23 (1H, t, J=9.3), 7.15-7.31 (4H, m), 7.55-7.60 (1H, m).

Elemental analysis for $C_{27}H_{37}ClN_6O_3 \cdot 0.1H_2O$.
Calcd. (%): C, 61.09; H, 7.06; N, 15.83.
Found (%): C, 60.97; H, 7.02; N, 15.78.

EXAMPLE 95

N-(4-chlorophenyl)-N'-((1R)-1-((4-(2-(5,7-dimethyl-3-oxo-1H-imidazo[1,5-c]imidazol-2(3H)-yl)ethyl)-1-piperazinyl)carbonyl)-2,2-dimethylpropyl)urea

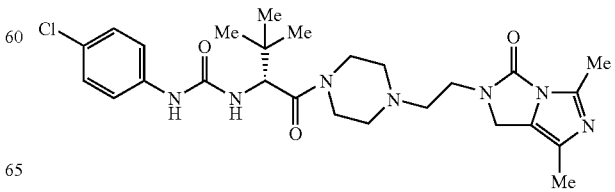

95a) (4-benzyl-1-piperazinyl)acetonitrile

To a suspension of 1-benzylpiperazine (18 g) and sodium carbonate (8.3 g) in acetone (50 ml) was added chloroacetonitrile (12 g) under ice-cooling, and mixed at room temperature for 2 hours. The reaction solution was concentrated under reduced pressure, to the residue were added water and diethyl ether, and the organic layer was collected by separation. The organic layer was washed with water and dried over anhydrous sodium sulfate, and then concentrated under reduced pressure. The residue was purified with silica gel column (ethyl acetate) to obtain the title compound as pale yellow liquid (17 g, 80%).

NMR (CDCl$_3$) δ: 2.51 (4H, s), 2.62 (4H, t, J=4.8), 3.50 (2H, s), 3.52 (2H, s), 7.23-7.33 (5H, m).

95b) 2-(4-benzyl-1-piperazinyl)ethanamine

To a suspension of lithium aluminum hydride (5.0 g) in anhydrous THF (150 ml) was added a solution of (4-benzyl-1-piperazinyl)acetonitrile (11 g) obtained in Example 95a) in anhydrous THF (50 ml) under ice-cooling. The reaction solution was refluxed for 3 hours, to the reaction solution was then added sodium sulfate decahydrate (420 g) under ice-cooling, and mixed for 15 hours. The reaction solution was diluted with THF, the precipitate obtained by decantation was filtered off, and the solvent was distilled off under reduced pressure to obtain the title compound as pale yellow liquid (10 g, 95%).

NMR (CDCl$_3$) δ: 2.41 (2H, t, J=6.0), 2.44-2.60 (8H, m), 2.78 (2H, J=6.0), 3.51 (2H, s), 7.24-7.35 (5H, m).

95c) 2-(2-(4-benzyl-1-piperazinyl)ethyl)-5,7-dimethyl-1,2-dihydro-3H-imidazo[1,5-c]imidazol-3-one In the same manner as in Example 94a), the title compound as pale yellow liquid (2.4 g, 34%) was obtained from 2-(4-benzyl-1-piperazinyl)ethanamine (4.4 g) obtained in Example 95b).

NMR (CDCl$_3$) δ: 2.16 (3H, s), 2.48-2.58 (8H, m), 2.56 (3H, s), 2.59 (2H, t, J=6.0), 3.49 (2H, s), 3.54 (2H, t, J=6.0), 4.34 (2H, s), 7.20-7.35 (5H, m).

95d) 5,7-dimethyl-2-(2-(1-piperazinyl)ethyl)-1,2-dihydro-3H-imidazo[1,5-c]imidazol-3-one In the same manner as in Example 94b), the title compound as pale yellow liquid (0.65 g, quantitative) was obtained from 2-(2-(4-benzyl-1-piperazinyl)ethyl)-5,7-dimethyl-1,2-dihydro-3H-imidazo[1,5-c]imidazol-3-one (0.88 g) obtained in Example 95c).

NMR (CDCl$_3$) δ: 2.16 (3H, s), 2.50-2.55 (4H, m), 2.57 (3H, s), 2.60 (2H, t, J=6.3), 2.92 (4H, t, J=4.8), 3.56 (2H, t, J=6.3), 4.36 (2H, s).

95e) tert-butyl(1R)-1-((4-(2-(5,7-dimethyl-3-oxo-1H-imidazo[1,5-c]imidazol-2(3H)-yl)ethyl)-1-piperazinyl)carbonyl)-2,2-dimethylpropylcarbamate In the same manner as in Example 11a), the title compound as colorless powder (0.68 g, 63%) was obtained from 5,7-dimethyl-2-(2-(1-piperazinyl)ethyl)-1,2-dihydro-3H-imidazo[1,5-c]imidazol-3-one (0.60 g) obtained in Example 95d).

NMR (CD$_3$OD) δ: 0.97 (9H, s), 1.44 (9H, s), 2.12 (3H, s), 2.42-2.55 (4H, m), 2.48 (3H, s), 2.63 (2H, t, J=6.0), 3.40-3.55 (2H, m), 3.61 (2H, J=6.0), 3.70-3.85 (2H, m), 4.43 (2H, s), 4.49 (1H, s).

95f) N-(4-chlorophenyl)-N'-((1R)-1-((4-(2-(5,7-dimethyl-3-oxo-1H-imidazo[1,5-c]imidazol-2(3H)-yl)ethyl)-1-piperazinyl)carbonyl)-2,2-dimethylpropyl)urea In the same manner as in Example 15b), the title compound as colorless powder (recrystallization from ethyl acetate-hexane-diethyl ether: 0.23 g, 36%) was obtained from tert-butyl (1R)-1-((4-(2-(5,7-dimethyl-3-oxo-1H-imidazo[1,5-c]imidazol-2(3H)-yl)ethyl)-1-piperazinyl)carbonyl)-2,2-dimethylpropylcarbamate (0.58 g) obtained in Example 95e).

NMR (CDCl$_3$) δ: 1.02 (9H, s), 2.15 (3H, s), 2.38-2.55 (4H, m), 2.56 (3H, s), 2.59 (2H, t, J=6.0), 3.47-3.61 (2H, m), 3.55 (2H, t, J=6.0), 3.72-3.82 (2H, m), 4.31 (2H, s), 4.84 (1H, d, J=6.3), 6.02 (1H, d, J=6.3), 7.16-7.22 (4H, m).

Elemental analysis for $C_{26}H_{36}ClN_7O_3 \cdot 0.3H_2O \cdot 0.4Et_2O$.
Calcd. (%): C, 58.66; H, 7.24; N, 17.35.
Found (%): C, 58.89; H, 7.38; N, 17.38.

EXAMPLE 96

1-(4-chlorophenyl)-3-((1R)-2,2-dimethyl-1-((4-(2-(5-methyl-3-oxo-1H-imidazo[1,5-c]imidazol-2-yl)ethyl)-1-piperidinyl)carbonyl)propyl)urea

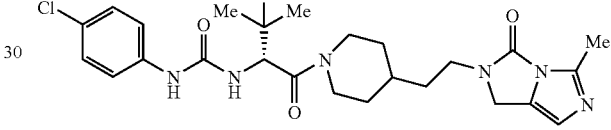

96a) 2-(2-(1-benzyl-4-piperidinyl)ethyl)-5-methyl-1,2-dihydroimidazo[1,5-c]imidazol-3-one To a suspension of 2-(1-benzyl-4-piperidinyl)ethanamine (5.5 g), 2-methylimidazole-4-carbaldehyde (2.8 g) and acetic acid (1.7 ml) in 1,2-dichloroethane (50 ml) was added sodium triacetoxyborohydride (8.1 g) under ice-cooling. The reaction mixture was returned to room temperature and mixed for 15 hours. Then, the reaction solution was washed with an aqueous potassium carbonate solution and dried over anhydrous magnesium sulfate. The solvent was distilled off under reduced pressure, and the residue was dissolved in THF (50 ml). To the reaction solution were added N,N'-carbonyldiimidazole (4.5 g) and DBU (4.2 g), and mixed at room temperature for 3 hours. The solvent was distilled off under reduced pressure, and the residue was dissolved in ethyl acetate, washed with water, dried over anhydrous magnesium sulfate, and then concentrated under reduced pressure. The residue was purified with basic silica gel column (ethyl acetate) to obtain the title compound as a colorless oil (4.0 g, 48%).

NMR (CDCl$_3$) δ: 1.26-1.41 (2H, m), 1.50-1.81 (5H, m), 1.89-2.05 (2H, m), 2.61 (3H, s), 2.85-2.91 (2H, m), 3.45-3.53 (4H, m), 4.30 (2H, s), 6.69 (1H, m), 7.23-7.32 (5H, m).

96b) 5-methyl-2-(2-(4-piperidinyl)ethyl)-1,2-dihydroimidazo[1,5-c]imidazol-3-one 2-(2-(1-Benzyl-4-piperidinyl)ethyl)-5-methyl-1,2-dihydroimidazo[1,5-c]imidazol-3-one (4.0 g) obtained in Example 96a) and 10% palladium carbon (0.8 g) were added to methanol (100 ml), and mixed under hydrogen atmosphere at room temperature for 2 days. The catalyst was filtered off, and the filtrate was concentrated under reduced pressure. The residue was purified with basic silica gel column (ethyl acetate, ethyl acetate/methanol=20/1). The product was recrystallized from ethyl acetate-hexane to obtain the title compound (1.4 g, 48%).

NMR (CDCl$_3$) δ: 1.12-1.77 (7H, m), 2.53-2.66 (5H, m), 3.04-3.10 (2H, m), 3.51 (2H, t, J=7.4), 4.31 (2H, s), 6.70 (1H, m).

96c) tert-butyl(1R)-2,2-dimethyl-1-((4-(2-(5-methyl-3-oxo-1H-imidazo[1,5-c]imidazol-2-yl)ethyl)-1-piperidinyl)carbonyl)propylcarbamate To a solution of Boc-D-tert-leucine (0.69 g) in methylene chloride (15 ml) were added HOBt (0.61 g), WSC (0.86 g) and triethylamine (0.84 ml) under ice-cooling. The reaction mixture was mixed at 0° C. for 2.5 hours. Then, 5-methyl-2-(2-(4-piperidinyl)ethyl)-1,2-dihydroimidazo[1,5-c]imidazol-3-one (0.74 g) obtained in Example 96b) was added thereto, and further mixed at room temperature for 15 hours. The solvent was distilled off under reduced pressure, and the residue was dissolved in ethyl acetate. The ethyl acetate solution was washed with an aqueous sodium hydrogen carbonate solution and dried over anhydrous magnesium sulfate. The solvent was distilled off under reduced pressure, and the residue was purified with silica gel column (ethyl acetate/methanol=20/1) to obtain the title compound as colorless powder (0.95 g, 69%).

NMR (CDCl$_3$) δ: 0.96-0.99 (9H, m), 1.10-1.34 (2H, m), 1.42-1.43 (9H, m), 1.56-1.60 (3H, m), 1.75-1.92 (2H, m), 2.51-2.66 (4H, m), 2.97-3.16 (1H, m), 3.48-3.54 (2H, t, J=5.9), 4.08-4.18 (1H, m), 4.31 (2H, s), 4.50-4.72 (2H, m), 5.33-5.37 (1H, m), 6.70 (1H, m).

96d) 1-(4-chlorophenyl)-3-((1R)-2,2-dimethyl-1-((4-(2-(5-methyl-3-oxo-1H-imidazo[1,5-c]imidazol-2-yl)ethyl)-1-piperidinyl)carbonyl)propyl)urea A solution of tert-butyl(1R)-2,2-dimethyl-1-((4-(2-(5-methyl-3-oxo-1H-imidazo[1,5-c]imidazol-2-yl)ethyl)-1-piperidinyl)carbonyl)propylcarbamate (0.95 g) obtained in Example 96c) in toluene (10 ml)-trifluoroacetic acid (10 ml) was mixed at room temperature for 1.5 hours, and then concentrated under reduced pressure. The residue was dissolved in water, and the reaction mixture was basified with potassium carbonate and extracted with ethyl acetate. The extract was dried over anhydrous magnesium sulfate, and the solvent was distilled off under reduced pressure. The one-half amount of the resulting amine was dissolved in THF (20 ml), 4-chlorophenyl isocyanate (0.15 g) was added thereto, and mixed at room temperature for 2 days. The solvent was distilled off under reduced pressure, and the residue was purified with basic silica gel column (ethyl acetate, ethyl acetate/methanol=20/1). The product was recrystallized from ethyl acetate-hexane to obtain the title compound (0.40 g, 75%).

NMR (CDCl$_3$) δ: 1.02-1.05 (9H, m), 1.12-1.30 (2H, m), 1.45-1.93 (5H, m), 2.60 (4H, m), 3.10-3.20 (1H, m), 3.42-3.56 (2H, m), 4.18-4.32 (3H, m), 4.54-4.70 (1H, m), 4.86-4.93 (1H, m), 6.05-6.15 (1H, m), 6.70 (1H, m), 7.15-7.34 (5H, m).

Elemental analysis for C$_{26}$H$_{35}$ClN$_6$O$_3$.0.2AcOEt.
Calcd. (%): C, 60.32; H, 7.10; N, 15.79.
Found (%): C, 60.13; H, 7.86; N, 15.55.

EXAMPLE 97

N-(4-chlorophenyl)-N'-((1R)-2,2-dimethyl-1-((4-(2-(5-methyl-3-oxo-1H-imidazo[1,5-c]imidazol-2(3H)-yl)ethyl)-1-piperazinyl)carbonyl)propyl)urea

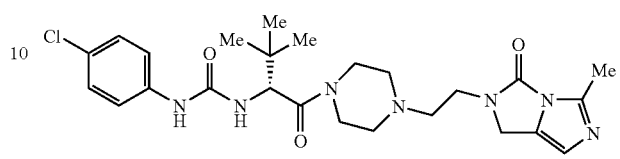

97a) 2-(1-benzyl-4-piperazinyl)ethanamine trihydrochloride

To a solution of 1-benzylpiperazine (4.4 g), tert-butyl N-(2-oxoethyl)carbamate (3.8 g) and acetic acid (1.7 ml) in 1,2-dichloroethane (50 ml) was added sodium triacetoxyborohydride (8.1 g) under ice-cooling. The reaction mixture was mixed at room temperature for 2 days. Then, the reaction solution washed with an aqueous potassium carbonate solution and dried over anhydrous magnesium sulfate. The solvent was distilled off under reduced pressure, and the residue was dissolved in methanol (50 ml). A 4 N solution of hydrogen chloride in ethanol (40 ml) was added thereto, and mixed at room temperature for 5 hours. The precipitate was collected by filtration and washed with diethyl ether and hexane to obtain the title compound (5.0 g, 61%).

NMR (DMSO-d$_6$) δ: 2.6-3.7 (12H, m), 4.35-4.40 (2H, m), 7.47 (3H, m), 7.67 (2H, m), 8.33 (3H, NH$_3$).

97b) 2-(2-(1-benzyl-4-piperazinyl)ethyl)-5-methyl-1,2-dihydroimidazo[1,5-c]imidazol-3-one A suspension of 2-(1-benzyl-4-piperazinyl)ethanamine trihydrochloride (2.5 g) obtained in Example 97a), 2-methylimidazole-4-carbaldehyde (0.84 g) and acetic acid (0.5 ml) in 1,2-dichloroethane (50 ml) was mixed at room temperature for 40 minutes, and then sodium triacetoxyborohydride (2.4 g) was added thereto under ice-cooling. The reaction mixture was returned to room temperature, and mixed for 2 days. Then, the reaction solution was washed with an aqueous potassium carbonate solution and dried over anhydrous magnesium sulfate. The solvent was distilled off under reduced pressure, and the residue was dissolved in THF (60 ml). To the reaction solution were added N,N'-carbonyldiimidazole (1.4 g) and DBU (1.3 g), and mixed at room temperature for 4 days. The solvent was distilled off under reduced pressure, and the residue was dissolved in ethyl acetate, then washed with water, dried over anhydrous magnesium sulfate, and then concentrated under reduced pressure. The residue was purified with basic silica gel column (ethyl acetate) to obtain the title compound as a colorless oil (0.22 g, 8.5%).

NMR (CDCl$_3$) δ: 2.28-2.73 (15H, m), 3.43-3.65 (6H, m), 4.44 (2H, s), 6.68 (1H, m), 7.28-7.32 (5H, m).

97c) 5-methyl-2-(2-(1-piperazinyl)ethyl)-1,2-dihydroimidazo[1,5-c]imidazol-3-one 2-(2-(1-Benzyl-4-piperazinyl)ethyl)-5-methyl-1,2-dihydroimidazo[1,5-c]imidazol-3-one (0.22 g) obtained in Example 97b), 1 N hydrochloric acid (1 ml) and 10% palladium carbon (74 mg) were added to methanol (10 ml), and mixed under hydrogen atmosphere at room temperature for 3 days. The catalyst was filtered off, and the filtrate was concentrated under reduced pressure. The residue was dissolved in a small amount of water, and the reaction mixture was basified with potassium carbonate and extracted with ethyl acetate. The extract was dried over anhydrous magnesium sulfate, and the solvent was distilled off under reduced pressure to obtain the title compound (0.10 g, 63%).

NMR (CDCl$_3$) δ: 2.4-3.0 (13H, m), 3.57 (2H, t, J=6), 4.45 (2H, s), 6.68 (1H, s).

97d) tert-butyl(1R)-2,2-dimethyl-1-(4-(2-(5-methyl-3-oxo-1H-imidazo[1,5-c]imidazol-2-yl)ethyl)-1-piperazinyl)carbonyl)propylcarbamate To a solution of Boc-D-tert-leucine (93 mg) in methylene chloride (2 ml) were added HOBt (81 mg), WSC (114 mg) and triethylamine (0.11 ml) under ice-cooling, and the reaction mixture was mixed at 0° C. for 30 minutes. Then, a solution of 5-methyl-2-(2-(1-piperazinyl)ethyl)-1,2-dihydroimidazo[1,5-c]imidazol-3-one (0.10 g) obtained in Example 97c) in methylene chloride (3 ml) was added, and further mixed at room temperature for 15 hours. The solvent was distilled off under reduced pressure, and the residue was dissolved in ethyl acetate. The ethyl acetate solution was washed with an aqueous potassium carbonate solution and dried over anhydrous magnesium sulfate. The solvent was distilled off under reduced pressure, and the residue was purified with basic silica gel column (ethyl acetate/methanol=30/1) to obtain the title compound as a colorless oil (0.15 g, 79%).

NMR (CDCl$_3$) δ: 0.97 (9H, s), 1.43 (9H, s), 2.4-2.7 (9H, m), 3.40-3.85 (6H, m), 4.43 (2H, s), 4.49 (1H, d, J=10.2), 5.25-5.40 (1H, br), 6.69 (1H, s).

97e) N-(4-chlorophenyl)-N'-((1R)-2,2-dimethyl-1-((4-(2-(5-methyl-3-oxo-1H-imidazo[1,5-c]imidazol-2(3H)-yl)ethyl)-1-piperazinyl)carbonyl)propyl)urea A solution of tert-butyl(1R)-2,2-dimethyl-1-(4-(2-(5-methyl-3-oxo-1H-imidazo[1,5-c]imidazol-2-yl)ethyl)-1-piperazinyl)carbonyl)propylcarbamate (0.15 g) obtained in Example 97d) in methylene chloride (1.5 ml)-trifluoroacetic acid (1.5 ml) was mixed at room temperature for 1 hour, and then concentrated under reduced pressure. The residue was dissolved in THF (5 ml), triethylamine (0.3 ml) and 4-chlorophenyl isocyanate (0.10 g) were added thereto, and mixed at room temperature for 1.5 hours. The solvent was distilled off under reduced pressure, and the residue was dissolved in ethyl acetate. The ethyl acetate solution was washed with an aqueous potassium carbonate solution and dried over anhydrous magnesium sulfate. The solvent was distilled off under reduced pressure, and the residue was purified with basic silica gel column (ethyl acetate/methanol=30/1) to obtain the title compound as colorless powder (54 mg, 32%).

NMR (CDCl$_3$) δ: 1.02 (9H, s), 2.32-2.66 (9H, m), 3.40-3.68 (4H, m), 3.70-3.86 (2H, m), 4.41 (2H, s), 4.85 (1H, d, J=9.6), 6.15 (1H, d, J=9.6), 7.20 (4H, m), 7.49 (1H, s).

Elemental analysis for C$_{25}$H$_{34}$ClN$_7$O$_3$.0.4AcOEt.0.3H$_2$O.
Calcd. (%): C, 57.39; H, 6.84; N, 17.61.
Found (%): C, 57.24; H, 7.02; N, 17.74.

EXAMPLE 98

N-(4-chlorophenyl)-N'-((1R)-2,2-dimethyl-1-((4-(1-methyl-4-piperidinyl)-1-piperazinyl)carbonyl)propyl)urea

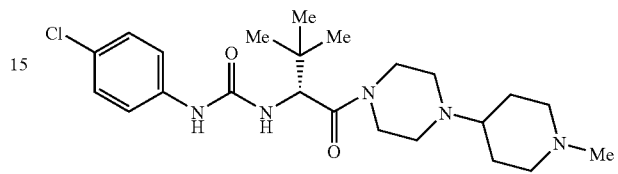

98a) tert-butyl(1R)-2,2-dimethyl-1-((4-(1-methyl-4-piperidinyl)-1-piperazinyl)carbonyl)propylcarbamate To a solution of Boc-D-tert-leucine (0.46 g) and HOBt (0.46 g) in acetonitrile (20 ml) was added WSC (0.58 g), and the reaction mixture was mixed at room temperature for 15 minutes. Then, 1-(1-methyl-4-piperidyl)piperazine (0.70 g) and triethylamine (0.61 g) were added, and the reaction mixture was mixed at room temperature for 15 hours. The solvent was distilled off under reduced pressure, and the residue was dissolved in ethyl acetate. The ethyl acetate solution was washed with an aqueous sodium hydrogen carbonate solution and dried over anhydrous sodium sulfate. The solvent was distilled off under reduced pressure to obtain the title compound as a colorless oil (0.80 g, quantitative).

NMR (CDCl$_3$) δ: 0.97 (9H, m), 1.43 (9H, s), 1.58-1.64 (2H, m), 1.89-1.97 (2H, m), 2.23-2.26 (3H, m), 2.32-2.58 (5H, m), 2.88-2.92 (2H, m), 3.20-3.29 (2H, m), 3.45-3.58 (2H, m), 3.67-3.83 (2H, m), 4.49-4.52 (1H, m), 5.34-5.37 (1H, m).

98b) N-(4-chlorophenyl)-N'-((1R)-2,2-dimethyl-1-((4-(1-methyl-4-piperidinyl)-1-piperazinyl)carbonyl)propyl)urea In the same manner as in Example 15b), the title compound as colorless powder (0.44 g, 55%) was obtained from tert-butyl(1R)-2,2-dimethyl-1-((4-(1-methyl-4-piperidinyl)-1-piperazinyl)carbonyl)propylcarbamate (0.70 g) obtained in Example 98a).

NMR (CDCl$_3$) δ: 1.03 (9H, s), 1.50-1.58 (3H, m), 1.87-1.95 (2H, m), 2.05-2.25 (5H, m), 2.43-2.63 (4H, m), 2.86-2.90 (2H, m), 3.45-3.60 (2H, m), 3.78-3.82 (2H, m), 4.88 (1H, d, J=9.1), 6.16 (1H, d, J=9.1), 7.16-7.36 (5H, m).

Elemental analysis for C$_{23}$H$_{36}$ClN$_5$O$_2$.1.2H$_2$O.
Calcd. (%): C, 58.57; H, 8.21; N, 14.85.
Found (%): C, 58.42; H, 8.29; N, 14.76.

EXAMPLE 99

N-(4-chlorophenyl)-N'-((1R)-2,2-dimethyl-1-((2-oxo-1,4'-bipiperidin-1'-yl)carbonyl)propyl)urea

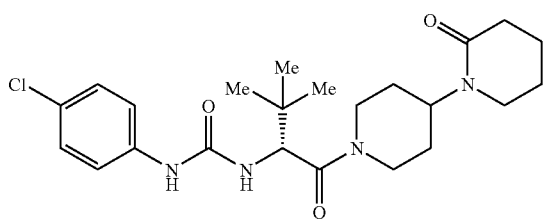

99a) tert-butyl(1R)-2,2-dimethyl-1-((2-oxo-1,4'-bipiperidin-1'-yl)carbonyl)propylcarbamate In the same manner as in Example 98a), the title compound as colorless powder (0.33 g, 83%) was obtained from 1,4'-bipiperidin-2-one hydrochloride (PCT Japanese Translation Patent Publication No. 2001524466; 0.22 g).

NMR (CDCl$_3$) δ: 0.96-1.00 (9H, m), 1.42-1.43 (9H, m), 1.53-1.79 (8H, m), 2.41-2.43 (2H, m), 2.60-2.69 (1H, m), 3.12-3.19 (3H, m), 4.17-4.21 (1H, m), 4.51-4.55 (1H, m), 4.72-4.83 (2H, m), 5.32-5.36 (1H, m).

99b) N-(4-chlorophenyl)-N'-((1R)-2,2-dimethyl-1-((2-oxo-1,4'-bipiperidin-1'-yl)carbonyl)propyl)urea In the same manner as in Example 15b), the title compound as colorless powder (0.22 g, 61%) was obtained from tert-butyl(1R)-2,2-dimethyl-1-((2-oxo-1,4'-bipiperidin-1'-yl)carbonyl)propylcarbamate (0.32 g) obtained in Example 99a).

NMR (CDCl$_3$) δ: 1.01-1.05 (9H, m), 1.50-1.76 (7H, m), 2.39-2.43 (2H, m), 2.64-2.72 (1H, m), 2.99-3.23 (3H, m), 4.26-4.31 (1H, m), 4.73-4.89 (3H, m), 5.93-6.03 (1H, m), 7.11-7.61 (6H, m).

Elemental analysis for $C_{23}H_{33}ClN_4O_3 \cdot 0.5H_2O$.
Calcd. (%): C, 60.32; H, 7.48; N, 12.23.
Found (%): C, 60.45; H, 7.54; N, 12.03.

EXAMPLE 100

N-(4-chlorophenyl)-N'-((1R)-2,2-dimethyl-1-((4-(2-oxo-1-pyrrolidinyl)-1-piperidinyl)carbonyl)propyl)urea

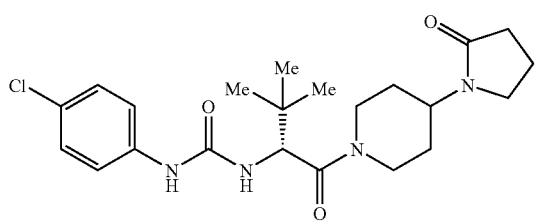

100a) tert-butyl(1R)-2,2-dimethyl-1-((4-(2-oxo-1-pyrrolidinyl)-1-piperidinyl)carbonyl)propylcarbamate In the same manner as in Example 98a), the title compound as colorless powder (0.43 g, quantitative) was obtained from 1-(4-piperidinyl)-2-pyrrolidinone (PCT Japanese Translation Patent Publication No. 08502511; 0.17 g).

NMR (CDCl$_3$) δ: 0.97-1.00 (9H, m), 1.42-1.44 (9H, m), 1.67-1.80 (4H, m), 1.98-2.03 (2H, m), 2.37-2.44 (2H, m), 2.58-2.67 (1H, m), 3.09-3.17 (1H, m), 3.26-3.34 (2H, m), 4.20-4.27 (2H, m), 4.51-4.55 (1H, m), 4.74-4.78 (1H, m), 5.33-5.36 (1H, m).

100b) N-(4-chlorophenyl)-N'-((1R)-2,2-dimethyl-1-((4-(2-oxo-1-pyrrolidinyl)-1-piperidinyl)carbonyl)propyl)urea In the same manner as in Example 15b), the title compound as colorless powder (0.43 g, 99%) was obtained from tert-butyl(1R)-2,2-dimethyl-1-((4-(2-oxo-1-pyrrolidinyl)-1-piperidinyl)carbonyl)propylcarbamate (0.38 g) obtained in Example 10a).

NMR (CDCl$_3$) δ: 1.02-1.05 (9H, m), 1.46-2.00 (6H, m), 2.35-2.45 (2H, m), 2.59-2.71 (1H, m), 3.12-3.36 (3H, m), 4.16-4.32 (2H, m), 4.73-4.89 (2H, m), 6.06-6.14 (1H, m), 7.16-7.38 (5H, m).

Elemental analysis for $C_{22}H_{31}ClN_4O_3 \cdot H_2O$.
Calcd. (%): C, 58.33; H, 7.34; N, 12.37.
Found (%): C, 58.61; H, 7.42; N, 12.05.

EXAMPLE 101

N-(4-chlorophenyl)-N'-((1R)-2,2-dimethyl-1-((4-(2-oxo-1-imidazolidinyl)-1-piperidinyl)carbonyl)propyl)urea

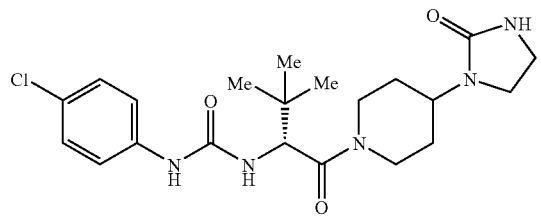

101a) tert-butyl(1R)-2,2-dimethyl-1-((4-(2-oxo-1-imidazolidinyl)-1-piperidinyl)carbonyl)propylcarbamate In the same manner as in Example 98a), the title compound as a colorless oil (0.29 g, quantitative) was obtained from 1-(4-piperidinyl)-2-imidazolidinone (PCT Japanese Translation Patent Publication No. 57081483; 0.12 g).

NMR (CDCl$_3$) δ: 0.97-1.00 (9H, m), 1.42-1.43 (9H, m), 1.51-1.81 (4H, m), 2.58-2.67 (1H, m), 3.12-3.17 (1H, m), 3.35-3.45 (4H, m), 3.96-4.04 (1H, m), 4.18-4.22 (1H, m), 4.52-4.55 (2H, m), 4.73-4.78 (1H, m), 5.34-5.37 (1H, m).

101b) N-(4-chlorophenyl)-N'-((1R)-2,2-dimethyl-1-((4-(2-oxo-1-imidazolidinyl)-1-piperidinyl)carbonyl)propyl)urea In the same manner as in Example 15b), the title compound as pale yellow powder (0.23 g, 78%) was obtained from tert-butyl(1R)-2,2-dimethyl-1-((4-(2-oxo-1-imidazolidinyl)-1-piperidinyl)carbonyl)propylcarbamate (0.26 g) obtained in Example 101a).

NMR (CDCl$_3$) δ: 1.02-1.05 (9H, m), 1.45-1.85 (4H, m), 2.59-2.70 (1H, m), 3.14-3.43 (5H, m), 3.98-3.99 (1H, m), 4.29-4.34 (1H, m), 4.74-4.78 (1H, m), 4.87-4.90 (1H, m), 4.98-5.06 (1H, m), 6.32-6.39 (1H, m), 7.16-7.26 (4H, m), 7.51 (1H, s).

Elemental analysis for $C_{21}H_{30}ClN_5O_3 \cdot 0.6H_2O$.
Calcd. (%): C, 56.46; H, 7.04; N, 15.68.
Found (%): C, 56.25; H, 7.22; N, 15.43.

EXAMPLE 102

N-(4-chlorophenyl)-N'-((1R)-2,2-dimethyl-1-((4-(3-methyl-2-oxo-1-imidazolidinyl)-1-piperidinyl)carbonyl)propyl)urea

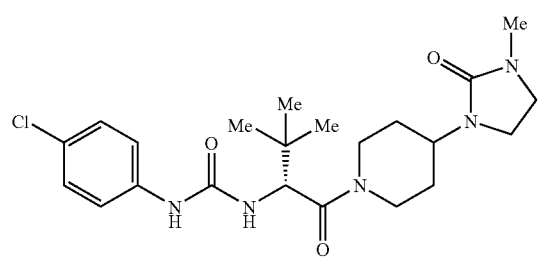

102a) tert-butyl(1R)-2,2-dimethyl-1-((4-(3-methyl-2-oxo-1-imidazolidinyl)-1-piperidinyl)carbonyl)propylcarbamate In the same manner as in Example 98a), the title compound as a colorless oil (0.47 g, 59%) was obtained from 3-methyl-1-(4-piperidinyl)-2-imidazolidinone (Eur. Pat. Appl. EP485; 0.37 g).

NMR (CDCl$_3$) δ: 0.96-1.00 (9H, m), 1.42-1.43 (9H, m), 1.47-1.83 (5H, m), 2.58-2.67 (1H, m), 2.78 (3H, s), 3.12-3.30 (4H, m), 3.94-4.16 (2H, m), 4.52-4.55 (1H, m), 4.71-4.76 (1H, m), 5.33-5.36 (1H, m).

102b) N-(4-chlorophenyl)-N'-((1R)-2,2-dimethyl-1-((4-(3-methyl-2-oxo-1-imidazolidinyl)-1-piperidinyl)carbonyl)propyl)urea In the same manner as in Example 15b), the title compound as pale yellow powder (0.52 g, 99%) was obtained from tert-butyl(1R)-2,2-dimethyl-1-((4-(3-methyl-2-oxo-1-imidazolidinyl)-1-piperidinyl)carbonyl)propylcarbamate (0.46 g) obtained in Example 102a).

NMR (CDCl$_3$) δ: 1.02-1.05 (9H, m), 1.38-1.85 (4H, m), 2.62-2.71 (1H, m), 2.77-2.79 (3H, m), 3.14-3.31 (5H, m), 3.94-3.99 (1H, m), 4.26-4.31 (1H, m), 4.72-4.77 (1H, m), 4.86-4.91 (1H, m), 6.07-6.16 (1H, m), 7.16-7.37 (5H, m).

Elemental analysis for $C_{22}H_{32}ClN_5O_3 \cdot H_2O \cdot 0.1AcOEt$.
Calcd. (%): C, 56.43; H, 7.36; N, 14.69.
Found (%): C, 56.64; H, 7.31; N, 14.55.

EXAMPLE 103

N-(4-chlorophenyl)-N'-((1R)-2,2-dimethyl-1-((4-(4-methyl-2-oxo-1-piperazinyl)-1-piperidinyl)carbonyl)propyl)urea

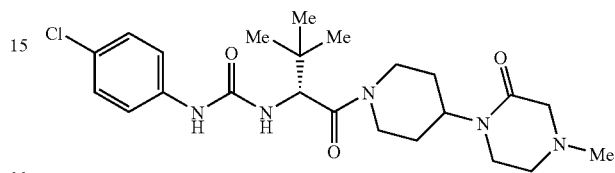

103a) tert-butyl 3-oxo-4-(4-piperidinyl)-1-piperazinecarboxylate tert-Butyl 4-(1-benzyl-4-piperidinyl)-3-oxo-1-piperazinecarboxylate (PCT Japanese Translation Patent Publication No. 2002533451; 1.4 g) was dissolved in ethanol (30 ml), 10% palladium carbon (50% water content; 0.12 g) was added thereto, and mixed under hydrogen atmosphere at room temperature for 16 hours. The reaction mixture was filtered, and the filtrate was concentrated under reduced pressure to obtain the title compound as a green oil (0.95 g, quantitative).

NMR (CDCl$_3$) δ: 1.47 (9H, s), 1.57-1.65 (3H, m), 2.08 (1H, m), 2.69-2.78 (2H, m), 3.12-3.16 (2H, m), 3.27-3.31 (2H, m), 3.58-3.62 (2H, m), 4.08 (2H, s), 4.54-4.61 (1H, m), 4.83 (1H, br).

103b) tert-butyl 4-((2R)-2-(benzyloxycarbonylamino)-3,3-dimethylbutyroyl)-4-piperidinyl)-3-oxo-1-piperazinecarboxylate To a solution of Z-D-tert-leucine (0.64 g) and HOBt (0.55 g) in acetonitrile (20 ml) was added WSC (0.69 g), and the reaction mixture was mixed at room temperature for 15 minutes. Then, tert-butyl 3-oxo-4-(4-piperidinyl)-1-piperazinecarboxylate (0.68 g) obtained in Example 103a) and triethylamine (0.73 g) were added thereto. The reaction mixture was mixed at room temperature for 15 hours, and then the solvent was distilled off under reduced pressure. The residue was dissolved in ethyl acetate, and the reaction mixture was washed sequentially with an aqueous sodium hydrogen carbonate solution, water, a 5% aqueous citric acid solution and saturated brine and dried over anhydrous sodium sulfate. Then, the solvent was distilled off under reduced pressure, and the residue was purified with silica gel column (ethyl acetate) to obtain the title compound as a colorless oil (1.3 g, quantitative).

NMR (CDCl$_3$) δ: 0.98-1.01 (9H, m), 1.47 (9H, s), 1.56-1.78 (4H, m), 2.59-2.68 (1H, m), 3.12-3.22 (3H, m), 3.53-3.62 (2H, m), 4.09-4.23 (3H, m), 4.56-4.59 (1H, m), 4.71-4.75 (2H, m), 5.09-5.10 (2H, m), 5.55-5.60 (1H, m), 7.35-7.37 (5H, m).

103c) benzyl(1R)-2,2-dimethyl-1-((4-(4-methyl-2-oxo-1-piperazinyl)-1-piperidinyl)carbonyl)propylcarbamate A solution of tert-butyl 4-((2R)-2-(benzyloxycarbonylamino)-3,3-dimethylbutyroyl)-4-piperidinyl)-3-oxo-1-piperazinecarboxylate (0.23 g) obtained in Example 103b) in trifluoroacetic acid (2 ml) and dichloromethane (2 ml) was mixed at room temperature for 1 hour. The reaction mixture was alkalified with an aqueous potassium carbonate solution, and then extracted with dichloromethane. The extract was dried over anhydrous sodium sulfate, and the solvent was distilled off under reduced pressure. The residue was dissolved in 1,2-dichloroethane (20 ml) and methanol (1 ml). Formalin (0.50 ml) and acetic acid (25 mg) were added thereto, and mixed at room temperature for 1 hour. Then, sodium triacetoxyborohydride (0.22 g) was added thereto, and mixed at room temperature for 3 hours. The reaction mixture was alkalified with an aqueous potassium carbonate solution, and then the organic layer was collected by separation. The organic layer was dried over anhydrous sodium sulfate, and the solvent was distilled off under reduced pressure to obtain the title compound as a colorless oil (0.19 g, quantitative).

NMR (CDCl$_3$) δ: 0.97-1.01 (9H, m), 1.61-1.67 (5H, m), 2.32 (3H, s), 2.59-2.65 (3H, m), 3.12-3.20 (4H, m), 4.16-4.23 (1H, m), 4.57-5.14 (5H, m), 5.56-5.62 (1H, m), 7.31-7.35 (5H, m).

103d) 1-(1-((2R)-2-amino-3,3-dimethylbutyroyl)-4-piperidinyl)-4-methylpiperazin-2-one Benzyl(1R)-2,2-dimethyl-1-((4-(4-methyl-2-oxo-1-piperazinyl)-1-piperidinyl)carbonyl)propylcarbamate (0.18 g) obtained in Example 103c) was dissolved in ethanol (10 ml), 10% palladium carbon (50% water content; 20 mg) was added thereto, and mixed under hydrogen atmosphere at room temperature for 2 hours. The reaction mixture was filtered, and the filtrate was concentrated under reduced pressure to obtain the title compound as a colorless oil (0.12 g, 91%).

NMR (CDCl$_3$) δ: 0.96-1.00 (9H, m), 1.47-1.70 (7H, m), 2.33 (3H, s), 2.63-2.64 (3H, m), 3.13-3.21 (5H, m), 4.11-4.15 (1H, m), 4.71-4.81 (2H, m).

103e) N-(4-chlorophenyl)-N'-((1R)-2,2-dimethyl-1-((4-(4-methyl-2-oxo-1-piperazinyl)-1-piperidinyl)carbonyl)propyl)urea To a solution of 1-(1-((2R)-2-amino-3,3-dimethylbutyroyl)-4-piperidinyl)-4-methylpiperazin-2-one (0.12 g) obtained in Example 103d) in acetonitrile (5 ml) was added 4-chlorophenyl isocyanate (57 mg), and mixed at room temperature for 1 hour. The reaction mixture was concentrated under reduced pressure, and the residue was purified with silica gel column (ethyl acetate) to obtain the title compound as colorless powder (46 mg, 27%).

NMR (CDCl$_3$) δ: 1.01-1.05 (9H, m), 1.63-1.76 (4H, m), 2.30-2.33 (3H, m), 2.52-2.66 (3H, m), 3.03-3.23 (5H, m), 4.27-4.33 (1H, m), 4.74-4.89 (3H, m), 5.98-6.09 (1H, m), 7.15-7.30 (5H, m).

Elemental analysis for C$_{23}$H$_{34}$ClN$_5$O$_3$.0.3H$_2$O.0.4AcOEt.
Calcd. (%): C, 58.55; H, 7.55; N, 13.88.
Found (%): C, 58.73; H, 7.78; N, 13.66.

EXAMPLE 104

N-(4-chlorophenyl)-N'-((1R)-2,2-dimethyl-1-((4-(3-oxo-4-morpholinyl)-1-piperidinyl)carbonyl)propyl)urea

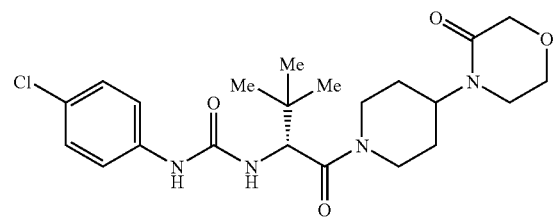

104a) tert-butyl 4-(3-oxo-4-morpholinyl)-1-piperidinecarboxylate tert-Butyl 4-(2-hydroxyethyl)amino-1-piperidinecarboxylate (2.4 g) obtained in Example 91a) and triethylamine (1.0 g) were dissolved in THF (70 ml). While the mixture was cooled to 0° C., chloroacetyl chloride (0.72 ml) was added dropwise thereto, and mixed at 0° C. for 2 hours. Sodium hydride (60%; 1.0 g) and DMF (30 ml) were added to the reaction mixture, and mixed at 80° C. for 15 hours. The reaction mixture was concentrated under reduced pressure, water was added thereto, and then extracted with ethyl acetate. The extract was washed with water, a 5% aqueous citric acid solution and saturated brine and dried over anhydrous sodium sulfate. The solvent was distilled off under reduced pressure, and the residue was purified with silica gel column (ethyl acetate/hexane=1/1 to ethyl acetate) to obtain the title compound as a colorless oil (0.51 g, 18%).

NMR (CDCl$_3$) δ: 1.46 (9H, s), 1.58-1.67 (4H, m), 2.77-2.85 (2H, m), 3.26 (2H, t, J=5.1), 3.88 (2H, t, J=5.1), 4.19 (2H, s), 4.22 (2H, br), 4.60-4.68 (2H, m).

104b) benzyl(1R)-2,2-dimethyl-1-((4-(3-oxo-4-morpholinyl)-1-piperidinyl)carbonyl)propylcarbamate tert-Butyl 4-(3-oxo-4-morpholinyl)-1-piperidinecarboxylate (0.28 g) obtained in Example 104a) was dissolved in trifluoroacetic acid (2 ml) and dichloromethane (2 ml), and mixed at room temperature for 2 hours. The reaction mixture was concentrated under reduced pressure, and the residue was dissolved in acetonitrile (3 ml). The reaction solution was added to a solution of Z-D-tert-leucine (0.27 g), HOBt (0.23 g), triethylamine (0.51 g) and WSC (0.29 g) in acetonitrile (10 ml) was added, and the reaction mixture was mixed at room temperature for 15 hours. The reaction mixture was concentrated under reduced pressure, and the residue was dissolved in ethyl acetate, washed sequentially with an aqueous sodium hydrogen carbonate solution, water, a 5% aqueous citric acid solution and saturated brine, and dried over anhydrous sodium sulfate. The solvent was distilled off under reduced pressure to obtain the title compound as a colorless oil (0.39 g, 90%).

NMR (CDCl$_3$) δ: 0.98-1.01 (9H, m), 1.54-1.76 (4H, m), 2.61-2.69 (1H, m), 3.15-3.25 (3H, m), 3.82-3.90 (2H, m), 4.19-4.24 (3H, m), 4.57-4.60 (1H, m), 4.71-4.81 (2H, m), 5.08-5.10 (2H, m), 5.58-5.61 (1H, m), 7.35-7.36 (5H, m).

104c) N-(4-chlorophenyl)-N'-((1R)-2,2-dimethyl-1-((4-(3-oxo-4-morpholinyl)-1-piperidinyl)carbonyl)propyl)urea Benzyl(1R)-2,2-dimethyl-1-((4-(3-oxo-4-morpholinyl)-1-piperidinyl)carbonyl)propylcarbamate (0.38 g) obtained in Example 104b) was dissolved in ethanol (10 ml), 10% palladium carbon (50 mg) was added thereto, and mixed under hydrogen atmosphere at room temperature for 2 hours. The reaction mixture was filtered, and the filtrate was concentrated under reduced pressure. The residue was dissolved in acetonitrile (10 ml), 4-chlorophenyl isocyanate (0.14 g) was added thereto, and mixed at room temperature for 1 hour. The reaction mixture was concentrated under reduced pressure, and the residue was purified with silica gel column (ethyl acetate to ethyl acetate/methanol=10/1) to obtain the title compound as colorless powder (0.37 g, 93%).

NMR (CDCl$_3$) δ: 1.03-1.05 (9H, m), 1.45-1.81 (4H, m), 2.60-2.73 (1H, m), 3.05-3.28 (3H, m), 3.76-3.91 (2H, m), 4.17-4.20 (2H, m), 4.31-4.35 (1H, m), 4.70-4.79 (2H, m), 4.86-4.90 (1H, m), 6.05-6.16 (1H, m), 7.15-7.35 (5H, m).

Elemental analysis for $C_{23}H_{34}ClN_5O_3 \cdot 0.3H_2O \cdot 0.4AcOEt$.
Calcd. (%): C, 58.55; H, 7.55; N, 13.88.
Found (%): C, 58.73; H, 7.78; N, 13.66.

EXAMPLE 105

N-(4-chlorophenyl)-N'-((1R)-1-((4-(1,1-dioxide-2-isothiazolidinyl)-1-piperidinyl)carbonyl)-2,2-dimethylpropyl)urea

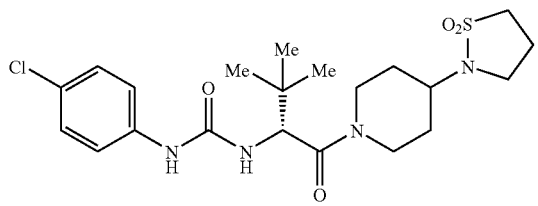

105a) tert-butyl 4-(1,1-dioxide-2-isothiazolidinyl)-1-piperidinecarboxylate tert-Butyl 4-amino-1-piperidinecarboxylate (1.6 g) and pyridine (0.93 g) were dissolved in dichloromethane (20 ml). While the mixture was cooled to 0° C., 3-chloropropanesulfonyl chloride (1.1 ml) was added dropwise thereto, and mixed 0° C. for 2 hours. To the reaction mixture was added a saturated aqueous ammonium chloride solution, and the organic layer was collected by separation. The organic layer was washed with saturated brine, and the solvent was distilled off under reduced pressure. The residue was dissolved in DMF (50 ml), cesium carbonate (2.6 g) was added thereto, and mixed at 80° C. for 15 hours. The reaction mixture was concentrated under reduced pressure, water was added thereto, and then extracted with ethyl acetate. The extract was washed with water, a 5% aqueous citric acid solution and saturated brine and dried over anhydrous sodium sulfate. The solvent was distilled off under reduced pressure, and the residue was purified with silica gel column (ethyl acetate/hexane=3/1 to ethyl acetate) to obtain the title compound as a colorless oil (0.69 g, 34%).

NMR (CDCl$_3$) δ: 1.46 (9H, s), 1.56-1.69 (2H, m), 1.86-1.90 (2H, m), 2.30-2.40 (1H, m), 2.80 (2H, m), 3.15 (2H, t, J=7.6), 3.27 (2H, t, J=6.7), 3.53-3.61 (1H, m), 4.11-4.16 (2H, m).

105b) benzyl(1R)-2,2-dimethyl-1-((4-(1,1-dioxide-2-isothiazolidinyl)-1-piperidinyl)carbonyl)propylcarbamate To tert-butyl 4-(1,1-dioxide-2-isothiazolidinyl)-1-piperidinecarboxylate (0.30 g) obtained in Example 105a) was added a 4 N solution of hydrogen chloride in ethyl acetate (10 ml), and mixed at room temperature for 15 hours. The reaction mixture was concentrated under reduced pressure, and water was removed from the residue by azeotropy with ethanol. The residue was added to a solution of Z-D-tert-leucine (0.27 g), HOBt (0.23 g), triethylamine (0.30 g) and WSC (0.29 g) in acetonitrile (10 ml), and mixed at room temperature for 15 hours. The reaction mixture was concentrated under reduced pressure, and the residue was dissolved in ethyl acetate. The reaction mixture was washed sequentially with an aqueous sodium hydrogen carbonate solution, water, a 5% aqueous citric acid solution and saturated brine and dried over anhydrous sodium sulfate. The solvent was distilled off under reduced pressure to obtain the title compound as colorless powder (0.37 g, 82%).

NMR (CDCl$_3$) δ: 0.97-1.00 (9H, m), 1.56-1.72 (3H, m), 1.89-2.05 (2H, m), 2.30-2.38 (2H, m), 2.62-2.71 (1H, m), 3.11-3.27 (4H, m), 3.60-3.70 (1H, m), 4.09-4.16 (1H, m), 4.56-4.60 (1H, m), 4.71-4.72 (1H, m), 5.03-5.13 (2H, m), 5.58-5.61 (1H, m), 7.35-7.36 (5H, m).

105c) N-(4-chlorophenyl)-N'-((1R)-1-((4-(1,1-dioxide-2-isothiazolidinyl)-1-piperidinyl)carbonyl)-2,2-dimethylpropyl)urea In the same manner as in Example 104c), the title compound as colorless powder (0.33 g, 85%) was obtained from benzyl (1R)-2,2-dimethyl-1-((4-(1,1-dioxide-2-isothiazolidinyl)-1-piperidinyl)carbonyl)propylcarbamate (0.37 g) obtained in Example 105b).

NMR (CDCl$_3$) δ: 0.98-1.05 (9H, m), 1.48-1.97 (4H, m), 2.24-2.39 (2H, m), 2.66-2.78 (1H, m), 3.05-3.29 (5H, m), 3.59-3.70 (1H, m), 4.26-4.32 (1H, m), 4.53-4.71 (1H, m), 4.85-4.91 (1H, m), 6.02-6.14 (1H, m), 7.15-7.28 (5H, m).

Elemental analysis for $C_{21}H_{31}ClN_4O_4S \cdot 0.5H_2O \cdot 0.1AcOEt$.
Calcd. (%): C, 52.58; H, 6.76; N, 11.46.
Found (%): C, 52.61; H, 6.36; N, 11.11.

EXAMPLE 106

N-(4-chlorophenyl)-N'-((1R)-2-(4-(((2Z)-3-methyl-2-(methylimino)-2,3-dihydro-1,3-thiazol-4-yl)methyl)-1-piperazinyl)-2-oxo-1-phenylethyl)urea

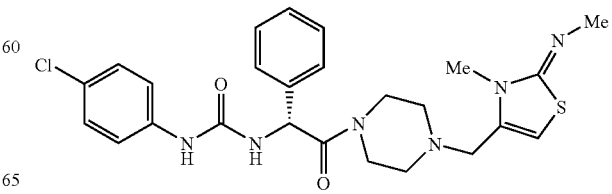

106a) tert-butyl(1R)-2-(4-(((2Z)-3-methyl-2-(methylimino)-2,3-dihydro-1,3-thiazol-4-yl)methyl)-1-piperazinyl)-2-oxo-1-phenylethylcarbamate To a solution of Boc-D-phenylglycine (0.50 g) and HOBt (0.46 g) in acetonitrile (15 ml) was added WSC (0.58 g), and the reaction mixture was mixed at room temperature for 15 minutes. Then, a solution of N-((2Z)-3-methyl-4-(1-piperazinyl)methyl-1,3-thiazol-2(3H)-ylidene)methanamine trihydrochloride (0.67 g) obtained in Reference Example 3, DBU (0.91 g) and triethylamine (0.84 ml) in acetonitrile (5 ml) was added thereto. The reaction mixture was mixed at room temperature for 15 hours, and then the solvent was distilled off under reduced pressure. The residue was dissolved in ethyl acetate, and the mixture was washed with an aqueous sodium hydrogen carbonate solution and dried over anhydrous sodium sulfate. The solvent was distilled off under reduced pressure, and the residue was purified with basic silica gel column (ethyl acetate) to obtain the title compound as pale brown powder (0.90 g, 99%).

NMR (CDCl$_3$) δ: 1.41 (9H, m), 1.87-1.91 (1H, m), 2.26-2.44 (3H, m), 2.98 (3H, s), 3.14 (2H, s), 3.29 (3H, s), 3.37-3.64 (4H, m), 5.54 (1H, d, J=7.8), 5.67 (1H, s), 6.04 (1H, d, J=7.8), 7.29-7.37 (5H, m).

106b) N-(4-chlorophenyl)-N'-((1R)-2-(4-(((2Z)-3-methyl-2-(methylimino)-2,3-dihydro-1,3-thiazol-4-yl)methyl)-1-piperazinyl)-2-oxo-1-phenylethyl)urea In the same manner as in Example 15b), the title compound as colorless powder (0.43 g, 92%) was obtained from tert-butyl(1R)-2-(4-(((2Z)-3-methyl-2-(methylimino)-2,3-dihydro-1,3-thiazol-4-yl)methyl)-1-piperazinyl)-2-oxo-1-phenylethylcarbamate (0.42 g) obtained in Example 106a).

NMR (CDCl$_3$) δ: 1.73-2.43 (4H, m), 2.98 (3H, s), 3.15 (2H, s), 3.29 (3H, s), 3.42-3.65 (4H, m), 5.67 (1H, s), 5.83-5.86 (1H, m), 6.50 (1H, m), 6.75 (1H, m), 7.21-7.34 (9H, m).

Elemental analysis for C$_{25}$H$_{29}$ClN$_6$O$_2$S.0.5H$_2$O.0.2AcOEt
Calcd. (%): C, 57.80; H, 5.87; N, 15.68.
Found (%): C, 58.06; H, 6.17; N, 15.46.

EXAMPLE 107

N-(4-chlorophenyl)-N'-(2-(4-(((2Z)-3-methyl-2-(methylimino)-2,3-dihydro-1,3-thiazol-4-yl)methyl)-1-piperazinyl)-2-oxoethyl)urea

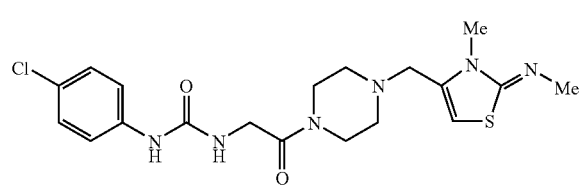

107a) tert-butyl 2-(4-(((2Z)-3-methyl-2-(methylimino)-2,3-dihydro-1,3-thiazol-4-yl)methyl)-1-piperazinyl)-2-oxoethylcarbamate In the same manner as in Example 106a), the title compound as a yellow solid (0.84 g, 88%) was obtained from Boc-glycine (0.44 g).

NMR (CDCl$_3$) δ: 1.45 (9H, s), 2.42-2.45 (4H, m), 3.00 (3H, s), 3.26 (2H, s), 3.36 (3H, s), 3.37-3.98 (7H, m), 5.50 (1H, br), 5.74 (1H, s).

107b) N-(4-chlorophenyl)-N'-(2-(4-(((2Z)-3-methyl-2-(methylimino)-2,3-dihydro-1,3-thiazol-4-yl)methyl)-1-piperazinyl)-2-oxoethyl)urea In the same manner as in Example 15b), the title compound as colorless powder (66 mg, 29%) was obtained from tert-butyl 2-(4-(((2Z)-3-methyl-2-(methylimino)-2,3-dihydro-1,3-thiazol-4-yl)methyl)-1-piperazinyl)-2-oxoethylcarbamate (0.20 g) obtained in Example 107a).

NMR (CDCl$_3$) δ: 2.42-2.45 (4H, m), 2.98 (3H, s), 3.29 (2H, s), 3.35 (3H, s), 3.46-3.49 (2H, m), 3.66-3.69 (2H, m), 4.25 (2H, s), 5.80 (1H, s), 6.99 (1H, d, J=0.9), 7.22 (2H, dd, J=1.8, 8.7), 7.35 (2H, d, J=8.7), 7.63 (1H, d, J=1.5).

Elemental analysis for C$_{19}$H$_{25}$ClN$_6$O$_2$S.0.5H$_2$O
Calcd. (%): C, 51.17; H, 5.88; N, 18.84.
Found (%): C, 51.43; H, 5.70; N, 18.69.

EXAMPLE 108

N'-(4-chlorophenyl)-N-methyl-N-(2-(4-(((2Z)-3-methyl-2-(methylimino)-2,3-dihydro-1,3-thiazol-4-yl)methyl)-1-piperazinyl)-2-oxoethyl)urea

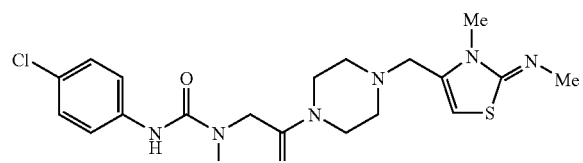

108a) tert-butyl methyl(2-(4-(((2Z)-3-methyl-2-(methylimino)-2,3-dihydro-1,3-thiazol-4-yl)methyl)-1-piperazinyl)-2-oxoethyl)carbamate In the same manner as in Example 106a), the title compound as a yellow oil (0.95 g, 96%) was obtained from Boc-sarcosine (0.47 g).

NMR (CDCl$_3$) δ: 1.47 (9H, s), 2.42 (4H, m), 2.92 (3H, s), 3.00 (3H, s), 3.25 (2H, s), 3.36 (3H, s), 3.37-4.05 (6H, m), 5.74 (1H, s).

108b) N'-(4-chlorophenyl)-N-methyl-N-(2-(4-(((2Z)-3-methyl-2-(methylimino)-2,3-dihydro-1,3-thiazol-4-yl)methyl)-1-piperazinyl)-2-oxoethyl)urea In the same manner as in Example 15b), the title compound as colorless powder (52 mg, 21%) was obtained from tert-butyl methyl(2-(4-(((2Z)-3-methyl-2-(methylimino)-2,3-dihydro-1,3-thiazol-4-yl)methyl)-1-piperazinyl)-2-oxoethyl)carbamate (0.22 g) obtained in Example 108a).

NMR (CDCl$_3$) δ: 2.43-2.46 (4H, m), 3.00 (3H, s), 3.11 (3H, s), 3.26 (2H, s), 3.36 (3H, s), 3.46-3.49 (2H, m), 3.61-3.64 (2H, m), 4.19 (2H, s), 5.74 (1H, s), 6.97 (1H, br), 7.22 (2H, dt, J=1.8, 8.7), 7.32 (2H, dt, J=1.8, 8.7).

Elemental analysis for C$_{20}$H$_{27}$ClN$_6$O$_2$S.0.2H$_2$O.0.2AcOEt
Calcd. (%): C, 52.91; H, 6.19; N, 17.80.
Found (%): C, 52.75; H, 6.18; N, 17.84.

EXAMPLE 109

N-(4-chlorophenyl)-N'-(3-(4-(((2Z)-3-methyl-2-(methylimino)-2,3-dihydro-1,3-thiazol-4-yl)methyl)-1-piperazinyl)-3-oxopropyl)urea

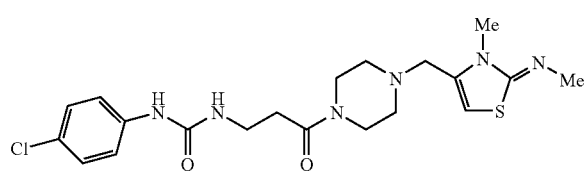

109a) tert-butyl 3-(4-(((2Z)-3-methyl-2-(methylimino)-2,3-dihydro-1,3-thiazol-4-yl)methyl)-1-piperazinyl)-3-oxopropylcarbamate In the same manner as in Example 106a), the title compound as a yellow oil (0.97 g, 98%) was obtained from Boc-β-alanine (0.47 g).
NMR (CDCl$_3$) δ: 1.43 (9H, s), 2.40-2.44 (4H, m), 2.48-2.52 (2H, m), 3.00 (3H, s), 3.25 (2H, s), 3.36 (3H, s), 3.41-3.47 (4H, m), 3.59-3.63 (2H, m), 5.29 (1H, m), 5.74 (1H, s).

109b) N-(4-chlorophenyl)-N'-(3-(4-(((2Z)-3-methyl-2-(methylimino)-2,3-dihydro-1,3-thiazol-4-yl)methyl)-1-piperazinyl)-3-oxopropyl)urea In the same manner as in Example 15b), the title compound as colorless powder (50 mg, 20%) was obtained from tert-butyl 3-(4-(((2Z)-3-methyl-2-(methylimino)-2,3-dihydro-1,3-thiazol-4-yl)methyl)-1-piperazinyl)-3-oxopropylcarbamate (0.22 g) obtained in Example 109a).
NMR (CDCl$_3$) δ: 2.38-2.44 (4H, m), 2.58 (2H, t, J=5.4), 2.99 (3H, s), 3.24 (2H, s), 3.34 (3H, s), 3.45 (2H, t, J=4.8), 3.53-3.61 (4H, m), 5.72 (1H, s), 5.76 (1H, br), 7.19-7.30 (4H, m).
Elemental analysis for C$_{20}$H$_{27}$ClN$_6$ O$_2$S.0.6H$_2$O.0.1AcOEt
Calcd. (%): C, 52.06; H, 6.21; N, 17.86.
Found (%): C, 51.85; H, 6.25; N, 17.74.

EXAMPLE 110

N-((1R)-1-benzyl-2-(4-(((2Z)-3-methyl-2-(methylimino)-2,3-dihydro-1,3-thiazol-4-yl)methyl)-1-piperazinyl)-2-oxoethyl)-N'-(4-chlorophenyl)urea

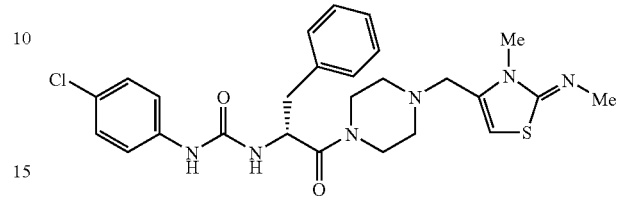

110a) tert-butyl(1R)-1-benzyl-2-(4-(((2Z)-3-methyl-2-(methylimino)-2,3-dihydro-1,3-thiazol-4-yl)methyl)-1-piperazinyl)-2-oxoethylcarbamate In the same manner as in Example 106a), the title compound as a yellow oil (0.20 g, 42%) was obtained from Boc-D-phenylalanine (0.27 g).
NMR (CDCl$_3$) δ: 1.42 (9H, s), 1.80-2.40 (5H, m), 2.92-2.96 (3H, m), 2.99 (3H, s), 3.20-3.29 (2H, m), 3.30 (3H, s), 3.53 (2H, m), 4.80-4.82 (2H, m), 5.39-5.42 (1H, m), 5.68 (1H, s), 7.17-7.29 (5H, m).

110b) N-((1R)-1-benzyl-2-(4-(((2Z)-3-methyl-2-(methylimino)-2,3-dihydro-1,3-thiazol-4-yl)methyl)-1-piperazinyl)-2-oxoethyl)-N'-(4-chlorophenyl)urea In the same manner as in Example 15b), the title compound as pale brown powder (0.11 g, 52%) was obtained from tert-butyl(1R)-1-benzyl-2-(4-(((2Z)-3-methyl-2-(methylimino)-2,3-dihydro-1,3-thiazol-4-yl)methyl)-1-piperazinyl)-2-oxoethylcarbamate (0.19 g) obtained in Example 110a).
NMR (CDCl$_3$) δ: 1.64-2.35 (4H, m), 2.93-3.14 (2H, m), 3.00 (3H, s), 3.12 (2H, s), 3.30 (3H, s), 3.38-3.59 (4H, m), 5.14-5.18 (1H, m), 5.69 (1H, s), 6.75 (1H, d, J=9.0), 7.16-7.33 (9H, m), 7.62 (1H, s).
Elemental analysis for C$_{26}$H$_{31}$ClN$_6$O$_2$S.0.5H$_2$O
Calcd. (%): C, 58.25; H, 6.02; N, 15.68.
Found (%): C, 58.05; H, 6.11; N, 15.39.

EXAMPLE 111

N-(4-chlorophenyl)-N'-((1R)-2,2-dimethyl-1-((4-(((2Z)-3-methyl-2-(methylimino)-2,3-dihydro-1,3-thiazol-4-yl)methyl)-1-piperazinyl)carbonyl)propyl)urea

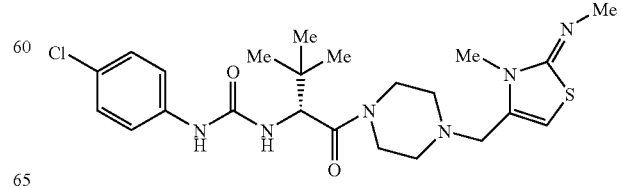

111a) tert-butyl(1R)-2,2-dimethyl-1-((4-(((2Z)-3-methyl-2-(methylimino)-2,3-dihydro-1,3-thiazol-4-yl)methyl)-1-piperazinyl)carbonyl)propylcarbamate In the same manner as in Example 106a), the title compound as yellow powder (0.39 g, 89%) was obtained from Boc-D-tert-leucine (0.23 g).
NMR (CDCl$_3$) δ: 0.97 (9H, s), 1.43 (9H, s), 2.40-2.52 (4H, m), 3.00 (3H, s), 3.25 (2H, s), 3.36 (3H, s), 3.50-3.85 (4H, m), 4.48-4.51 (1H, m), 5.32-5.35 (1H, m), 5.74 (1H, s).

111b) N-(4-chlorophenyl)-N'-((1R)-2,2-dimethyl-1-((4-(((2Z)-3-methyl-2-(methylimino)-2,3-dihydro-1,3-thiazol-4-yl)methyl)-1-piperazinyl)carbonyl)propyl)urea In the same manner as in Example 15b), the title compound as colorless powder (0.12 g, 28%) was obtained from tert-butyl(1R)-2,2-dimethyl-1-((4-(((2Z)-3-methyl-2-(methylimino)-2,3-dihydro-1,3-thiazol-4-yl)methyl)-1-piperazinyl)carbonyl)propylcarbamate (0.39 g) obtained in Example 111a).
NMR (CDCl$_3$) δ: 1.02 (9H, s), 2.29-2.58 (4H, m), 3.00 (3H, s), 3.23 (2H, s), 3.36 (3H, s), 3.40-3.90 (4H, m), 4.82-4.85 (1H, m), 5.73 (1H, s), 5.97-6.00 (1H, m), 7.19-7.26 (5H, m).
Elemental analysis for $C_{23}H_{33}ClN_6O_2S \cdot H_2O \cdot 0.2AcOEt$
Calcd. (%): C, 54.07; H, 6.98; N, 15.90.
Found (%): C, 53.87; H, 6.88; N, 15.60.

EXAMPLE 112

N-(4-chlorophenyl)-N'-((1R)-2-(4-(2-methylimidazo[1,2-a]pyridin-5-yl)-1-piperazinyl)-2-oxo-1-phenylethyl)urea

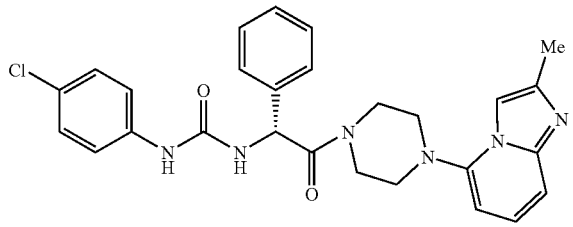

112a) tert-butyl(1R)-2-(4-(2-methylimidazo[1,2-a]pyridin-5-yl)-1-piperazinyl)-2-oxo-1-phenylethylcarbamate To a solution of Boc-D-phenylglycine (0.25 g) and HOBt (0.23 g) in acetonitrile (10 ml) was added WSC (0.29 g), and the reaction mixture was mixed at room temperature for 15 minutes. Then, a solution of 2-methyl-5-(1-piperazinyl)imidazo[1,2-a]pyridine dihydrochloride (0.29 g) obtained in Reference Example 4, DBU (0.30 g) and triethylamine (0.42 ml) in acetonitrile (5 ml) was added thereto. The reaction mixture was mixed at room temperature for 15 hours, and then the solvent was distilled off under reduced pressure. The residue was dissolved in ethyl acetate, and the reaction mixture was washed with an aqueous sodium hydrogen carbonate solution and dried over anhydrous sodium sulfate. The solvent was distilled off under reduced pressure, and then the residue was purified with basic silica gel column (ethyl acetate) to obtain the title compound as a yellow oil (0.41 g, 91%).
NMR (CDCl$_3$) δ: 1.43 (9H, m), 2.44 (3H, s), 2.93-3.65 (8H, m), 5.64 (1H, d, J=7.5), 6.02-6.13 (1H, m), 7.06-7.42 (9H, m).

112b) N-(4-chlorophenyl)-N'-((1R)-2-(4-(2-methylimidazo[1,2-a]pyridin-5-yl)-1-piperazinyl)-2-oxo-1-phenylethyl)urea In the same manner as in Example 15b), the title compound as colorless powder (0.45 g, quantitative, 21% ee) was obtained from tert-butyl(1R)-2-(4-(2-methylimidazo[1,2-a]pyridin-5-yl)-1-piperazinyl)-2-oxo-1-phenylethylcarbamate (0.40 g) obtained in Example 112a).
NMR (CDCl$_3$) δ: 1.72-1.94 (2H, m), 2.45 (3H, s), 2.51-3.99 (6H, m), 5.93 (1H, d, J=7.2), 6.12 (1H, d, J=7.1), 6.50-6.56 (1H, m), 7.07-7.40 (9H, m).
Elemental analysis for $C_{27}H_{27}ClN_6O_2 \cdot 1.4H_2O$
Calcd. (%): C, 61.39; H, 5.69; N, 15.91.
Found (%): C, 61.64; H, 5.96; N, 15.53.

EXAMPLE 113

N-(4-chlorophenyl)-N'-((1R)-2,2-dimethyl-1-((4-(2-methylimidazo[1,2-a]pyridin-5-yl)-1-piperazinyl)carbonyl)propyl)urea

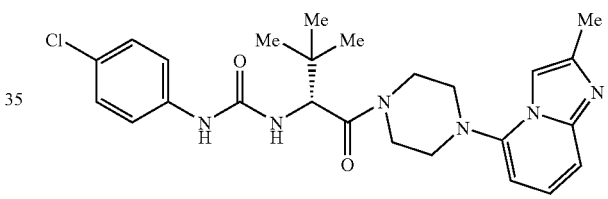

113a) tert-butyl(1R)-2,2-dimethyl-1-((4-(2-methylimidazo[1,2-a]pyridin-5-yl)-1-piperazinyl)carbonyl)propylcarbamate In the same manner as in Example 112a), the title compound as yellow powder (0.24 g, 56%) was obtained from Boc-D-tert-leucine (0.23 g).
NMR (CDCl$_3$) δ: 1.02 (9H, s), 1.45 (9H, s), 2.48 (3H, s), 3.14 (4H, m), 3.84-4.00 (4H, m), 4.57 (1H, d, J=9.8), 5.35 (1H, d, J=10.2), 6.25 (1H, d, J=7.1), 7.11-7.33 (3H, m).

113b) N-(4-chlorophenyl)-N'-((1R)-2,2-dimethyl-1-((4-(2-methylimidazo[1,2-a]pyridin-5-yl)-1-piperazinyl)carbonyl)propyl)urea In the same manner as in Example 15b), the title compound as colorless powder (0.11 g, 41%) was obtained from tert-butyl(1R)-2,2-dimethyl-1-((4-(2-methylimidazo[1,2-a]pyridin-5-yl)-1-piperazinyl)carbonyl)propylcarbamate (0.24 g) obtained in Example 113a).
NMR (CDCl$_3$) δ: 1.06 (9H, s), 2.48 (3H, s), 3.03-3.16 (4H, m), 3.74-4.14 (4H, m), 4.90 (1H, d, J=9.4), 6.00 (1H, d, J=9.5), 6.22 (1H, d, J=7.2), 7.10-7.34 (8H, m).
Elemental analysis for $C_{25}H_{31}ClN_6O_2 \cdot 0.6H_2O \cdot 0.3Et_2O$
Calcd. (%): C, 61.34; H, 6.92; N, 16.38.
Found (%): C, 61.13; H, 6.81; N, 16.22.

EXAMPLE 114

1-(4-chlorophenyl)-3-((1R)-2,2-dimethyl-1-((4-(2-methyl-4-pyridinyl)-1-piperazinyl)carbonyl)propyl)urea

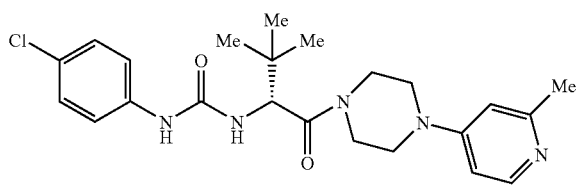

114a) 1-benzyl-4-(2-methyl-4-pyridinyl)piperazine

A solution of 1-benzylpiperazine (6.8 g) and 4-chloro-2-methylpyridine (4.9 g) in acetic acid (20 ml) was heated under reflux for 15 hours, and then concentrated under reduced pressure. The residue was dissolved in water, and the reaction mixture was basified with potassium carbonate and extracted with ethyl acetate. The extract was dried over anhydrous magnesium sulfate, and the solvent was distilled off under reduced pressure. The residue was purified with basic silica gel column (ethyl acetate) to obtain the title compound as a brown oil (10 g, quantitative).

NMR (CDCl$_3$) δ: 2.44 (3H, s), 2.53-2.58 (4H, m), 3.29-3.34 (4H, m), 3.55 (2H, s), 6.46-6.53 (2H, m), 7.29-7.35 (5H, m), 8.16 (1H, d, J=6.2).

114b) 1-(2-methyl-4-pyridinyl)piperazine

1-Benzyl-4-(2-methyl-4-pyridinyl)piperazine (10.3 g) obtained in Example 114a) and 10% palladium carbon (1.0 g) were added to methanol (200 ml), and mixed under hydrogen atmosphere at room temperature for 7 days. The catalyst was filtered off, and the filtrate was concentrated under reduced pressure. The residue was purified with basic silica gel column (ethyl acetate) and recrystallized from ethyl acetate-hexane to obtain the title compound as a colorless needle-like crystal (2.58 g, 38%).

NMR (CDCl$_3$) δ: 2.45 (3H, s), 2.96-3.01 (4H, m), 3.25-3.30 (4H, m), 6.48-6.55 (2H, m), 8.17 (1H, d, J=6.0).

114c) tert-butyl((1R)-2,2-dimethyl-1-((4-(2-methyl-4-pyridinyl)-1-piperazinyl)carbonyl)propyl)carbamate To a solution of Boc-D-tert-leucine (0.23 g) in methylene chloride (5 ml) were added HOBt (0.20 g), WSC (0.29 g) and triethylamine (0.28 ml) under ice-cooling, and the reaction mixture was mixed at 0° C. for 15 minutes. Then, 1-(2-methyl-4-pyridinyl)piperazine (0.18 g) obtained in Example 114b) was added thereto, and further mixed at room temperature for 13 hours. The solvent was distilled off under reduced pressure, and the residue was dissolved in ethyl acetate. The reaction mixture was washed with an aqueous potassium carbonate solution and dried over anhydrous magnesium sulfate. The solvent was distilled off under reduced pressure, and then the residue was purified with basic silica gel column (ethyl acetate) to obtain the title compound as a colorless solid (0.35 g, 90%).

NMR (CDCl$_3$) δ: 1.00 (9H, s), 1.43 (9H, s), 2.47 (3H, s), 3.20-3.50 (4H, m), 3.58-3.80 (2H, m), 3.82-3.98 (2H, m), 4.52 (1H, d, J=10.2), 5.31 (1H, d, J=10.2), 6.49-6.53 (2H, m), 8.21 (1H, d, J=5.8).

114d) 1-(4-chlorophenyl)-3-((1R)-2,2-dimethyl-1-((4-(2-methyl-4-pyridinyl)-1-piperazinyl)carbonyl)propyl)urea A solution of tert-butyl((1R)-2,2-dimethyl-1-((4-(2-methyl-4-pyridinyl)-1-piperazinyl)carbonyl)propyl)carbamate (0.35 g) obtained in Example 114c) in trifluoroacetic acid (2 ml) was mixed at room temperature for 1 hour, and then concentrated under reduced pressure. The residue was dissolved in THF (5 ml), triethylamine (0.3 ml) and 4-chlorophenyl isocyanate (0.14 g) were added thereto, and mixed at room temperature for 1 hour. The solvent was distilled off under reduced pressure, and the residue was dissolved in ethyl acetate. The reaction mixture was washed with an aqueous sodium hydrogen carbonate solution and dried over anhydrous magnesium sulfate. The solvent was distilled off under reduced pressure, and the residue was purified with basic silica gel column (ethyl acetate). The product was recrystallized from ethyl acetate-hexane to obtain the title compound as a colorless needle-like crystal (0.26 g, 59%).

NMR (CDCl$_3$) δ: 1.04 (9H, s), 2.47 (3H, s), 3.12-3.48 (4H, m), 3.60-4.10 (4H, m), 4.86 (1H, d, J=9.4), 5.98 (1H, d, J=9.4), 6.47-6.51 (2H, m), 7.22 (4H, m), 7.37 (1H, s), 8.21 (1H, d, J=5.8).

Elemental analysis for $C_{23}H_{30}ClN_5O_2 \cdot 0.5AcOEt$
Calcd. (%): C, 61.53; H, 7.02; N, 14.35.
Found (%): C, 61.90; H, 7.28; N, 14.14.

EXAMPLE 115

N-(2-(4-(5-methyl-3-oxo-1H-imidazo[1,5-c]imidazol-2(3H)-yl)-1-piperidinyl)-2-oxo-1-phenylethyl)-N'-phenylurea

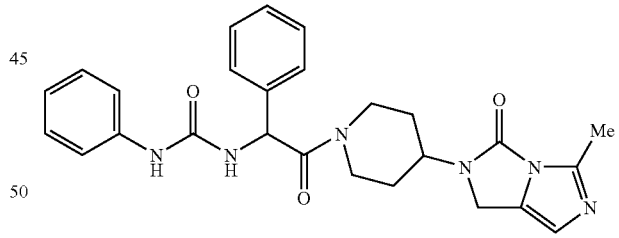

115a) 2-(1-(2-amino-2-phenylacetyl)-4-piperidinyl)-5-methyl-1,2-dihydro-3H-imidazo[1,5-c]imidazol-3-one dihydrochloride tert-Butyl 2-(4-(5-methyl-3-oxo-1H-imidazo[1,5-c]imidazol-2(3H)-yl)-1-piperidinyl)-2-oxo-1-phenylethylcarbamate (13 g) obtained in Example 50a) was dissolved in concentrated hydrochloric acid (30 ml) and ethanol (30 ml). The reaction mixture was mixed at room temperature for 30 minutes, and then the solvent was distilled off under reduced pressure. Water in the residue was removed by azeotropy with ethanol to obtain the title compound as pale yellow powder (12 g, quantitative).

NMR (DMSO-d$_6$) δ: 1.41-2.09 (4H, m), 2.71-2.76 (3H, m), 2.79-2.81 (1H, m), 3.12-3.40 (1H, m), 3.63-4.12 (3H, m), 4.40-4.55 (2H, m), 4.64 (1H, s), 5.59-5.60 (1H, m), 7.45-7.57 (5H, m), 8.72-8.82 (3H, m).

115b) N-((2-(4-(5-methyl-3-oxo-1H-imidazo[1,5-c]imidazol-2(3H)-yl)-1-piperidinyl)-2-oxo-1-phenyl-ethyl)-N'-phenylurea 2-(1-(2-Amino-2-phenylacetyl)-4-piperidinyl)-5-methyl-1,2-dihydro-3H-imidazo[1,5-c]imidazol-3-one dihydrochloride (0.21 g) obtained in Example 115a) and DBU (0.15 g) were dissolved in acetonitrile (10 ml). Phenyl isocyanate (66 mg) was added thereto, and mixed at room temperature for 2 hours. The solvent was distilled off under reduced pressure and the residue was dissolved in ethyl acetate. The reaction mixture was washed with an aqueous sodium hydrogen carbonate solution and dried over anhydrous sodium sulfate. The solvent was distilled off under reduced pressure, and the residue was purified with silica gel column (ethyl acetate to ethyl acetate/methanol=5/1) and solidified with ethyl acetate and diethyl ether to obtain the title compound (0.14 g, 59%) as colorless powder.

NMR (CDCl$_3$) δ: 1.34-1.87 (5H, m), 2.56-2.59 (3H, m), 2.64-3.16 (2H, m), 3.77-4.23 (4H, m), 4.77-4.81 (1H, m), 5.89-5.99 (1H, m), 6.55-6.71 (2H, m), 6.90-7.45 (10H, m).

Elemental analysis for C$_{26}$H$_{28}$N$_6$O$_3$.0.5H$_2$O
Calcd. (%): C, 64.85; H, 6.07; N, 17.45.
Found (%): C, 65.04; H, 6.01; N, 17.24.

EXAMPLE 116

N-(2-(4-(5-methyl-3-oxo-1H-imidazo[1,5-c]imidazol-2(3H)-yl)-1-piperidinyl)-2-oxo-1-phenylethyl)-N'-(4-methylphenyl)urea

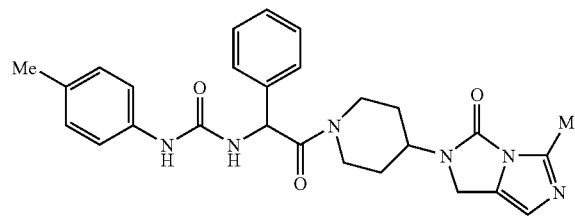

In the same manner as in Example 115b), the title compound as colorless powder (92 mg, 19%) was obtained from 4-methylphenyl isocyanate (73 mg).

NMR (CDCl$_3$) δ: 1.62-1.87 (4H, m), 2.29 (3H, s), 2.56-2.60 (3H, m), 2.64-3.16 (2H, m), 3.77-4.23 (4H, m), 4.77-4.81 (1H, m), 5.88-5.98 (1H, m), 6.60-6.95 (3H, m), 7.06-7.17 (4H, m), 7.35-7.42 (5H, m).

Elemental analysis for C$_{27}$H$_{30}$N$_6$O$_3$.0.5H$_2$O
Calcd. (%): C, 65.44; H, 6.31; N, 16.96.
Found (%): C, 65.45; H, 6.52; N, 16.81.

EXAMPLE 117

N-(4-methoxyphenyl)-N'-(2-(4-(5-methyl-3-oxo-1H-imidazo[1,5-c]imidazol-2(3H)-yl)-1-piperidinyl)-2-oxo-1-phenylethyl)urea

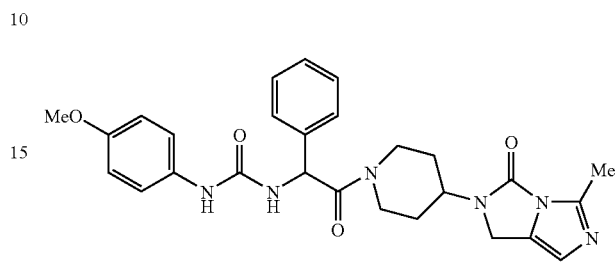

In the same manner as in Example 115b), the title compound as colorless powder (0.18 g, 72%) was obtained from 4-methoxyphenyl isocyanate (82 mg).

NMR (CDCl$_3$) δ: 1.30-1.90 (4H, m), 2.56-2.59 (3H, m), 2.64-3.15 (2H, m), 3.77 (3H, s), 3.76-4.23 (4H, m), 4.76-4.80 (1H, m), 5.87-5.96 (1H, m), 6.42-6.84 (3H, m), 7.16-7.42 (9H, m).

Elemental analysis for C$_{27}$H$_{30}$N$_6$O$_4$.0.5H$_2$O
Calcd. (%): C, 63.39; H, 6.11; N, 16.43.
Found (%): C, 63.53; H, 6.13; N, 16.13.

EXAMPLE 118

N-(4-fluorophenyl)-N'-((1R)-2-(4-(5-methyl-3-oxo-1H-imidazo[1,5-c]imidazol-2(3H)-yl)-1-piperidinyl)-2-oxo-1-phenylethyl)urea

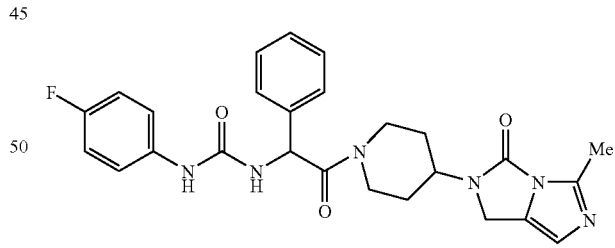

In the same manner as in Example 115b), the title compound as colorless powder (0.12 g, 49%) was obtained from 4-fluorophenyl isocyanate (69 mg).

NMR (CDCl$_3$) δ: 1.29-1.93 (4H, m), 2.56-2.59 (3H, m), 2.64-3.18 (2H, m), 3.79-4.24 (4H, m), 4.76-4.81 (1H, m), 5.88-5.97 (1H, m), 6.63-6.72 (2H, m), 6.91-7.38 (10H, m).

Elemental analysis for C$_{26}$H$_{27}$FN$_6$O$_3$.0.5H$_2$O.0.1Et$_2$O
Calcd. (%): C, 62.67; H, 5.78; N, 16.61.
Found (%): C, 62.89; H, 5.77; N, 16.42.

EXAMPLE 119

N-(4-bromophenyl)-N'-(2-(4-(5-methyl-3-oxo-1H-imidazo[1,5-c]imidazol-2(3H)-yl)-1-piperidinyl)-2-oxo-1-phenylethyl)urea

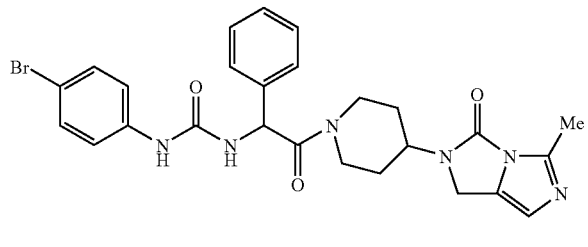

In the same manner as in Example 115b), the title compound as colorless powder (0.21 g, 76%) was obtained from 4-bromophenyl isocyanate (99 mg).

NMR (CDCl$_3$) δ: 1.32-1.93 (4H, m), 2.56-2.60 (3H, m), 2.73-3.22 (2H, m), 3.82-4.30 (4H, m), 4.78-4.82 (1H, m), 5.88-5.95 (1H, m), 6.67-6.87 (2H, m), 7.30-8.04 (10H, m).

Elemental analysis for $C_{26}H_{27}BrN_6O_3 \cdot 0.5H_2O$
Calcd. (%): C, 55.72; H, 5.04; N, 15.00.
Found (%): C, 55.80; H, 5.01; N, 14.79.

EXAMPLE 120

N-(4-cyanophenyl)-N'-(2-(4-(5-methyl-3-oxo-1H-imidazo[1,5-c]imidazol-2(3H)-yl)-1-piperidinyl)-2-oxo-1-phenylethyl)urea

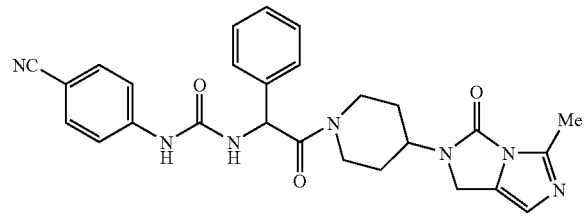

In the same manner as in Example 115b), the title compound as colorless powder (0.21 g, 70%) was obtained from 4-cyanophenyl isocyanate (72 mg).

NMR (CDCl$_3$) δ: 1.32-1.93 (4H, m), 2.56-2.60 (3H, m), 2.65-3.18 (2H, m), 3.79-4.25 (4H, m), 4.76-4.81 (1H, m), 5.89-5.97 (1H, m), 6.66-6.76 (2H, m), 7.13-7.50 (10H, m).

Elemental analysis for $C_{27}H_{27}N_7O_3 \cdot 0.5H_2O$
Calcd. (%): C, 64.02; H, 5.57; N, 19.36.
Found (%): C, 63.96; H, 5.75; N, 18.98.

EXAMPLE 121

N-(3-chlorophenyl)-N'-(2-(4-(5-methyl-3-oxo-1H-imidazo[1,5-c]imidazol-2(3H)-yl)-1-piperidinyl)-2-oxo-1-phenylethyl)urea

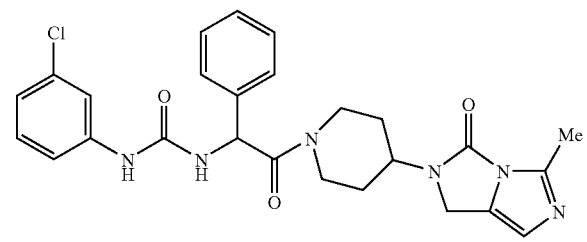

In the same manner as in Example 115b), the title compound as colorless powder (0.20 g, 79%) was obtained from 3-chlorophenyl isocyanate (77 mg).

NMR (CDCl$_3$) δ: 1.32-1.95 (4H, m), 2.56-2.60 (3H, m), 2.68-3.19 (2H, m), 3.80-4.29 (4H, m), 4.78-4.84 (1H, m), 5.91-5.99 (1H, m), 6.66-7.69 (12H, m).

Elemental analysis for $C_{26}H_{27}ClN_6O_3 \cdot 0.5H_2O$
Calcd. (%): C, 60.52; H, 5.47; N, 16.29.
Found (%): C, 60.81; H, 5.49; N, 16.05.

EXAMPLE 122

N-(2-chlorophenyl)-N'-(2-(4-(5-methyl-3-oxo-1H-imidazo[1,5-c]imidazol-2(3H)-yl)-1-piperidinyl)-2-oxo-1-phenylethyl)urea

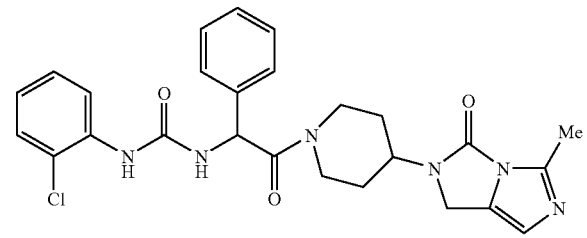

In the same manner as in Example 115b), the title compound as colorless powder (0.17 g, 65%) was obtained from 2-chlorophenyl isocyanate (77 mg).

NMR (CDCl$_3$) δ: 1.32-1.92 (4H, m), 2.56-2.59 (3H, m), 2.67-3.14 (2H, m), 3.99-4.26 (4H, m), 4.81-4.85 (1H, m), 5.88-6.00 (1H, m), 6.67-6.72 (1H, m), 6.85-7.48 (10H, m), 8.05-8.08 (1H, m).

Elemental analysis for $C_{26}H_{27}ClN_6O_3 \cdot 0.5H_2O$
Calcd. (%): C, 60.52; H, 5.47; N, 16.29.
Found (%): C, 60.70; H, 5.58; N, 16.02.

EXAMPLE 123

N-(2-(4-(5-methyl-3-oxo-1H-imidazo[1,5-c]imidazol-2(3H)-yl)-1-piperidinyl)-2-oxo-1-phenylethyl)-N'-(4-trifluoromethylphenyl)urea

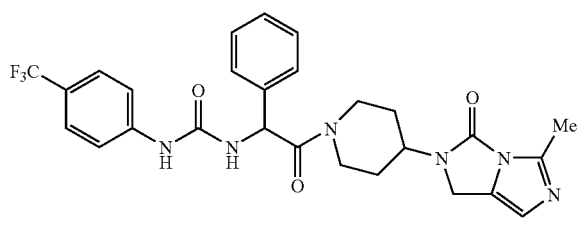

In the same manner as in Example 115b), the title compound as colorless powder (0.22 g, 82%) was obtained from 4-trifluoromethylphenyl isocyanate (0.10 g).

NMR (CDCl$_3$) δ: 1.32-1.90 (4H, m), 2.56-2.60 (3H, m), 2.70-3.23 (2H, m), 3.81-4.28 (4H, m), 4.79-4.83 (1H, m), 5.90-5.98 (1H, m), 6.67-6.75 (1H, m), 6.83-6.85 (1H, m), 7.30-7.41 (9H, m), 7.78-7.87 (1H, m).

Elemental analysis for C$_{27}$H$_{27}$F$_3$N$_6$O$_3$.0.5H$_2$O.0.1Et$_2$O

Calcd. (%): C, 59.19; H, 5.26; N, 15.12.

Found (%): C, 59.30; H, 5.24; N, 14.83.

EXAMPLE 124

N-(4-chloro-2-methylphenyl)-N'-(2-(4-(5-methyl-3-oxo-1H-imidazo[1,5-c]imidazol-2(3H)-yl)-1-piperidinyl)-2-oxo-1-phenylethyl)urea

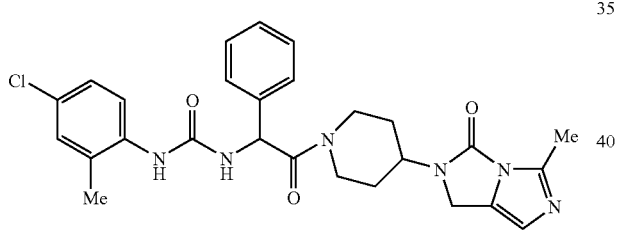

2-(1-(2-Amino-2-phenylacetyl)-4-piperidinyl)-5-methyl-1,2-dihydro-3H-imidazo[1,5-c]imidazol-3-one dihydrochloride (0.21 g) obtained in Example 115a) was dissolved in acetonitrile (5.0 ml). Triethylamine (0.14 ml) and 4-chloro-2-methylphenyl isocyanate (80 mg) were added thereto, and mixed at room temperature for 15 hours. The solvent was distilled off under reduced pressure, and the residue was dissolved in ethyl acetate. The reaction mixture was washed with an aqueous sodium hydrogen carbonate solution and dried over anhydrous magnesium sulfate. The solvent was distilled off under reduced pressure, and the residue was purified with basic silica gel column (ethyl acetate/hexane=1/1 to ethyl acetate). The product was crystallized from ethyl acetate-diethyl ether to obtain the title compound as colorless powder (0.16 g, 61%).

NMR (CDCl$_3$) δ: 1.33-1.92 (3H, m), 2.15 (3H, s), 2.56-2.84 (4H, m), 3.78-4.24 (4H, m), 4.77 (1H, d, J=12.4), 5.85-5.94 (1H, m), 6.58-6.73 (3H, m), 7.10-7.13 (2H, m), 7.30-7.43 (6H, m).

Elemental analysis for C$_{27}$H$_{29}$ClN$_6$O$_3$.0.5H$_2$O

Calcd. (%): C, 61.18; H, 5.71; N, 15.86.

Found (%): C, 61.31; H, 5.96; N, 15.61.

EXAMPLE 125

N-(2,4-dichlorophenyl)-N'-(2-(4-(5-methyl-3-oxo-1H-imidazo[1,5-c]imidazol-2(3H)-yl)-1-piperidinyl)-2-oxo-1-phenylethyl)urea

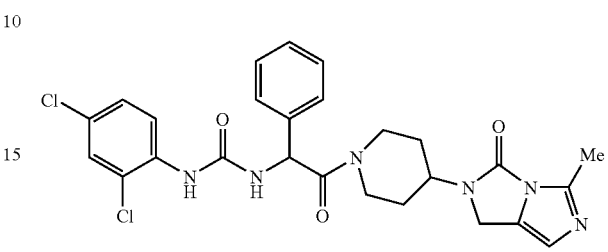

In the same manner as in Example 124, the title compound as colorless powder (0.13 g, 47%) was obtained from 2,4-dichlorophenyl isocyanate (0.09 g).

NMR (CDCl$_3$) δ: 1.18-1.88 (4H, m), 2.56-2.59 (3H, m), 2.67-3.20 (2H, m), 3.80-4.26 (4H, m), 4.81 (1H, d, J=13.4), 5.89-6.00 (1H, m), 6.67-6.73 (1H, m), 7.08-7.46 (10H, m), 8.01-8.05 (1H, m).

Elemental analysis for C$_{26}$H$_{26}$Cl$_2$N$_6$O$_3$.0.25H$_2$O

Calcd. (%): C, 57.20; H, 4.89; N, 15.39.

Found (%): C, 57.19; H, 5.01; N, 15.03.

EXAMPLE 126

N-(2-(4-(5-methyl-3-oxo-1H-imidazo[1,5-c]imidazol-2(3H)-yl)-1-piperidinyl)-2-oxo-1-phenylethyl)-N'-(4-(methylthio)phenyl)urea

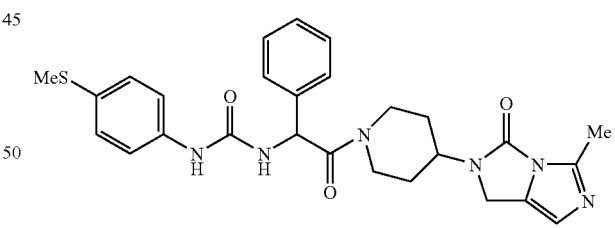

In the same manner as in Example 124, the title compound as colorless powder (0.46 g, 60%) was obtained from 4-methylthiophenyl isocyanate (0.22 ml).

NMR (CDCl$_3$) δ: 1.19-1.83 (4H, m), 2.42 (3H, s), 2.56-2.59 (3H, m), 2.65-3.13 (2H, m), 3.78-4.22 (4H, m), 4.77 (1H, d, J=13.2), 5.92-6.02 (1H, m), 6.66-6.86 (2H, m), 7.12-7.19 (4H, m), 7.33-7.40 (5H, m), 7.50-7.66 (1H, m).

Elemental analysis for C$_{27}$H$_{30}$N$_6$O$_3$S.0.5H$_2$O

Calcd. (%): C, 61.46; H, 5.92; N, 15.93.

Found (%): C, 61.62; H, 6.13; N, 15.66.

EXAMPLE 127

N-(2-(4-(5-methyl-3-oxo-1H-imidazo[1,5-c]imidazol-2(3H)-yl)-1-piperidinyl)-2-oxo-1-phenylethyl)-N'-(4-(methylsulfinyl)phenyl)urea

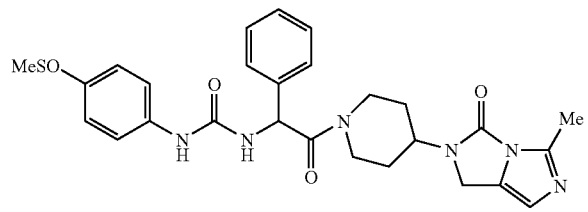

In the same manner as in Example 67, the title compound as colorless powder (0.08 g, 73%) was obtained from N-(2-(4-(5-methyl-3-oxo-1H-imidazo[1,5-c]imidazol-2(3H)-yl)-1-piperidinyl)-2-oxo-1-phenylethyl)-N'-(4-(methylthio)phenyl)urea (0.10 g) obtained in Example 126 and 3-chlorobenzoic acid (0.05 g).

NMR (CDCl$_3$) δ: 1.42-1.85 (4H, m), 2.56-2.59 (3H, m), 2.69 (3H, s), 2.83-3.16 (1H, m), 3.80-4.27 (5H, m), 4.79 (1H, d, J=12.6), 5.89-5.97 (1H, m), 6.67-6.74 (1H, m), 7.01-7.04 (1H, m), 7.34-7.47 (9H, m), 8.26-8.33 (1H, m).

Elemental analysis for C$_{27}$H$_{30}$N$_6$O$_4$S.0.5AcOEt.0.5H$_2$O
Calcd. (%): C, 59.27; H, 6.00; N, 14.30.
Found (%): C, 59.31; H, 5.78; N, 14.51.

EXAMPLE 128

N-(2-(4-(5-methyl-3-oxo-1H-imidazo[1,5-c]imidazol-2(3H)-yl)-1-piperidinyl)-2-oxo-1-phenylethyl)-N'-(4-(methylsulfonyl)phenyl)urea

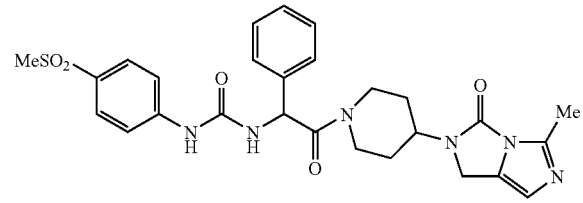

In the same manner as in Example 68, the title compound as colorless powder (0.07 g, 67%) was obtained from N-(2-(4-(5-methyl-3-oxo-1H-imidazo[1,5-c]imidazol-2(3H)-yl)-1-piperidinyl)-2-oxo-1-phenylethyl)-N'-(4-(methylthio)phenyl)urea (0.10 g) obtained in Example 126 and 3-chlorobenzoic acid (0.11 g).

NMR (CDCl$_3$) δ: 1.48-2.05 (4H, m), 2.56-2.64 (3H, m), 2.77-2.90 (1H, m), 3.00 (3H, s), 3.15-3.28 (1H, m), 3.87-4.30 (4H, m), 4.81 (1H, d, J=13.4), 5.88-5.96 (1H, m), 6.68-6.76 (1H, m), 6.96-6.98 (1H, m), 7.36-7.42 (7H, m), 7.61-7.71 (2H, m), 8.26-8.33 (1H, m).

Elemental analysis for C$_{27}$H$_{30}$N$_6$O$_4$S.1.5H$_2$O
Calcd. (%): C, 56.14; H, 5.76; N, 14.55.
Found (%): C, 56.11; H, 5.59; N, 14.43.

EXAMPLE 129 ethyl 4-((((2-(4-(5-methyl-3-oxo-1H-imidazo[1,5-c]imidazol-2(3H)-yl)-1-piperidinyl)-2-oxo-1-phenylethyl)amino)carbonyl)amino)benzoate

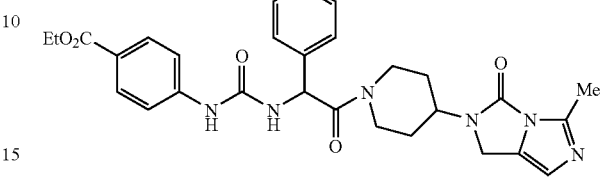

In the same manner as in Example 124, the title compound as colorless powder (0.54 g, 60%) was obtained from ethyl 4-isocyanatobenzoate (0.30 g).

NMR (CDCl$_3$) δ: 1.36 (3H, t, J=7.2), 1.51-1.90 (4H, m), 2.56-2.60 (3H, m), 2.73-3.16 (2H, m), 3.80-4.26 (4H, m), 4.33 (2H, q, J=7.2), 4.80 (1H, d, J=9.0), 5.94-6.03 (1H, m), 6.66-6.74 (1H, m), 6.95-6.99 (1H, m), 7.32-7.37 (7H, m), 7.85-8.04 (3H, m).

Elemental analysis for C$_{29}$H$_{32}$N$_6$O$_5$.0.5H$_2$O
Calcd. (%): C, 62.92; H, 6.01; N, 15.18.
Found (%): C, 63.00; H, 5.98; N, 15.16.

EXAMPLE 130

N-(5-chloro-2-pyridinyl)-N'-(2-(4-(5-methyl-3-oxo-1H-imidazo[1,5-c]imidazol-2(3H)-yl)-1-piperidinyl)-2-oxo-1-phenylethyl)urea

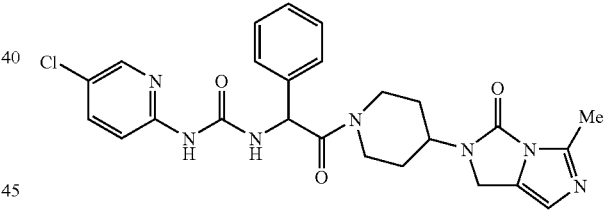

2-Amino-5-chloropyridine (0.64 g) and DBU (1.5 g) were dissolved in acetonitrile (10 ml), N,N'-carbonyldiimidazole (0.97 g) was added thereto, and mixed at room temperature for 15 hours. 2-(1-(2-Amino-2-phenylacetyl)-4-piperidinyl)-5-methyl-1,2-dihydro-3H-imidazo[1,5-c]imidazol-3-one dihydrochloride (0.85 g) obtained in Example 115a) and DBU (0.91 g) were added thereto, and the reaction mixture was mixed at room temperature for 15 hours. The reaction mixture was concentrated under reduced pressure, and the residue was dissolved in chloroform. The mixture was washed with an aqueous potassium carbonate solution and dried over anhydrous sodium sulfate. The solvent was distilled off under reduced pressure, and the residue was purified with basic silica gel column (ethyl acetate) and crystallized from ethyl acetate to obtain the title compound (55 mg, 5%) as colorless powder.

NMR (CDCl$_3$) δ: 1.38-1.87 (4H, m), 2.57-2.60 (3H, m), 2.72-3.19 (2H, m), 3.79-4.24 (4H, m), 4.85-4.90 (1H, m), 5.95-6.03 (1H, m), 6.67-6.70 (1H, m), 6.96-6.99 (1H, m), 7.36-7.55 (6H, m), 8.20-8.23 (2H, m), 9.78-9.84 (1H, m).

Elemental analysis for $C_{25}H_{26}ClN_7O_3 \cdot 0.5H_2O$
Calcd. (%): C, 58.08; H, 5.26; N, 18.97.
Found (%): C, 58.35; H, 5.19; N, 19.09.

EXAMPLE 131

N-(6-chloro-3-pyridinyl)-N'-(2-(4-(5-methyl-3-oxo-1H-imidazo[1,5-c]imidazol-2(3H)-yl)-1-piperidinyl)-2-oxo-1-phenylethyl)urea

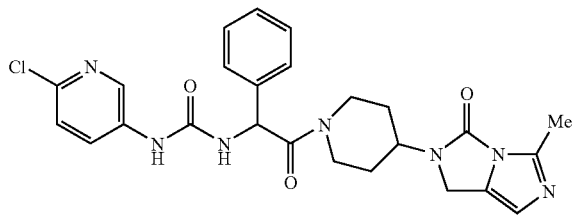

In the same manner as in Example 130, the title compound as colorless powder (0.40 g, 26%) was obtained from 3-amino-6-chloropyridine (0.39 g).

NMR (CDCl$_3$) δ: 1.38-1.93 (4H, m), 2.56-2.60 (3H, m), 2.69-3.22 (2H, m), 3.82-4.34 (4H, m), 4.77-4.81 (1H, m), 5.89-5.95 (1H, m), 6.67-6.85 (2H, m), 7.11-7.14 (1H, m), 7.37-7.40 (5H, m), 7.94-8.04 (3H, m).

Elemental analysis for $C_{25}H_{26}ClN_7O_3 \cdot 0.8H_2O \cdot 0.2IPE$
Calcd. (%): C, 57.97; H, 5.64; N, 18.06.
Found (%): C, 57.86; H, 5.36; N, 18.05.

EXAMPLE 132

N-(5-chloro-2-pyrimidinyl)-N'-(2-(4-(5-methyl-3-oxo-1H-imidazo[1,5-c]imidazol-2(3H)-yl)-1-piperidinyl)-2-oxo-1-phenylethyl)urea

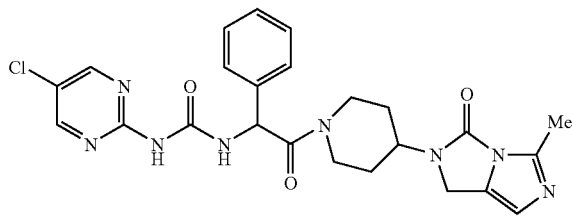

In the same manner as in Example 130, the title compound as colorless powder (0.50 g, 33%) was obtained from 2-amino-5-chloropyrimidine (0.39 g).

NMR (CDCl$_3$) δ: 1.38-1.93 (4H, m), 2.57-2.60 (3H, m), 2.69-3.22 (2H, m), 3.82-4.27 (4H, m), 4.84-4.87 (1H, m), 5.91-6.00 (1H, m), 6.67-6.72 (1H, m), 7.38-7.65 (6H, m), 8.50 (2H, s), 9.97-10.09 (1H, m).

Elemental analysis for $C_{24}H_{25}ClN_8O_3 \cdot 0.3H_2O$
Calcd. (%): C, 56.04; H, 5.02; N, 21.78.
Found (%): C, 56.05; H, 5.20; N, 21.58.

EXAMPLE 133

N-(4-chlorophenyl)-N'-((1R)-2,2-dimethyl-1-((4-(2-((2Z)-2-(methylimino)-1,3-thiazol-3(2H)-yl)ethyl)-1-piperidinyl)carbonyl)propyl)urea hydrochloride

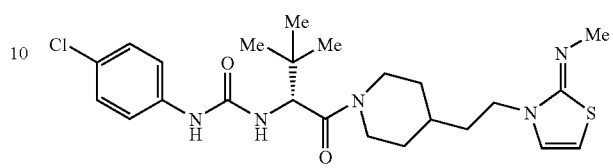

133a) tert-butyl 4-(2-((2Z)-2-(methylimino)-1,3-thiazol-3(2H)-yl)ethyl)-1-piperidinecarboxylate To a solution of tert-butyl 4-(2-bromoethyl)-1-piperidinecarboxylate (D. Brundish et al., J. Med. Chem., 42, 4584 (1999); 5.0 g) and 2-methylaminothiazole (O. Kemal et al., J. Chem. Soc. Perkin I, 5, 1569 (1981); 3.9 g) in DMF (50 ml) was added potassium iodide (5.7 g), and mixed at 80° C. for 12 hours. The reaction mixture was concentrated under reduced pressure, and the residue was dissolved in chloroform and a saturated aqueous potassium hydrogen carbonate solution. The organic layer was collected by separation, dried over anhydrous sodium sulfate, and then concentrated under reduced pressure. The residue was purified with silica gel column to obtain the title compound as a brown oil (1.25 g, 22%).

NMR (CDCl$_3$) δ: 1.06-1.21 (2H, m), 1.45 (9H, s), 1.47 (1H, m), 1.58-1.69 (4H, m), 2.59-2.74 (2H, m), 2.97 (3H, s), 3.75 (2H, t, J=7.4), 4.00-4.16 (2H, br), 5.90 (1H, d, J=4.9), 6.51 (1H, d, J=4.9).

133b) N-(4-chlorophenyl)-N'-((1R)-2,2-dimethyl-1-((4-(2-((2Z)-2-(methylimino)-1,3-thiazol-3(2H)-yl)ethyl)-1-piperidinyl)carbonyl)propyl)urea hydrochloride To tert-butyl 4-(2-((2Z)-2-(methylimino)-1,3-thiazol-3(2H)-yl)ethyl)-1-piperidinecarboxylate (1.3 g) obtained in Example 133a) was added concentrated hydrochloric acid (2 ml), subsequently, the mixture was diluted with ethanol, and then concentrated under reduced pressure to the residue was added triethylamine (1.7 ml) and dissolved in acetonitrile (20 ml). WSC (1.1 g), HOBt (0.90 g) and Boc-D-tert-leucine (1.4 g) were added thereto, and mixed at room temperature for 12 hours. The reaction mixture was concentrated under reduced pressure, and the residue was dissolved in chloroform and a saturated aqueous sodium hydrogen carbonate solution. The organic layer was collected by separation and dried over anhydrous sodium sulfate, and the solvent was distilled off under reduced pressure. To the residue was added trifluoroacetic acid (10 ml), and mixed for 30 minutes. The reaction mixture was poured into chloroform and a saturated aqueous sodium hydrogen carbonate solution, and the isolated organic layer was collected by separation. The organic layer was dried over anhydrous sodium sulfate, and then concentrated under reduced pressure. The residue was dissolved in acetonitrile, 4-chlorophenyl isocyanate (0.60 g) was added thereto, and mixed for 2 hours. The reaction mixture was concentrated under reduced pressure, and the residue was purified with silica gel column to obtain N-(4-chlorophenyl)-N'-((1R)-2,2- dimethyl-1-((4-(2-((2Z)-2-(methylimino)-1,3-thiazol-3(2H)-yl)ethyl)-1-piperidinyl)carbonyl)propyl)urea as a white solid (0.98 g, 47%). The resulting compound was treated with a 4 N solution of hydrochloric acid/ethyl acetate to obtain the title compound as white powder.

NMR (DMSO-d$_6$) δ: 0.88-0.99 (9H, m), 0.99-1.18 (2H, m), 1.56-1.81 (5H, m), 2.57 (1H, m), 2.99 (3H, s), 3.05 (1H, m), 4.04-4.19 (3H, m), 4.41 (1H, m), 4.67 (1H, t, J=9.1), 6.57 (1H, m), 7.13 (1H, m), 7.22-7.29 (2H, m), 7.36-7.46 (2H, m), 7.60 (1H, m), 9.07 (1H, m).

EXAMPLE 134

N-(4-chlorophenyl)-N'-((1R)-2,2-dimethyl-1-((4-(((2Z)-2-(methylimino)-1,3-thiazol-3(2H)-yl)methyl)-1-piperidinyl)carbonyl)propyl)urea

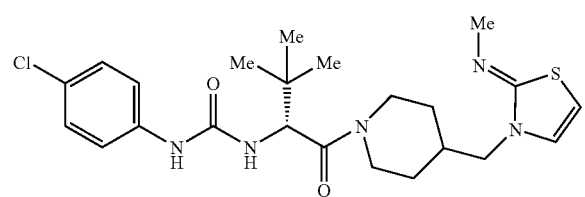

134a) tert-butyl 4-(((2Z)-2-(methylimino)-1,3-thiazol-3(2H)-yl)methyl)-1-piperidinecarboxylate In the same manner as in Example 133a), the title compound as a brown oil (0.75 g, 14%) was obtained from tert-butyl 4-bromomethyl-1-piperidinecarboxylate (R. J. DeVita et al., Bioorg. Med. Chem. Lett., 9, 261 (1999); 4.8 g) and 2-methylaminothiazole (3.9 g).

NMR (CDCl$_3$) δ: 1.05-1.53 (2H, m), 1.45 (9H, s), 1.62-1.67 (2H, m), 2.01 (1H, m), 2.67 (2H, t, J=15.0), 2.97 (3H, s), 3.59 (2H, br), 4.12 (2H, br), 5.90 (1H, d, J=4.8), 6.47 (1H, d, J=4.8).

134b) N-(4-chlorophenyl)-N'-((1R)-2,2-dimethyl-1-((4-(((2Z)-2-(methylimino)-1,3-thiazol-3(2H)-yl)methyl)-1-piperidinyl)carbonyl)propyl)urea In the same manner as in Example 133b), the title compound as a white solid (0.56 g, 49%) was obtained from tert-butyl 4-(((2Z)-2-(methylimino)-1,3-thiazol-3(2H)-yl)methyl)-1-piperidinecarboxylate (0.70 g) obtained in Example 134a).

NMR (CDCl$_3$) δ: 0.95-1.08 (9H, m), 1.16-1.35 (2H, m), 1.61-1.88 (2H, m), 2.21 (1H, m), 2.55 (1H, m), 2.97 (3H, s), 3.02 (1H, m), 3.59-3.74 (2H, m), 4.14 (1H, m), 4.62 (1H, m), 4.86 (1H, m), 5.74 (1H, m), 6.15 (1H, m), 6.32 (1H, m), 6.50 (1H, m), 7.15-7.34 (5H, m).

EXAMPLE 135

N-(4-chlorophenyl)-N'-((1R)-2,2-dimethyl-1-((4-(((2Z)-3-methyl-1,3-thiazol-2(3H)-ylidene)amino)-1-piperidinyl)carbonyl)propyl)urea

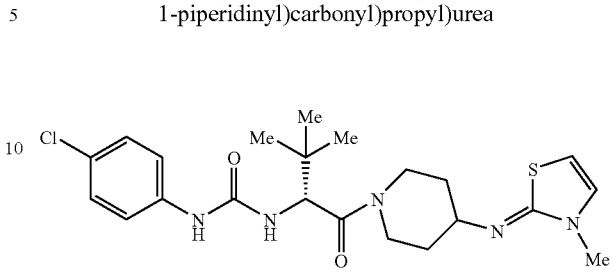

135a) tert-butyl 4-(1,3-thiazol-2-yl)amino-1-piperidinecarboxylate

To a solution of N-Boc-4-aminopiperidine (6.0 g) in THF (100 ml) was added benzoyl isothiocyanate (4.1 ml), and mixed for 2 hours. The reaction mixture was concentrated under reduced pressure, and the residue was dissolved in methanol, potassium carbonate was added thereto, and mixed at 50° C. for 1 hour. The reaction mixture was concentrated under reduced pressure, and then the residue was dissolved in ethyl acetate. The mixture was washed with 1 N hydrochloric acid, a saturated aqueous sodium hydrogen carbonate solution and saturated brine. The ethyl acetate solution was dried over anhydrous sodium sulfate and concentrated under reduced pressure to obtain the title compound as a pale yellow solid (7.3 g, 94%).

NMR (CDCl$_3$) δ: 1.26-1.45 (2H, m), 1.45 (9H, s), 1.98-2.08 (2H, m), 2.90 (2H, t, J=9.8), 3.98-4.10 (3H, m), 6.10 (2H, s), 6.74 (1H, d, J=7.2).

135b) tert-butyl 4-(1,3-thiazol-2-yl)amino-1-piperidinecarboxylate tert-Butyl 4-(1,3-thiazol-2-yl)amino-1-piperidinecarboxylate (5.0 g) obtained in Example 135a) was dissolved in ethanol (50 ml), chloroacetaldehyde (40% water content: 5.7 ml) was added thereto, and heated under reflux for 12 hours. The reaction mixture was concentrated under reduced pressure, the residue was dissolved in ethyl acetate and water, and the aqueous layer was collected by separation. The residue was basified with an aqueous potassium carbonate solution and extracted with chloroform. The extract was dried over anhydrous sodium sulfate and concentrated under reduced pressure to obtain the title compound as a pale yellow solid (3.2 g, 61%).

NMR (CDCl$_3$) δ: 1.33-1.49 (2H, m), 1.46 (9H, s), 2.06 (2H, m), 2.92 (2H, m), 3.56 (1H, m), 4.02 (2H, d, J=10.5), 4.95 (1H, br), 5.71 (1H, d, J=4.8), 6.72 (1H, d, J=4.8).

135c) tert-butyl 4-(((2Z)-3-methyl-1,3-thiazol-2(3H)-ylidene)amino)-1-piperidinecarboxylate To a solution of tert-butyl 4-(1,3-thiazol-2-yl)amino-1-piperidinecarboxylate (2.5 g) obtained in Example 135b) in DMF (50 ml) was added methyl iodide (1.1 ml), and mixed at 80° C. for 4 hours. The reaction mixture was concentrated under reduced pressure, and the residue was dissolved in chloroform and an aqueous potassium carbonate solution. The organic layer was collected by separation, dried over anhydrous sodium sulfate, and then concentrated under reduced pressure. The residue was purified with silica gel column to obtain the title compound as a pale yellow solid (0.54 g, 21%).

NMR (CDCl$_3$) δ: 1.46 (9H, s), 1.51-1.85 (4H, m), 2.82-3.08 (3H, m), 3.26 (3H, s), 3.96 (2H, br), 5.83 (1H, d, J=4.8), 6.45 (1H, d, J=4.8).

135d) N-(4-chlorophenyl)-N'-((1R)-2,2-dimethyl-1-((4-(((2Z)-3-methyl-1,3-thiazol-2(3H)-ylidene)amino)-1-piperidinyl)carbonyl)propyl)urea In the same manner as in Example 133b), the title compound as a white solid (0.48 g, 61%) was obtained from tert-butyl 4-(((2Z)-3-methyl-1,3-thiazol-2(3H)-ylidene)amino)-1-piperidinecarboxylate (0.50 g) obtained in Example 135c).

NMR (CDCl$_3$) δ: 1.03 (9H, s), 1.51-2.00 (4H, m), 3.02 (1H, m), 3.20 (1H, m), 3.22 (3H, s), 3.46 (1H, m), 4.07-4.20 (2H, m), 4.96 (1H, m), 5.87 (1H, d, J=4.7), 6.37 (1H, d, J=9.0), 6.47 (1H, d, J=4.7), 7.14-7.29 (4H, m), 7.90 (1H, s).

EXAMPLE 136

N-(4-chlorophenyl)-N'-((1R)-2-(4-(((2Z)-3-methyl-1,3-thiazol-2(3H)-ylidene)amino)-1-piperidinyl)-2-oxo-1-phenylethyl)urea

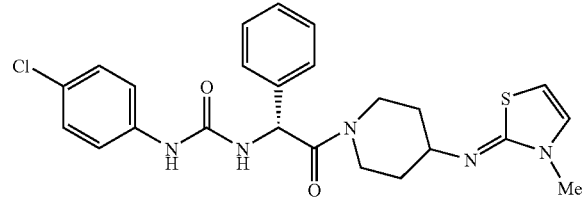

In the same manner as in Example 133b), the title compound as colorless powder (0.22 g, 46%) was obtained from tert-butyl 4-(((2Z)-3-methyl-1,3-thiazol-2(3H)-ylidene)amino)-1-piperidinecarboxylate (0.30 g) obtained in Example 135c).

NMR (CDCl$_3$) δ: 1.24-1.83 (4H, m), 2.89-2.97 (1H, m), 3.18-3.25 (3H, m), 3.30-3.49 (2H, m), 3.82 (1H, m), 4.00-4.20 (1H, m), 5.80-5.83 (1H, m), 5.99-6.02 (1H, m), 6.41-6.45 (1H, m), 7.07-7.37 (10H, m), 7.77-7.80 (1H, m).

Elemental analysis for C$_{24}$H$_{26}$ClN$_5$O$_2$S

Calcd. (%): C, 59.56; H, 5.41; N, 14.47.

Found (%): C, 59.42; H, 5.40; N, 14.36.

EXAMPLE 137

N-(4-chlorophenyl)-N'-((1R)-2,2-dimethyl-1-((4-((2Z)-3-methyl-2-(methylimino)-2,3-dihydro-1,3-thiazol-5-yl)-1-piperidinyl)carbonyl)propyl)urea

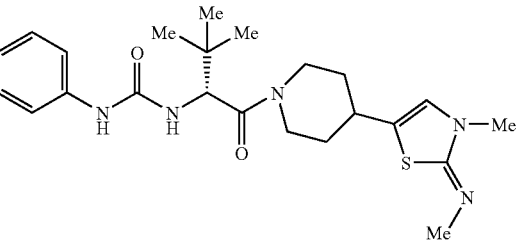

137a) tert-butyl 4-((2Z)-3-methyl-2-(methylimino)-2,3-dihydro-1,3-thiazol-5-yl)-1-piperidinecarboxylate A solution of tert-butyl 4-(1-bromo-2-oxoethyl)-1-piperidinecarboxylate (21 g) and N,N'-dimethylthiourea (6.0 g) in ethanol (300 ml) was heated under reflux. The reaction mixture was concentrated under reduced pressure, the residue was dissolved in ethyl acetate and water, and the aqueous layer was collected by separation. The residue was basified with an aqueous potassium carbonate solution and extracted with chloroform. The extract was dried over anhydrous sodium sulfate and the solvent was distilled off under reduced pressure to obtain the title compound as a pale yellow solid (12 g, 57%).

NMR (CDCl$_3$) δ: 1.47 (9H, s), 1.46-1.55 (2H, m), 1.83-1.87 (2H, m), 2.55 (1H, m), 2.78 (2H, m), 2.98 (3H, s), 3.23 (3H, s), 4.14 (2H, br), 6.17 (1H, s).

137b) N-(4-chlorophenyl)-N'-((1R)-2,2-dimethyl-1-((4-((2Z)-3-methyl-2-(methylimino)-2,3-dihydro-1,3-thiazol-5-yl)-1-piperidinyl)carbonyl)propyl)urea In the same manner as in Example 133b), the title compound as a pale yellow solid (0.23 g, 52%) was obtained from tert-butyl 4-((2Z)-3-methyl-2-(methylimino)-2,3-dihydro-1,3-thiazol-5-yl)-1-piperidinecarboxylate (0.29 g) obtained in Example 137a).

NMR (CDCl$_3$) δ: 0.96-1.08 (9H, m), 1.36-1.52 (2H, m), 1.90-2.03 (2H, m), 2.60-2.76 (2H, m), 2.93-3.03 (3H, m), 3.17 (1H, m), 3.44 (3H, s), 4.30 (1H, m), 4.60 (1H, m), 4.83 (1H, d, J=9.0), 6.25-6.39 (2H, m), 7.12-7.22 (2H, m), 7.22-7.33 (3H, m), 7.93 (1H, m).

EXAMPLE 138

N-(4-chlorophenyl)-N'-((1R)-2-(4-((2Z)-3-methyl-2-(methylimino)-2,3-dihydro-1,3-thiazol-5-yl)-1-piperidinyl)-2-oxo-1-phenylethyl)urea hydrochloride

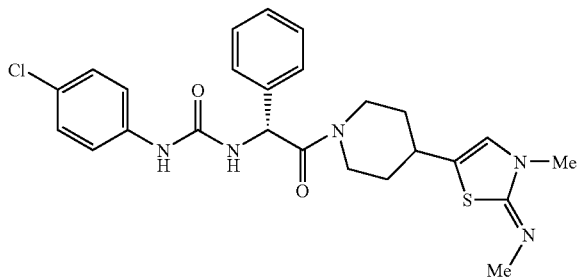

In the same manner as in Example 133b), the title compound (0.19 g, 71%, 70% ee) as colorless powder was obtained from tert-butyl 4-((2Z)-3-methyl-2-(methylimino)-2,3-dihydro-1,3-thiazol-5-yl)-1-piperidinecarboxylate (0.16 g) obtained in Example 137a).

NMR (DMSO-$d_6$) δ: 1.44-1.91 (4H, m), 2.68-3.40 (7H, m), 3.51-3.56 (3H, m), 3.90-4.10 (1H, m), 4.44-4.48 (1H, m), 5.75-5.81 (1H, m), 7.05-7.11 (1H, m), 7.23-7.44 (9H, m), 9.07-9.09 (1H, m), 9.88 (1H, br).

Elemental analysis for $C_{25}H_{29}Cl_2N_5O_2S \cdot H_2O$
Calcd. (%): C, 54.35; H, 5.66; N, 12.68.
Found (%): C, 54.39; H, 5.65; N, 12.60.

EXAMPLE 139

N-(4-chlorophenyl)-N'-((1R)-2,2-dimethyl-1-((4-((2-imino-1,3-thiazol-3(2H)-yl)methyl)-1-piperidinyl)carbonyl)propyl)urea

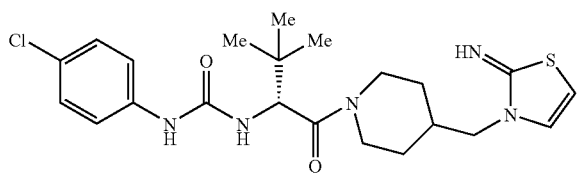

139a) tert-butyl 4-((2-imino-1,3-thiazol-3(2H)-yl)methyl)-1-piperidinecarboxylate In the same manner as in Example 133a), the title compound as a brown oil (0.90 g, 18%) was obtained from tert-butyl 4-bromomethyl-1-piperidinecarboxylate (4.8 g) and 2-aminothiazole (3.4 g).

NMR (CDCl$_3$) δ: 1.08-1.22 (2H, m), 1.45 (9H, s), 1.67 (2H, d, J=12.9), 2.05 (1H, m), 2.68 (2H, t, J=13.2), 3.57 (2H, br), 4.12 (2H, br), 5.77 (1H, d, J=4.8), 6.33 (1H, d, J=4.8).

139b) tert-butyl 4-(((2Z)-2-(((allyloxy)carbonyl)imino)-1,3-thiazol-3(2H)-yl)methyl)-1-piperidinecarboxylate To a solution of tert-butyl 4-((2-imino-1,3-thiazol-3(2H)-yl)methyl)-1-piperidinecarboxylate (0.9 g) obtained in Example 139a) and triethylamine (0.93 ml) in dichloromethane (10 ml) was added allyl chloroformate (0.35 ml) under ice-cooling, and mixed at 0° C. for 12 hours. Ice chips were added to the reaction mixture to stop the reaction, and diluted with ethyl acetate and water. The organic layer was collected by separation, washed with saturated sodium bicarbonate water and saturated brine, and dried over anhydrous sodium sulfate. The solvent was distilled off under reduced pressure to obtain the title compound as a colorless solid (1.1 g, 96%).

NMR (CDCl$_3$) δ: 1.10-1.28 (2H, m), 1.45 (9H, s), 2.10 (1H, m), 2.65 (2H, t, J=11.0), 3.98 (2H, d, J=7.2), 4.69-4.74 (2H, m), 5.23 (1H, d, J=10.2), 5.35 (1H, d, J=15.8), 6.05 (1H, m), 6.58 (1H, d, J=4.8), 6.81 (1H, d, J=4.8).

139c) allyl (2Z)-3-(1-(2-(N'-(4-chlorophenyl)ureido)-3,3-dimethylbutyroyl)-4-piperidinyl)methyl-1,3-thiazol-2(3H)-ylidenecarbamate tert-Butyl 4-(((2Z)-2-(((allyloxy)carbonyl)imino)-1,3-thiazol-3(2H)-yl)methyl)-1-piperidinecarboxylate (0.49 g) obtained in Example 139b) was dissolved in a 4 N solution of hydrochloric acid in dioxane (10 ml), and mixed at room temperature for 4 hours. To the reaction mixture was added an aqueous potassium carbonate solution and extracted with chloroform. The extract was dried over anhydrous sodium sulfate, and then concentrated under reduced pressure. The residue was dissolved in acetonitrile, triethylamine (0.36 ml), WSC (0.37 g), HOBt (0.29 g) and Boc-D-tert-leucine (0.44 g) were added thereto, and mixed at room temperature for 12 hours. The reaction mixture was concentrated under reduced pressure, and the residue was dissolved in chloroform and a saturated aqueous sodium hydrogen carbonate solution. The organic layer was collected by separation and dried over anhydrous sodium sulfate, and the solvent was distilled off under reduced pressure. The residue was dissolved in a 4 N solution of hydrochloric acid in dioxane and mixed at room temperature for 4 hours. To the reaction mixture was added an aqueous potassium carbonate solution and extracted with chloroform. The extract was dried over anhydrous sodium sulfate, and then concentrated under reduced pressure. The residue was dissolved in acetonitrile, 4-chlorophenyl isocyanate was added thereto, and mixed for 2 hours. The reaction mixture was concentrated under reduced pressure, and the residue was purified with silica gel column to obtain the title compound as a white solid (0.35 g, 50%).

NMR (CDCl$_3$) δ: 0.96-1.08 (9H, m), 1.20-1.35 (2H, m), 1.63-1.79 (2H, m), 2.29 (1H, m), 2.55 (1H, m), 3.03 (1H, m), 3.85 (1H, m), 4.03 (1H, d, J=7.7), 4.22 (1H, m), 4.61-4.74 (3H, m), 4.87 (1H, t, J=9.8), 5.23 (1H, d, J=10.4), 5.35 (1H, d, J=17.2), 6.06 (1H, m), 6.59-6.84 (2H, m), 7.16-7.23 (4H, m).

139d) N-(4-chlorophenyl)-N'-((1R)-2,2-dimethyl-1-((4-((2-imino-1,3-thiazol-3(2H)-yl)methyl)-1-piperidinyl)carbonyl)propyl)urea Allyl(2Z)-3-(1-(2-(N'-(4-chlorophenyl)ureido)-3,3-dimethylbutyroyl)-4-piperidinyl)methyl-1,3-thiazol-2(3H)-ylidenecarbamate (0.33 g) obtained in Example 139c) and meldrum's acid (0.13 g) were dissolved in THF (10 ml). The solution was deaerated and substituted with argon. Tetrakis(triphenylphosphine)palladium (0.07 g) was added thereto, and mixed under argon atmosphere for 12 hours. The precipitated insolubles were filtered off, and the filtrate was concentrated under reduced pressure. The residue was purified with silica gel column to obtain the title compound as a pale yellow solid (0.14 g, 51%).

NMR (CDCl₃) δ: 0.95-1.08 (9H, m), 1.18-1.33 (2H, m), 1.61-1.86 (2H, m), 2.20 (1H, m), 2.58 (1H, m), 3.12 (1H, m), 3.43-3.63 (3H, m), 4.23 (1H, m), 4.63 (1H, m), 4.90 (1H, m), 5.74 (1H, m), 6.15-6.34 (2H, m), 7.15-7.34 (5H, m), 7.65 (1H, s).

EXAMPLE 140

N-(4-chlorophenyl)-N'-((1R)-2,2-dimethyl-1-((4-(2-(2-imino-1,3-thiazol-3(2H)-yl)ethyl)-1-piperidinyl)carbonyl)propyl)urea

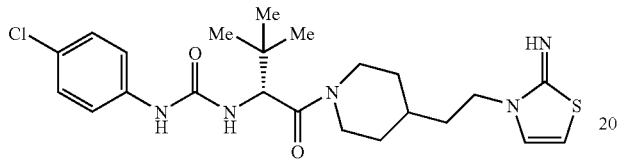

140a) tert-butyl 4-(2-(2-imino-1,3-thiazol-3(2H)-yl)ethyl)-1-piperidinecarboxylate In the same manner as in Example 133a), the title compound as a brown oil (1.1 g, 20%) was obtained from tert-butyl 4-(2-bromoethyl)-1-piperidinecarboxylate (5.0 g) and 2-aminothiazole (3.4 g).

NMR (CDCl₃) δ: 1.04-1.25 (2H, m), 1.45 (9H, s), 1.50 (1H, m), 1.60-1.74 (4H, m), 2.67 (2H, t, J=11.0), 3.74 (2H, t, J=7.2), 4.07 (2H, d, J=11.0), 5.77 (1H, d, J=4.8), 6.37 (1H, d, J=4.8), 7.15-7.34 (5H, m), 7.65 (1H, s).

140b) tert-butyl 4-(2-((2Z)-2-(((allyloxy)carbonyl)imino)-1,3-thiazol-3(2H)-yl)ethyl)-1-piperidinecarboxylate In the same manner as in Example 139b), the title compound as a white solid (1.3 g, 96%) was obtained from tert-butyl 4-(2-(2-imino-1,3-thiazol-3(2H)-yl)ethyl)-1-piperidinecarboxylate (1.0 g) obtained in Example 140a).

NMR (CDCl₃) δ: 1.12-1.22 (2H, m), 1.38 (1H, m), 1.45 (9H, s), 1.69-1.76 (4H, m), 2.66 (2H, t, J=13.5), 4.08-4.20 (4H, m), 4.69-4.72 (2H, m), 5.20-5.25 (2H, m), 5.32-5.40 (2H, m), 5.97-6.11 (1H, m), 6.60 (1H, d, J=4.8), 6.86 (1H, d, J=4.8).

140c) allyl (2Z)-3-(1-(2-(N'-(4-chlorophenyl)ureido)-3,3-dimethylbutyroyl)-4-piperidinyl)ethyl)-1,3-thiazol-2(3H)-ylidenecarbamate In the same manner as in Example 139c), the title compound as a white solid (0.40 g, 59%) was obtained from tert-butyl 4-(2-((2Z)-2-(((allyloxy)carbonyl)imino)-1,3-thiazol-3(2H)-yl)ethyl)-1-piperidinecarboxylate (0.48 g) obtained in Example 140b).

NMR (CDCl₃) δ: 0.97-1.06 (9H, m), 1.18-1.33 (2H, m), 1.53-1.87 (5H, m), 2.59 (1H, m), 3.03 (1H, m), 4.07-4.20 (3H, m), 4.60 (1H, m), 4.67-4.72 (2H, m), 4.89 (t, J=8.7), 5.23 (1H, d, J=10.4), 5.36 (1H, d, J=17.1), 6.10 (1H, m), 6.61 (1H, m), 6.83 (1H, m), 7.16-7.25 (4H, m), 7.33 (1H, d, J=10.4).

140d) N-(4-chlorophenyl)-N'-((1R)-2,2-dimethyl-1-((4-(2-(2-imino-1,3-thiazol-3(2H)-yl)ethyl)-1-piperidinyl)carbonyl)propyl)urea In the same manner as in Example 139d), the title compound as a pale yellow solid (0.24 g, 74%) was obtained from allyl (2Z)-3-(1-(2-(N'-(4-chlorophenyl)ureido)-3,3-dimethylbutyroyl)-4-piperidinyl)ethyl)-1,3-thiazol-2(3H)-ylidenecarbamate (0.38 g) obtained in Example 140c).

NMR (CDCl₃) δ: 1.00 (9H, s), 1.17-1.32 (2H, m), 1.55-1.86 (5H, m), 2.58 (1H, m), 3.02 (1H, m), 3.64-3.78 (2H, m), 4.16 (1H, d, J=13.4), 4.58 (1H, m), 4.88 (1H, t, J=9.1), 5.76 (1H, t, J=5.2), 6.19 (1H, d, J=9.2), 6.34 (1H, dd, J=4.9, 13.4), 7.15-7.29 (4H, m), 7.51 (1H, m).

EXAMPLE 141

N-(4-chlorophenyl)-N'-((1R)-2,2-dimethyl-1-((4-((2-imino-3-methyl-2,3-dihydro-1,3-thiazol-4-yl)methyl)-1-piperazinyl)carbonyl)propyl)urea

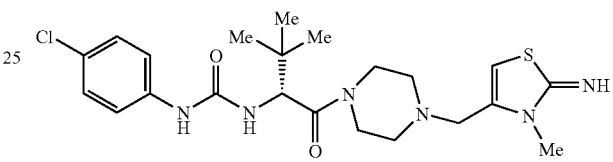

141a) tert-butyl 4-((2-amino-1,3-thiazol-4-yl)methyl)piperazine-1-carboxylate A solution of Boc-piperazine (4.67 g), 2-amino-4-chloromethylthiazole hydrochloride (WO 0190090; 5.1 g) and potassium carbonate (8.4 g) in DMF (100 ml) was mixed at 65° C. for 12 hours. The precipitated insolubles were filtered off, and then the filtrate was concentrated under reduced pressure. The residue was purified with silica gel column to obtain the title compound as a brown solid (5.6 g, 74%).

NMR (CDCl₃) δ: 1.45 (9H, s), 2.36-2.46 (4H, m), 3.42-3.49 (4H, m), 4.94 (2H, s), 6.32 (1H, s).

141b) tert-butyl 4-((2-imino-3-methyl-2,3-dihydro-1,3-thiazol-4-yl)methyl)-1-piperazinecarboxylate In the same manner as in Example 135c), the title compound as a pale yellow solid (0.56 g, 10%) was obtained from tert-butyl 4-((2-amino-1,3-thiazol-4-yl)methyl)piperazine-1-carboxylate (5.5 g) obtained in Example 141a).

NMR (CDCl₃) δ: 1.46 (9H, s), 2.36-2.41 (4H, m), 3.20 (2H, s), 3.39 (3H, s), 3.39-3.45 (4H, m), 5.30 (1H, s), 5.64 (1H, s).

141c) tert-butyl 4-(((2Z)-2-(((allyloxy)carbonyl)imino)-3-methyl-2,3-dihydro-1,3-thiazol-4-yl)methyl)-1-piperazinecarboxylate In the same manner as in Example 139b), the title compound as a white solid (0.63 g, 83%) was obtained from tert-butyl 4-((2-imino-3-methyl-2,3-dihydro-1,3-thiazol-4-yl)methyl)-1-piperazinecarboxylate (0.59 g) obtained in Example 141b).

NMR (CDCl₃) δ: 1.46 (9H, s), 2.34-2.42 (4H, m), 3.37-3.43 (4H, m), 3.41 (3H, s), 3.73 (2H, s), 4.69 (2H, d, J=6.0), 5.21 (1H, d, J=11.5), 5.35 (1H, d, J=17.1), 5.98-6.08 (1H, m), 6.38 (1H, s).

141d) allyl (2Z)-3-(4-(2-(N'-(4-chlorophenyl)ureido)-3,3-dimethylbutyroyl)-1-piperazinyl)methyl)-3-methyl-1,3-thiazol-2(3H)-ylidenecarbamate In the same manner as in Example 139c), the title compound as a white solid (0.23 g, 35%) was obtained from tert-butyl 4-(((2Z)-2-(((allyloxy)carbonyl)imino)-3-methyl-2,3-dihydro-1,3-thiazol-4-yl)methyl)-1-piperazinecarboxylate (0.46 g) obtained in Example 141c).

NMR (CDCl$_3$) δ: 1.01 (9H, s), 2.28-2.59 (4H, m), 3.34-3.45 (3H, m), 3.55 (1H, m), 3.72 (3H, s), 3.69-3.76 (2H, m), 4.71 (2H, d, J=5.7), 4.81 (1H, d, J=9.2), 5.22 (1H, dd, J=1.1, 10.4), 5.36 (1H, d, J=17.4), 5.75 (1H, d, J=9.4), 6.03 (1H, m), 6.39 (1H, s), 6.78 (1H, s), 7.21-7.25 (4H, m).

141e) N-(4-chlorophenyl)-N'-((1R)-2,2-dimethyl-1-((4-((2-imino-3-methyl-2,3-dihydro-1,3-thiazol-4-yl)methyl)-1-piperazinyl)carbonyl)propyl)urea In the same manner as in Example 139d), the title compound as a pale yellow solid (0.14 g, 81%) was obtained from allyl (2Z)-3-(4-(2-(N'-(4-chlorophenyl)ureido)-3,3-dimethylbutyroyl)-1-piperazinyl)methyl)-3-methyl-1,3-thiazol-2(3H)-ylidenecarbamate (0.21 g) obtained in Example 141d).

NMR (CDCl$_3$) δ: 1.02 (9H, s), 2.21-2.52 (4H, m), 3.17 (2H, s), 3.34 (3H, s), 3.41 (1H, m), 3.56 (1H, m), 3.78-3.93 (2H, m), 4.84 (1H, d, J=9.4), 5.61 (1H, s), 6.13 (1H, d, J=9.4), 7.17-7.27 (4H, m), 7.45 (1H, s).

PREPARATION EXAMPLE 1

FXa inhibitors (e.g., therapeutic agent for deep vein thrombosis, therapeutic agent for cardiogenic cerebral infarction, etc.) comprising the compound represented by Formula (1) in the invention or a salt thereof as an active ingredient can be prepared by, for example, the following formulation.

In addition, as ingredients (additives) other than the active ingredients in the following formulation, the list of ingredients according to Japanese Pharmacopoeia, Pharmaceutical Specification out of Japanese Pharmacopoeia or Pharmaceutical Additives Specification can be used.

| 1. Capsule | |
|---|---|
| (1) Compound obtained in Example 20 | 120 mg |
| (2) Lactose | 210 mg |
| (3) Microcrystalline cellulose | 27 mg |
| (4) Magnesium stearate | 3 mg |
| 1 Capsule | 360 mg |

(1), (2), (3) and ½ of (4) were mixed and then granulated. The remaining (4) was added thereto, and the whole mixture was encapsulated in a gelatin capsule.

| 2. Capsule | |
|---|---|
| (1) Compound obtained in Example 74 | 120 mg |
| (2) Lactose | 210 mg |
| (3) Microcrystalline cellulose | 27 mg |
| (4) Magnesium stearate | 3 mg |
| 1 Capsule | 360 mg |

(1), (2), (3) and ½ of (4) were mixed and then granulated. The remaining (4) was added thereto, and the whole mixture was encapsulated in a gelatin capsule.

| 3. Tablet | |
|---|---|
| (1) Compound obtained in Example 20 | 120 mg |
| (2) Lactose | 174 mg |
| (3) Corn starch | 54 mg |
| (4) Microcrystalline cellulose | 10.5 mg |
| (5) Magnesium stearate | 1.5 mg |
| 1 Tablet | 360 mg |

(1), (2), (3), ⅔ of (4) and ½ of (5) were mixed and then granulated. The remaining (4) and (5) were added to the granules, and the mixture was compressed to give tablets.

| 4. Tablet | |
|---|---|
| (1) Compound obtained in Example 74 | 120 mg |
| (2) Lactose | 174 mg |
| (3) Corn starch | 54 mg |
| (4) Microcrystalline cellulose | 10.5 mg |
| (5) Magnesium stearate | 1.5 mg |
| 1 Tablet | 360 mg |

(1), (2), (3), ⅔ of (4) and ½ of (5) were mixed and then granulated. The remaining (4) and (5) were added to the granules, and the mixture was compressed to give tablets.

PREPARATION EXAMPLE 2

50 mg of the compound obtained in Example 74 was dissolved in 50 mL of the distilled water for injection according to Japanese Pharmacopoeia, and then the distilled water for injection according to Japanese Pharmacopoeia was added to a volume of 100 mL. The solution was filtered under the sterilized condition, and then taken out in 1 mL-portions, and under sterilized condition, charged into a vial for injection. The vials were freeze-dried for sealing.

EXPERIMENTAL EXAMPLE 1

(1) Human Activated Blood Coagulation Factor X (FXa) Inhibitory Action

Method of experiment: 225 μl of a 0.05 M Tris hydrochloride buffer (pH 8.3) containing 0.145 M sodium chloride and 2 mM calcium chloride, 5 μl of a sample (the test compound is dissolved in dimethylsulfoxide), and 10 μl of human FXa (0.3 unit/ml) were added to a 96-well microplate to react at 37° C. for about 10 minutes, and then 10 μl of a substrate (3 mM, S-2765) was added thereto to react at 37° C. for about 10 minutes. Subsequently, 25 μl of a 50% aqueous acetic acid solution was added to terminate the reaction, and then the change in the absorbance at 405 nm was measured with a spectrophotometer to calculate the concentration inhibiting 50% of the FXa action (IC$_{50}$).

(2) Method of Measuring In Vitro Coagulation Time (2-1) Method of Measuring Extrinsic Coagulation Time (PT):

The extrinsic coagulation time was measured with an automatic blood coagulation time measuring device (STA compact, Diagnostica stago, Inc.) using a PT reagent (Diagnostica Stago, Inc.). 3 μl of the drug was added to 97 μl of human normal plasma (fresh human plasma FFP, Sekisui Chemical Co., Ltd.), and the mixture was pre-warmed to 37° C. for 4 minutes. To 50 µl of the aforementioned plasma, 100 µl of a solution of tissue thromboplastin derived from rabbit brain was added, and then the time to coagulate was measured. The drug was dissolved in dimethylsulfoxide (DMSO) for use. The concentration for doubling the coagulation time was calculated based on the coagulation time for the case of adding DMSO instead of the drug.

(2-2) Method of Measuring Intrinsic Coagulation Time (APTT)

The intrinsic coagulation time was measured with an automatic blood coagulation time measuring device using STA-APTT-LT (Diagnostica Stago, Inc.). 3 µl of the drug was added to 97 µl of human normal plasma. To 50 µl of the plasma, 50 µl of a solution of activated partial thromboplastin was added, and the mixture was pre-warmed to 37° C. for 4 minutes. 50 µl of a 25 mmol/l $CaCl_2$ solution was added, and the time to coagulate was measured. The drug was dissolved in DMSO for use. The concentration for doubling the coagulation time was calculated in the same manner as in (2-1).

(2-3) Method of Measuring Thrombin Coagulation Time (TT):

The thrombin coagulation time was measured with an automatic blood coagulation time measuring device using a fibrinogen reagent (Diagnostica Stago, Inc.). The fibrinogen reagent (containing thrombin) was dissolved in 5 ml of distilled water, and then was adjusted by diluting to a 20-fold volume with 0.5% bovine serum albumin-added physiological saline. 3 µl of the drug was added to 97 µl of human normal plasma (fresh human plasma FFP, Sekisui Chemical Co., Ltd.), and the mixture was pre-warmed to 37° C. for 3 minutes. To 50 µl of the above-mentioned plasma, 100 µl of a thrombin solution was added, and the time to coagulate was measured. The drug was dissolved in DMSO for use. The concentration for doubling the coagulation time was calculated in the same manner as in (2-1).

(3) Method of Measuring Ex Vivo Coagulation Time (Mouse)

(3-1) Intravenous Administration:

Male ICR mice (25 to 35 g, Crea Japan Inc.) were used. Under pentobarbital (50 mg/kg, i.p.) anesthesia, the drug was administered a singe time through the tail vein in a dose of 5 ml/kg. After five minutes of administration, 0.8 ml of blood was collected in a tube containing a 1/10 volume of a 3.8% sodium citrate solution (Chitoral, Yamanouchi Pharmaceutical Co., Ltd.) from the abdominal aorta or from the heart, and was centrifuged at 3000 rpm for 15 minutes to obtain the plasma. To 50 µl of the plasma, 100 µl of a solution of thromboplastin derived from rabbit brain tissue was added, and then the time to coagulate was measured. The coagulation time was measured with an automatic blood coagulation time measuring device (STA compact) using a PT reagent (Diagnostica Stago, Inc.). The drug was dissolved in a solution prepared by mixing dimethylacetamide, 1/10 N hydrochloric acid and physiological saline for use, and for the control, a solution formed by mixing dimethylacetamide, 1/10 N hydrochloric acid and physiological saline was administered. The drug activity was referred to as a ratio (%) of the coagulation time in the drug administered group to the coagulation time in the control group.

(3-2) Oral Administration:

Male ICR mice (25 to 35 g, Crea Japan, Inc.) were used. Mice which had fasted for over 12 hours were forced to take oral administration of the drug at a dose of 5 ml/kg. After 1 hour of administration, blood was collected from abdominal aorta under pentobarbital (50 mg/kg, i.p.) anesthesia. The drug was used as a suspension in 0.5% methylcellulose, and for the control, 0.5% methylcellulose was administered instead of the drug. The other procedure was carried out in the same manner as in (3-1).

(4) Method of Measuring In Vivo Antithrombotic Action (4-1) Rat Arteriovenous Shunt Method:

The method was carried out according to the method of Umetsu, et al. (Thromb. Haemostas., 39, 74-73 (1978)). Male SD rats (200 to 350 g, Crea Japan, Inc.) were employed, and an extracorporeal circulation route of a polyethylene tube having a silk thread was placed in between the left jugular vein and the right jugular vein in each rat, under pentobarbital (50 mg/kg, i.p.) anesthesia. In order to prevent blood coagulation, the tube was filled in advance with physiological saline containing heparin (50 U/ml). The blood was circulated for 15 minutes, and the wet weight of the thrombi attached to the silk thread during the circulation was measured. The drug administration was performed orally or intravenously. In the case of oral administration, the drug was administered (2 ml/kg) as a suspension in 0.5% methylcellulose under fasting, and for the control, 0.5% methylcellulose was administered instead of the drug. In the case of intravenous administration, the drug was dissolved in physiological saline and was administered through the tail vein at a dose of 1 ml/kg, and for the control, physiological saline was administered instead of the drug. The drug activity was calculated as a ratio (%) of the wet weight of thrombi in the drug administered group to the wet weight of thrombi in the control group.

(4-2) Rat Abdominal Vena Cava Partial Ligation Model

Male SD rats (200 to 400 g, Crea Japan, Inc.) were used. In each rat, the abdominal vena cava was carefully detached under pentobarbital (50 mg/kg, i.p.) anesthesia, and then threads were used to ligate all of the rami present between the renal vein bifurcation of the abdominal vena cava and a spot 1 cm downstream therefrom. A balloon catheter (Fogarty 2F, Baxter, Inc.) was inserted from the left femoral vein, and the part between the two pieces of threads was injured three times using a balloon filled with 200 to 300 ml of air. The balloon catheter was removed, and a partial ligation was produced by tying the thread tied at the renal vein bifurcation together with a 26G needle and then removing the needle. After 30 minutes, a piece of thread was tied, and the thrombi caught between the two pieces of threads were carefully isolated. The wet weight of thrombi was measured by using an analytic balance equipped with windshield (BP1100S, Sartorius AG). The drug administration was performed orally or intravenously in the same manner as in (4-1). The drug activity was calculated in the same manner as in (4-1).

(4-3) Rat Deep Vein Thrombosis (DVT) Model

Male SD rats (200 to 350 g, Crea Japan, Inc.) were employed. In each rat, a polyethylene tube was inserted to the left femoral vein under pentobarbital (50 mg/kg, i.p.) anesthesia. A silk thread (length 5 cm) connected in advance to a guide wire was inserted to the polyethylene tube, and the polyethylene tube was filled physiological saline containing heparin (50 U/ml) in order to prevent blood coagulation. The polyethylene tube was inserted until it reached the abdominal vena cava, and the silk thread was placed to stand still in the abdominal vena cava by using the guide wire. After standing for 30 minutes, heparin (200 U/kg) was intravenously administered through the tail vein. After bleeding by means of brachial artery incision, the abdominal cavity was surgically opened to take out the silk thread, and the wet weight of attached thrombi (including the weight of silk thread) was measured. The drug administration was performed orally or intravenously in the same manner as in (4-1). The wet weight of thrombi only was determined from the formula: (wet weight of thrombi attached to the silk thread)−(wet weight of the silk thread measured by immersing the silk thread in the venous blood collected with heparin). The drug activity was calculated in the same manner as in (4-1).

Experiment Results

The $IC_{50}$ values determined from Experiment Example 1(1) are presented in Table 1. From these results, it is clear that the compound of the invention has excellent FXa inhibitory action.

TABLE 1

| Example No. | $IC_{50}$ (nM) |
|---|---|
| 20 | 18 |
| 37 | 26 |
| 40 | 10 |
| 74 | 50 |

INDUSTRIAL APPLICABILITY

The Compound (I) of the present invention or a salt thereof has excellent FXa inhibitory action with low side effect of hemorrhage, is useful as an orally absorbable anticoagulant, and is advantageously used in the prevention and/or treatment of various diseases caused by thrombosis or infarction.

The invention claimed is:

1. A compound represented by Formula (1):

[Formula 1]

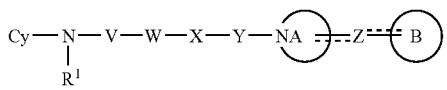

(I)

wherein Cy is a phenyl which may be substituted with a halogen atom or a $C_{2-4}$ alkylene; $R^1$ is a hydrogen atom; V is —C(O); W is —NH—; X is a methylene which may be substituted with (1) a $C_{1-6}$ alkyl, (2) a $C_{2-6}$ alkenyl, (3) a $C_{2-6}$ alkynyl, (4) a phenyl, (5) a $C_{3-7}$ cycloalkyl, (6) a $C_{3-6}$ cycloalkenyl, (7) a $C_{7-16}$ aralkyl or (8) a 5- to 6-membered aromatic monocyclic heterocyclic group, where each of the $C_{1-6}$ alkyl of (1), the $C_{2-6}$ alkenyl of (2), the $C_{2-6}$ alkynyl of (3), the phenyl of (4), the $C_{3-7}$ cycloalkyl of (5), the $C_{3-6}$ cycloalkenyl of (6), the $C_{7-16}$ aralkyl of (7) and the 5- to 6-membered aromatic monocyclic heterocyclic group of (8) may be substituted with (i) a hydroxyl group, (ii) a thiol group which may be substituted with $C_{1-6}$ alkyl, (iii) a carboxyl, (iv) a $C_{1-6}$ alkoxycarbonyl, (v) an acyl, (vi) an amino which may be substituted with lower alkyl, carboxyl, $C_{1-6}$ alkoxycarbonyl or acyl, (vii) a halogen atom, (viii) a carbamoyloxy, (ix) a nitro group, (x) a cyano group, (xi) a lower alkyl which may be substituted with 1 to 5 halogen atoms, (xii) a phenyl which may be substituted with 1 to 5 halogen atoms, (xiii) a lower alkoxy which may be substituted with a phenyl or 1 to 5 halogen atoms, (xiv) a 5- to 6-membered aromatic monocyclic heterocyclic group or (xv) a thioxo; Y is —C(O); Z is a bond or a $C_{1-6}$ alkylene; ring A is a piperadine ring which may be substituted, or a piperazine ring which may be substituted; ring B is a piperazine ring which may be substituted, an imidazoline ring which may be substituted, an imidazole ring which may be substituted, a thiazoline ring which may be substituted, or a fused nitrogen-containing heterocyclic ring which may be substituted; and ⚌,⚌ is each independently a single bond or a double bond, or a salt thereof.

2. The compound according to claim 1, wherein Cy is a phenyl which may be substituted with a halogen atom.

3. The compound according to claim 1, wherein ring B is a fused nitrogen-containing heterocyclic ring which may be substituted.

4. The compound according to claim 3, wherein the fused nitrogen-containing heterocyclic ring is a fused pyridine ring which may be substituted, a fused imidazole ring which may be substituted, a fused pyrazole ring which may be substituted, or a fused thiazoline ring which may be substituted.

5. A compound selected from the group consisting of N-(4-chlorophenyl)-N'-((1R)-2,2-dimethyl-1-((4-(5-methyl-3-oxo-1H-imidazo[1,5-c]imidazol-2(3H)-yl)-1-piperazinyl)carbonyl)propyl)urea, N-(4-chlorophenyl)-N'-(2-ethyl-2-hydroxy-1-((4-(5-methyl-3-oxo -1H-imidazo[1,5-c]imidazol-2(3H)-yl)-1-piperazinyl)carbonyl)butyl)urea, N-(4-chlorophenyl) -N'-((1S)-2-methyl-1-((4-(5-methyl-3-oxo-1H-imidazo[1,5-c]imidazol-2(3H)-yl)-1-piperazinyl)carbonyl)-2-(methylthio)propyl)urea, and N-(4-chlorophenyl)-N'- (2-methoxy-2-methyl-1-((4-(5-methyl-3-oxo-1H-imidazo[1,5-c]imidazol-2(3H)-yl)-1-piperazinyl)carbonyl)propyl)urea, or a salt thereof.

6. A pharmaceutical composition comprising the compound according to claim 1.

7. A method of treating myocardial infarction, cerebral infarction, deep vein thrombosis, pulmonary thromboembolism or arteriosclerosis obliterans in mammal which comprises administering an effective amount of the compound according to claim 1 to the mammal.

8. The compound according to claim 1, wherein ⚌,⚌ are both single bonds.

* * * * *